United States Patent [19]
Godfrey et al.

[11] Patent Number: 5,952,359
[45] Date of Patent: Sep. 14, 1999

[54] THIAZOLES AND THEIR AGRICULTURAL COMPOSITIONS

[75] Inventors: Christopher Richard Ayles Godfrey, Bracknell; Matthew Brian Hotson, Binfield; Nan Catherine Sillars, Camberley; Alan John Dowling, Maidenhead; Michael Drysdale Turnbull, Reading; Harjinder Singh Bansal, Bracknell; Allison Mary Smith, Richmond; Roger Salmon, Bracknell; Steven Fitzjohn, Bracknell, all of United Kingdom

[73] Assignee: ZENECA Limited, London, United Kingdom

[21] Appl. No.: 08/887,858

[22] Filed: Jul. 3, 1997

Related U.S. Application Data

[62] Division of application No. 08/400,912, Mar. 8, 1995, Pat. No. 5,705,516.

[51] Int. Cl.$^6$ ...................... A61K 31/425; C07D 275/03; C07D 277/36
[52] U.S. Cl. .......................... 514/369; 514/372; 548/183; 548/213
[58] Field of Search ..................... 514/369, 372; 548/183, 213

[56] References Cited

U.S. PATENT DOCUMENTS

| | | | |
|---|---|---|---|
| 3,223,707 | 12/1965 | Brokke | 544/315 |
| 3,780,050 | 12/1973 | Brokke | 544/315 |
| 4,059,635 | 11/1997 | Sugiyama et al. | 424/270 |
| 4,089,964 | 5/1978 | Sugiyama et al. | 424/270 |
| 4,097,669 | 6/1978 | Reisdorff et al. | 542/413 |
| 4,694,014 | 9/1987 | Ernst | 514/363 |
| 4,770,692 | 9/1988 | Stetter et al. | 548/376 |
| 4,771,066 | 9/1988 | Gehring et al. | 514/404 |
| 4,804,675 | 2/1989 | Jensen-Korte et al. | 514/407 |
| 4,810,720 | 3/1989 | Jensen-Korte et al. | 514/407 |
| 4,910,210 | 3/1990 | Beriger et al. | 514/363 |
| 4,952,580 | 8/1990 | Martinez et al. | 514/236.2 |
| 5,075,326 | 12/1991 | Beck et al. | 514/369 |
| 5,095,024 | 3/1992 | Muller et al. | 514/363 |
| 5,246,938 | 9/1993 | Turnbull et al. | 514/274 |
| 5,250,536 | 10/1993 | Turnbull | 514/269 |
| 5,270,318 | 12/1993 | Turnbull | 514/269 |
| 5,273,988 | 12/1993 | Turnbull | 514/375 |

FOREIGN PATENT DOCUMENTS

| | | |
|---|---|---|
| 2021919 | 1/1991 | Canada . |
| 249033 | 12/1987 | European Pat. Off. . |
| 287851 | 10/1988 | European Pat. Off. . |
| 342150 | 11/1989 | European Pat. Off. . |
| 25 33 605 | 2/1977 | Germany . |
| 38 21 953 | 12/1989 | Germany . |
| 1261381 | 10/1989 | Japan . |
| 1395955 | 5/1975 | United Kingdom . |
| 86/7590 | 12/1986 | WIPO . |
| WO 94/6783 | 3/1994 | WIPO . |
| WO 95/4727 | 2/1995 | WIPO . |

Primary Examiner—Yogendra N. Gupta

[57] ABSTRACT

A compound of formula (I),

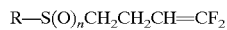

or a salt thereof, wherein n is 0, 1 or 2; and R is a group of formula (V) or (VII)

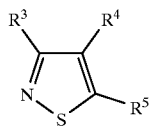

(V)

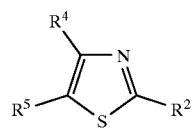

(VII)

wherein:

at least one of $R^2$, $R^3$, $R^4$ or $R^5$ is a $S(O)_nCH_2CH_2CH=CF_2$ group; and the remainder of $R^2$, $R^3$, $R^4$ and $R^5$ are each independently hydrogen, optionally substituted alkyl, optionally substituted alkenyl, alkynyl, cycloalkyl, alkylcycloalkyl, alkoxy, alkenyloxy, alkynyloxy, hydroxyalkyl, alkoxyalkyl, optionally substituted aryl, optionally substituted arylalkyl, optionally substituted heteroaryl, optionally substituted heteroarylalkyl, optionally substituted aryloxy, optionally substituted arylalkoxy, optionally substituted aryloxyalkyl, optionally substituted heteroaryloxy, optionally substituted heteroarylalkoxy, optionally substituted heteroaryloxyalkyl, haloalkyl, haloalkenyl, haloalkynyl, haloalkoxy, haloalkenyloxy, haloalkynyloxy, halogen, hydroxy, cyano, nitro, $-NR^7R^8$, $-NR^7COR^8$, $-NR^7CSR^8$, $-NR^7SO_2R^8$, $-NR^7SO_2R^8$, $-N(SO_2R^7)(SO_2R^8)$, $-COR^7$, $-CONR^7R^8$, -alkylCONR$^7R^8$, $-CR^7NR^8$, $-COR^7$, $-OCOR^7$, $-SR^7$, $-SOR^7$, $-SO_2R^7$, -alkylSR$^7$, -alkylSOR$^7$, -alkylSO$_2R^7$, $-OSO_2R^7$, $-SO_2NR^7R^8$, $-CSNR^7R^8$, $-CSNR^7R^8$, $-SiR^7R^8R^9$, $-OCH_2CO_2R^7$, $-OCH_2CH_2SO_2R^7$, $-CONR^7SO_2R^8$, -alkylCONR$^7SO_2R^8$, $-NHCONR^7R^8$, $-NHCSNR^7R^8$; and $R^7$, $R^8$ and $R^9$ are each independently hydrogen, optionally substituted alkyl, optionally substituted alkenyl, alkynyl, optionally substituted aryl or optionally substituted arylalkyl, haloalkyl, haloalkenyl, haloalkynyl, halogen, or hydroxy; and agricultural compositions, and processes for preparing agricultural compositions made thereby.

14 Claims, No Drawings

THIAZOLES AND THEIR AGRICULTURAL COMPOSITIONS

This application is a divisional of application Ser. No. 08/400,912, filed Mar. 8, 1995 U.S. Pat. No. 5,705,516.

The present invention relates to novel heterocyclic and phenyl derivatives having nematicidal, insecticidal and acaricidal activity, to processes for their preparation, to compositions containing them, and to methods for killing or controlling nematode, insect or acarid pests using them.

According to the present invention there is provided a compound of formula (I), or a salt thereof, wherein n is 0, 1 or 2; and R is a group of formula (II) to (XXI), wherein:

the $S(O)_nCH_2CH_2CH=CF_2$ group is at least one of R1 (when attached to a carbon atom), R2, R3, R4, R5 or R6;

R1 (when attached to a carbon atom), R2, R3, R4, R5 and R6 are each independently hydrogen, optionally substituted alkyl, optionally substituted alkenyl, alkynyl, cycloalkyl, alkylcycloalkyl, alkoxy, alkenyloxy, alkynyloxy, hydroxyalkyl, alkoxyalkyl, optionally substituted aryl, optionally substituted arylalkyl, optionally substituted heteroaryl, optionally substituted heteroarylalkyl, optionally substituted aryloxy, optionally substituted arylalkoxy, optionally substituted aryloxyalkyl, optionally substituted heteroaryloxyalkyl, optionally substituted heteroarylalkoxy, optionally substituted heteroaryloxyalkyl, haloalkyl, haloalkenyl, haloalkynyl, haloalkoxy, haloalkenyloxy, haloalkynyloxy, halogen, hydroxy, cyano, nitro, —NR7R8, —NR7COR8, —NR7CSR8, —NR7SO2R8, —N(SO2R7)(SO2R8), —COR7, —CONR7R8, -alkylCONR7R8, —CR7NR8, —COOR7, —OCOR7, —SR7, —SOR7, —SO2R7, -alkylSR7, -alkylSOR7, -alkylSO2R7, —SO2NR7R8, —CSNR7R8, —SiR7R8R9, —OCH2CO2R7, —OCH2CH2CO2R7, —CONR7SO2R8, -alkylCONR7SO2R8, —NHCONR7R8, —NHCSNR7R8, or an adjacent pair of R1, R2, R3, R4, R5 and R6 when taken together form a fused 5- or 6-membered carbocyclic or heterocyclic ring;

R1 (when attached to a nitrogen atom) is hydrogen, optionally substituted alkyl, cycloalkyl, alkylcycloalkyl, hydroxyalkyl, alkoxyalkyl, optionally substituted aryl, optionally substituted arylalkyl, optionally substituted aryloxyalkyl, optionally substituted heteroaryl, optionally substituted heteroarylalkyl, optionally substituted heteroaryloxyalkyl, haloalkyl, hydroxy, cyano, nitro, —NR7R8, —NR7COR8, NR7CSR8, —NR7COOR8, —NR7SO2R8, —N(SO2R7)(SO2R8), —COR7, —CONR7R8, -alkylCONR7R8, —CR7NR8, —COOR7, —OCOR7, —SOR7, —SO2R7, -alkylSR7, -alkylSOR7, -alkylSO2R7, —OSO2R7, —SO2NR7NR8, —SR7, —SOR7, —SO2R7, —CSNR7R8, —SiR7R8R7, —OCH2CO2R7, —OCH2CH2CO2R7, —CONR7SO2R8, -alkylCONR7SO2R8, —NHCOR7R8, or —NHCSR7R8; and R7, R8 and R9 are each independently hydrogen, optionally substituted alkyl, optionally substituted alkenyl, alkynyl, optionally substituted aryl, optionally substituted arylalkyl, haloalkyl, haloalkenyl, haloalkynyl, halogen, or hydroxy.

We would explain that, for ease of reference only, the substituents on the R group have been named in accordance with their position on this R group. For example, when R has the formula (II), substituents R2, R3, R4 and R5 are in positions 2, 3, 4, and 5, respectively, on the ring. For the avoidance of doubt, the —S(O)nCH2CH2CH=CF2 group can be at any of the substituent positions indicated by R1 (when attached to a carbon atom) to R6.

When any one of R1 to R9 is an alkyl group, or contains an alkyl moiety, it may be straight or branched chain and is preferably C1–6 alkyl, even more preferably C1–4 alkyl, for example methyl, ethyl, propyl, iso-propyl, n-butyl, iso-butyl, sec-butyl or t-butyl. When the alkyl group is acting as a "linking" group, ie R-alkyl-, for example in R-alkyl SR7, C1–4 alkyl or C1–2 alkyl are particularly preferred.

When any one of R1 to R8 is a substituted alkyl group, or contains a substituted alkyl moiety, it may comprise one or more substituents chosen from halogen, nitro, cyano, —COOR7 or a salt thereof, hydroxy, alkoxy, alkoxyimino, alkoxycarbonyl, carbamoyl, mono- or di-alkylcarbamoyl, amino, mono- or di-alkylamino, acylamido (preferably C1–6 acylamido), alkanesulfonyl, and arylsulfonyl, which may itself be substituted with halogen, alkoxy or nitro.

When any one of R1 to R8 is an alkenyl or alkynyl group, or contains an alkenyl or alkynyl moiety, it may be straight or branched chain and is preferably C2–6 alkenyl or C2–6 alkynyl, even more preferably C2–4 alkenyl or C2–4 alkynyl, for example vinyl, allyl, but-3-enyl, 3-methyl-but-3-enyl, ethynyl or propargyl.

When any one of R1 to R8 is a substituted alkenyl group, or contains a substituted alkenyl moiety, it may comprise one or more substituents chosen from halogen, COOR7 or a salt thereof, hydroxy, nitro and cyano.

When any one of R1 to R6 is a cycloalkyl or alkylcycloalkyl group, or contains a cycloalkyl or alkylcycloalkyl moiety, it is preferably C3–6 cycloalkyl or C4–7 alkylcycloalkyl, for example, cyclopropyl, cyclopentyl, cyclohexyl or methylcyclopropyl.

When any one of R1 to R6 is an alkoxy, alkenyloxy, alkynyloxy or alkoxyalkyl group, or contains such a moiety, it is preferably C1–6 alkoxy, for example, methoxy, ethoxy, n-propoxy, iso-propoxy, n-butyoxy, iso-butoxy, sec-butoxy and t-butyoxy; C2–6 alkenyloxy, for example, vinyloxy, allyloxy, but-3-enyloxy and 3-methylbut-3-enyloxy; C2–6 alkynyloxy, for example, propargyloxy; C2–6 monoalkoxyalkyl, for example, methoxymethyl, methoxyethyl and ethoxymethyl; or C3–6 dialkoxyalkyl, for example, dimethoxymethyl and diethoxymethyl.

When any one of R1 to R9 is aryl, or contains an aryl moiety, it is preferably C6–10 aryl, more preferably it is phenyl. When any one of R1 to R9 is arylalkyl, it is preferably C6–10 aryl-methyl or C6–10 aryl-ethyl, even more preferably benzyl or phenethyl.

When any one of R1 to R6 is heteroaryl, or contains a heteroaryl moiety, it is preferably a 5 or 6 membered ring containing at least one O, N or S atom as the heteroatom, for example, pyridine, pyrrole, pyrazine, furan or thiophene. When any one of R1 to R6 is heteroarylalkyl, it is preferably heteroaryl-C1–2 alkyl.

When any one of R1 to R9 is a substituted aryl, arylalkyl, heteroaryl, or heteroarylalkyl group, it may comprise one or more substituents chosen from alkyl, alkoxy, haloalkyl, halogen, hydroxy, COOR7 (or a salt thereof), aminosulfonyl, cyano or nitro. Examples of these groups are 4-methylphenyl, 4-chlorophenyl, 4-fluorophenyl, 4-nitrophenyl, 3-trifluoromethylphenyl, 4-trifluoromethylphenyl, 4-aminosulfonylphenyl, 4-chlorobenzyl, 4-fluorobenzyl, 3-trifluoromethylbenzyl, 4-trifluoromethylbenzyl, 4-nitrobenzyl and 4-methylbenzyl.

When any one of R1 to R6 is a aryloxy or arylalkoxy group, it is preferably phenoxy, benzyloxy or phenethoxy.

When any one of R1 to R6 is a substituted aryloxy, arylalkoxy, heteroaryloxy or heteroarylalkoxy group, it may comprise one or more substituents chosen from alkyl, alkoxy, haloalkyl, hydroxy, cyano or nitro. Examples of these groups are 4-methylphenoxy, 4-chlorophenoxy, 4-fluorophenoxy, 4-nitrophenoxy, 3-trifluoromethylphenoxy, 4-trifluoromethylphenoxy 4-chlorobenzyloxy, 4-fluorobenzyloxy, 3-trifluoromethylbenzyloxy, 4-trifluoromethylbenzyloxy, 4-nitrobenzyloxy and 4-methylbenzyloxy.

When any one of R1 to R9 is halogen, or contains a halogen moiety, it is preferably fluorine, chlorine, bromine or iodine. Even more preferably, it is fluorine, chlorine or bromine.

When any one of R1 to R9 is a haloalkyl, haloalkenyl or haloalkynyl group, it may contain one or more halogen atoms, preferably chlorine, fluorine or bromine. Examples of these groups are fluoromethyl, difluoromethyl, trifluoromethyl, chloromethyl, dichloromethyl, trichloromethyl, 2-fluoroethyl, 2,2,2-trifluoroethyl, pentafluoroethyl, 2,2-difluoroethenyl, 3,3-dichloroprop-2-enyl, 2-chloroprop-2-enyl, 3,4,4-trifluorobut-3-enyl, 4-fluorobut-3-enyl, 4,4-difluorobut-3-enyl and 3-methyl-4,4-difluorobut-3-enyl.

When any one of R1 to R6 is a haloalkoxy group, a haloalkenyloxy group or a haloalkynyloxy group, it may contain one or more halogen atoms, preferably chlorine, fluorine or bromine. Examples of the preferred C1–6 alkoxy, C2–6 alkenyloxy and C2–6 alkynyloxy groups are trichloromethoxy, fluoromethoxy, difluoromethoxy, trifluoromethoxy, 2-fluoroethoxy, 2,2,2-trifluoroethoxy, pentafluoroethoxy, 1,1,2,2-tetrafluoroethoxy, 2,2-difluoroethenyloxy, 3,4,4-trifluorobut-3-enyloxy, 4-fluorobut-3-enyloxy, 4,4-difluorobut-3-enyloxy, 3-methyl-4,4-difluorobut-3-enyloxy, 2-chloroprop-2-enyloxy and 3,3-dichloroprop-2-enyloxy.

When any one of R1 to R6 is the group —NR7R8, it is preferably —NH2; a mono-alkylamino group, for example, methylamino and ethylamino; or a di-alkylamino group, for example, dimethylamino and diethylamino.

When any one of R1 to R6 is the group —NR7COR8, it is preferably —NHCHO; a C2–6 acylamino group, for example —NHCOCH3, —NHCOC2H5; or benzamido, which may be substituted with one or more substituents chosen from halogen, for example, chlorine, fluorine and bromine; alkyl, for example, methyl and ethyl; alkoxy, for example, methoxy and ethoxy; haloalkyl, for example, chloromethyl, fluoromethyl, trifluoromethyl and 2,2,2-trifluoroethyl; haloalkoxy, for example, trifluoromethoxy and 2,2,2-trifluoroethoxy; hydroxy; cyano and nitro.

When any one of R1 to R6 is —NR7CSF8, R7 and R8 are preferably alkyl, for example methyl and ethyl.

When any one of R1 to R6 is the group —NR7SO2R8, it is preferably an alkanesulfonamido group, for example, —NHSO2CH3 and —NHSO2C2H5.

When any one of R1 to R6 is the group —N(SO2R7)(SO2R8), it is preferably a di-(alkanesulfonyl)amino group, for example, —N(SO2CH3)2 and —N(SO2C2H5)2.

When any one of R1 to R6 is the group —COR7, it is preferably a C1–6 acyl group; or an optionally substituted benzoyl group. The benzoyl may be substituted with one or more substituents chosen from halogen, for example, chlorine, fluorine and bromine; alkyl, for example, methyl and ethyl; alkoxy, for example, methoxy and ethoxy; haloalkyl, for example, chloromethyl, fluoromethyl, trifluoromethyl and 2,2,2-trifluoroethyl; haloalkoxy, for example, trifluoromethoxy and 2,2,2-trifluoroethoxy; hydroxy; cyano and nitro. Examples of preferred —COR7 groups are acetyl, propionyl, n-butanoyl, 4-chlorobenzoyl, 4-fluorobenzoyl, 4-bromobenzoyl, 4-methylbenzoyl and 4-trifluoromethylbenzoyl.

When any one of R1 to R6 is the group —CONR7R8, it is preferably —CONH2; an N-alkyl-carboxamido group, for example —CONHCH3, —CONHC2H5 and —CONHCH2CH2CH3; or an N,N-dialkyl-carboxamido group, for example —CON(CH3)2, —CON(CH3)(C2H5) and —CON(C2H5)2.

When any one of R1 to R6 is the group -alkylCONR7R8, it is preferably —C1–4 alkylCONR7R8.

When any one of more of R1 to R6 is the group —CR7NR8, it is preferably —CH=NOH.

When any one of R1 to R6 is the group —COOR7, it is preferably —COOH; an alkoxycarbonyl group, for example methoxycarbonyl and ethoxycarbonyl; or a haloalkenyloxy-carbonyl group, for example 3,4,4-trifluorobut-3-enyloxycarbonyl, 4-fluorobut-3-enyloxycarbonyl, 4,4-difluorobut-3-enyloxycarbonyl and 3-methyl-4,4-difluorobut-3-enyloxycarbonyl.

When any one of R1 to R6 is the group —OCOR7, it is preferably a C2–6 acyloxy group, for example —OCOCH3 and —OCOC2H5; or an optionally substituted benzoyloxy group. The benzoyloxy group may comprise one or more substituents chosen from halogen, for example, chlorine, fluorine and bromine; alkyl, for example, methyl and ethyl; alkoxy, for example, methoxy and ethoxy; haloalkyl, for example, chloromethyl, fluoromethyl, trifluoromethyl and 2,2,2-trifluoroethyl; haloalkoxy, for example, trifluoromethoxy and 2,2,2-trifluoroethoxy; hydroxy; cyano; and nitro.

When any one of R1 to R6 is the group —SR7, R7 is preferably hydrogen, optionally substituted alkyl, optionally substituted alkenyl, alkynyl, haloalkyl, haloalkenyl, haloalkynyl, optionally substituted aryl, or optionally substituted arylalkyl. Examples of the preferred C1–6 alkylthio (C1–4 alkyl being especially preferred), C2–6 alkenylthio or C2–6 alkynylthio groups are methylthio, ethylthio, n-propylthio, iso-propylthio, n-butylthio, iso-butylthio, sec-butylthio, t-butylthio, allylthio, but-3-enylthio, 3-methylbut-3-enylthio and propargylthio. Examples of the preferred C1–6 haloalkylthio (C1–4 alkyl being especially preferred), C2–6 haloalkenylthio or C2–6 haloalkynylthio groups are fluoromethylthio, difluoromethylthio, trifluoromethylthio, trichloromethylthio, 2-fluoroethylthio, 2,2,2-trifluoroethylthio, 3-fluoro-n-propylthio, pentafluoroethylthio, 2-chloroprop-2-enylthio, 3,3-dichloroprop-2-enylthio, 3,4,4-trifluorobut-3-enylthio, 4-fluorobut-3-enylthio, 4,4-difluorobut-3-enylthio and 3-methyl-4,4-difluorobut-3-enylthio. An example of the preferred C6–10 arylthio and C6–10 aryl-C1–2 alkylthio groups is 3-trifluoromethylbenzylthio.

When any one of R1 to R6 is the group —SOR7, it is preferably an alkanesulfinyl, alkenylsulfinyl or alkynylsulfinyl group, for example methanesulfinyl or ethanesulfinyl; or a haloalkanesulfinyl, haloalkenylsulfinyl or haloalkynylsulfinyl group, for example trifluoromethanesulfinyl. In another preferred embodiment —SOR7 is preferably —SOF, —SOBr or —SOCl.

When any one of R1 to R6 is the group —SO2R7, it is preferably an alkanesulfonyl, alkenylsulfonyl, alkynylsulfonyl, a haloalkanesulfonyl, haloalkenylsulfonyl, haloalkynylsulfonyl group; or an optionally substituted benzenesulfonyl group. The benzenesulfonyl group may comprise one or more substituents chosen from halogen, for example, chlorine, fluorine and bromine; alkyl, for example, methyl and ethyl; alkoxy, for example, methoxy and ethoxy; haloalkyl, for example, chloromethyl, fluoromethyl, trifluoromethyl and 2,2,2-trifluoroethyl; haloalkoxy such as trifluoromethoxy and 2,2,2-trifluoroethoxy; hydroxy; cyano and nitro. Examples of such groups are methanesulfonyl, ethanesulfonyl, trifluoromethanesulfonyl, and 4-methylbenzenesulfonyl. In another preferred embodiment —SO2R7 is preferably —SO2F, —SO2Br or —SO2Cl.

It will thus be appreciated that the R group of formula (II) to (XXI) can comprise more than one —S(O)nCH2CH2CH=CF2 group. Preferably the R group contains one or two such substituents.

When any one of R1 to R6 is the group —OSO2R7, it is preferably an alkanesulfonyloxy group or an optionally substituted benzenesulfonyloxy group. The benzenesulfonyl may be substituted with one or more substituents chosen from halogen, for example, chlorine, fluorine and bromine; alkyl, for example, methyl and ethyl; alkoxy, for example, methoxy and ethoxy; haloalkyl, for example, chloromethyl, fluoromethyl, trifluoromethyl and 2,2,2-trifluoroethyl; haloalkoxy, for example, trifluoromethoxy and 2,2,2-trifluoroethoxy; hydroxy; cyano; and nitro.

When any one of R1 to R6 is the group —SO2NR7R8, it is preferably —SO2NH2; an alkylaminosulfonyl group, for example, —SO2NHCH3 and —SO2NHC2H5; or a dialkylaminosulfonyl group, for example, —SO2N(CH3)2 and —SO2N(C2H5)2.

When any one of R1 to R6 is the group —CSNR7R8 it is preferably —CSNH2, —CSNHCH3 or —CSN(CH3)2.

When any one of R1 to R6 is the group —SiR7R8R9, it is preferably a trialkylsilyl group, for example, trimethylsilyl and triethylsilyl.

When any one of R1 to R6 is the group —OCH2CO2R7, it is preferably an alkoxycarbonylmethoxy group, for example, methoxycarbonyl methoxy and ethoxycarbonylmethoxy.

When any one of R1 to R6 is the group —OCH2CH2CO2R7, it is preferably a alkoxycarbonylethoxy group, for example, methoxycarbonylethoxy and ethoxycarbonylethoxy.

When any one of R1 to R6 is the group —CONR7SO2R8, it is preferably an N-alkanesulfonylcarboxamido group or an N-alkyl-N-alkanesulfonylcarboxamido group, for example, N-(methanesulfonyl)-carboxamide and N-methyl-N-(methanesulfonyl)carboxamido.

When any one or more of R1 to R6 is the group -alkylCONR7SO2R8, R7 and R8 are preferably alkyl groups, for example, ethyl and methyl.

When any one of R1 to R6 is —NHCONR7R8, R7 and R8 are preferably alkyl groups, for example, ethyl and methyl.

When any one of R1 to R6 is —NHCSNR7R8, R7 and R8 are preferably alkyl groups, for example, ethyl and methyl.

When an adjacent pair of R1, R2, R3, R4, R5 and R6 taken together form a fused 5- or 6-membered carbocyclic or heterocyclic ring, preferably containing two oxygen atoms, the pair of substituents taken together is preferably —(CH2)3—, —(CH2)4—, —CH=CH—CH=CH—, —O—CH2—O—, optionally substituted with one or two halogen atoms or methyl groups, for example —O—CHF—O— or —O—CF2—O—, —O—CH(CH3)—O—, —O—C(CH3)2—O— or —O—(CH2)2—O—.

According to an especially preferred embodiment of the present invention R1 (when attached to a carbon atom) to R6 are each independently hydrogen; nitro; halogen; cyano; —CH=NOH; C1–4 alkyl; C1–4 haloalkyl; C1–4 alkenyl; C1–4 haloalkenyl; cyclopropyl; hydroxy; C1–4 alkoxy; C2–4 alkoxyalkyl; —COOH; C2–4 alkoxycarbonyl; C2–4 haloalkenyloxycarbonyl; —CONH2; mono or di-C1–2 alkylaminocarbonyl; C2–4 alkanecarbonyl; —CONHSO2 C1–4 alkyl, preferably —CONHSO2CH3; phenyl optionally mono- or di-substituted with groups independently chosen from halogen, nitro, C1–4 alkyl, C1–4 alkoxy or aminosulfonyl; benzyl optionally mono- or di-substituted with groups independently chosen from halogen, nitro, C1–4 alkyl or C1–4 alkoxy; phenoxy optionally mono- or di-substituted with groups independently chosen from halogen, cyano, C1–4 alkyl or C1–4 alkoxy; amino optionally mono- or di-substituted with C1–4 alkyl groups; —SH; C1–4 alkylthio; benzylthio optionally mono- or di-substituted with groups independently chosen from halogen or C1–4 haloalkyl; C1–4 alkenylthio; C2–4 haloalkenylthio; a second S(O)nCH2CH2CH=CF2 group; C1–4 alkanesulfonyl; C1–4 haloalkanesulfonyl; fluorosulfonyl; mono- or di-C1–4 alkylsulfamoyl; a 5 or 6 membered heteroaryl group, for example, furyl, pyrazinyl, pyridinyl or thienyl, optionally substituted with halogen, or any adjacent pair forms a fused 5- or 6-carbocyclic or heterocyclic ring; and R1 (when attached to a nitrogen atom) is hydrogen; nitro; cyano, —CH=NOH; C1–4 alkyl; C1–4 haloalkyl; cyclopropyl; hydroxy; —COOH; C2–4 alkoxycarbonyl; C2–4 haloalkenyloxycarbonyl; —CONH2; mono or di-C1–2 alkylaminocarbonyl; C2–4 alkanecarbonyl; —CONHSO2 C1-4 alkyl, preferably —CONHSO2CH3; phenyl optionally mono- or di-substituted with groups independently chosen from halogen, cyano, C1–4 alkyl, C1–4 alkoxy or aminosulfonyl; benzyl optionally mono- or di-substituted with groups independently chosen from halogen, nitro, C1–4 aklyl or C1–4 alkoxy; phenoxy optionally mono- or di-substituted with groups independently chosen from halogen, cyano, C1–4 alkyl or C1–4 alkoxy; amino optionally mono- or di-substituted with C1–4 alkyl groups; —SH; C1–4 alkylthio; benzylthio optionally mono- or di-substituted with groups independently chosen from halogen or C1–4 haloalkyl; C1–4 alkenylthio; C2–4 haloalkenylthio; a second S(O)nCH2CH2CH=CF2 group; C1–4 alkanesulfonyl; C1–4 haloalkanesulfonyl; fluorosulfonyl; mono- or di-C1–4 alkylsulfamoyl; a 5 or 6 membered heteroaryl group, for example, furyl, pyrazinyl, pyridinyl or thienyl, optionally substituted with halogen. The following Tables give examples of compounds according to the invention. Examples of compounds of Formula (II) according to the invention are set out in Table II.

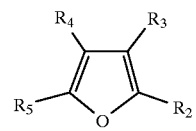

TABLE II

| No.   | R2                  | R3                  | R4 | R5    |
|-------|---------------------|---------------------|----|-------|
| II.1  | 2-SCH2CH2CH=CF2     | 3-H                 | 4-H| 5-H   |
| II.2  | 2-SOCH2CH2CH=CF2    | 3-H                 | 4-H| 5-H   |
| II.3  | 2-SO2CH2CH2CH=CF2   | 3-H                 | 4-H| 5-H   |
| II.4  | 2-SCHCH2CH=CF2      | 3-H                 | 4-H| 5-CH3 |
| II.5  | 2-SOCH2CH2CH=CF2    | 3-H                 | 4-H| 5-CH3 |
| II.6  | 2-SO2CH2CH2CH=CF2   | 3-H                 | 4-H| 5-CH3 |
| II.7  | 2-CH3               | 3-SCH2CH2CH=CF2     | 4-H| 5-H   |
| II.8  | 2-CH3               | 3-SOCH2CH2CH=CF2    | 4-H| 5-H   |
| II.9  | 2-CH3               | 3-SO2CH2CH2CH=CF2   | 4-H| 5-H   |

Examples of compounds of Formula (III) according to the invention are set out in Table III.

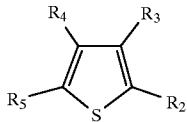

TABLE III

| No.    | R2                | R3  | R4  | R5          |
|--------|-------------------|-----|-----|-------------|
| III.1  | 2-SCH2CH2CH=CF2   | 3-H | 4-H | 5-H         |
| III.2  | 2-SOCH2CH2CH=CF2  | 3-H | 4-H | 5-H         |
| III.3  | 2-SO2CH2CH2CH=CF2 | 3-H | 4-H | 5-H         |
| III.4  | 2-SCH2CH2CH=CF2   | 3-H | 4-H | 5-CHO       |
| III.5  | 2-SCH2CH2CH=CF2   | 3-H | 4-H | 5-CH2OH     |
| III.6  | 2-SCH2CH2CH=CF2   | 3-H | 4-H | (E) 5-CH=NOH|
| III.7  | 2-SCH2CH2CH=CF2   | 3-H | 4-H | (Z) 5-CH=NOH|
| III.8  | 2-SCH2CH2CH=CF2   | 3-H | 4-H | 5-CN        |
| III.9  | 2-SCH2CH2CH=CF2   | 3-H | 4-H | 5-COCH3     |

TABLE III-continued

| No.    | R2                | R3  | R4            | R5 |
|--------|-------------------|-----|---------------|----|
| III.10 | 2-SCH2CH2CH=CF2   | 3-H | —CH=CH—CH=CH— |    |
| III.11 | 2-SOCH2CH2CH=CF2  | 3-H | —CH=CH—CH=CH— |    |
| III.12 | 2-SO2CH2CH2CH=CF2 | 3-H | —CH=CH—CH=CH— |    |

Examples of compound of Formula (IV) according to the invention are set out in table IV.

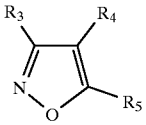

TABLE IV

| No.   | R3                 | R4              | R5                  |
|-------|--------------------|-----------------|---------------------|
| IV.1  | 3-C6H5             | 4-H             | 5-SCH2CH2CH=CF2     |
| IV.2  | 3-C6H5             | 4-H             | 5-SOCH2CH2CH=CF2    |
| IV.3  | 3-C6H5             | 4-H             | 5-SO2CH2CH2CH=CF2   |
| IV.4  | 3-CN               | 4-H             | 5-SCH2CH2CH=CF2     |
| IV.5  | 3-Cl               | 4-H             | 5-SCH2CH2CH=CF2     |
| IV.6  | 3-CF3              | 4-H             | 5-SCH2CH2CH=CF2     |
| IV.7  | 3-CH3              | 4-CONH2         | 5-SCH2CH2CH=CF2     |
| IV.8  | 3-CH3              | 4-COOCH2CH3     | 5-SCH2CH2CH=CF2     |
| IV.9  | 3-CH3              | 4-COOH          | 5-SCH2CH2CH=CF2     |
| IV.10 | 3-CH3              | 4-H             | 5-SCH2CH2CH=CF2     |
| IV.11 | 3-H                | 4-Cl            | 5-SCH2CH2CH=CF2     |
| IV.12 | 3-H                | 4-CN            | 5-SCH2CH2CH=CF2     |
| IV.13 | 3-H                | 4-CN            | 5-SOCH2CH2CH=CF2    |
| IV.14 | 3-H                | 4-CN            | 5-SO2CH2CH2CH=CF2   |
| IV.15 | 3-H                | 4-CF3           | 5-SCH2CH2CH=CF2     |
| IV.16 | 3-H                | 4-H             | 5-SCH2CH2CH=CF2     |
| IV.17 | 3-H                | 4-NO2           | 5-SCH2CH2CH=CF2     |
| IV.18 | 3-H                | 4-SCH2CH2CH=CF2 | 5-CN                |
| IV.19 | 3-H                | 4-SCH2CH2CH=CF2 | 5-CF3               |
| IV.20 | 3-SCH2CH2CH=CF2    | 4-H             | 5-Cl                |
| IV.21 | 3-SCH2CH2CH=CF2    | 4-Cl            | 5-H                 |
| IV.22 | 3-SO2CH2CH2CH=CF2  | 4-CN            | 5-SO2CH2CH2CH=CF2   |
| IV.23 | 3-(5-Cl—Fur-2-yl)  | 4-H             | 5-SCH2CH2CH=CF2     |
| IV.24 | 3-(5-Cl-Fur-2-yl)  | 4-H             | 5-SO2CH2CH2CH=CF2   |
| IV.25 | 3-(Thien-2-yl)     | 4-H             | 5-SCH2CH2CH=CF2     |
| IV.26 | 3-(Thien-2-yl)     | 4-H             | 5-SO2CH2CH2CH=CF2   |

Examples of compounds of Formula (V) according to the invention are set out in Table V.

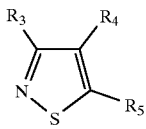

TABLE V

| No. | R3 | R4 | R5 |
|---|---|---|---|
| V.1 | 3-CF3 | 4-H | 5-SCH2CH2CH=CF2 |
| V.2 | 3-Cl | 4-CN | 5-SCH2CH2CH=CF2 |
| V.3 | 3-Cl | 4-H | 5-SCH2CH2CH=CF2 |
| V.4 | 3-Cl | 4-H | 5-SO2CH2CH2CH=CF2 |
| V.5 | 3-H | 4-CN | 5-SCH2CH2CH=CF2 |
| V.6 | 3-H | 4-CN | 5-SO2CH2CH2CH=CF2 |
| V.7 | 3-H | 4-SCH2CH2CH=CF2 | 5-CF3 |
| V.8 | 3-H | 4-SOCH2CH2CH=CF2 | 5-CF3 |
| V.9 | 3-H | 4-SCH2CH2CH=CF2 | 5-CN |
| V.10 | 3-NO2 | 4-H | 5-SCH2CH2CH=CF2 |
| V.11 | 3-SCH2CH2CH=CF2 | 4-Cl | 5-H |
| V.12 | 3-SCH2CH2CH=CF2 | 4-CN | 5-SCH2CH2CH=CF2 |
| V.13 | 3-SO2CH2CH2CH=CF2 | 4-CN | 5-SOCH2CH2CH=CF2 |
| V.14 | 3-SOCH2CH2CH=CF2 | 4-CN | 5-SO2CH2CH2CH=CF2 |
| V.15 | 3-SO2CH2CH2CH=CF2 | 4-CN | 5-SO2CH2CH2CH=CF2 |
| V.16 | 3-SCH2CH2CH=CF2 | 4-H | 5-Cl |

Examples of compounds of Formula (VI) according to the invention are set out in Table VI.

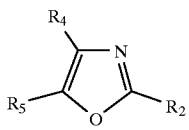

TABLE VI

| No. | R2 | R4 | R5 |
|---|---|---|---|
| VI.1 | 2-SCH2CH2CH=CF2 | 4-H | 5-H |
| VI.2 | 2-SOCH2CH2CH=CF2 | 4-H | 5-H |
| VI.3 | 2-SO2CH2CH2CH=CF2 | 4-H | 5-H |
| VI.4 | 2-SCH2CH2CH=CF2 | 4-CF3 | 5-H |
| VI.5 | 2-SO2CH2CH2CH=CF2 | 4-CF3 | 5-H |
| VI.6 | 2-SCH2CH2CH=CF2 | 4-CH3 | 5-H |
| VI.7 | 2-SCH2CH2CH=CF2 | 4-CN | 5-H |
| VI.8 | 2-SCH2CH2CH=CF2 | 4-CONH2 | 5-H |
| VI.9 | 2-SCH2CH2CH=CF2 | 4-COOCH2CH3 | 5-H |
| VI.10 | 2-SO2CH2CH2CH=CF2 | 4-COOCH2CH3 | 5-H |
| VI.11 | 2-SCH2CH2CH=CF2 | 4-COOH | 5-H |
| VI.12 | 2-SO2CH2CH2CH=CF2 | 4-H | 5-Br |
| VI.13 | 2-SCH2CH2CH=CF2 | 4-H | 5-Cl |
| VI.14 | 2-SO2CH2CH2CH=CF2 | 4-H | 5-Cl |
| VI.15 | 2-SCH2CH2CH=CF2 | 4-CH3 | 5-Cl |
| VI.16 | 2-SO2CH2CH2CH=CF2 | 4-CH3 | 5-Cl |
| VI.17 | 2-SCH2CH2CH=CF2 | 4-H | 5-F |
| VI.18 | 2-SCH2CH2CH=CF2 | 4-H | 5-C6H5 |
| VI.19 | 2-SOCH2CH2CH=CF2 | 4-H | 5-C6H5 |
| VI.20 | 2-SO2CH2CH2CH=CF2 | 4-H | 5-C6H5 |
| VI.21 | 2-SCH2CH2CH=CF2 | 4-H | 5-CF3 |
| VI.22 | 2-SCH2CH2CH=CF2 | 4-H | 5-CN |
| VI.23 | 2-SOCH2CH2CH=CF2 | 4-H | 5-CN |
| VI.24 | 2-SO2CH2CH2CH=CF2 | 4-H | 5-CN |
| VI.25 | 2-SCH2CH2CH=CF2 | 4-CH3 | 5-CN |

TABLE VI-continued

| No. | R2 | R4 | R5 |
|---|---|---|---|
| VI.26 | 2-SO2CH2CH2CH=CF2 | 4-CH3 | 5-CN |
| VI.27 | 2-SO2CH2CH2CH=CF2 | 4-CH3 | 5-CN |
| VI.28 | 2-SCH2CH2CH=CF2 | 4-H | 5-COOCH2CH3 |
| VI.29 | 2-SOCH2CH2CH=CF2 | 4-H | 5-COOCH2CH3 |
| VI.30 | 2-SO2CH2CH2CH=CF2 | 4-H | 5-COOCH2CH3 |
| VI.31 | 2-SCH2CH2CH=CF2 | 4-CF3 | 5-COOCH2CH3 |
| VI.32 | 2-SCH2CH2CH=CF2 | 4-CH3 | 5-COOCH3 |
| VI.33 | 2-SOCH2CH2CH=CF2 | 4-CH3 | 5-COOCH3 |
| VI.34 | 2-SO2CH2CH2CH=CF2 | 4-CH3 | 5-COOCH3 |
| VI.35 | 2-SCH2CH2CH=CF2 | 4-H | 5-COOH |
| VI.36 | 2-SCH2CH2CH=CF2 | 4-CF3 | 5-COOH |
| VI.37 | 2-SCH2CH2CH=CF2 | 5-COOH | |
| VI.24 | 2-SO2CH2C=CH=CF2 | 4-H | 5-CN |
| VI.38 | 2-SCH2CH2CH=CF2 | 4-CH3 | 5-CONHSO2CH3 |
| VI.39 | 2-SCH2CH2CH=CF2 | 4-H | 5-CONH2 |
| VI.40 | 2-SCH2CH2CH=CF2 | 4-CH3 | 5-CONH2 |
| VI.41 | 2-SOCH2CH2CH=CF2 | 4-CH3 | 5-CONH2 |
| VI.42 | 2-SCH2CH2CH=CF2 | 4-H | 5-NO2 |
| VI.43 | 2-SOCH2CH2CH=CF2 | 4-H | 5-NO2 |
| VI.44 | 2-SO2CH2CH2CH=CF2 | 4-H | 5-NO2 |
| VI.45 | 2-SCH2CH2CH=CF2 | 4-H | 5-SO2F |
| VI.46 | 2-SOCH2CH2CH=CF2 | 4-H | 5-SO2F |
| VI.47 | 2-SCH2CH2CH=CF2 | 4-H | 5-SO2NH2 |
| VI.48 | 2-SO2CH2CH2CH=CF2 | 4-H | 5-SO2NH2 |
| VI.49 | 2-H | 4-SCH2CH2CH=CF2 | 5-Br |
| VI.50 | 2-H | 4-SCH2CH2CH=CF2 | 5-C6H5 |
| VI.51 | 2-H | 4-SOCH2CH2CH=CF2 | 5-C6H5 |
| VI.52 | 2-H | 4-SCH2CH2CH=CF2 | 5-CF3 |
| VI.53 | 2-H | 4-SOCH2CH2CH=CF2 | 5-CF3 |
| VI.54 | 2-H | 4-SCH2CH2CH=CF2 | 5-Cl |
| VI.55 | 2-H | 4-SOCH2CH2CH=CF2 | 5-Cl |
| VI.56 | 2-H | 4-SO2CH2CH2CH=CF2 | 5-Cl |
| VI.57 | 2-H | 4-SCH2CH2CH=CF2 | 5-CN |
| VI.58 | 2-CH3 | 4-SCH2CH2CH=CF2 | 5-CN |
| VI.59 | 2-CH3 | 4-SOCH2CH2CH=CF2 | 5-CN |
| VI.60 | 2-CH3 | 4-SO2CH2CH2CH=CF2 | 5-CN |
| VI.61 | 2-H | 4-SCH2CH2CH=CF2 | 5-CONH2 |
| VI.62 | 2-CH3 | 4-SCH2CH2CH=CF2 | 5-CONH2 |
| VI.63 | 2-H | 4-SCH2CH2CH=CF2 | 5-COOCH2CH3 |
| VI.64 | 2-CH3 | 4-SCH2CH2CH=CF2 | 5-COOCH3 |
| VI.65 | 2-CH3 | 4-SO2CH2CH2CH=CF2 | 5-COOCH3 |
| VI.66 | 2-H | 4-SCH2CH2CH=CF2 | 5-COOH |
| VI.67 | 2-H | 4-SCH2CH2CH=CF2 | 5-F |
| VI.68 | 2-H | 4-SCH2CH2CH=CF2 | 5-H |
| VI.69 | 2-H | 4-SOCH2CH2CH=CF2 | 5-H |
| VI.70 | 2-H | 4-SO2CH2CH2CH=CF2 | 5-H |
| VI.71 | 2-H | 4-SCH2CH2CH=CF2 | 5-NO2 |
| VI.72 | 2-H | 4-SCH2CH2CH=CF2 | 5-SO2F |
| VI.73 | 2-H | 4-SCH2CH2CH=CF2 | 5-SO2NH2 |
| VI.74 | 2-H | 4-Br | 5-SCH2CH2CH=CF2 |
| VI.75 | 2-H | 4-C6H5 | 5-SCH2CH2CH=CF2 |
| VI.76 | 2-H | 4-CF3 | 5-SCH2CH2CH=CF2 |
| VI.77 | 2-H | 4-CF3 | 5-SO2CH2CH2CH=CF2 |
| VI.78 | 2-H | 4-Cl | 5-SCH2CH2CH=CF2 |
| VI.79 | 2-H | 4-CN | 5-SCH2CH2CH=CF2 |
| VI.80 | 2-H | 4-CN | 5-SOCH2CH2CH=CF2 |
| VI.81 | 2-H | 4-CN | 5-SO2CH2CH2CH=CF2 |
| VI.82 | 2-CH3 | 4-CN | 5-SCH2CH2CH=CF2 |
| VI.83 | 2-H | 4-CONH2 | 5-SCH2CH2CH=CF2 |
| VI.84 | 2-H | 4-CONH2 | 5-SOCH2CH2CH=CF2 |
| VI.85 | 2-H | 4-CONH2 | 5-SO2CH2CH2CH=CF2 |
| VI.86 | 2-CH3 | 4-CONH2 | 5-SCH2CH2CH=CF2 |
| VI.87 | 2-H | 4-COOCH3 | 5-SCH2CH2CH=CF2 |
| VI.88 | 2-H | 4-COOCH2CH3 | 5-SOCH2CH2CH=CF2 |
| VI.89 | 2-H | 4-COOCH2CH3 | 5-SO2CH2CH2CH=CF2 |
| VI.90 | 2-CH3 | 4-COOCH3 | 5-SCH2CH2CH=CF2 |
| VI.91 | 2-H | 4-COOH | 5-SCH2CH2CH=CF2 |
| VI.92 | 2-H | 4-F | 5-SCH2CH2CH=CF2 |
| VI.93 | 2-H | 4-H | 5-SCH2CH2CH=CF2 |
| VI.94 | 2-H | 4-H | 5-SOCH2CH2CH=CF2 |
| VI.95 | 2-H | 4-H | 5-SO2CH2CH2CH=CF2 |
| VI.96 | 2-H | 4-NO2 | 5-SCH2CH2CH=CF2 |
| VI.97 | 2-H | 4-NO2 | 5-SOCH2CH2CH=CF2 |
| VI.98 | 2-H | 4-SO2F | 5-SCH2CH2CH=CF2 |
| VI.99 | 2-H | 4-SO2NH2 | 5-SCH2CH2CH=CF2 |
| VI.100 | 2-Br | 4-H | 5-SCH2CH2CH=CF2 |
| VI.101 | 2-C6H5 | 4-H | 5-SCH2CH2CH=CF2 |

TABLE VI-continued

| No. | R2 | R4 | R5 |
|---|---|---|---|
| VI.102 | 2-C6H5 | 4-H | 5-SOCH2CH2CH=CF2 |
| VI.103 | 2-C6H5 | 4-H | 5-SO2CH2CH2CH=CF2 |
| VI.104 | 2-CF3 | 4-H | 5-SCH2CH2CH=CF2 |
| VI.105 | 2-CF3 | 4-H | 5-SO2CH2CH2CH=CF2 |
| VI.106 | 2-Cl | 4-H | 5-SCH2CH2CH=CF2 |
| VI.107 | 2-CN | 4-H | 5-SCH2CH2CH=CF2 |
| VI.108 | 2-CN | 4-CH3 | 5-SCH2CH2CH=CF2 |
| VI.109 | 2-CONH2 | 4-H | 5-SCH2CH2CH=CF2 |
| VI.110 | 2-CONH2 | 4-H | 5-SOCH2CH2CH=CF2 |
| VI.111 | 2-CONH2 | 4-H | 5-SO2CH2CH2CH=CF2 |
| VI.112 | 2-CONH2 | 4-CH3 | 5-SO2CH2CH2CH=CF2 |
| VI.113 | 2-COOCH2CH3 | 4-H | 5-SCH2CH2CH=CF2 |
| VI.114 | 2-COOCH3 | 4-CH3 | 5-SCH2CH2CH=CF2 |
| VI.115 | 2-COOH | 4-H | 5-SCH2CH2CH=CF2 |
| VI.116 | 2-F | 4-H | 5-SCH2CH2CH=CF2 |
| VI.117 | 2-F | 4-H | 5-SOCH2CH2CH=CF2 |
| VI.118 | 2-NO2 | 4-H | 5-SCH2CH2CH=CF2 |
| VI.119 | 2-SO2F | 4-H | 5-SCH2CH2CH=CF2 |
| VI.120 | 2-SO2NH2 | 4-H | 5-SCH2CH2CH=CF2 |

Examples of compounds of Formula (VII) according to the invention are set out in Table VII.

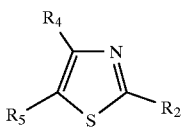

TABLE VII

| No. | R2 | R4 | R5 |
|---|---|---|---|
| VII.1 | 2-SCH2CH2CH=CF2 | 4-H | 5-H |
| VII.2 | 2-SOCH2CH2CH=CF2 | 4-H | 5-H |
| VII.3 | 2-SO2CH2CH2CH=CF2 | 4-H | 5-H |
| VII.4 | 2-SCH2CH2CH=CF2 | 4-CF3 | 5-H |
| VII.5 | 2-SO2CH2CH2CH=CF2 | 4-CF3 | 5-H |
| VII.6 | 2-SCH2CH2CH=CF2 | 4-CN | 5-H |
| VII.7 | 2-SCH2CH2CH=CF2 | 4-CONH2 | 5-H |
| VII.8 | 2-SCH2CH2CH=CF2 | 4-COOCH2CH3 | 5-H |
| VII.9 | 2-SO2CH2CH2CH=CF2 | 4-COOCH2CH3 | 5-H |
| VII.10 | 2-SCH2CH2CH=CF2 | 4-COOH | 5-H |
| VII.11 | 12-SCH2CH2CH=CF2 | 4-COOCH2CH3 | 5-Br |
| VII.12 | 2-SO2CH2CH2CH=CF2 | 4-COOCH2CH3 | 5-Br |
| VII.13 | 2-SCH2CH2CH=CF2 | 4-COOH | 5-Br |
| VII.14 | 2-SCH2CH2CH=CF2 | 4-H | 5-Br |
| VII.15 | 2-SOCH2CH2CH=CF2 | 4-H | 5-Br |
| VII.16 | 2-SO2CH2CH2CH=CF2 | 4-H | 5-Br |
| VII.17 | 2-SCH2CH2CH=CF2 | 4-H | 5-C6H5 |
| VII.18 | 2-SOCH2CH2CH=CF2 | 4-H | 5-C6H5 |
| VII.19 | 2-SO2CH2CH2CH=CF2 | 4-H | 5-C6H5 |
| VII.20 | 2-SCH2CH2CH=CF2 | 4-H | 5-CF3 |
| VII.21 | 2-SCH2CH2CH=CF2 | 4-H | 5-CH3 |
| VII.22 | 2-SOCH2CH2CH=CF2 | 4-H | 5-CH3 |
| VII.23 | 2-SO2CH2CH2CH=CF2 | 4-H | 5-CH3 |
| VII.24 | 2-SCH2CH2CH=CF2 | 4-H | 5-Cl |
| VII.25 | 2-SO2CH2CH2CH=CF2 | 4-H | 5-Cl |
| VII.26 | 2-SO2CH2CH2CH=CF2 | 4-H | 5-Cl |
| VII.27 | 2-SCH2CH2CH=CF2 | 4-CH3 | 5-Cl |
| VII.28 | 2-SO2CH2CH2CH=CF2 | 4-CH3 | 5-Cl |
| VII.29 | 2-SCH2CH2CH=CF2 | 4-H | 5-CN |
| VII.30 | 2-SOCH2CH2CH=CF2 | 4-H | 5-CN |
| VII.31 | 2-SO2CH2CH2CH=CF2 | 4-H | 5-CN |
| VII.32 | 2-SCH2CH2CH=CF2 | 4-CH3 | 5-CN |
| VII.33 | 2-SOCH2CH2CH=CF2 | 4-CH3 | 5-CN |
| VII.34 | 2-SO2CH2CH2CH=CF2 | 4-CH3 | 5-CN |
| VII.35 | 2-SCH2CH2CH=CF2 | 4-H | 5-CONH2 |
| VII.36 | 2-SCH2CH2CH=CF2 | 4-CH3 | 5-CONH2 |

TABLE VII-continued

| No. | R2 | R4 | R5 |
|---|---|---|---|
| VII.37 | 2-SOCH2CH2CH=CF2 | 4-CH3 | 5-CONH2 |
| VII.38 | 2-SCH2CH2CH=CF2 | 4-H | 5-COOCH2CH3 |
| VII.39 | 2-SOCH2CH2CH=CF2 | 4-H | 5-COOCH2CH3 |
| VII.40 | 2-SO2CH2CH2CH=CF2 | 4-H | 5-COOCH2CH3 |
| VII.41 | 2-SCH2CH2CH=CF2 | 4-CH3 | 5-COOCH3 |
| VII.42 | 2-SOCH2CH2CH=CF2 | 4-CH3 | 5-COOCH3 |
| VII.43 | 2-SO2CH2CH2CH=CF2 | 4-CH3 | 5-COOCH3 |
| VII.44 | 2-SCH2CH2CH=CF2 | 4-H | 5-COOH |
| VII.45 | 2-SCH2CH2CH=CF2 | 4-CH3 | 5-COOH |
| VII.46 | 2-SCH2CH2CH=CF2 | 4-H | 5-F |
| VII.47 | 2-SCH2CH2CH=CF2 | 4-H | 5-NO2 |
| VII.48 | 2-SOCH2CH2CH=CF2 | 4-H | 5-NO2 |
| VII.49 | 2-SO2CH2CH2CH=CF2 | 4-H | 5-NO2 |
| VII.50 | 2-SCH2CH2CH=CF2 | 4-H | 5-SO2F |
| VII.51 | 2-SOCH2CH2CH=CF2 | 4-H | 5-SO2F |
| VII.52 | 2-SCH2CH2CH=CF2 | 4-CH3 | 5-SO2F |
| VII.53 | 2-SO2CH2CH2CH=CF2 | 4-CH3 | 5-SO2F |
| VII.54 | 2-SCH2CH2CH=CF2 | 4-H | 5-SO2NH2 |
| VII.55 | 2-SO2CH2CH2CH=CF2 | 4-H | 5-SO2NH2 |
| VII.56 | 2-SCH2CH2CH=CF2 | 4-CH3 | 5-SO2N(CH2CH3)2 |
| VII.57 | 2-H | 4-SCH2CH2CH=CF2 | 5-H |
| VII.58 | 2-H | 4-SOCH2CH2CH=CF2 | 5-H |
| VII.59 | 2-H | 4-SO2CH2CH2CH=CF2 | 5-H |
| VII.60 | 2-H | 4-SCH2CH2CH=CF2 | 5-Br |
| VII.61 | 2-H | 4-SCH2CH2CH=CF2 | 5-C6H5 |
| VII.62 | 2-H | 4-SOCH2CH2CH=CF2 | 5-C6H5 |
| VII.63 | 2-H | 4-SCH2CH2CH=CF2 | 5-CF3 |
| VII.64 | 2-H | 4-SOCH2CH2CH=CF2 | 5-CF3 |
| VII.65 | 2-H | 4-SCH2CH2CH=CF2 | 5-Cl |
| VII.66 | 2-H | 4-SOCH2CH2CH=CF2 | 5-Cl |
| VII.67 | 2-H | 4-SO2CH2CH2CH=CF2 | 5-Cl |
| VII.68 | 2-H | 4-SCH2CH2CH=CF2 | 5-CN |
| VII.69 | 2-CH3 | 4-SCH2CH2CH=CF2 | 5-CN |
| VII.70 | 2-CH3 | 4-SOCH2CH2CH=CF2 | 5-CN |
| VII.71 | 2-CH3 | 4-SO2CH2CH2CH=CF2 | 5-CN |
| VII.72 | 2-H | 4-SCH2CH2CH=CF2 | 5-CONH2 |
| VII.73 | 2-CH3 | 4-SCH2CH2CH=CF2 | 5-CONH2 |
| VII.74 | 2-H | 4-SCH2CH2CH=CF2 | 5-COOCH2CH3 |
| VII.75 | 2-CH3 | 4-SCH2CH2CH=CF2 | 5-COOCH3 |
| VII.76 | 2-CH3 | 4-SO2CH2CH2CH=CF2 | 5-COOCH3 |
| VII.77 | 2-H | 4-SCH2CH2CH=CF2 | 5-COOH |
| VII.78 | 2-H | 4-SCH2CH2CH=CF2 | 5-F |
| VII.79 | 2-H | 4-SCH2CH2CH=CF2 | 5-NO2 |
| VII.80 | 2-H | 4-SCH2CH2CH=CF2 | 5-SO2F |
| VII.81 | 2-H | 4-SCH2CH2CH=CF2 | 5-SO2NH2 |
| VII.82 | 2-H | 4-H | 5-SCH2CH2CH=CF2 |
| VII.83 | 2-H | 4-H | 5-SOCH2CH2CH=CF2 |
| VII.84 | 2-H | 4-H | 5-SO2CH2CH2CH=CF2 |
| VII.85 | 2-H | 4-Br | 5-SCH2CH2CH=CF2 |
| VII.86 | 2-H | 4-C6H5 | 5-SCH2CH2CH=CF2 |
| VII.87 | 2-H | 4-CF3 | 5-SCH2CH2CH=CF2 |
| VII.88 | 2-H | 4-CF3 | 5-SO2CH2CH2CH=CF2 |
| VII.89 | 2-H | 4-Cl | 5-SCH2CH2CH=CF2 |
| VII.90 | 2-H | 4-CN | 5-SCH2CH2CH=CF2 |
| VII.91 | 2-H | 4-CN | 5-SOCH2CH2CH=CF2 |
| VII.92 | 2-H | 4-CN | 5-SO2CH2CH2CH=CF2 |
| VII.93 | 2-CH3 | 4-CN | 5-SCH2CH2CH=CF2 |
| VII.94 | 2-H | 4-CONH2 | 5-SCH2CH2CH=CF2 |
| VII.95 | 2-H | 4-CONH2 | 5-SOCH2CH2CH=CF2 |
| VII.96 | 2-H | 4-CONH2 | 5-SO2CH2CH2CH=CF2 |
| VII.97 | 2-CH3 | 4-CONH2 | 5-SCH2CH2CH=CF2 |
| VII.98 | 2-H | 4-COOCH2CH3 | 5-SCH2CH2CH=CF2 |
| VII.99 | 2-H | 4-COOCH2CH3 | 5-SOCH2CH2CH=CF2 |
| VII.100 | 2-H | 4-COOCH2CH3 | 5-SO2CH2CH2CH=CF2 |
| VII.101 | 2-CH3 | 4-COOCH3 | 5-SCH2CH2CH=CF2 |
| VII.102 | 2-H | 4-COOH | 5-SCH2CH2CH=CF2 |
| VII.103 | 2-H | 4-F | 5-SCH2CH2CH=CF2 |
| VII.104 | 2-H | 4-NO2 | 5-SCH2CH2CH=CF2 |
| VII.105 | 2-H | 4-NO2 | 5-SOCH2CH2CH=CF2 |
| VII.106 | 2-H | 4-SO2F | 5-SCH2CH2CH=CF2 |
| VII.107 | 2-H | 4-SO2NH2 | 5-SCH2CH2CH=CF2 |
| VII.108 | 2-Br | 4-H | 5-SCH2CH2CH=CF2 |
| VII.109 | 2-C6H5 | 4-H | 5-SCH2CH2CH=CF2 |
| VII.110 | 2-C6H5 | 4-H | 5-SOCH2CH2CH=CF2 |
| VII.111 | 2-C6H5 | 4-H | 5-SO2CH2CH2CH=CF2 |
| VII.112 | 2-CF3 | 4-H | 5-SCH2CH2CH=CF2 |
| VII.113 | 2-CF3 | 4-H | 5-SO2CH2CH2CH=CF2 |

TABLE VII-continued

| No. | R2 | R4 | R5 |
|---|---|---|---|
| VII.114 | 2-Cl | 4-H | 5-SCH2CH2CH=CF2 |
| VII.115 | 2-Cl | 4-H | 5-SOCH2CH2CH=CF2 |
| VII.116 | 2-Cl | 4-H | 5-SO2CH2CH2CH=CF2 |
| VII.117 | 2-CN | 4-H | 5-SCH2CH2CH=CF2 |
| VII.118 | 2-CN | 4-CH3 | 5-SCH2CH2CH=CF2 |
| VII.119 | 2-CONH2 | 4-H | 5-SCH2CH2CH=CF2 |
| VII.120 | 2-CONH2 | 4-H | 5-SOCH2CH2CH=CF2 |
| VII.121 | 2-CONH2 | 4-H | 5-SO2CH2CH2CH=CF2 |
| VII.122 | 2-CONH2 | 4-CH3 | 5-SO2CH2CH2CH=CF2 |
| VII.123 | 2-COOCH2CH3 | 4-H | 5-SCH2CH2CH=CF2 |
| VII.124 | 2-COOCH3 | 4-CH3 | 5-SCH2CH2CH=CF2 |
| VII.125 | 2-COOH | 4-H | 5-SCH2CH2CH=CF2 |
| VII.126 | 2-F | 4-H | 5-SCH2CH2CH=CF2 |
| VII.127 | 2-F | 4-H | 5-SOCH2CH2CH=CF2 |
| VII.128 | 2-NH2 | 4-H | 5-SCH2CH2CH=CF2 |
| VII.129 | 2-NO2 | 4-H | 5-SCH2CH2CH=CF2 |
| VII.130 | 2-O(4-CN-C6H4) | 4-H | 5-SCH2CH2CH=CF2 |
| VII.131 | 2-SO2F | 4-H | 5-SCH2CH2CH=CF2 |
| VII.132 | 2-SO2NH2 | 4-H | 5-SCH2CH2CH=CF2 |
| VII.133 | 2-5-(2)-(5-Cl Thiazole) | 4-H | 5-SCH2CH2CH=CF2 |
| VII.134 | 2-SCH2CH2CH=CF2 | 4-dihydro | 5-dihydro |

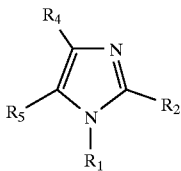

Examples of compounds of Formula (VIII) according to the invention are set out in Table VIII.

TABLE VIII

| No. | R1 | R2 | R4 | R5 |
|---|---|---|---|---|
| VIII.1 | 1-H | 2-SCH2CH2CH=CF2 | 4-H | 5-H |
| VIII.2 | 1-H | 2-SO2CH2CH2CH=CF2 | 4-H | 5-H |
| VIII.3 | 1-C6H5 | 2-SCH2CH2CH=CF2 | 4-H | 5-H |
| VIII.4 | 1-C6H5 | 2-SO2CH2CH2CH=CF2 | 4-H | 5-H |
| VIII.5 | 1-CH3 | 2-SCH2CH2CH=CF2 | 4-H | 5-H |
| VIII.6 | 1-CH3 | 2-SOCH2CH2CH=CF2 | 4-H | 5-H |
| VIII.7 | 1-CH3 | 2-SO2CH2CH2CH=CF2 | 4-H | 5-H |
| VIII.8 | 1-CH2CH2CH=CF2 | 2-SCH2CH2CH=CF2 | 4-H | 5-H |
| VIII.9 | 1-CH2CH2CH=CF2 | 2-SO2CH2CH2CH=CF2 | 4-H | 5-H |
| VIII.10 | 1-CH2CH3 | 2-SCH2CH2CH=CF2 | 4-H | 5-H |
| VIII.11 | 1-CH2CH3 | 2-SO2CH2CH2CH=CF2 | 4-H | 5-H |
| VIII.12 | 1-CH2CH2CH3 | 2-SCH2CH2CH=CF2 | 4-H | 5-H |
| VIII.13 | 1-CH2CH2CH3 | 2-SO2CH2CH2CH=CF2 | 4-H | 5-H |
| VIII.14 | 1-CH(CH3)2 | 2-SCH2CH2CH=CF2 | 4-H | 5-H |
| VIII.15 | 1-CH(CH3)2 | 2-SO2CH2CH2CH=CF2 | 4-H | 5-H |
| VIII.16 | 1-C(CH3)2 | 2-SCH2CH2CH=CF2 | 4-H | 5-H |
| VIII.17 | 1-C(CH3)2 | 2-SO2CH2CH2CH=CF2 | 4-H | 5-H |
| VIII.18 | 1-SO2CH3 | 2-SCH2CH2CH=CF2 | 4-H | 5-H |
| VIII.19 | 1-H | 2-SCH2CH2CH=CF2 | 5-C6H5 | 5-H |
| VIII.20 | 1-H | 2-SOCH2CH2CH=CF2 | 4-C6H5 | 5-H |
| VIII.21 | 1-H | 2-SO2CH2CH2CH=CF2 | 4-C6H5 | 5-H |
| VIII.22 | 1-CH3 | 2-SCH2CH2CH=CF2 | 4-C6H5 | 5-H |
| VIII.23 | 1-CH3 | 2-SOCH2CH2CH=CF2 | 4-C6H5 | 5-H |
| VIII.24 | 1-CH3 | 2-SO2CH2CH2CH=CF2 | 4-C6H5 | 5-H |
| VIII.25 | 1-CH3 | 2-SO2CH2CH2CH=CF2 | 4-H | 5-Br |
| VIII.26 | 1-CH3 | 2-SCH2CH2CH=CF2 | 4-H | 5-CF3 |
| VIII.27 | 1-H | 2-SCH2CH2CH=CF2 | 4-CH2CH3 | 5-CH3 |
| VIII.28 | 1-H | 2-SO2CH2CH2CH=CF2 | 4-CH2CH3 | 5-CH3 |
| VIII.29 | 1-H | 2-SCH2CH2CH=CF2 | 4-CH3 | 5-CH3 |
| VIII.30 | 1-H | 2-SO2CH2CH2CH=CF2 | 4-CH3 | 5-CH3 |
| VIII.31 | 1-CH3 | 2-SCH2CH2CH=CF2 | 4-CH3 | 5-CH3 |
| VIII.32 | 1-CH3 | 2-SO2CH2CH2CH=CF2 | 4-CH3 | 5-CH3 |
| VIII.33 | 1-CH2CH3 | 2-SCH2CH2CH=CF2 | 4-CH3 | 5-CH3 |
| VIII.34 | 1-CH2CH3 | 2-SO2CH2CH2CH=CF2 | 4-CH3 | 5-CH3 |

TABLE VIII-continued

| No. | R1 | R2 | R4 | R5 |
|---|---|---|---|---|
| VIII.35 | 1-CH3 | 2-SCH2CH2CH=CF2 | 4-H | 5-CH3 |
| VIII.36 | 1-CH3 | 2-SO2CH2CH2CH=CF2 | 4-H | 5-CH3 |
| VIII.37 | 1-CH(CH3)2 | 2-SCH2CH2CH=CF2 | 4-H | 5-CH3 |
| VIII.38 | 1-CH(CH3)2 | 2-SO2CH2CH2CH=CF2 | 4-H | 5-CH3 |
| VIII.39 | 1-CH3 | 2-SCH2CH2CH=CF2 | 4-H | 5-Cl |
| VIII.40 | 1-CH3 | 2-SO2CH2CH2CH=CF2 | 4-H | 5-Cl |
| VIII.41 | 1-CH3 | 2-SCH2CH2CH=CF2 | 4-H | 5-CN |
| VIII.42 | 1-CH3 | 2-SOCH2CH2CH=CF2 | 4-H | 5-CN |
| VIII.43 | 1-CH3 | 2-SO2CH2CH2CH=CF2 | 4-H | 5-CN |
| VIII.44 | 1-CH3 | 2-SCH2CH2CH=CF2 | 4-CH3 | 5-CN |
| VIII.45 | 1-CH3 | 2-SOCH2CH2CH=CF2 | 4-CH3 | 5-CN |
| VIII.46 | 1-CH3 | 2-SO2CH2CH2CH=CF2 | 4-CH3 | 5-CN |
| VIII.47 | 1-CH3 | 2-SCH2CH2CH=CF2 | 4-H | 5-CONH2 |
| VIII.48 | 1-CH3 | 2-SCH2CH2CH=CF2 | 4-CH3 | 5-CONH2 |
| VIII.49 | 1-CH3 | 2-SOCH2CH2CH=CF2 | 4-CH3 | 5-CONH2 |
| VIII.50 | 1-H | 2-SOCH2CH2CH=CF2 | 4-H | 5-COOCH2CH3 |
| VIII.51 | 1-H | 2-SO2CH2CH2CH=CF2 | 4-H | 5-COOCH2CH3 |
| VIII.52 | 1-CH3 | 2-SCH2CH2CH=CF2 | 4-H | 5-COOCH2CH3 |
| VIII.53 | 1-CH3 | 2-SO2CH2CH2CH=CF2 | 4-H | 5-COOCH2CH3 |
| VIII.54 | 1-CH3 | 2-SCH2CH2CH=CF2 | 4-H | 5-COOH |
| VIII.55 | 1-CH3 | 2-SCH2CH2CH=CF2 | 4-CH2CH3 | 5-COOCH3 |
| VIII.56 | 1-CH3 | 2-SO2CH2CH2CH=CF2 | 4-CH2CH3 | 5-COOCH3 |
| VIII.57 | 1-CH3 | 2-SCH2CH2CH=CF2 | 4-H | 5-F |
| VIII.58 | 1-H | 2-SCH2CH2CH=CF2 | 4-CH3 | 5-H |
| VIII.59 | 1-H | 2-SO2CH2CH2CH=CF2 | 4-CH3 | 5-H |
| VIII.60 | 1-CH3 | 2-SCH2CH2CH=CF2 | 4-CH3 | 5-H |
| VIII.61 | 1-CH3 | 2-SO2CH2CH2CH=CF2 | 4-CH3 | 5-H |
| VIII.62 | 1-CH(CH3)2 | 2-SCH2CH2CH=CF2 | 4-CH3 | 5-H |
| VIII.63 | 1-CH(CH3)2 | 2-SO2CH2CH2CH=CF2 | 4-CH3 | 5-H |
| VIII.64 | 1-H | 2-SCH2CH2CH=CF2 | 4-COOCH2CH3 | 5-H |
| VIII.65 | 1-CH3 | 2-SCH2CH2CH=CF2 | 4-COOCH2CH3 | 5-H |
| VIII.66 | 1-CH3 | 2-SOCH2CH2CH=CF2 | 4-COOCH2CH3 | 5-H |
| VIII.67 | 1-CH3 | 2-SO2CH2CH2CH=CF2 | 4-COOCH2CH3 | 5-H |
| VIII.68 | 1-CH3 | 2-SCH2CH2CH=CF2 | 4-COOCH3 | 5-CH2CH3 |
| VIII.69 | 1-CH3 | 2-SCH2CH2CH=CF2 | 4-H | 5-NO2 |
| VIII.70 | 1-CH3 | 2-SOCH2CH2CH=CF2 | 4-H | 5-NO2 |
| VIII.71 | 1-CH3 | 2-SO2CH2CH2CH=CF2 | 4-H | 5-NO2 |
| VIII.72 | 1-CH3 | 2-SCH2CH2CH=CF2 | 4-H | 5-SO2F |
| VIII.73 | 1-CH3 | 2-SOCH2CH2CH=CF2 | 4-H | 5-SO2F |
| VIII.74 | 1-CH3 | 2-SCH2CH2CH=CF2 | 4-H | 5-SO2NH2 |
| VIII.75 | 1-CH3 | 2-SO2CH2CH2CH=CF2 | 4-H | 5-SO2NH2 |
| VIII.76 | 1-CH3 | 2-H | 4-SCH2CH2CH=CF2 | 5-H |
| VIII.77 | 1-CH3 | 2-H | 4-SOCH2CH2CH=CF2 | 5-H |
| VIII.78 | 1-CH3 | 2-H | 4-SO2CH2CH2CH=CF2 | 5-H |
| VIII.79 | 1-CH3 | 2-H | 4-SCH2CH2CH=CF2 | 5-CN |
| VIII.80 | 1-CH3 | 2-CH3 | 4-SCH2CH2CH=CF2 | 5-CN |
| VIII.81 | 1-CH3 | 2-CH3 | 4-SOCH2CH2CH=CF2 | 5-CN |
| VIII.82 | 1-CH3 | 2-CH3 | 4-SO2CH2CH2CH=CF2 | 5-CN |
| VIII.83 | 1-CH3 | 2-H | 4-SCH2CH2CH=CF2 | 5-C6H5 |
| VIII.84 | 1-CH3 | 2-H | 4-SOCH2CH2CH=CF2 | 5-C6H5 |
| VIII.85 | 1-CH3 | 2-H | 4-SCH2CH2CH=CF2 | 5-COOCH2CH3 |
| VIII.86 | 1-CH3 | 2-CH3 | 4-SCH2CH2CH=CF2 | 5-COOCH3 |
| VIII.87 | 1-CH3 | 2-CH3 | 4-SO2CH2CH2CH=CF2 | 5-COOCH3 |
| VIII.88 | 1-CH3 | 2-H | 4-SCH2CH2CH=CF2 | 5-COOH |
| VIII.89 | 1-H | 2-H | 4-SCH2CH2CH=CF2 | 5-CONH2 |
| VIII.90 | 1-CH3 | 2-CH3 | 4-SCH2CH2CH=CF2 | 5-CONH2 |
| VIII.91 | 1-CH3 | 2-H | 4-SCH2CH2CH=CF2 | 5-Cl |
| VIII.92 | 1-CH3 | 2-H | 4-SOCH2CH2CH=CF2 | 5-Cl |
| VIII.93 | 1-CH3 | 2-H | 4-SO2CH2CH2CH=CF2 | 5-Cl |
| VIII.94 | 1-CH3 | 2-H | 4-SCH2CH2CH=CF2 | 5-F |
| VIII.95 | 1-CH3 | 2-H | 4-SCH2CH2CH=CF2 | 5-Br |
| VIII.96 | 1-CH3 | 2-H | 4-SCH2CH2CH=CF2 | 5-SO2NH2 |
| VIII.97 | 1-CH3 | 2-H | 4-SCH2CH2CH=CF2 | 5-SO2F |
| VIII.98 | 1-CH3 | 2-H | 4-SCH2CH2CH=CF2 | 5-NO2 |
| VIII.99 | 1-CH3 | 2-H | 4-SCH2CH2CH=CF2 | 5-CF3 |
| VIII.100 | 1-CH3 | 2-H | 4-SOCH2CH2CH=CF2 | 5-CF3 |
| VIII.101 | 1-CH3 | 2-H | 4-H | 5-SCH2CH2CH=CF2 |
| VIII.102 | 1-CH3 | 2-H | 4-H | 5-SOCH2CH2CH=CF2 |
| VIII.103 | 1-CH3 | 2-H | 4-H | 5-SO2CH2CH2CH=CF2 |
| VIII.104 | 1-CH3 | 2-H | 4-CN | 5-SCH2CH2CH=CF2 |
| VIII.105 | 1-CH3 | 2-H | 4-CN | 5-SOCH2CH2CH=CF2 |
| VIII.106 | 1-CH3 | 2-H | 4-CN | 5-SO2CH2CH2CH=CF2 |
| VIII.107 | 1-CH3 | 2-CH3 | 4-CN | 5-SCH2CH2CH=CF2 |
| VIII.108 | 1-CH3 | 2-H | 4-C6H5 | 5-SCH2CH2CH=CF2 |
| VIII.109 | 1-CH3 | 2-H | 4-COOCH2CH3 | 5-SCH2CH2CH=CF2 |
| VIII.110 | 1-CH3 | 2-H | 4-COOCH2CH3 | 5-SOCH2CH2CH=CF2 |
| VIII.111 | 1-CH3 | 2-H | 4-COOCH2CH3 | 5-SO2CH2CH2CH=CF2 |

TABLE VIII-continued

| No. | R1 | R2 | R4 | R5 |
|---|---|---|---|---|
| VIII.112 | 1-CH3 | 2-CH3 | 4-COOCH3 | 5-SCH2CH2CH=CF2 |
| VIII.113 | 1-CH3 | 2-H | 4-COOH | 5-SCH2CH2CH=CF2 |
| VIII.114 | 1-CH3 | 2-H | 4-CONH2 | 5-SCH2CH2CH=CF2 |
| VIII.115 | 1-CH3 | 2-H | 4-CONH2 | 5-SOCH2CH2CH=CF2 |
| VIII.116 | 1-CH3 | 2-H | 4-CONH2 | 5-SO2CH2CH2CH=CF2 |
| VIII.117 | 1-CH3 | 2-CH3 | 4-CONH2 | 5-SCH2CH2CH=CF2 |
| VIII.118 | 1-CH3 | 2-H | 4-Cl | 5-SCH2CH2CH=CF2 |
| VIII.119 | 1-CH3 | 2-H | 4-F | 5-SCH2CH2CH=CF2 |
| VIII.120 | 1-CH3 | 2-H | 4-Br | 5-SCH2CH2CH=CF2 |
| VIII.121 | 1-CH3 | 2-H | 4-SO2NH2 | 5-SCH2CH2CH=CF2 |
| VIII.122 | 1-CH3 | 2-H | 4-SO2F | 5-SCH2CH2CH=CF2 |
| VIII.123 | 1-CH3 | 2-H | 4-NO2 | 5-SCH2CH2CH=CF2 |
| VIII.124 | 1-CH3 | 2-H | 4-NO2 | 5-SOCH2CH2CH=CF2 |
| VIII.125 | 1-CH3 | 2-H | 4-CF3 | 5-SCH2CH2CH=CF2 |
| VIII.126 | 1-CH3 | 2-H | 4-CF3 | 5-SO2CH2CH2CH=CF2 |
| VIII.127 | 1-CH3 | 2-H | 4-H | 5-SCH2CH2CH=CF2 |
| VIII.128 | 1-CH3 | 2-H | 4-H | 5-SOCH2CH2CH=CF2 |
| VIII.129 | 1-CH3 | 2-H | 4-H | 5-SO2CH2CH2CH=CF2 |
| VIII.130 | 1-CH3 | 2-CN | 4-H | 5-SCH2CH2CH=CF2 |
| VIII.131 | 1-CH3 | 2-CN | 4-CH3 | 5-SCH2CH2CH=CF2 |
| VIII.132 | 1-CH3 | 2-C6H5 | 4-H | 5-SCH2CH2CH=CF2 |
| VIII.133 | 1-CH3 | 2-C6H5 | 4-H | 5-SOCH2CH2CH=CF2 |
| VIII.134 | 1-CH3 | 2-C6H5 | 4-H | 5-SO2CH2CH2CH=CF2 |
| VIII.135 | 1-CH3 | 2-COOCH2CH3 | 4-H | 5-SCH2CH2CH=CF2 |
| VIII.136 | 1-CH3 | 2-COOCH3 | 4-CH3 | 5-SCH2CH2CH=CF2 |
| VIII.137 | 1-CH3 | 2-COOH | 4-H | 5-SCH2CH2CH=CF2 |
| VIII.138 | 1-CH3 | 2-CONH2 | 4-H | 5-SCH2CH2CH=CF2 |
| VIII.139 | 1-CH3 | 2-CONH2 | 4-H | 5-SOCH2CH2CH=CF2 |
| VIII.140 | 1-CH3 | 2-CONH2 | 4-H | 5-SO2CH2CH2CH=CF2 |
| VIII.141 | 1-CH3 | 2-CONH2 | 4-CH3 | 5-SO2CH2CH2CH=CF2 |
| VIII.142 | 1-CH3 | 2-Cl | 4-H | 5-SCH2CH2CH=CF2 |
| VIII.143 | 1-CH3 | 2-F | 4-H | 5-SCH2CH2CH=CF2 |
| VIII.144 | 1-CH3 | 2-F | 4-H | 5-SOCH2CH2CH=CF2 |
| VIII.145 | 1-CH3 | 2-Br | 4-H | 5-SCH2CH2CH=CF2 |
| VIII.146 | 1-CH3 | 2-SO2NH2 | 4-H | 5-SCH2CH2CH=CF2 |
| VIII.147 | 1-CH3 | 2-SO2F | 4-H | 5-SCH2CH2CH=CF2 |
| VIII.148 | 1-CH3 | 2-NO2 | 4-H | 5-SCH2CH2CH=CF2 |
| VIII.149 | 1-CH3 | 2-CF3 | 4-H | 5-SCH2CH2CH=CF2 |
| VIII.150 | 1-CH3 | 2-CF3 | 4-H | 5-SO2CH2CH2CH=CF2 |
| VIII.151 | 1–5 linked | 2-SCH2CH2CH=CF2 | 4-H | —CH=CH—CH=CH— |
| VIII.152 | 1–5 linked | 2-SO2CH2CH2CH=CF2 | 4-H | —CH=CH—CH=CH— |

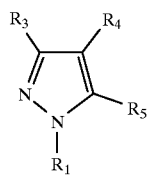

TABLE IX

| No. | R1 | R3 | R4 | R5 |
|---|---|---|---|---|
| IX.1 | 1-CH3 | 3-H | 4-H | 5-SCH2CH2CH=CF2 |
| IX.2 | 1-CH3 | 3-H | 4-H | 5-SOCH2CH2CH=CF2 |
| IX.3 | 1-CH3 | 3-H | 4-H | 5-SO2CH2CH2CH=CF2 |
| IX.4 | 1-CH3 | 3-Cl | 4-H | 5-SCH2CH2CH=CF2 |
| IX.5 | 1-CH3 | 3-Cl | 4-H | 5-SOCH2CH2CH=CF2 |
| IX.6 | 1-CH3 | 3-Cl | 4-H | 5-SO2CH2CH2CH=CF2 |
| IX.7 | 1-CH3 | 3-COOC2H5 | 4-H | 5-SCH2CH2CH=CF2 |
| IX.8 | 1-CH3 | 3-COOC2H5 | 4-H | 5-SOCH2CH2CH=CF2 |
| IX.9 | 1-CH3 | 3-COOC2H5 | 4-H | 5-SO2CH2CH2CH=CF2 |
| IX.10 | 1-CH3 | 3-COOH | 4-H | 5-SCH2CH2CH=CF2 |
| IX.11 | 1-CH3 | 3-COOH | 4-H | 5-SOCH2CH2CH=CF2 |
| IX.12 | 1-CH3 | 3-COOH | 4-H | 5-SO2CH2CH2CH=CF2 |
| IX.13 | 1-CH3 | 3-CONH2 | 4-H | 5-SCH2CH2CH=CF2 |
| IX.14 | 1-CH3 | 3-CONH2 | 4-H | 5-SOCH2CH2CH=CF2 |

TABLE IX-continued

| No. | R1 | R3 | R4 | R5 |
|---|---|---|---|---|
| IX.15 | 1-CH3 | 3-CONH2 | 4-H | 5-SO2CH2CH2CH=CF2 |
| IX.16 | 1-CH3 | 3-CN | 4-H | 5-SCH2CH2CH=CF2 |
| IX.17 | 1-CH3 | 3-CN | 4-H | 5-SOCH2CH2CH=CF2 |
| IX.18 | 1-CH3 | 3-CN | 4-H | 5-SO2CH2CH2CH=CF2 |
| IX.19 | 1-CH3 | 3-SO2F | 4-H | 5-SCH2CH2CH=CF2 |
| IX.20 | 1-CH3 | 3-SO2F | 4-H | 5-SOCH2CH2CH=CF2 |
| IX.21 | 1-CH3 | 3-SO2F | 4-H | 5-SO2CH2CH2CH=CF2 |
| IX.22 | 1-CH3 | 3-SO2NH2 | 4-H | 5-SCH2CH2CH=CF2 |
| IX.23 | 1-CH3 | 3-SO2NH2 | 4-H | 5-SOCH2CH2CH=CF2 |
| IX.24 | 1-CH3 | 3-SO2NH2 | 4-H | 5-SO2CH2CH2CH=CF2 |
| IX.25 | 1-CH3 | 3-H | 4-H | 5-SCH2CH2CH=CF2 |
| IX.26 | 1-CH3 | 3-H | 4-H | 5-SOCH2CH2CH=CF2 |
| IX.27 | 1-CH3 | 3-H | 4-H | 5-SO2CH2CH=CF2 |
| IX.28 | 1-CH3 | 3-H | 4-Cl | 5-SCH2CH2CH=CF2 |
| IX.29 | 1-CH3 | 3-H | 4-Cl | 5-SOCH2CH2CH=CF2 |
| IX.30 | 1-CH3 | 3-H | 4-Cl | 5-SO2CH2CH2CH=CF2 |
| IX.31 | 1-CH3 | 3-H | 4-Br | 5-SCH2CH2CH=CF2 |
| IX.32 | 1-CH3 | 3-H | 4-Br | 5-SOCH2CH2CH=CF2 |
| IX.33 | 1-CH3 | 3-H | 4-Br | 5-SO2CH2CH2CH=CF2 |
| IX.34 | 1-CH3 | 3-H | 4-COOC2H5 | 5-SCH2CH2CH=CF2 |
| IX.35 | 1-CH3 | 3-H | 4-COOC2H5 | 5-SOCH2CH2CH=CF2 |
| IX.36 | 1-CH3 | 3-H | 4-COOC2H5 | 5-SO2CH2CH2CH=CF2 |
| IX.37 | 1-CH3 | 3-H | 4-COOCH(CH3)2 | 5-SCH2CH2CH=CF2 |
| IX.38 | 1-CH3 | 3-H | 4-COOCH(CH3)2 | 5-SOCH2CH2CH=CF2 |
| IX.39 | 1-CH3 | 3-H | 4-COOCH(CH3)2 | 5-SO2CH2CH2CH=CF2 |
| IX.40 | 1-CH3 | 3-H | 4-COOH | 5-SCH2CH2CH=CF2 |
| IX.41 | 1-CH3 | 3-H | 4-COOH | 5-SOCH2CH2CH=CF2 |
| IX.42 | 1-CH3 | 3-H | 4-COOH | 5-SO2CH2CH2CH=CF2 |
| IX.43 | 1-CH3 | 3-H | 4-CONH2 | 5-SCH2CH2CH=CF2 |
| IX.44 | 1-CH3 | 3-H | 4-CONH2 | 5-SOCH2CH2CH=CF2 |
| IX.45 | 1-CH3 | 3-H | 4-CONH2 | 5-SO2CH2CH2CH=CF2 |
| IX.46 | 1-CH3 | 3-H | 4-CN | 5-SCH2CH2CH=CF2 |
| IX.47 | 1-CH3 | 3-H | 4-CN | 5-SOCH2CH2CH=CF2 |
| IX.48 | 1-CH3 | 3-H | 4-CN | 5-SO2CH2CH2CH=CF2 |
| IX.49 | 1-CH3 | 3-H | 4-SO2F | 5-SCH2CH2CH=CF2 |
| IX.50 | 1-CH3 | 3-H | 4-SO2F | 5-SOCH2CH2CH=CF2 |
| IX.51 | 1-CH3 | 3-H | 4-SO2F | 5-SO2CH2CH2CH=CF2 |
| IX.52 | 1-CH3 | 3-H | 4-SO2NH2 | 5-SCH2CH2CH=CF2 |
| IX.53 | 1-CH3 | 3-H | 4-SO2NH2 | 5-SOCH2CH2CH=CF2 |
| IX.54 | 1-CH3 | 3-H | 4-SO2NH2 | 5-SO2CH2CH2CH=CF2 |
| IX.55 | 1-CH3 | 3-CH3 | 4-H | 5-SCH2CH2CH=CF2 |
| IX.56 | 1-CH3 | 3-CH3 | 4-H | 5-SOCH2CH2CH=CF2 |
| IX.57 | 1-CH3 | 3-CH3 | 4-H | 5-SO2CH2CH2CH=CF2 |
| IX.58 | 1-CH3 | 3-CH3 | 4-Cl | 5-SCH2CH2CH=CF2 |
| IX.59 | 1-CH3 | 3-CH3 | 4-Cl | 5-SOCH2CH2CH=CF2 |
| IX.60 | 1-CH3 | 3-CH3 | 4-Cl | 5-SO2CH2CH2CH=CF2 |
| IX.61 | 1-CH3 | 3-CH3 | 4-I | 5-SCH2CH2CH=CF2 |
| IX.62 | 1-CH3 | 3-CH3 | 4-I | 5-SOCH2CH2CH=CF2 |
| IX.63 | 1-CH3 | 3-CH3 | 4-I | 5-SO2CH2CH2CH=CF2 |
| IX.64 | 1-CH3 | 3-CH3 | 4-COOC2H5 | 5-SCH2CH2CH=CF2 |
| IX.65 | 1-CH3 | 3-CH3 | 4-COOC2H5 | 5-SOCH2CH2CH=CF2 |
| IX.66 | 1-CH3 | 3-CH3 | 4-COOC2H5 | 5-SO2CH2CH2CH=CF2 |
| IX.67 | 1-CH3 | 3-CH3 | 4-COOH | 5-SCH2CH2CH=CF2 |
| IX.68 | 1-CH3 | 3-CH3 | 4-COOH | 5-SOCH2CH2CH=CF2 |
| IX.69 | 1-CH3 | 3-CH3 | 4-COOH | 5-SO2CH2CH2CH=CF2 |
| IX.70 | 1-CH3 | 3-CH3 | 4-CONH2 | 5-SCH2CH2CH=CF2 |
| IX.71 | 1-CH3 | 3-CH3 | 4-CONH2 | 5-SOCH2CH2CH=CF2 |
| IX.72 | 1-CH3 | 3-CH3 | 4-CONH2 | 5-SO2CH2CH2CH=CF2 |
| IX.73 | 1-CH3 | 3-CH3 | 4-CN | 5-SCH2CH2CH=CF2 |
| IX.74 | 1-CH3 | 3-CH3 | 4-CN | 5-SOCH2CH2CH=CF2 |
| IX.75 | 1-CH3 | 3-CH3 | 4-CN | 5-SO2CH2CH2CH=CF2 |
| IX.76 | 1-CH3 | 3-CH3 | 4-SO2F | 5-SCH2CH2CH=CF2 |
| IX.77 | 1-CH3 | 3-CH3 | 4-SO2F | 5-SOCH2CH2CH=CF2 |
| IX.78 | 1-CH3 | 3-CH3 | 4-SO2F | 5-SO2CH2CH2CH=CF2 |
| IX.79 | 1-CH3 | 3-CH3 | 4-SO2NH2 | 4-SCH2CH2CH=CF2 |
| IX.80 | 1-CH3 | 3-CH3 | 4-SO2NH2 | 5-SOCH2CH2CH=CF2 |
| IX.81 | 1-CH3 | 3-CH3 | 4-SO2NH2 | 5-SO2CH2CH2CH=CF2 |
| IX.82 | 1-CH3 | 3-CH3 | 4-NO2 | 5-SCH2CH2CH=CF2 |
| IX.83 | 1-CH3 | 3-CH3 | 4-NO2 | 5-SOCH2CH2CH=CF2 |
| IX.84 | 1-CH3 | 3-CH3 | 4-NO2 | 5-SO2CH2CH2CH=CF2 |
| IX.85 | 1-CH3 | 3-CF3 | 4-H | 5-SCH2CH2CH=CF2 |
| IX.86 | 1-CH3 | 3-CF3 | 4-H | 5-SOCH2CH2CH=CF2 |
| IX.87 | 1-CH3 | 3-CF3 | 4-H | 5-SO2CH2CH2CH=CF2 |
| IX.88 | 1-CH3 | 3-C6H5 | 4-H | 5-SCH2CH2CH=CF2 |
| IX.89 | 1-CH3 | 3-C6H5 | 4-H | 5-SOCH2CH2CH=CF2 |
| IX.90 | 1-CH3 | 3-C6H5 | 4-H | 5-SO2CH2CH2CH=CF2 |
| IX.91 | 1-CH3 | 3-C6H5 | 4-CN | 5-SCH2CH2CH=CF2 |

TABLE IX-continued

| No. | R1 | R3 | R4 | R5 |
|---|---|---|---|---|
| IX.92 | 1-CH3 | 3-C6H5 | 4-CN | 5-SOCH2CH2CH=CF2 |
| IX.93 | 1-CH3 | 3-C6H5 | 4-CN | 5-SO2CH2CH2CH=CF2 |
| IX.94 | 1-CH3 | 3-SCH2CH2CH=CF2 | 4-CN | 5-H |
| IX.95 | 1-CH3 | 3-SOCH2CH2CH=CF2 | 4-CN | 5-H |
| IX.96 | 1-CH3 | 3-SO2CH2CH2CH=CF2 | 4-CN | 5-H |
| IX.97 | 1-CH3 | 3-SCH2CH2CH=CF2 | 4-H | 5-Cl |
| IX.98 | 1-CH3 | 3-SOCH2CH2CH=CF2 | 4-H | 5-Cl |
| IX.99 | 1-CH3 | 3-SO2CH2CH2CH=CF2 | 4-H | 5-Cl |
| IX.100 | 1-CH3 | 3-SCH2CH2CH=CF2 | 4-H | 5-CN |
| IX.101 | 1-CH3 | 3-SOCH2CH2CH=CF2 | 4-H | 5-CN |
| IX.102 | 1-CH3 | 3-SO2CH2CH2CH=CF2 | 4-H | 5-CN |
| IX.103 | 1-CH3 | 3-SCH2CH2CH=CF2 | 4-H | 5-COOC2H5 |
| IX.104 | 1-CH3 | 3-SOCH2CH2CH=CF2 | 4-H | 5-COOC2H5 |
| IX.105 | 1-CH3 | 3-SO2CH2CH2CH=CF2 | 4-H | 5-COOC2H5 |
| IX.106 | 1-CH3 | 3-SCH2CH2CH=CF2 | 4-H | 5-CF3 |
| IX.107 | 1-CH3 | 3-SOCH2CH2CH=CF2 | 4-H | 5-CF3 |
| IX.108 | 1-CH3 | 3-SO2CH2CH2CH=CF2 | 4-H | 5-CF3 |
| IX.109 | 1-CH2COOH | 3-SCH2CH2CH=CF2 | 4-H | 5-CH3 |
| IX.110 | 1-CH2COOH | 3-SOCH2CH2CH=CF2 | 4-H | 5-CH3 |
| IX.111 | 1-CH2COOH | 3-SO2CH2CH2CH=CF2 | 4-H | 5-CH3 |
| IX.112 | 1-CH2COOC2H5 | 3-SCH2CH2CH=CF2 | 4-H | 5-C6H5 |
| IX.113 | 1-CH2COOC2H5 | 3-SOCH2CH2CH=CF2 | 4-H | 5-C6H5 |
| IX.114 | 1-CH2COOC2H5 | 3-SO2CH2CH2CH=CF2 | 4-H | 5-C6H5 |
| IX.115 | 1-CH2CN | 3-SCH2CH2CH=CF2 | 4-H | 5-(2-Thienyl) |
| IX.116 | 1-CH2CN | 3-SOCH2CH2CH=CF2 | 4-H | 5-(2-Thienyl) |
| IX.117 | 1-CH2CN | 3-SO2CH2CH2CH=CF2 | 4-H | 5-(2-Thienyl) |
| IX.118 | 1-C6H5 | 3-H | 4-H | 5-SCH2CH2CH=CF2 |
| IX.119 | 1-C6H5 | 3-H | 4-H | 5-SOCH2CH2CH=CF2 |
| IX.120 | 1-C6H5 | 3-H | 4-H | 5-SO2CH2CH2CH=CF2 |
| IX.121 | 1-C6H5 | 3-H | 4-CN | 5-SCH2CH2CH=CF2 |
| IX.122 | 1-C6H5 | 3-H | 4-CN | 5-SOCH2CH2CH=CF2 |
| IX.123 | 1-C6H5 | 3-H | 4-CN | 5-SO2CH2CH2CH=CF2 |
| IX.124 | 1-C6H5 | 3-H | 4-COOC2H5 | 5-SCH2CH2CH=CF2 |
| IX.125 | 1-C6H5 | 3-H | 4-COOC2H5 | 5-SOCH2CH2CH=CF2 |
| IX.126 | 1-C6H5 | 3-H | 4-COOC2H5 | 5-SO2CH2CH2CH=CF2 |
| IX.127 | 1-C6H5 | 3-H | 4-COOH | 5-SCH2CH2CH=CF2 |
| IX.128 | 1-C6H5 | 3-H | 4-COOH | 5-SOCH2CH2CH=CF2 |
| IX.129 | 1-C6H5 | 3-H | 4-COOH | 5-SO2CH2CH2CH=CF2 |
| IX.130 | 1-C6H5 | 3-H | 4-Cl | 5-SCH2CH2CH=CF2 |
| IX.131 | 1-C6H5 | 3-H | 4-Cl | 5-SOCH2CH2CH=CF2 |
| IX.132 | 1-C6H5 | 3-H | 4-Cl | 5-SO2CH2CH2CH=CF2 |
| IX.133 | 1-C6H5 | 3-H | 4-SO2F | 5-SCH2CH2CH=CF2 |
| IX.134 | 1-C6H5 | 3-H | 4-SO2F | 5-SOCH2CH2CH=CF2 |
| IX.135 | 1-C6H5 | 3-H | 4-SO2F | 5-SO2CH2CH2CH=CF2 |
| IX.136 | 1-C6H5 | 3-CH3 | 4-H | 5-SCH2CH2CH=CF2 |
| IX.137 | 1-C6H5 | 3-CH3 | 4-H | 5-SOCH2CH2CH=CF2 |
| IX.138 | 1-C6H5 | 3-CH3 | 4-H | 5-SO2CH2CH2CH=CF2 |
| IX.139 | 1-C6H5 | 3-CH3 | 4-CN | 5-SCH2CH2CH=CF2 |
| IX.140 | 1-C6H5 | 3-CH3 | 4-CN | 5-SOCH2CH2CH=CF2 |
| IX.141 | 1-C6H5 | 3-CH3 | 4-CN | 5-SO2CH2CH2CH=CF2 |
| IX.142 | 1-C6H5 | 3-CH3 | 4-COOC2H5 | 5-SCH2CH2CH=CF2 |
| IX.143 | 1-C6H5 | 3-CH3 | 4-COOC2H5 | 5-SOCH2CH2CH=CF2 |
| IX.144 | 1-C6H5 | 3-CH3 | 4-COOC2H5 | 5-SO2CH2CH2CH=CF2 |
| IX.145 | 1-C6H5 | 3-CH3 | 4-COOH | 5-SCH2CH2CH=CF2 |
| IX.146 | 1-C6H5 | 3-CH3 | 4-COOH | 5-SOCH2CH2CH=CF2 |
| IX.147 | 1-C6H5 | 3-CH3 | 4-COOH | 5-SO2CH2CH2CH=CF2 |
| IX.148 | 1-C6H5 | 3-CH3 | 4-Cl | 5-SCH2CH2CH=CF2 |
| IX.149 | 1-C6H5 | 3-CH3 | 4-Cl | 5-SOCH2CH2CH=CF2 |
| IX.150 | 1-C6H5 | 3-CH3 | 4-Cl | 5-SO2CH2CH2CH=CF2 |
| IX.151 | 1-C6H5 | 3-CH3 | 4-SO2F | 5-SCH2CH2CH=CF2 |
| IX.152 | 1-C6H5 | 3-CH3 | 4-SO2F | 5-SOCH2CH2CH=CF2 |
| IX.153 | 1-C6H5 | 3-CH3 | 4-SO2F | 5-SO2CH2CH2CH=CF2 |
| IX.154 | 1-C6H5 | 3-Cl | 4-H | 5-SCH2CH2CH=CF2 |
| IX.155 | 1-C6H5 | 3-Cl | 4-H | 5-SOCH2CH2CH=CF2 |
| IX.156 | 1-C6H5 | 3-Cl | 4-H | 5-SO2CH2CH2CH=CF2 |
| IX.157 | 1-C6H5 | 3-COOC2H5 | 4-H | 5-SCH2CH2CH=CF2 |
| IX.158 | 1-C6H5 | 3-COOC2H5 | 4-H | 5-SOCH2CH2CH=CF2 |
| IX.159 | 1-C6H5 | 3-COOC2H5 | 4-H | 5-SO2CH2CH2CH=CF2 |
| IX.160 | 1-C6H5 | 3-COOH | 4-H | 5-SCH2CH2CH=CF2 |
| IX.161 | 1-C6H5 | 3-COOH | 4-H | 5-SOCH2CH2CH=CF2 |
| IX.162 | 1-C6H5 | 3-COOH | 4-H | 5-SO2CH2CH2CH=CF2 |
| IX.163 | 1-C6H5 | 3-CONH2 | 4-H | 5-SCH2CH2CH=CF2 |
| IX.164 | 1-C6H5 | 3-CONH2 | 4-H | 5-SOCH2CH2CH=CF2 |
| IX.165 | 1-C6H5 | 3-CONH2 | 4-H | 5-SO2CH2CH2CH=CF2 |
| IX.166 | 1-C6H5 | 3-CN | 4-H | 5-SCH2CH2CH=CF2 |
| IX.167 | 1-C6H5 | 3-CN | 4-H | 5-SOCH2CH2CH=CF2 |
| IX.168 | 1-C6H5 | 3-CN | 4-H | 5-SO2CH2CH2CH=CF2 |

TABLE IX-continued

| No. | R1 | R3 | R4 | R5 |
|---|---|---|---|---|
| IX.169 | 1-C6H5 | 3-SO2F | 4-H | 5-SCH2CH2CH=CF2 |
| IX.170 | 1-C6H5 | 3-SO2F | 4-H | 5-SOCH2CH2CH=CF2 |
| IX.171 | 1-C6H5 | 3-SO2F | 4-H | 5-SO2CH2CH2CH=CF2 |
| IX.172 | 1-C6H5 | 3-SO2NH2 | 4-H | 5-SCH2CH2CH=CF2 |
| IX.173 | 1-C6H5 | 3-SO2NH2 | 4-H | 5-SOCH2CH2CH=CF2 |
| IX.174 | 1-C6H5 | 3-SO2NH2 | 4-H | 5-SO2CH2CH2CH=CF2 |
| IX.175 | 1-CH3 | 3-H | 4-SCH2CH2CH=CF2 | 5-CN |
| IX.176 | 1-CH3 | 3-H | 4-SOCH2CH2CH=CF2 | 5-CN |
| IX.177 | 1-CH3 | 3-H | 4-SO2CH2CH2CH=CF2 | 5-CN |
| IX.178 | 1-CH3 | 3-H | 4-SCH2CH2CH=CF2 | 5-COOC2H5 |
| IX.179 | 1-CH3 | 3-H | 4-SOCH2CH2CH=CF2 | 5-COOC2H5 |
| IX.180 | 1-CH3 | 3-H | 4-SO2CH2CH2CH=CF2 | 5-COOC2H5 |
| IX.181 | 1-CH3 | 3-H | 4-SCH2CH2CH=CF2 | 5-CF3 |
| IX.182 | 1-CH3 | 3-H | 4-SOCH2CH2CH=CF2 | 5-CF3 |
| IX.183 | 1-CH3 | 3-H | 4-SO2CH2CH2CH=CF2 | 5-CF3 |
| IX.184 | 1-CH3 | 3-CN | 4-SCH2CH2CH=CF2 | 5-H |
| IX.185 | 1-CH3 | 3-CN | 4-SOCH2CH2CH=CF2 | 5-H |
| IX.186 | 1-CH3 | 3-CN | 4-SO2CH2CH2CH=CF2 | 5-H |
| IX.187 | 1-CH3 | 3-COOC2H5 | 4-SCH2CH2CH=CF2 | 5-H |
| IX.188 | 1-CH3 | 3-COOC2H5 | 4-SOCH2CH2CH=CF2 | 5-H |
| IX.189 | 1-CH3 | 3-COOC2H5 | 4-SO2CH2CH2CH=CF2 | 5-H |
| IX.190 | 1-CH3 | 3-CF3 | 4-SCH2CH2CH=CF2 | 5-H |
| IX.191 | 1-CH3 | 3-CF3 | 4-SOCH2CH2CH=CF2 | 5-H |
| IX.192 | 1-CH3 | 3-CF3 | 4-SO2CH2CH2CH=CF2 | 5-H |

Examples of compounds of Formula (X) according to the invention are set out in Table X.

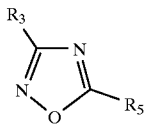

TABLE X

| No. | R3 | R5 |
|---|---|---|
| X.1 | 3-c-C3H5 | 5-SCH2CH2CH=CF2 |
| X.2 | 3-C≡CH | 5-SCH2CH2CH=F2 |
| X.3 | 3-C6H5 | 5-SCH2CH2CH=CF2 |
| X.4 | 3-C6H5 | 5-SOCH2CH2CH=CF2 |
| X.5 | 3-C6H5 | 5-SO2CH2CH2CH=CF2 |
| X.6 | 3-CF2H | 5-SCH2CH2CH=CF2 |
| X.7 | 3-CF3 | 5-SCH2CH2CH=CF2 |
| X.8 | 3-CH(CH3)2 | 5-SCH2CH2CH=CF2 |
| X.9 | 3-CH=CH2 | 5-SCH2CH2CH=CF2 |
| X.10 | 3-CH2Br | 5-SCH2CH2CH=CF2 |
| X.11 | 3-CH2C6H5 | 5-SCH2CH2CH=CF2 |
| X.12 | 3-CH2C6H5 | 5-SOCH2CH2CH=CF2 |
| X.13 | 3-CH2CF3 | 5-SCH2CH2CH=CF2 |
| X.14 | 3-CH2CF3 | 5-SOCH2CH2CH=CF2 |
| X.15 | 3-CH2CF3 | 5-SO2CH2CH2CH=CF2 |
| X.16 | 3-CH2CH=CH2 | 5-SCH2CH2CH=CF2 |
| X.17 | 3-CH2CH2F | 5-SCH2CH2CH=CF2 |
| X.18 | 3-CH2CH3 | 5-SCH2CH2CH=CF2 |
| X.19 | 3-CH2CN | 5-SCH2CH2CH=CF2 |
| X.20 | 3-CH2CN | 5-SOCH2CH2CH=CF2 |
| X.21 | 3-CH2CONH2 | 5-SCH2CH2CH=CF2 |
| X.22 | 3-CH2COOCH2CH3 | 5-SCH2CH2CH=CF2 |
| X.23 | 3-CH2N(CH3)2 | 5-SCH2CH2CH=CF2 |
| X.24 | 3-CH2NHCOCH3 | 5-SCH2CH2CH=CF2 |
| X.25 | 3-CH2NHCOOCH3 | 5-SCH2CH2CH=CF2 |
| X.26 | 3-CH2OCH3 | 5-SCH2CH2CH=CF2 |
| X.27 | 3-CH2OCH3 | 5-SO2CH2CH2CH=CF2 |
| X.28 | 3-CH2OH | 5-SCH2CH2CH=CF2 |
| X.29 | 3-CH2OH | 5-SOCH2CH2CH=CF2 |
| X.30 | 3-CH2SO2C6H5 | 5-SCH2CH2CH=CF2 |
| X.31 | 3-CH2SO2C6H5 | 5-SO2CH2CH2CH=CF2 |
| X.32 | 3-CH3 | 5-SCH2CH2CH=CF2 |
| X.33 | 3-CH3 | 5-SOCH2CH2CH=CF2 |
| X.34 | 3-CH3 | 5-SO2CH2CH2CH=CF2 |
| X.35 | 3-COC6H5 | 5-SCH2CH2CH=CF2 |
| X.36 | 3-COCH3 | 5-SCH2CH2CH=CF2 |
| X.37 | 3-CON(CH3)2 | 5-SCH2CH2CH=CF2 |
| X.38 | 3-CONH2 | 5-SCH2CH2CH=CF2 |
| X.39 | 3-CONHCH2C6H5 | 5-SCH2CH2CH=CF2 |
| X.40 | 3-CONHCH2C6H5 | 5-SOCH2CH2CH=CF2 |
| X.41 | 3-CONHCH2CH2CH=CF2 | 5-SCH2CH2CH=CF2 |
| X.42 | 3-CONHCH3 | 5-SCH2CH2CH=CF2 |
| X.43 | 3-CONHSO2CH3 | 5-SCH2CH2CH=CF2 |
| X.44 | 3-COOC6H5 | 5-SCH2CH2CH=CF2 |
| X.45 | 3-COOC6H5 | 5-SOCH2CH2CH=CF2 |
| X.46 | 3-COOC6H5 | 5-SO2CH2CH2CH=CF2 |
| X.47 | 3-COOCH2CH2CH=CF2 | 5-SCH2CH2CH=CF2 |
| X.48 | 3-COOCH2CH2CH=CF2 | 5-SOCH2CH2CH=CF2 |
| X.49 | 3-COOCH2CH2CH=CF2 | 5-SO2CH2CH2CH=CF2 |
| X.50 | 3-COOCH2CH2F | 5-SCH2CH2CH=CF2 |
| X.51 | 3-COOCH3 | 5-SCH2CH2CH=CF2 |
| X.52 | 3-COOH | 5-SCH2CH2CH=CF2 |
| X.53 | 3-COSCH2CH2CH=CF2 | 5-SCH2CH2CH=CF2 |
| X.54 | 3-CSNH2 | 5-SCH2CH2CH=CF2 |
| X.55 | 3-H | 5-SCH2CH2CH=CF2 |
| X.56 | 3-H | 5-SOCH2CH2CH=CF2 |
| X.57 | 3-H | 5-SO2CH2CH2CH=CF2 |
| X.58 | 3-N(SO2CH3)2 | 5-SCH2CH2CH=CF2 |
| X.59 | 3-NHCH2CH3 | 5-SCH2CH2CH=CF2 |
| X.60 | 3-NHCHO | 5-SCH2CH2CH=CF2 |
| X.61 | 3-NHCOOCH3 | 5-SCH2CH2CH=CF2 |
| X.62 | 3-HNCOCF3 | 5-SCH2CH2CH=CF2 |
| X.63 | 3-HNCOCF3 | 5-SOCH2CH2CH=CF2 |
| X.64 | 3-NHCOCH3 | 5-SCH2CH2CH=CF2 |
| X.65 | 3-NHCOCH3 | 5-SO2CH2CH2CH=CF2 |
| X.66 | 3-NHCSCH2CH3 | 5-SCH2CH2CH=CF2 |
| X.67 | 3-NHCSNHCH2CH3 | 5-SCH2CH2CH=CF2 |
| X.68 | 3-NHSO2CH3 | 5-SCH2CH2CH=CF2 |
| X.69 | 3-OCF2CF2H | 5-SCH2CH2CH=CF2 |
| X.70 | 3-OCF3 | 5-SCH2CH2CH=CF2 |
| X.71 | 3-OCF3 | 5-SOCH2CH2CH=CF2 |
| X.72 | 3-OCH2C6H5 | 5-SCH2CH2CH=CF2 |
| X.73 | 3-OCH2C6H5 | 5-SO2CH2CH2CH=CF2 |
| X.74 | 3-OCH2CF3 | 5-SCH2CH2CH=CF2 |
| X.75 | 3-OCH2CF3 | 5-SOCH2CH2CH=CF2 |
| X.76 | 3-OCH2CF3 | 5-SO2CH2CH2CH=CF2 |

TABLE X-continued

| No. | R3 | R5 |
|---|---|---|
| X.77 | 3-OCH2CH=CCl2 | 5-SCH2CH2CH=CF2 |
| X.78 | 3-OCH2CH2CH=CF2 | 5-SCH2CH2CH=CF2 |
| X.79 | 3-OCH2CH2CH=CF2 | 5-SOCH2CH2CH=CF2 |
| X.80 | 3-OCH2CH2CH=CF2 | 5-SO2CH2CH2CH=CF2 |
| X.81 | 3-OCH2CF2H | 5-SCH2CH2CH=CF2 |
| X.82 | 3-OCH2COOH | 5-SCH2CH2CH=CF2 |
| X.83 | 3-OCH3 | 5-SCH2CH2CH=CF2 |
| X.84 | 3-OCOC6H5 | 5-SCH2CH2CH=CF2 |
| X.85 | 3-OCOCH3 | 5-SCH2CH2CH=CF2 |
| X.86 | 3-OC6H5 | 5-SCH2CH2CH=CF2 |
| X.87 | 3-OC6H5 | 5-SOCH2CH2CH=CF2 |
| X.88 | 3-OC6H5 | 5-SO2CH2CH2CH=CF2 |
| X.89 | 3-OSO2CH3 | 5-SCH2CH2CH=CF2 |
| X.90 | 3-OSO2CH3 | 5-SOCH2CH2CH=CF2 |
| X.91 | 3-SCF3 | 5-SCH2CH2CH=CF2 |
| X.92 | 3-SCH2CH2CH=CF2 | 5-C6H5 |
| X.93 | 3-SOCH2CH2CH=CF2 | 5-C6H5 |
| X.94 | 3-SO2CH2CH2CH=CF2 | 5-C6H5 |
| X.95 | 3-SCH2CH2CH=CF2 | 5-CF2H |
| X.96 | 3-SCH2CH2CH=CF2 | 5-CF3 |
| X.97 | 3-SCH2CH2CH=CF2 | 5-CH2C6H5 |
| X.98 | 3-SOCH2CH2CH=CF2 | 5-CH2C6H5 |
| X.99 | 3-SCH2CH2CH=CF2 | 5-CH2CF3 |
| X.100 | 3-SCH2CH2CH=CF2 | 5-CH2CH2F |
| X.101 | 3-SCH2CH2CH=CF2 | 5-CH2Cl |
| X.102 | 3-SCH2CH2CH=CF2 | 5-CH2CN |
| X.103 | 3-SCH2CH2CH=CF2 | 5-CH2OCH3 |
| X.104 | 3-SCH2CH2CH=CF2 | 5-CH2OH |
| X.105 | 3-SCH2CH2CH=CF2 | 5-CH3 |
| X.106 | 3-SO2CH2CH2CH=CF2 | 5-CH3 |
| X.107 | 3-SCH2CH2CH=CF2 | 5-Cl |
| X.108 | 3-SCH2CH2CH=CF2 | 5-CN |
| X.109 | 3-SCH2CH2CH=CF2 | 5-CON(CH3)2 |
| X.110 | 3-SCH2CH2CH=CF2 | 5-COOCH2CH2CH=CF2 |
| X.111 | 3-SCH2CH2CH=CF2 | 5-COOCH2CH2F |
| X.112 | 3-SCH2CH2CH=CF2 | 5-COOCH3 |
| X.113 | 3-SCH2CH2CH=CF2 | 5-F |
| X.114 | 3-SCH2CH2CH=CF2 | 5-H |
| X.115 | 3-SCH2CH2CH=CF2 | 5-N(SO2CH3)2 |
| X.116 | 3-SCH2CH2CH=CF2 | 5-NHCHO |
| X.117 | 3-SCH2CH2CH=CF2 | 5-NHCOCF3 |
| X.118 | 3-SCH2CH2CH=CF2 | 5-NHCOOCH3 |
| X.119 | 3-SCH2CH2CH=CF2 | 5-NHSO2CH3 |
| X.120 | 3-SCH2CH2CH=CF2 | 5-NO2 |
| X.121 | 3-SCH2CH2CH=CF2 | 5-OC6H5 |
| X.122 | 3-SCH2CH2CH=CF2 | 5-OCF2H |
| X.123 | 3-SCH2CH2CH=CF2 | 5-OCF3 |
| X.124 | 3-SCH2CH2CH=CF2 | 5-OCH2CF3 |
| X.125 | 3-SOCH2CH2CH=CF2 | 5-OCH2CF3 |
| X.126 | 3-SO2CH2CH2CH=CF2 | 5-OCH2CF3 |
| X.127 | 3-SCH2CH2CH=CF2 | 5-OCOCH3 |
| X.128 | 3-SCH2CH2CH=CF2 | 5-OSO2CH3 |
| X.129 | 3-SCH2CH2CH=CF2 | 5-SCH2CH2CH=CF2 |
| X.130 | 3-SOCH2CH2CH=CF2 | 5-SCH2CH2CH=CF2 |
| X.131 | 3-SO2CH2CH2CH=CF2 | 5-SCH2CH2CH=CF2 |
| X.132 | 3-SCH2CH2CH=CF2 | 5-SCH3 |
| X.133 | 3-SCH2CH2CH=CF2 | 5-SO2CF3 |
| X.134 | 3-SOCH2CH2CH=CF2 | 5-SO2CH2CH2CH=CF2 |
| X.135 | 3-SO2CH2CH2CH=CF2 | 5-SO2CH2CH2CH=CF2 |
| X.136 | 3-SCH2CH2CH=CF2 | 5-SO2CH3 |
| X.137 | 3-SO2CH2CH2CH=CF2 | 5-SO2CH3 |
| X.138 | 3-SCH2CH2CH=CF2 | 5-SO2N(CH3)2 |
| X.139 | 3-SCH2CH2CH=CF2 | 5-SOCF3 |
| X.140 | 3-SOCH2CH2CH=CF2 | 5-SOCH2CH2CH=CF2 |
| X.141 | 3-SCH3 | 5-SCH2CH2CH=CF2 |
| X.142 | 3-SO2CF3 | 5-SCH2CH2CH=CF2 |
| X.143 | 3-SO2CF3 | 5-SO2CH2CH2CH=CF2 |
| X.144 | 3-SO2CH3 | 5-SCH2CH2CH=CF2 |
| X.145 | 3-SO2N(CH3)2 | 5-SCH2CH2CH=CF2 |
| X.146 | 3-SO2NH2 | 5-SCH2CH2CH=CF2 |
| X.147 | 3-SO2NHCH3 | 5-SCH2CH2CH=CF2 |
| X.148 | 3-SO2NHCH3 | 5-SO2CH2CH2CH=CF2 |
| X.149 | 3-SOCF3 | 5-SCH2CH2CH=CF2 |
| X.150 | 3-SOCF3 | 5-SOCH2CH2CH=CF2 |
| X.151 | 3-SOCH3 | 5-SCH2CH2CH=CF2 |
| X.152 | 3-SOCH3 | 5-SO2CH2CH2CH=CF2 |
| X.153 | 3-(4-CF3—C6H4) | 5-SCH2CH2CH=CF2 |
| X.154 | 3-(4-CF3—C6H4) | 5-SO2CH2CH2CH=CF2 |
| X.155 | 3-(4-CH3—C6H4) | 5-SCH2CH2CH=CF2 |
| X.156 | 3-(4-CN—C6H4) | 5-SCH2CH2CH=CF2 |
| X.157 | 3-(4-CONH2—C6H4) | 5-SCH2CH2CH=CF2 |
| X.158 | 3-(4-CONH2—C6H4) | 5-SO2CH2CH2CH=CF2 |
| X.159 | 3-(4-NO2—C6H4) | 5-SCH2CH2CH=CF2 |
| X.160 | 3-(4-OCH3—C6H4) | 5-SCH2CH2CH=CF2 |

Examples of compounds of Formula (XI) according to the invention are set out in Table XI.

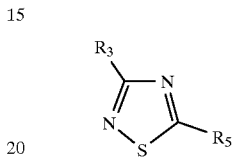

TABLE XI

| No. | R3 | R5 |
|---|---|---|
| XI.1 | 3-Br | 5-SCH2CH2CH=CF2 |
| XI.2 | 3-c-C5H9 | 5-SCH2CH2CH=CF2 |
| XI.3 | 3-c-C5H9 | 5-SOCH2CH2CH=CF2 |
| XI.4 | 3-C≡CH | 5-SCH2CH2CH=CF2 |
| XI.5 | 3-C6H5 | 5-SCH2CH2CH=CF2 |
| XI.6 | 3-C6H5 | 5-SOCH2CH2CH=CF2 |
| XI.7 | 3-C6H5 | 5-SO2CH2CH2CH=CF2 |
| XI.8 | 3-CF2H | 5-SCH2CH2CH=CF2 |
| XI.9 | 3-CF3 | 5-SCH2CH2CH=CF2 |
| XI.10 | 3-CH=CH2 | 5-SCH2CH2CH=CF2 |
| XI.11 | 3-CH=CHCH3 | 5-SCH2CH2CH=CF2 |
| XI.12 | 3-CH=CHCN | 5-SCH2CH2CH=CF2 |
| XI.13 | 3-CH=CHNO2 | 5-SCH2CH2CH=CF2 |
| XI.14 | 3-CH=NOCH3 | 5-SCH2CH2CH=CF2 |
| XI.15 | 3-CH2(3-CF3—C6H4) | 5-SCH2CH2CH=CF2 |
| XI.16 | 3-CH2(3-CF3—C6H4) | 5-SCH2CH2CH=CF2 |
| XI.17 | 3-CH2C6H5 | 5-SCH2CH2CH=CF2 |
| XI.18 | 3-CH2C6H5 | 5-SOCH2CH2CH=CF2 |
| XI.19 | 3-CH2C6H5 | 5-SO2CH2CH2CH=CF2 |
| XI.20 | 3-CH2CF3 | 5-SCH2CH2CH=CF2 |
| XI.21 | 3-CH2CF3 | 5-SOCH2CH2CH=CF2 |
| XI.22 | 3-CH2CH=CH2 | 5-SCH2CH2CH=CF2 |
| XI.23 | 3-CH2CH3 | 5-SCH2CH2CH=CF2 |
| XI.24 | 3-CH2CH3 | 5-SO2CH2CH2CH=CF2 |
| XI.25 | 3-CH2Cl | 5-SCH2CH2CH=CF2 |
| XI.26 | 3-CH2CN | 5-SCH2CH2CH=CF2 |
| XI.27 | 3-CH2CONH2 | 5-SCH2CH2CH=CF2 |
| XI.28 | 3-CH2N(CH3)2 | 5-SCH2CH2CH=CF2 |
| XI.29 | 3-CH2NHCOCH3 | 5-SCH2CH2CH=CF2 |
| XI.30 | 3-CH2OCH2CH2CH2CH3 | 5-SCH2CH2CH=CF2 |
| XI.31 | 3-CH2OCH2CH2CH3 | 5-SCH2CH2CH=CF2 |
| XI.32 | 3-CH2OCH2CH3 | 5-SCH2CH2CH=CF2 |
| XI.33 | 3-CH2OCH2CH3 | 5-SOCH2CH2CH=CF2 |
| XI.34 | 3-CH2OCH3 | 5-SCH2CH2CH=CF2 |
| XI.35 | 3-CH2OCH3 | 5-SOCH2CH2CH=CF2 |
| XI.36 | 3-CH2OCH3 | 5-SO2CH2CH2CH=CF2 |
| XI.37 | 3-CH2OH | 5-SCH2CH2CH=CF2 |
| XI.38 | 3-CH2SCH2CH2CH=CF2 | 5-SCH2CH2CH=CF2 |
| XI.39 | 3-CH2SO2C6H5 | 5-SCH2CH2CH=CF2 |
| XI.40 | 3-CH3 | 5-SCH2CH2CH=CF2 |
| XI.41 | 3-CH3 | 5-SOCH2CH2CH=CF2 |
| XI.42 | 3-CH3 | 5-SO2CH2CH2CH=CF2 |
| XI.43 | 3-Cl | 5-SCH2CH2CH=CF2 |
| XI.44 | 3-Cl | 5-SO2CH2CH2CH=CF2 |
| XI.45 | 3-CN | 5-SCH2CH2CH=CF2 |
| XI.46 | 3-COC6H5 | 5-SCH2CH2CH=CF2 |
| XI.47 | 3-COCH3 | 5-SCH2CH2CH=CF2 |
| XI.48 | 3-CON(CH3)2 | 5-SCH2CH2CH=CF2 |
| XI.49 | 3-CON(CH3)C2H5 | 5-SCH2CH2CH=CF2 |
| XI.50 | 3-CONH2 | 5-SCH2CH2CH=CF2 |

TABLE XI-continued

| No. | R3 | R5 |
|---|---|---|
| XI.51 | 3-CONHCH2C6H5 | 5-SCH2CH2CH=CF2 |
| XI.52 | 3-CONHCH2CH2CH=CF2 | 5-SCH2CH2CH=CF2 |
| XI.53 | 3-CONHCH2CH2CH3 | 5-SCH2CH2CH=CF2 |
| XI.54 | 3-CONHCH3 | 5-SCH2CH2CH=CF2 |
| XI.55 | 3-CONHCH3 | 5-SOCH2CH2CH=CF2 |
| XI.56 | 3-CONHCH3 | 5-SO2CH2CH2CH=CF2 |
| XI.57 | 3-CONHSO2CH3 | 5-SCH2CH2CH=CF2 |
| XI.58 | 3-COOC6H5 | 5-SCH2CH2CH=CF2 |
| XI.59 | 3-COOCH2CH2CH=CF2 | 5-SCH2CH2CH=CF2 |
| XI.60 | 3-COOCH2CH2F | 5-SCH2CH2CH=CF2 |
| XI.61 | 3-COOCH2CH3 | 5-SCH2CH2CH=CF2 |
| XI.62 | 3-COOCH3 | 5-SCH2CH2CH=CF2 |
| XI.63 | 3-COOH | 5-SCH2CH2CH=CF2 |
| XI.64 | 3-COSCH2CH2CH=CF2 | 5-SCH2CH2CH=CF2 |
| XI.65 | 3-CSNH2 | 5-SCH2CH2CH=CF2 |
| XI.66 | 3-F | 5-SCH2CH2CH=CF2 |
| XI.67 | 3-H | 5-SCH2CH2CH=CF2 |
| XI.68 | 3-H | 5-SOCH2CH2CH=CF2 |
| XI.69 | 3-H | 5-SO2CH2CH2CH=CF2 |
| XI.70 | 3-N(SO2CH3)2 | 5-SCH2CH2CH=CF2 |
| XI.71 | 3-NHCHO | 5-SCH2CH2CH=CF2 |
| XI.72 | 3-NHCOC2H5 | 5-SCH2CH2CH=CF2 |
| XI.73 | 3-NHCOCF3 | 5-SCH2CH2CH=CF2 |
| XI.74 | 3-NHCOCH3 | 5-SCH2CH2CH=CF2 |
| XI.75 | 3-NHCSCH2CH3 | 5-SCH2CH2CH=CF2 |
| XI.76 | 3-NHCSNHCH2CH3 | 5-SCH2CH2CH=CF2 |
| XI.77 | 3-NHSO2CH3 | 5-SCH2CH2CH=CF2 |
| XI.78 | 3-NO2 | 5-SCH2CH2CH=CF2 |
| XI.79 | 3-OC6H5 | 5-SCH2CH2CH=CF2 |
| XI.80 | 3-OCF2CF2H | 5-SCH2CH2CH=CF2 |
| XI.81 | 3-OCF2H | 5-SCH2CH2CH=CF2 |
| XI.82 | 3-OCF3 | 5-SCH2CH2CH=CF2 |
| XI.83 | 3-OCH2CF3 | 5-SCH2CH2CH=CF2 |
| XI.84 | 3-OCH2CF3 | 5-SOCH2CH2CH=CF2 |
| XI.85 | 3-OCH2CF3 | 5-SO2CH2CH2CH=CF2 |
| XI.86 | 3-OCH2CH=CCl2 | 5-SCH2CH2CH=CF2 |
| XI.87 | 3-OCH3 | 5-SCH2CH2CH=CF2 |
| XI.88 | 3-OCOC2H5 | 5-SCH2CH2CH=CF2 |
| XI.89 | 3-OCOC6H5 | 5-SCH2CH2CH=CF2 |
| XI.90 | 3-OCOCH3 | 5-SCH2CH2CH=CF2 |
| XI.91 | 3-OSO2CH3 | 5-SCH2CH2CH=CF2 |
| XI.92 | 3-SCF3 | 5-SCH2CH2CH=CF2 |
| XI.93 | 3-SCH2CH2CH=CF2 | 5-CF3 |
| XI.94 | 3-SCH2CH2CH=CF2 | 5-CH2C6H5 |
| XI.95 | 3-SCH2CH2CH=CF2 | 5-CH2CF3 |
| XI.96 | 3-SCH2CH2CH=CF2 | 5-CH2CH=CH2 |
| XI.97 | 3-SCH2CH2CH=CF2 | 5-CH2CN |
| XI.98 | 3-SCH2CH2CH=CF2 | 5-CH2CONH2 |
| XI.99 | 3-SCH2CH2CH=CF2 | 5-CH2NHCOCH3 |
| XI.100 | 3-SCH2CH2CH=CF2 | 5-CH2OCH3 |
| XI.101 | 3-SCH2CH2CH=CF2 | 5-CH3 |
| XI.102 | 3-SCH2CH2CH=CF2 | 5-Cl |
| XI.103 | 3-SCH2CH2CH=CF2 | 5-CN |
| XI.104 | 3-SCH2CH2CH=CF2 | 5-COOCH3 |
| XI.105 | 3-SCH2CH2CH=CF2 | 5-NHCHO |
| XI.106 | 3-SCH2CH2CH=CF2 | 5-OC6H5 |
| XI.107 | 3-SCH2CH2CH=CF2 | 5-OCH2CF3 |
| XI.108 | 3-SCH2CH2CH=CF2 | 5-OCH3 |
| XI.109 | 3-SCH2CH2CH=CF2 | 5-SCH2CH2CH=CF2 |
| XI.110 | 3-SCH3 | 5-SCH2CH2CH=CF2 |
| XI.111 | 3-SO2C2H5 | 5-SCH2CH2CH=CF2 |
| XI.112 | 3-SO2CF3 | 5-SCH2CH2CH=CF2 |
| XI.113 | 3-SO2CH2CH2CH=CF2 | 5-OCH2CF3 |
| XI.114 | 3-SO2CH2CH2CH=CF2 | 5-SCH2CH2CH=CF2 |
| XI.115 | 3-SO2CH2CH2CH=CF2 | 5-SOCH2CH2CH=CF2 |
| XI.116 | 3-SO2F | 5-SCH2CH2CH=CF2 |
| XI.117 | 3-SO2N(CH3)2 | 5-SCH2CH2CH=CF2 |
| XI.118 | 3-SO2NH2 | 5-SCH2CH2CH=CF2 |
| XI.119 | 3-SO2NHCH3 | 5-SCH2CH2CH=CF2 |
| XI.120 | 3-SOCF3 | 5-SCH2CH2CH=CF2 |
| XI.121 | 3-SOCH2CH2CH=CF2 | 5-CH2CN |
| XI.122 | 3-SOCH2CH2CH=CF2 | 5-OCH2CF3 |
| XI.123 | 3-SOCH2CH2CH=CF2 | 5-SCH2CH2CH=CF2 |
| XI.124 | 3-SOCH3 | 5-SCH2CH2CH=CF2 |
| XI.125 | 3-(2-Pyrazinyl) | 5-SCH2CH2CH=CF2 |
| XI.126 | 3-(3-F—C6H4) | 5-SCH2CH2CH=CF2 |
| XI.127 | 3-(3-NO2—C6H4) | 5-SCH2CH2CH=CF2 |
| XI.128 | 3-(3-NO2—C6H4) | 5-SOCH2CH2CH=CF2 |
| XI.129 | 3-(3-NO2—C6H4) | 5-SO2CH2CH2CH=CF2 |
| XI.130 | 3-(4-F—C6H4) | 5-SCH2CH2CH=CF2 |
| XI.131 | 3-(4-F—C6H4) | 5-SOCH2CH2CH=CF2 |
| XI.132 | 3-(4-F—C6H4) | 5-SO2CH2CH2CH=CF2 |

Examples of compounds of Formula (XII) according to the invention are set out in Table XII.

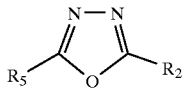

TABLE XII

| No. | R2 | R5 |
|---|---|---|
| XII.1 | 2-SCH2CH2CH=CF2 | 5-c-C3H5 |
| XII.2 | 2-SCH2CH2CH=CF2 | 5-C≡CH |
| XII.3 | 2-SCH2CH2CH=CF2 | 5-C6H5 |
| XII.4 | 2-SOCH2CH2CH=CF2 | 5-C6H5 |
| XII.5 | 2-SO2CH2CH2CH=CF2 | 5-C6H5 |
| XII.6 | 2-SCH2CH2CH=CF2 | 5-CF2H |
| XII.7 | 2-SCH2CH2CH=CF2 | 5-CF3 |
| XII.8 | 2-SCH2CH2CH=CF2 | 5-CH(CH3)2 |
| XII.9 | 2-SO2CH2CH2CH=CF2 | 5-CH(CH3)2 |
| XII.10 | 2-SCH2CH2CH=CF2 | 5-CH=CH2 |
| XII.11 | 2-SCH2CH2CH=CF2 | 5-CH2(2,6-di F-C6H3) |
| XII.12 | 2-SCH2CH2CH=CF2 | 5-CH2(4-NO2-C6H4) |
| XII.13 | 2-SOCH2CH2CH=CF2 | 5-CH2(4-NO2-C6H4) |
| XII.14 | 2-SOCH2CH2CH=CF2 | 5-CH2(4-OCH3-C6H4) |
| XII.15 | 2-SO2CH2CH2CH=CF2 | 5-CH2(4-OCH3-C6H4) |
| XII.16 | 2-SCH2CH2CH=CF2 | 5-CH2Br |
| XII.17 | 2-SCH2CH2CH=CF2 | 5-CH2C6H5 |
| XII.18 | 2-SOCH2CH2CH=CF2 | 5-CH2C6H5 |
| XII.19 | 2-SO2CH2CH2CH=CF2 | 5-CH2C6H5 |
| XII.20 | 2-SCH2CH2CH=CF2 | 5-CH2CF3 |
| XII.21 | 2-SOCH2CH2CH=CF2 | 5-CH2CF3 |
| XII.22 | 2-SO2CH2CH2CH=CF2 | 5-CH2CF3 |
| XII.23 | 2-SCH2CH2CH=CF2 | 5-CH2CH(CH3)2 |
| XII.24 | 2-SCH2CH2CH=CF2 | 5-CH2CH=CH2 |
| XII.25 | 2-SCH2CH2CH=CF2 | 5-CH2CH2CH2CH2CH3 |
| XII.26 | 2-SOCH2CH2CH=CF2 | 5-CH2CH2CH2CH2CH3 |
| XII.27 | 2-SO2CH2CH2CH=CF2 | 5-CH2CH2CH2CH2CH3 |
| XII.28 | 2-SCH2CH2CH=CF2 | 5-CH2CH2CH2CH3 |
| XII.29 | 2-SOCH2CH2CH=CF2 | 5-CH2CH2CH2CH3 |
| XII.30 | 2-SO2CH2CH2CH=CF2 | 5-CH2CH2CH2CH3 |
| XII.31 | 2-SCH2CH2CH=CF2 | 5-CH2CH2CH3 |
| XII.32 | 2-SOCH2CH2CH=CF2 | 5-CH2CH2CH3 |
| XII.33 | 2-SO2CH2CH2CH=CF2 | 5-CH2CH2CH3 |
| XII.34 | 2-SCH2CH2CH=CF2 | 5-CH2CH2F |
| XII.35 | 2-SCH2CH2CH=CF2 | 5-CH2CH3 |
| XII.36 | 2-SCH2CH2CH=CF2 | 5-CH2CN |
| XII.37 | 2-SOCH2CH2CH=CF2 | 5-CH2CN |
| XII.38 | 2-SCH2CH2CH=CF2 | 5-CH2CONH2 |
| XII.39 | 2-SCH2CH2CH=CF2 | 5-CH2COOCH2CH3 |
| XII.40 | 2-SCH2CH2CH=CF2 | 5-CH2N(CH3)2 |
| XII.41 | 2-SCH2CH2CH=CF2 | 5-CH2NHCOCH3 |
| XII.42 | 2-SCH2CH2CH=CF2 | 5-CH2NHCOOCH3 |
| XII.43 | 2-SCH2CH2CH=CF2 | 5-CH2OCH3 |
| XII.44 | 2-SO2CH2CH2CH=CF2 | 5-CH2OCH3 |
| XII.45 | 2-SCH2CH2CH=CF2 | 5-CH2OH |
| XII.46 | 2-SOCH2CH2CH=CF2 | 5-CH2OH |
| XII.47 | 2-SCH2CH2CH=CF2 | 5-CH2SO2C6H5 |
| XII.48 | 2-SO2CH2CH2CH=CF2 | 5-CH2SO2C6H5 |
| XII.49 | 2-SCH2CH2CH=CF2 | 5-CH3 |
| XII.50 | 2-SOCH2CH2CH=CF2 | 5-CH3 |
| XII.51 | 2-SO2CH2CH2CH=CF2 | 5-CH3 |
| XII.52 | 2-SCH2CH2CH=CF2 | 5-COC6H5 |
| XII.53 | 2-SCH2CH2CH=CF2 | 5-COCH3 |
| XII.54 | 2-SCH2CH2CH=CF2 | 5-CON(CH3)2 |

TABLE XII-continued

| No. | R2 | R5 |
|---|---|---|
| XII.55 | 2-SCH2CH2CH=CF2 | 5-CONH2 |
| XII.56 | 2-SCH2CH2CH=CF2 | 5-CONHCH2C6H5 |
| XII.57 | 2-SOCH2CH2CH=CF2 | 5-CONHCH2C6H5 |
| XII.58 | 2-SCH2CH2CH=CF2 | 5-CONHCH2CH2CH=CF2 |
| XII.59 | 2-SCH2CH2CH=CF2 | 5-CONHCH3 |
| XII.60 | 2-SCH2CH2CH=CF2 | 5-CONHSO2CH3 |
| XII.61 | 2-SCH2CH2CH=CF2 | 5-COOC6H5 |
| XII.62 | 2-SOCH2CH2CH=CF2 | 5-COOC6H5 |
| XII.63 | 2-SO2CH2CH2CH=CF2 | 5-COOC6H5 |
| XII.64 | 2-SCH2CH2CH=CF2 | 5-COOCH2CH2CH=CF2 |
| XII.65 | 2-SOCH2CH2CH=CF2 | 5-COOCH2CH2CH=CF2 |
| XII.66 | 2-SO2CH2CH2CH=CF2 | 5-COOCH2CH2CH=CF2 |
| XII.67 | 2-SCH2CH2CH=CF2 | 5-COOCH2CF2F |
| XII.68 | 2-SCH2CH2CH=CF2 | 5-COOCH2CH3 |
| XII.69 | 2-SCH2CH2CH=CF2 | 5-COOCH3 |
| XII.70 | 2-SCH2CH2CH=CF2 | 5-COOH |
| XII.71 | 2-SCH2CH2CH=CF2 | 5-COSCH2CH2CH=CF2 |
| XII.72 | 2-SCH2CH2CH=CF2 | 5-CSNH2 |
| XII.73 | 2-SCH2CH2CH=CF2 | 5-H |
| XII.74 | 2-SOCH2CH2CH=CF2 | 5-H |
| XII.75 | 2-SO2CH2CH2CH=CF2 | 5-H |
| XII.76 | 2-SCH2CH2CH=CF2 | 5-N(SO2CH3)2 |
| XII.77 | 2-SCH2CH2CH=CF2 | 5-NHCH2CH3 |
| XII.78 | 2-SCH2CH2CH=CF2 | 5-NHCHO |
| XII.79 | 2-SCH2CH2CH=CF2 | 5-NHCOOCH3 |
| XII.80 | 2-SCH2CH2CH=CF2 | 5-NHCOCF3 |
| XII.81 | 2-SOCH2CH2CH=CF2 | 5-NHCOCF3 |
| XII.82 | 2-SCH2CH2CH=CF2 | 5-NHCOCH3 |
| XII.83 | 2-SO2CH2CH2CH=CF2 | 5-NHCOCH3 |
| XII.84 | 2-SCH2CH2CH=CF2 | 5-NHCSCH2CH3 |
| XII.85 | 2-SCH2CH2CH=CF2 | 5-NHCSNHCH2CH3 |
| XII.86 | 2-SCH2CH2CH=CF2 | 5-NHSO2CH3 |
| XII.87 | 2-SCH2CH2CH=CF2 | 5-OCF2CF2H |
| XII.88 | 2-SCH2CH2CH=CF2 | 5-OCF3 |
| XII.89 | 2-SOCH2CH2CH=CF2 | 5-OCF3 |
| XII.90 | 2-SCH2CH2CH=CF2 | 5-OCH2C6H5 |
| XII.91 | 2-SO2CH2CH2CH=CF2 | 5-OCH2C6H5 |
| XII.92 | 2-SCH2CH2CH=CF2 | 5-OCH2CF3 |
| XII.93 | 2-SOCH2CH2CH=CF2 | 5-OCH2CF3 |
| XII.94 | 2-SO2CH2CH2CH=CF2 | 5-OCH2CF3 |
| XII.95 | 2-SCH2CH2CH=CF2 | 5-OCH2CH=CCl2 |
| XII.96 | 2-SCH2CH2CH=CF2 | 5-OCH2CH2CH=CF2 |
| XII.97 | 2-SOCH2CH2CH=CF2 | 5-OCH2CH2CH=CF2 |
| XII.98 | 2-SO2CH2CH2CH=CF2 | 5-OCH2CH2CH=CF2 |
| XII.99 | 2-SCH2CH2CH=CF2 | 5-OCH2CH2F |
| XII.100 | 2-SCH2CH2CH=CF2 | 5-OCH2COOH |
| XII.101 | 2-SCH2CH2CH=CF2 | 5-OCH3 |
| XII.102 | 2-SCH2CH2CH=CF2 | 5-OCOC6H5 |
| XII.103 | 2-SCH2CH2CH=CF2 | 5-OCOCH3 |
| XII.104 | 2-SCH2CH2CH=CF2 | 5-OC6H5 |
| XII.105 | 2-SOCH2CH2CH=CF2 | 5-OC6H5 |
| XII.106 | 2-SO2CH2CH2CH=CF2 | 5-OC6H5 |
| XII.107 | 2-SCH2CH2CH=CF2 | 5-OSO2CH3 |
| XII.108 | 2-SOCH2CH2CH=CF2 | 5-OSO2CH3 |
| XII.109 | 2-SCH2CH2CH=CF2 | 5-SCF3 |
| XII.110 | 2-SCH2CH2CH=CF2 | 5-SCH2CH2CH=CF2 |
| XII.111 | 2-SCH2CH2CH=CF2 | 5-SCH3 |
| XII.112 | 2-SCH2CH2CH=CF2 | 5-SO2CF3 |
| XII.113 | 2-SO2CH2CH2CH=CF2 | 5-SO2CF3 |
| XII.114 | 2-SCH2CH2CH=CF2 | 5-SO2CH2CH2CH=CF2 |
| XII.115 | 2-SO2CH2CH2CH=CF2 | 5-SO2CH2CH2CH=CF2 |
| XII.116 | 2-SCH2CH2CH=CF2 | 5-SO2CH3 |
| XII.117 | 2-SCH2CH2CH=CF2 | 5-SO2N(CH3)2 |
| XII.118 | 2-SCH2CH2CH=CF2 | 5-SO2NH2 |
| XII.119 | 2-SCH2CH2CH=CF2 | 5-SO2NHCH3 |
| XII.120 | 2-SO2CH2CH2CH=CF2 | 5-SO2NHCH3 |
| XII.121 | 2-SCH2CH2CH=CF2 | 5-SOCF3 |
| XII.122 | 2-SOCH2CH2CH=CF2 | 5-SOCF3 |
| XII.123 | 2-SCH2CH2CH=CF2 | 5-SOCH2CH2CH=CF2 |
| XII.124 | 2-SOCH2CH2CH=CF2 | 5-SOCH2CH2CH=CF2 |
| XII.125 | 2-SO2CH2CH2CH=CF2 | 5-SOCH2CH2CH=CF2 |
| XII.126 | 2-SCH2CH2CH=CF2 | 5-SOCH3 |
| XII.127 | 2-SO2CH2CH2CH=CF2 | 5-SOCH3 |
| XII.128 | 2-SCH2CH2CH=CF2 | 5-(2-CH3-C6H4) |
| XII.129 | 2-SOCH2CH2CH=CF2 | 5-(2-CH3-C6H4) |
| XII.130 | 2-SO2CH2CH2CH=CF2 | 5-(2-CH3-C6H4) |
| XII.131 | 2-SCH2CH2CH=CF2 | 5(2-Furyl) |
| XII.132 | 2-SCH2CH2CH=CF2 | 5-(2-OCH3-C6H4) |
| XII.133 | 2-SCH2CH2CH=CF2 | 5(2-Thiophenyl) |
| XII.134 | 2-SCH2CH2CH=CF2 | 5-(3-Furyl) |
| XII.135 | 2-SCH2CH2CH=CF2 | 5-(4-CF3-C6H4) |
| XII.136 | 2-SO2CH2CH2CH=CF2 | 5-(4-CF3-C6H4) |
| XII.137 | 2-SCH2CH2CH=CF2 | 5-(4-CH3-C6H4) |
| XII.138 | 2-SCH2CH2CH=CF2 | 5-(4-CN-C6H4) |
| XII.139 | 2-SCH2CH2CH=CF2 | 5-(4-CONH2-C6H4) |
| XII.140 | 2-SO2CH2CH2CH=CF2 | 5-(4-CONH2-C6H4) |
| XII.141 | 2-SCH2CH2CH=CF2 | 5-(4-NO2-C6H4) |
| XII.142 | 2-SOCH2CH2CH=CF2 | 5-(4-NO2-C6H4) |
| XII.143 | 2-SO2CH2CH2CH=CF2 | 5-(4-NO2-C6H4) |
| XII.144 | 2-SCH2CH2CH=CF2 | 5-(4-OCH3-C6H4) |
| XII.145 | 2-SOCH2CH2CH=CF2 | 5-(4-OCH3-C6H4) |
| XII.146 | 2-SO2CH2CH2CH=CF2 | 5-(4-OCH3-C6H4) |
| XII.147 | 2-SCH2CH2CH=CF2 | 5-(4-H-C6H4) |
| XII.148 | 2-SCH2CH2CH=CF2 | 5-(4-Pyridinyl) |

Examples of compounds of Formula (XIII) according to the invention are set out in Table XIII.

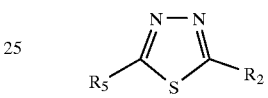

TABLE XIII

| No. | R2 | R5 |
|---|---|---|
| XIII.1 | 2-SCH2CH2CH=CF2 | 5-Br |
| XIII.2 | 2-SO2CH2CH2CH=CF2 | 5-Br |
| XIII.3 | 2-SCH2CH2CH=CF2 | 5-C(CH3)3 |
| XIII.4 | 2-SO2CH2CH2CH=CF2 | 5-C(CH3)3 |
| XIII.5 | 2-SCH2CH2CH=CF2 | 5-C(O)C6H5 |
| XIII.6 | 2-SCH2CH2CH=CF2 | 5-c-C3H5 |
| XIII.7 | 2-SO2CH2CH2CH=CF2 | 5-c-C3H5 |
| XIII.8 | 2-SCH2CH2CH=CF2 | 5-C≡H |
| XIII.9 | 2-SCH2CH2CH=CF2 | 5-C6H5 |
| XIII.10 | 2-SOCH2CH2CH=CF2 | 5-C6H5 |
| XIII.11 | 2-SO2CH2CH2CH=CF2 | 5-C6H5 |
| XIII.12 | 2-SCH2CH2CH=CF2 | 5-CF2H |
| XIII.13 | 2-SOCH2CH2CH=CF2 | 5-CF2H |
| XIII.14 | 2-SCH2CH2CH=CF2 | 5-CF3 |
| XIII.15 | 2-SO2CH2CH2CH=CF2 | 5-CF3 |
| XIII.16 | 2-SCH2CH2CH=CF2 | 5-CH(CH3)2 |
| XIII.17 | 2-SO2CH2CH2CH=CF2 | 5-CH(CH3)2 |
| XIII.18 | 2-SCH2CH2CH=CF2 | 5-CH=CH2 |
| XIII.19 | 2-SCH2CH2CH=CF2 | 5-CH2Br |
| XIII.20 | 2-SCH2CH2CH=CF2 | 5-CH2C6H5 |
| XIII.21 | 2-SOCH2CH2CH=CF2 | 5-CH2C6H5 |
| XIII.22 | 2-SO2CH2CH2CH=CF2 | 5-CH2C6H5 |
| XIII.23 | 2-SCH2CH2CH=CF2 | 5-CH2CF3 |
| XIII.24 | 2-SCH2CH2CH=CF2 | 5-CH2CH2F |
| XIII.25 | 2-SOCH2CH2CH=CF2 | 5-CH2CH2F |
| XIII.26 | 2-SO2CH2CH2CH=CF2 | 5-CH2CH2F |
| XIII.27 | 2-SCH2CH2CH=CF2 | 5-CH2CH3 |
| XIII.28 | 2-SOCH2CH2CH=CF2 | 5-CH2CH3 |
| XIII.29 | 2-SO2CH2CH2CH=CF2 | 5-CH2CH3 |
| XIII.30 | 2-SCH2CH2CH=CF2 | 5-CH2CHCH2 |
| XIII.31 | 2-SCH2CH2CH=CF2 | 5-CH2CN |
| XIII.32 | 2-SCH2CH2CH=CF2 | 5-CH2CONH2 |
| XIII.33 | 2-SCH2CH2CH=CF2 | 5-CH2COOCH2CH3 |
| XIII.34 | 2-SCH2CH2CH=CF2 | 5-CH2N(CH3)2 |
| XIII.35 | 2-SCH2CH2CH=CF2 | 5-CH2OCH3 |
| XIII.36 | 2-SOCH2CH2CH=CF2 | 5-CH2OCH3 |
| XIII.37 | 2-SO2CH2CH2CH=CF2 | 5-CH2OCH3 |
| XIII.38 | 2-SCH2CH2CH=CF2 | 5-CH2OH |
| XIII.39 | 2-SCH2CH2CH=CF2 | 5-CH2SO2C6H5 |
| XIII.40 | 2-SCH2CH2CH=CF2 | 5-CH3 |
| XIII.41 | 2-SOCH2CH2CH=CF2 | 5-CH3 |
| XIII.42 | 2-SO2CH2CH2CH=CF2 | 5-CH3 |

TABLE XIII-continued

| No. | R2 | R5 |
|---|---|---|
| XIII.43 | 2-SCH2CH2CH=CF2 | 5-COCH3 |
| XIII.44 | 2-SCH2CH2CH=CF2 | 5-CON(CH3)2 |
| XIII.45 | 2-SCH2CH2CH=CF2 | 5-CONH2 |
| XIII.46 | 2-SCH2CH2CH=CF2 | 5-CONHCH2C6H5 |
| XIII.47 | 2-SCH2CH2CH=CF2 | 5-CONHCH2CH2CH=CF2 |
| XIII.48 | 2-SOCH2CH2CH=CF2 | 5-CONHCH2CH2CH=CF2 |
| XIII.49 | 2-SO2CH2CH2CH=CF2 | 5-CONHCH2CH2CH=CF2 |
| XIII.50 | 2-SCH2CH2CH=CF2 | 5-CONHCH3 |
| XIII.51 | 2-SCH2CH2CH=CF2 | 5-CONHSO2CH3 |
| XIII.52 | 2-SO2CH2CH2CH=CF2 | 5-CONHSO2CH3 |
| XIII.53 | 2-SCH2CH2CH=CF2 | 5-COOC6H5 |
| XIII.54 | 2-SOCH2CH2CH=CF2 | 5-COOC6H5 |
| XIII.55 | 2-SCH2CH2CH=CF2 | 5-COOCH2CH2CH=CF2 |
| XIII.56 | 2-SOCH2CH2CH=CF2 | 5-COOCH2CH2CH=CF2 |
| XIII.57 | 2-SO2CH2CH2CH=CF2 | 5-COOCH2CH2CH=CF2 |
| XIII.58 | 2-SCH2CH2CH=CF2 | 5-COOCH2CH2F |
| XIII.59 | 2-SCH2CH2CH=CF2 | 5-COOCH3 |
| XIII.60 | 2-SCH2CH2CH=CF2 | 5-COOH |
| XIII.61 | 2-SCH2CH2CH=CF2 | 5-COSCH2CH2CH=CF2 |
| XIII.62 | 2-SCH2CH2CH=CF2 | 5-CSNH2 |
| XIII.63 | 2-SCH2CH2CH=CF2 | 5-H |
| XIII.64 | 2-SOCH2CH2CH=CF2 | 5-H |
| XIII.65 | 2-SO2CH2CH2CH=CF2 | 5-H |
| XIII.66 | 2-SCH2CH2CH=CF2 | 5-N(CH3)2 |
| XIII.67 | 2-SCH2CH2CH=CF2 | 5-N(SO2CH3)2 |
| XIII.68 | 2-SO2CH2CH2CH=CF2 | 5-N(SO2CH3)2 |
| XIII.69 | 2-SCH2CH2CH=CF2 | 5-NH2 |
| XIII.70 | 2-SCH2CH2CH=CF2 | 5-NHCH3 |
| XIII.71 | 2-SOCH2CH2CH=CF2 | 5-NHCH3 |
| XIII.72 | 2-SO2CH2CH2CH=CF2 | 5-NHCH3 |
| XIII.73 | 2-SCH2CH2CH=CF2 | 5-NHCHO |
| XIII.74 | 2-SOCH2CH2CH=CF2 | 5-NHCHO |
| XIII.75 | 2-SCH2CH2CH=CF2 | 5-NHCOCF3 |
| XIII.76 | 2-SO2CH2CH2CH=CF2 | 5-NHCOCF3 |
| XIII.77 | 2-SCH2CH2CH=CF2 | 5-NHCOCH3 |
| XIII.78 | 2-SCH2CH2CH=CF2 | 5-NHCOOCH3 |
| XIII.79 | 2-SOCH2CH2CH=CF2 | 5-NHCOOCH3 |
| XIII.80 | 2-SCH2CH2CH=CF2 | 5-NHCSCH2CH3 |
| XIII.81 | 2-SCH2CH2CH=CF2 | 5-NHCSNHCH2CH3 |
| XIII.82 | 2-SCH2CH2CH=CF2 | 5-NHSO2CH3 |
| XIII.83 | 2-SO2CH2CH2CH=CF2 | 5-NHSO2CH3 |
| XIII.84 | 2-SCH2CH2CH=CF2 | 5-OC6H5 |
| XIII.85 | 2-SOCH2CH2CH=CF2 | 5-OC6H5 |
| XIII.86 | 2-SO2CH2CH2CH=CF2 | 5-OC6H5 |
| XIII.87 | 2-SCH2CH2CH=CF2 | 5-OCF2CF2H |
| XIII.88 | 2-SCH2CH2CH=CF2 | 5-OCF3 |
| XIII.89 | 2-SOCH2CH2CH=CF2 | 5-OCF3 |
| XIII.90 | 2-SO2CH2CH2CH=CF2 | 5-OCF3 |
| XIII.91 | 2-SCH2CH2CH=CF2 | 5-OCH2C6H5 |
| XIII.92 | 2-SCH2CH2CH=CF2 | 5-OCH2CF3 |
| XIII.93 | 2-SOCH2CH2CH=CF2 | 5-OCH2CF3 |
| XIII.94 | 2-SO2CH2CH2CH=CF2 | 5-OCH2CF3 |
| XIII.95 | 2-SCH2CH2CH=CF2 | 5-OCH2CH=CCl2 |
| XIII.96 | 2-SCH2CH2CH=CF2 | 5-OCH2CH2CH=CF2 |
| XIII.97 | 2-SOCH2CH2CH=CF2 | 5-OCH2CH2CH=CF2 |
| XIII.98 | 2-SO2CH2CH2CH=CF2 | 5-OCH2CH2CH=CF2 |
| XIII.99 | 2-SCH2CH2CH=CF2 | 5-OCH2CH2F |
| XIII.100 | 2-SCH2CH2CH=CF2 | 5-OCH2COOCH3 |
| XIII.101 | 2-SCH2CH2CH=CF2 | 5-OCH3 |
| XIII.102 | 2-SOCH2CH2CH=CF2 | 5-OCH3 |
| XIII.103 | 2-SO2CH2CH2CH=CF2 | 5-OCH3 |
| XIII.104 | 2-SCH2CH2CH=CF2 | 5-OCOC6H5 |
| XIII.105 | 2-SCH2CH2CH=CF2 | 5-OCOCH3 |
| XIII.106 | 2-SCH2CH2CH=CF2 | 5-OSO2CH3 |
| XIII.107 | 2-SOCH2CH2CH=CF2 | 5-OSO2CH3 |
| XIII.108 | 2-SO2CH2CH2CH=CF2 | 5-OSO2CH3 |
| XIII.109 | 2-SCH2CH2CH=CF2 | 5-SCF3 |
| XIII.110 | 2-SCH2CH2CH=CF2 | 5-SCH2(3-CF3C6H4) |
| XIII.111 | 2-SOCH2CH2CH=CF2 | 5-SCH2(3-CF3C6H4) |
| XIII.112 | 2-SO2CH2CH2CH=CF2 | 5-SCH2(3-CF3C6H4) |
| XIII.113 | 2-SCH2CH2CH=CF2 | 5-SCH2(4-CF3-C6H4) |
| XIII.114 | 2-SCH2CH2CH=CF2 | 5-SCH2(c-C3H5) |
| XIII.115 | 2-SCH2CH2CH=CF2 | 5-SCH2C≡CH |
| XIII.116 | 2-SCH2CH2CH=CF2 | 5-SCH2CH=CH2 |
| XIII.117 | 2-SCH2CH2CH=CF2 | 5-SCH2CH2CH=CF2 |
| XIII.118 | 2-SOCH2CH2CH=CF2 | 5-SCH2CH2CH=CF2 |
| XIII.119 | 2-SCH2CH2CH=CF2 | 5-SCH3 |

TABLE XIII-continued

| No. | R2 | R5 |
|---|---|---|
| XIII.120 | 2-SOCH2CH2CH=CF2 | 5-SCH3 |
| XIII.121 | 2-SO2CH2CH2CH=CF2 | 5-SCH3 |
| XIII.122 | 2-SCH2CH2CH=CF2 | 5-SH |
| XIII.123 | 2-SCH2CH2CH=CF2 | 5-SO2CH2CH2CH=CF2 |
| XIII.124 | 2-SO2CH2CH2CH=CF2 | 5-SO2CH2CH2CH=CF2 |
| XIII.125 | 2-SCH2CH2CH=CF2 | 5-SO2CH3 |
| XIII.126 | 2-SO2CH2CH2CH=CF2 | 5-SO2CH3 |
| XIII.127 | 2-SCH2CH2CH=CF2 | 5-SO2N(CH3)2 |
| XIII.128 | 2-SCH2CH2CH=CF2 | 5-SO2NH2 |
| XIII.129 | 2-SCH2CH2CH=CF2 | 5-SO2NHCH3 |
| XIII.130 | 2-SCH2CH2CH=CF2 | 5-SOCF3 |
| XIII.131 | 2-SCH2CH2CH=CF2 | 5-SOCF3 |
| XIII.132 | 2-SCH2CH2CH=CF2 | 5-SOCH2CH2CH=CF2 |
| XIII.133 | 2-SOCH2CH2CH=CF2 | 5-SOCH2CH2CH=CF2 |
| XIII.134 | 2-SO2CH2CH2CH=CF2 | 5-SOCH2CH2CH=CF2 |
| XIII.135 | 2-SCH2CH2CH=CF2 | 5-SOCH3 |
| XIII.136 | 2-SCH2CH2CH=CF2 | 5-(4-CF3—C6H4) |
| XIII.137 | 2-SO2CH2CH2CH=CF2 | 5-(4-CF3—C6H4) |
| XIII.138 | 2-SCH2CH2CH=CF2 | 5-(4-CH3—C6H4) |
| XIII.139 | 2-SO2CH2CH2CH=CF2 | 5-(4-CH3—C6H4) |
| XIII.140 | 2-SCH2CH2CH=CF2 | 5-(4-CN—C6H4) |
| XIII.141 | 2-SOCH2CH2CH=CF2 | 5-(4-CN—C6H4) |
| XIII.142 | 2-SCH2CH2CH=CF2 | 5-(4-CONH2—C6H4) |
| XIII.143 | 2-SCH2CH2CH=CF2 | 5-(4-H2NSO2—C6H4) |
| XIII.144 | 2-SCH2CH2CH=CF2 | 5-(4-NO2—C6H4) |
| XIII.145 | 2-SCH2CH2CH=CF2 | 5-(4-OCH3—C6H4) |
| XIII.146 | 2-SOCH2CH2CH=CF2 | 5-(4-OCH3—C6H4) |
| XIII.147 | 2-SO2CH2CH2CH=CF2 | 5-(4-OCH3—C6H4) |

Examples of compounds of Formula (XIV) according to the invention are set out in Table XIV.

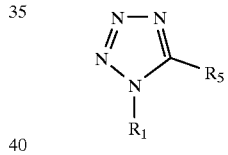

TABLE XIV

| No. | R1 | R5 |
|---|---|---|
| XIV.1 | 1-CH3 | 5-SCH2CH2CH=CF2 |

Examples of compounds of Formula (XV) according to the invention are set out in Table XV.

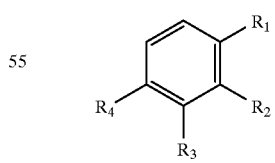

TABLE XV

| No. | R1 | R2 | R3 | R4 |
|---|---|---|---|---|
| XV.1 | 1-SCH2CH2CH=CF2 | 2-H | 3-H | 4-NO2 |

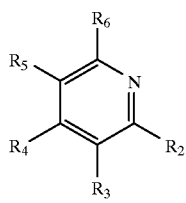

Examples of compounds of Formula (XVIII) according to the invention are set out in Table XVIII.

TABLE XVI

| No. | R2 | R3 | R4 | R5 | R6 |
|---|---|---|---|---|---|
| XVI.1 | 2-Cl | 3-H | 4-SCH2CH2CH=CF2 | 5-H | 6-H |
| XVI.2 | 2-F | 3-F | 4-SCH2CH2CH=CF2 | 5-F | 6-F |
| XVI.3 | 2-F | 3-F | 4-SOCH2CH2CH=CF2 | 5-F | 6-F |
| XVI.4 | 2-F | 3-F | 4-SO2CH2CH2CH=CF2 | 5-F | 6-F |
| XVI.5 | 2-H | 3-H | 4-SCH2CH2CH=CF2 | 5-H | 6-H |
| XVI.6 | 2-H | 3-H | 4-SO2CH2CH2CH=CF2 | 5-H | 6-H |
| XVI.7 | 2-SCH2CH2CH=CF2 | 3-CF3 | 4-H | 5-H | 6-H |
| XVI.8 | 2-SCH2CH2CH=CF2 | 3-CN | 4-H | 5-H | 6-H |
| XVI.9 | 2-SCH2CH2CH=CF2 | 3-CONH2 | 4-H | 5-H | 6-H |
| XVI.10 | 2-SCH2CH2CH=CF2 | 3-COOCH2CH2CH=CF2 | 4-H | 5-H | 6-H |
| XVI.11 | 2-SCH2CH2CH=CF2 | 3-H | 4-H | 5-CF3 | 6-H |
| XVI.12 | 2-SO2CH2CH2CH=CF2 | 3-H | 4-H | 5-CF3 | 6-H |
| XVI.13 | 2-SCH2CH2CH=CF2 | 3-H | 4-H | 5-Cl | 6-H |
| XVI.14 | 2-SO2CH2CH2CH=CF2 | 3-H | 4-H | 5-Cl | 6-H |
| XVI.15 | 2-SCH2CH2CH=CF2 | 3-H | 4-H | 5-CN | 6-H |
| XVI.16 | 2-SO2CH2CH2CH=CF2 | 3-H | 4-H | 5-CN | 6-H |
| XVI.17 | 2-SCH2CH2CH=CF2 | 3-H | 4-H | 5-CONH2 | 6-H |
| XVI.18 | 2-SCH2CH2CH=CF2 | 3-H | 4-H | 5-COOH | 6-H |
| XVI.19 | 2-SCH2CH2CH=CF2 | 3-H | 4-H | 5-H | 6-H |
| XVI.20 | 2-SO2CH2CH2CH=CF2 | 3-H | 4-H | 5-H | 6-H |
| XVI.21 | 2-SCH2CH2CH=CF2 | 3-H | 4-H | 5-NO2 | 6-H |
| XVI.22 | 2-SCH2CH2CH=CF2 | 3-H | 4-H | 5-SCH2CH2CH=CF2 | 6-H |
| XVI.23 | 2-SCH2CH2CH=CF2 | 3-H | 4-H | 5-H | 6-F |
| XVI.24 | 2-SCH2CH2CH=CF2 | 3-NO2 | 4-H | 5-H | 6-H |

Examples of compounds of Formula (XVII) according to the invention are set out in Table XVII.

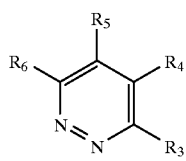

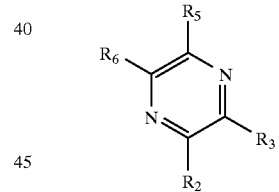

TABLE XVII

| No. | R3 | R4 | R5 | R6 |
|---|---|---|---|---|
| XVII.1 | 3-SCH2CH2CH=CF2 | 4-H | 5-H | 6-CH3 |
| XVII.2 | 3-SCH2CH2CH=CF2 | 4-H | 5-H | 6-Cl |
| XVII.3 | 3-SCH2CH2CH=CF2 | 4-H | 5-H | 6-OCH3 |
| XVII.4 | 3-SCH2CH2CH=CF2 | 4-H | 5-H | 6-C6H5 |
| XVII.5 | 3-SOCH2CH2CH=CF2 | 4-H | 5-H | 6-C6H5 |
| XVII.6 | 3-SO2CH2CH2CH=CF2 | 4-H | 5-H | 6-C6H5 |
| XVII.7 | 3-SCH2CH2CH=CF2 | —CH=CH—CH=CH— | | 6-H |

TABLE XVIII

| No. | R2 | R3 | R5 | R6 |
|---|---|---|---|---|
| XVIII.1 | 2-SCH2CH2CH=CF2 | 3-H | —CH=H—CH=CH— | |
| XVIII.2 | 2-SOCH2CH2CH=CF2 | 3-H | —CH=H—CH=CH— | |
| XVIII.3 | 2-SO2CH2CH2CH=CF2 | 3-H | —CH=H—CH=CH— | |
| XVIII.4 | 2-SCH2CH2CH=CF2 | 3-H | —CH=C(Cl)CH=CH— | |
| XVIII.5 | 2-SOCH2CH2CH=CF2 | 3-H | —CH=C(Cl)CH=CH— | |
| XVIII.6 | 2-SO2CH2CH2CH=CF2 | 3-H | —CH=C(Cl)CH=CH— | |
| XVIII.7 | 2-SCH2CH2CH=CF2 | 3-H | 5-H | 6-H |
| XVIII.8 | 2-SOCH2CH2CH=CF2 | 3-H | 5-H | 6-H |
| XVIII.9 | 2-SO2CH2CH2CH=CF2 | 3-H | 5-H | 6-H |
| XVIII.10 | 2-SCH2CH2CH=CF2 | 3-Cl | 5-H | 6-H |
| XVIII.11 | 2-SOCH2CH2CH=CF2 | 3-Cl | 5-H | 6-H |
| XVIII.12 | 2-SO2CH2CH2CH=CF2 | 3-Cl | 5-H | 6-H |
| XVIII.13 | 2-SCH2CH2CH=CF2 | 3-SCH2CH2CH=CF2 | 5-H | 6-H |
| XVIII.14 | 2-SCH2CH2CH=CF2 | 3-H | 5-H | 6-Cl |
| XVIII.15 | 2-SOCH2CH2CH=CF2 | 3-H | 5-H | 6-Cl |
| XVIII.16 | 2-SO2CH2CH2CH=CF2 | 3-H | 5-H | 6-Cl |

Examples of compounds of Formula (XIX) according to the invention are set out in Table XIX.

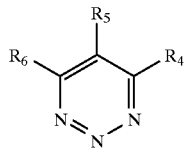

TABLE XIX

| No. | R4 | R5 | R6 |
|---|---|---|---|
| XIX.1 | 4-SCH2CH2CH=CF2 | —CH=CH—CH=CH— | |

Examples of compounds of Formula (XX) according to the invention are set out in Table XX.

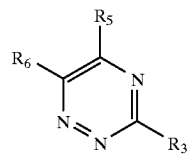

TABLE XX

| No. | R3 | R5 | R6 |
|---|---|---|---|
| XX.1 | 3-SCH2CH2CH=CF2 | 5-Br | 6-H |
| XX.2 | 3-SCH2CH2CH=CF2 | 5-c-C3H5 | 6-H |
| XX.3 | 3-SOCH2CH2CH=CF2 | 5-c-C3H5 | 6-H |
| XX.4 | 3-SCH2CH2CH=CF2 | 5-C6H5 | 6-CH3 |
| XX.5 | 3-SOCH2CH2CH=CF2 | 5-C6H5 | 6-CH3 |
| XX.6 | 3-SO2CH2CH2CH=CF2 | 5-C6H5 | 6-CH3 |
| XX.7 | 3-SOCH2CH2CH=CF2 | 5-C6H5 | 6-CN |
| XX.8 | 3-SCH2CH2CH=CF2 | 5-C6H5 | 6-H |
| XX.9 | 3-SO2CH2CH2CH=CF2 | 5-C6H5 | 6-H |
| XX.10 | 3-SCH2CH2CH=CF2 | 5-(4-F—C6H4) | 6-H |
| XX.11 | 3-SOCH2CH2CH=CF2 | 5-(4-F—C6H4) | 6-H |
| XX.12 | 3-SCH2CH2CH=CF2 | 5-CF2H | 6-CH3 |
| XX.13 | 3-SCH2CH2CH=CF2 | 5-CF3 | 6-H |
| XX.14 | 3-SOCH2CH2CH=CF2 | 5-CF3 | 6-OC6H5 |
| XX.15 | 3-SCH2CH2CH=CF2 | 5-CH(CH3)2 | 6-H |
| XX.16 | 3-SCH2CH2CH=CF2 | 5-CH=CH2 | 6-H |
| XX.17 | 3-SCH2CH2CH=CF2 | 5-CH=CHCN | 6-H |
| XX.18 | 3-SCH2CH2CH=CF2 | 5-CH=CHNO2 | 6-H |
| XX.19 | 3-SCH2CH2CH=CF2 | 5-CH=NOCH3 | 6-CH3 |
| XX.20 | 3-SCH2CH2CH=CF2 | 5-CH2C≡CH | 6-H |
| XX.21 | 3-SCH2CH2CH=CF2 | 5-CH2C6H5 | 6-H |
| XX.22 | 3-SOCH2CH2CH=CF2 | 5-CH2C6H5 | 6-H |
| XX.23 | 3-SCH2CH2CH=CF2 | 5-CH2CF3 | 6-H |
| XX.24 | 3-SCH2CH2CH=CF2 | 5-CH2CH=CH2 | 6-H |
| XX.25 | 3-SCH2CH2CH=CF2 | 5-CH2CH2CH2CH3 | 6-H |
| XX.26 | 3-SO2CH2CH2CH=CF2 | 5-CH2CH2CH2CH3 | 6-H |
| XX.27 | 3-SCH2CH2CH=CF2 | 5-CH2CH2CH3 | 6-H |
| XX.28 | 3-SO2CH2CH2CH=CF2 | 5-CH2CH2CH3 | 6-H |
| XX.29 | 3-SCH2CH2CH=CF2 | 5-CH2CH2F | 6-H |
| XX.30 | 3-SCH2CH2CH=CF2 | 5-CH2CH3 | 6-H |

TABLE XX-continued

| No. | R3 | R5 | R6 |
|---|---|---|---|
| XX.31 | 3-SCH2CH2CH=CF2 | 5-CH2CN | 6-CH3 |
| XX.32 | 3-SCH2CH2CH=CF2 | 5-CH2CONH2 | 6-H |
| XX.33 | 3-SCH2CH2CH=CF2 | 5-CH2N(CH3)2 | 6-CH3 |
| XX.34 | 3-SCH2CH2CH=CF2 | 5-CH2NHCOCH3 | 6-H |
| XX.35 | 3-SCH2CH2CH=CF2 | 5-CH2OCH2CH3 | 6-H |
| XX.36 | 3-SOCH2CH2CH=CF2 | 5-CH2OCH2CH3 | 6-H |
| XX.37 | 3-SCH2CH2CH=CF2 | 5-CH2OCH3 | 6-CH3 |
| XX.38 | 3-SCH2CH2CH=CF2 | 5-CH2OH | 6-H |
| XX.39 | 3-SCH2CH2CH=CF2 | 5-CH2SO2C6H5 | 6-H |
| XX.40 | 3-SCH2CH2CH=CF2 | 5-CH3 | 6-CF2H |
| XX.41 | 3-SCH2CH2CH=CF2 | 5-CH3 | 6-CH=CH2 |
| XX.42 | 3-SCH2CH2CH=CF2 | 5-CH3 | 6-CH2CH2F |
| XX.43 | 3-SCH2CH2CH=CF2 | 5-CH3 | 6-CH2CN |
| XX.44 | 3-SCH2CH2CH=CF2 | 5-CH3 | 6-CH2N(CH3)2 |
| XX.45 | 3-SCH2CH2CH=CF2 | 5-CH3 | 6-CH2OH |
| XX.46 | 3-SCH2CH2CH=CF2 | 5-CH3 | 6-CH3 |
| XX.47 | 3-SCH2CH2CH=CF2 | 5-CH3 | 6-CONH2 |
| XX.48 | 3-SCH2CH2CH=CF2 | 5-CH3 | 6-CONHCH3 |
| XX.49 | 3-SCH2CH2CH=CF2 | 5-CH3 | 6-CONHSO2CH3 |
| XX.50 | 3-SCH2CH2CH=CF2 | 5-CH3 | 6-COOCH2CH3 |
| XX.51 | 3-SCH2CH2CH=CF2 | 5-CH3 | 6-COOCH3 |
| XX.52 | 3-SCH2CH2CH=CF2 | 5-CH3 | 6-H |
| XX.53 | 3-SOCH2CH2CH=CF2 | 5-CH3 | 6-H |
| XX.54 | 3-SO2CH2CH2CH=CF2 | 5-CH3 | 6-H |
| XX.55 | 3-SCH2CH2CH=CF2 | 5-CH3 | 6-NHCHO |
| XX.56 | 3-SCH2CH2CH=CF2 | 5-CH3 | 6-NHCOCH3 |
| XX.57 | 3-SCH2CH2CH=CF2 | 5-CH3 | 6-NHCONH2 |
| XX.58 | 3-SCH2CH2CH=CF2 | 5-CH3 | 6-OCF2H |
| XX.59 | 3-SCH2CH2CH=CF2 | 5-CH3 | 6-OCH2CF3 |
| XX.60 | 3-SCH2CH2CH=CF2 | 5-CH3 | 6-OCH2CH2F |
| XX.61 | 3-SCH2CH2CH=CF2 | 5-CH3 | 6-OCOCH3 |
| XX.62 | 3-SCH2CH2CH=CF2 | 5-CH3 | 6-OSO2CH3 |
| XX.63 | 3-SCH2CH2CH=CF2 | 5-CH3 | 6-SO2NH2 |
| XX.64 | 3-SCH2CH2CH=CF2 | 5-CH3 | 6-SOCH3 |
| XX.65 | 3-SCH2CH2CH=CF2 | 5-CHCl2 | 6-H |
| XX.66 | 3-SCH2CH2CH=CF2 | 5-CHO | 6-CH3 |
| XX.67 | 3-SCH2CH2CH=CF2 | 5-Cl | 6-H |
| XX.68 | 3-SO2CH2CH2CH=CF2 | 5-Cl | 6-H |
| XX.69 | 3-SCH2CH2CH=CF2 | 5-CN | 6-H |
| XX.70 | 3-SOCH2CH2CH=CF2 | 5-CN | 6-H |
| XX.71 | 3-SCH2CH2CH=CF2 | 5-COCH3 | 6-H |
| XX.72 | 3-SCH2CH2CH=CF2 | 5-CON(CH3)2 | 6-H |
| XX.73 | 3-SCH2CH2CH=CF2 | 5-CONH2 | 6-H |
| XX.74 | 3-SCH2CH2CH=CF2 | 5-CONHCH2C6H5 | 6-H |
| XX.75 | 3-SOCH2CH2CH=CF2 | 5-CONHCH2CH2CH=CF2 | 6-H |
| XX.76 | 3-SCH2CH2CH=CF2 | 5-CONHCH3 | 6-H |
| XX.77 | 3-SCH2CH2CH=CF2 | 5-CONHSO2CH3 | 6-CH3 |
| XX.78 | 3-SO2CH2CH2CH=CF2 | 5-COOCH2CH2CH=CF2 | 6-H |
| XX.79 | 3-SCH2CH2CH=CF2 | 5-COOCH2F | 6-H |
| XX.80 | 3-SCH2CH2CH=CF2 | 5-COOCH2CH3 | 6-H |
| XX.81 | 3-SCH2CH2CH=CF2 | 5-COOCH3 | 6-CH3 |
| XX.82 | 3-SOCH2CH2CH=CF2 | 5-CCCCH3 | 6-H |
| XX.83 | 3-SCH2CH2CH=CF2 | 5-COOH | 6-H |
| XX.84 | 3-SOCH2CH2CH=CF2 | 5-COOH | 6-H |
| XX.85 | 3-SCH2CH2CH=CF2 | 5-F | 6-H |
| XX.86 | 3-SCH2CH2CH=CF2 | 5-H | 6-(1-CH3-cC3H4) |
| XX.87 | 3-SCH2CH2CH=CF2 | 5-H | 6-(4-F—C6H4) |
| XX.88 | 3-SO2CH2CH2CH=CF2 | 5-H | 6-(4-F—C6H4) |
| XX.89 | 3-SCH2CH2CH=CF2 | 5-H | 6-Br |
| XX.90 | 3-SCH2CH2CH=CF2 | 5-H | 6-C(CH3)3 |
| XX.91 | 3-SCH2CH2CH=CF2 | 5-H | 6-c-C3H5 |
| XX.92 | 3-SCH2CH2CH=CF2 | 5-H | 6-c-C5H9 |
| XX.93 | 3-SCH2CH2CH=CF2 | 5-H | 6-C≡CH |
| XX.94 | 3-SCH2CH2CH=CF2 | 5-H | 6-C6H5 |
| XX.95 | 3-SOCH2CH2CH=CF2 | 5-H | 6-C6H5 |
| XX.96 | 3-SCH2CH2CH=CF2 | 5-H | 6-CF3 |
| XX.97 | 3-SO2CH2CH2CH=CF2 | 5-H | 6-CF3 |
| XX.98 | 3-SCH2CH2CH=CF2 | 5-H | 6-CH(CH3)2 |
| XX.99 | 3-SCH2CH2CH=CF2 | 5-H | 6-CH=CHCN |
| XX.100 | 3-SCH2CH2CH=CF2 | 5-H | 6-CH=CHNO2 |
| XX.101 | 3-SCH2CH2CH=CF2 | 5-H | 6-CH=NOCH3 |
| XX.102 | 3-SOCH2CH2CH=CF2 | 5-H | 6-CH2(4-CF3—C6H4) |
| XX.103 | 3-SCH2CH2CH=CF2 | 5-H | 6-CH2C≡CH |
| XX.104 | 3-SCH2CH2CH=CF2 | 5-H | 6-CH2C6H5 |
| XX.105 | 3-SOCH2CH2CH=CF2 | 5-H | 6-CH2C6H5 |
| XX.106 | 3-SCH2CH2CH=CF2 | 5-H | 6-CH2CF3 |
| XX.107 | 3-SCH2CH2CH=CF2 | 5-H | 6-CH2CH=CH2 |

TABLE XX-continued

| No. | R3 | R5 | R6 |
|---|---|---|---|
| XX.108 | 3-SCH2CH2CH=CF2 | 5-H | 6-CH2CH2CH2CH3 |
| XX.109 | 3-SCH2CH2CH=CF2 | 5-H | 6-CH2CH2CH3 |
| XX.110 | 3-SCH2CH2CH=CF2 | 5-H | 6-CH2CH3 |
| XX.111 | 3-SCH2CH2CH=CF2 | 5-H | 6-CH2CONH2 |
| XX.112 | 3-SCH2CH2CH=CF2 | 5-H | 6-CH2NHCOCH3 |
| XX.113 | 3-SCH2CH2CH=CF2 | 5-H | 6-CH2OCH2CH3 |
| XX.114 | 3-SCH2CH2CH=CF2 | 5-H | 6-CH2OCH3 |
| XX.115 | 3-SCH2CH2CH=CF2 | 5-H | 6-CH2SO2C6H5 |
| XX.116 | 3-SCH2CH2CH=CF2 | 5-H | 6-CH3 |
| XX.117 | 3-SOCH2CH2CH=CF2 | 5-H | 6-CH3 |
| XX.118 | 3-SO2CH2CH2CH=CF2 | 5-H | 6-CH3 |
| XX.119 | 3-SCH2CH2CH=CF2 | 5-H | 6-CHO |
| XX.120 | 3-SCH2CH2CH=CF2 | 5-H | 6-Cl |
| XX.121 | 3-SOCH2CH2CH=CF2 | 5-H | 6-Cl |
| XX.122 | 3-SCH2CH2CH=CF2 | 5-H | 6-CN |
| XX.123 | 3-SCH2CH2CH=CF2 | 5-H | 6-COCH3 |
| XX.124 | 3-SCH2CH2CH=CF2 | 5-H | 6-CON(CH3)2 |
| XX.125 | 3-SO2CH2CH2CH=CF2 | 5-H | 6-CON(CH3)C2H5 |
| XX.126 | 3-SCH2CH2CH=CF2 | 5-H | 6-CONHCH2C6H5 |
| XX.127 | 3-SCH2CH2CH=CF2 | 5-H | 6-CONHCH2CH2CH=CF2 |
| XX.128 | 3-SCH2CH2CH=CF2 | 5-H | 6-CONHCH2CH2CH3 |
| XX.129 | 3-SCH2CH2CH=CF2 | 5-H | 6-COOC6H5 |
| XX.130 | 3-SCH2CH2CH=CF2 | 5-H | 6-COOCH2CH2CH=CF2 |
| XX.131 | 3-SCH2CH2CH=CF2 | 5-H | 6-COOCH2CH2F |
| XX.132 | 3-SCH2CH2CH=CF2 | 5-H | 6-COOCH3 |
| XX.133 | 3-SOCH2CH2CH=CF2 | 5-H | 6-COOCH3 |
| XX.134 | 3-SCH2CH2CH=CF2 | 5-H | 6-COOH |
| XX.135 | 3-SO2CH2CH2CH=CF2 | 5-H | 6-COOH |
| XX.136 | 3-SCH2CH2CH=CF2 | 5-H | 6-F |
| XX.137 | 3-SCH2CH2CH=CF2 | 5-H | 6-H |
| XX.138 | 3-SCH2CH2CH=CF2 | 5-H | 6-NHCH2CH3 |
| XX.139 | 3-SOCH2CH2CH=CF2 | 5-H | 6-NHCH2CH3 |
| XX.140 | 3-SCH2CH2CH=CF2 | 5-H | 6-NHCOC2H5 |
| XX.141 | 3-SCH2CH2CH=CF2 | 5-H | 6-NHCOC6H5 |
| XX.142 | 3-SCH2CH2CH=CF2 | 5-H | 6-NHCOCF3 |
| XX.143 | 3-SCH2CH2CH=CF2 | 5-H | 6-NHCOCH3 |
| XX.144 | 3-SCH2CH2CH=CF2 | 5-H | 6-NHCOOCH3 |
| XX.145 | 3-SCH2CH2CH=CF2 | 5-H | 6-NHCSCH2CH3 |
| XX.146 | 3-SCH2CH2CH=CF2 | 5-H | 6-NHCSNHCH2CH3 |
| XX.147 | 3-SCH2CH2CH=CF2 | 5-H | 6-NHSO2CH3 |
| XX.148 | 3-SCH2CH2CH=CF2 | 5-H | 6-NO2 |
| XX.149 | 3-SCH2CH2CH=CF2 | 5-H | 6-OC4H9 |
| XX.150 | 3-SOCH2CH2CH=CF2 | 5-H | 6-OC5H11 |
| XX.151 | 3-SCH2CH2CH=CF2 | 5-H | 6-OC6H5 |
| XX.152 | 3-SOCH2CH2CH=CF2 | 5-H | 6-OC6H5 |
| XX.153 | 3-SCH2CH2CH=CF2 | 5-H | 6-OCF2CF2H |
| XX.154 | 3-SCH2CH2CH=CF2 | 5-H | 6-OCF3 |
| XX.155 | 3-SOCH2CH2CH=CF2 | 5-H | 6-OCF3 |
| XX.156 | 3-SO2CH2CH2CH=CF2 | 5-H | 6-OCH(CH3)C2H5 |
| XX.157 | 3-SCH2CH2CH=CF2 | 5-H | 6-OCH2(4-Cl—C6H4) |
| XX.158 | 3-SO2CH2CH2CH=CF2 | 5-H | 6-OCH2(4-Cl—C6H4) |
| XX.159 | 3-SCH2CH2CH=CF2 | 5-H | 6-OCH2C6H5 |
| XX.160 | 3-SCH2CH2CH=CF2 | 5-H | 6-OCH2CCl=CH2 |
| XX.161 | 3-SCH2CH2CH=CF2 | 5-H | 6-OCH2CH=CCl2 |
| XX.162 | 3-SCH2CH2CH=CF2 | 5-H | 6-OCH2CH=CH2 |
| XX.163 | 3-SO2CH2CH2CH=CF2 | 5-H | 6-OCH2CH=CH2 |
| XX.164 | 3-SCH2CH2CH=CF2 | 5-H | 6-OCH2CH2CH3 |
| XX.165 | 3-SCH2CH2CH=CF2 | 5-H | 6-OCH2CH2COOCH3 |
| XX.166 | 3-SOCH2CH2CH=CF2 | 5-H | 6-OCH2CH2COOCH3 |
| XX.167 | 3-SCH2CH2CH=CF2 | 5-H | 6-OCH2CH2CH=CF2 |
| XX.168 | 3-SCH2CH2CH=CF2 | 5-H | 6-OCH2CH3 |
| XX.169 | 3-SCH2CH2CH=CF2 | 5-H | 6-OCH2COOH |
| XX.170 | 3-SCH2CH2CH=CF2 | 5-H | 6-OCH3 |
| XX.171 | 3-SOCH2CH2CH=CF2 | 5-H | 6-OCH3 |
| XX.172 | 3-SCH2CH2CH=CF2 | 5-H | 6-OCOC2H5 |
| XX.173 | 3-SCH2CH2CH=CF2 | 5-H | 6-OCOC6H5 |
| XX.174 | 3-SCH2CH2CH=CF2 | 5-H | 6-OH |
| XX.175 | 3-SOCH2CH2CH=CF2 | 5-H | 6-OH |
| XX.176 | 3-SCH2CH2CH=CF2 | 5-H | 6-SCF3 |
| XX.177 | 3-SOCH2CH2CH=CF2 | 5-H | 6-SCF3 |
| XX.178 | 3-SCH2CH2CH=CF2 | 5-H | 6-SCH2CH3 |
| XX.179 | 3-SCH2CH2CH=CF2 | 5-H | 6-SCH2CH2CH=CF2 |
| XX.180 | 3-SCH2CH2CH=CF2 | 5-H | 6-SCH3 |
| XX.181 | 3-SOCH2CH2CH=CF2 | 5-H | 6-SCH3 |
| XX.182 | 3-SCH2CH2CH=CF2 | 5-H | 6-SO2NHCH3 |
| XX.183 | 3-SCH2CH2CH=CF2 | 5-H | 6-SOCF3 |
| XX.184 | 3-SCH2CH2CH=CF2 | 5-H | 6-SOCH2CH2CH=CF2 |

TABLE XX-continued

| No. | R3 | R5 | R6 |
|---|---|---|---|
| XX.185 | 3-SCH2CH2CH=CF2 | 5-NH2 | 6-CH3 |
| XX.186 | 3-SO2CH2CH2CH=CF2 | 5-NHCH2CH3 | 6-C6H5 |
| XX.187 | 3-SCH2CH2CH=CF2 | 5-NHCH2CH3 | 6-H |
| XX.188 | 3-SCH2CH2CH=CF2 | 5-NHCHO | 6-H |
| XX.189 | 3-SCH2CH2CH=CF2 | 5-NHCOCF3 | 6-CH3 |
| XX.190 | 3-SOCH2CH2CH=CF2 | 5-NHCOCH3 | 6-C6H5 |
| XX.191 | 3-SCH2CH2CH=CF2 | 5-NHCOCH3 | 6-H |
| XX.192 | 3-SCH2CH2CH=CF2 | 5-NHCONH2 | 6-CH3 |
| XX.193 | 3-SCH2CH2CH=CF2 | 5-NHCOOCH3 | 6-H |
| XX.194 | 3-SCH2CH2CH=CF2 | 5-NHSO2CH3 | 6-CH3 |
| XX.195 | 3-SCH2CH2CH=CF2 | 5-NMe2 | 6-H |
| XX.196 | 3-SOCH2CH2CH=CF2 | 5-NO2 | 6-C6H5 |
| XX.197 | 3-SCH2CH2CH=CF2 | 5-NO2 | 6-H |
| XX.198 | 3-SCH2CH2CH=CF2 | 5-OC6H5 | 6-H |
| XX.199 | 3-SOCH2CH2CH=CF2 | 5-OC6H5 | 6-H |
| XX.200 | 3-SOCH2CH2CH=CF2 | 5-OC6H5 | 6-NHCOCH3 |
| XX.201 | 3-SCH2CH2CH=CF2 | 5-OCF2CF2H | 6-CH3 |
| XX.202 | 3-SCH2CH2CH=CF2 | 5-OCF2H | 6-H |
| XX.203 | 3-SCH2CH2CH=CF2 | 5-OCF3 | 6-H |
| XX.204 | 3-SOCH2CH2CH=CF2 | 5-OCF3 | 6-H |
| XX.205 | 3-SCH2CH2CH=CF2 | 5-OCH(CH3)2 | 6-H |
| XX.206 | 3-SOCH2CH2CH=CF2 | 5-OCH(CH3)C2H5 | 6-H |
| XX.207 | 3-SCH2CH2CH=CF2 | 5-OCH2(4-Cl—C6H4) | 6-H |
| XX.208 | 3-SO2CH2CH2CH=CF2 | 5-OCH2(4-Cl—C6H4) | 6-H |
| XX.209 | 3-SCH2CH2CH=CF2 | 5-OCH2C6H5 | 6-H |
| XX.210 | 3-SCH2CH2CH=CF2 | 5-OCH2CCl=CH2 | 6-H |
| XX.211 | 3-SCH2CH2CH=CF2 | 5-OCH2CF3 | 6-H |
| XX.212 | 3-SCH2CH2CH=CF2 | 5-OCH2CH=CH2 | 6-H |
| XX.213 | 3-SO2CH2CH2CH=CF2 | 5-OCH2CH2COOCH3 | 6-CH3 |
| XX.214 | 3-SCH2CH2CH=CF2 | 5-OCH2CH2COOCH3 | 6-H |
| XX.215 | 3-SO2CH2CH2CH=CF2 | 5-OCH2CH2COOCH3 | 6-H |
| XX.216 | 3-SCH2CH2CH=CF2 | 5-OCH2CH2CH=CF2 | 6-H |
| XX.217 | 3-SCH2CH2CH=CF2 | 5-OCH2CH2F | 6-CH3 |
| XX.218 | 3-SCH2CH2CH=CF2 | 5-OCH2CH3 | 6-H |
| XX.219 | 3-SCH2CH2CH=CF2 | 5-OCH2COOCH3 | 6-H |
| XX.220 | 3-SCH2CH2CH=CF2 | 5-OCH2COOH | 6-H |
| XX.221 | 3-SCH2CH2CH=CF2 | 5-OCH3 | 6-H |
| XX.222 | 3-SCH2CH2CH=CF2 | 5-OCOC2H5 | 6-H |
| XX.223 | 3-SOCH2CH2CH=CF2 | 5-OCOC6H5 | 6-H |
| XX.224 | 3-SCH2CH2CH=CF2 | 5-OCOCH3 | 6-CH3 |
| XX.225 | 3-SOCH2CH2CH=CF2 | 5-OH | 6-C6H5 |
| XX.226 | 3-SCH2CH2CH=CF2 | 5-OH | 6-CH3 |
| XX.227 | 3-SCH2CH2CH=CF2 | 5-OH | 6-H |
| XX.228 | 3-SCH2CH2CH=CF2 | 5-OSO2CH3 | 6-H |
| XX.229 | 3-SCH2CH2CH=CF2 | 5-SCF3 | 6-H |
| XX.230 | 3-SOCH2CH2CH=CF2 | 5-SCF3 | 6-H |
| XX.231 | 3-SCH2CH2CH=CF2 | 5-SCH2CH2CH=CF2 | 6-H |
| XX.232 | 3-SCH2CH2CH=CF2 | 5-SCH2CH2CH3 | 6-H |
| XX.233 | 3-SCH2CH2CH=CF2 | 5-SCH2CH2CH=CF2 | 6-H |
| XX.234 | 3-SCH2CH2CH=CF2 | 5-SCH3 | 6-H |
| XX.235 | 3-SOCH2CH2CH=CF2 | 5-SCH3 | 6-H |
| XX.236 | 3-SCH2CH2CH=CF2 | 5-SO2NH2 | 6-CH3 |
| XX.237 | 3-SCH2CH2CH=CF2 | 5-SO2NHCH3 | 6-H |
| XX.238 | 3-SCH2CH2CH=CF2 | 5-SOCF3 | 6-H |
| XX.239 | 3-SCH2CH2CH=CF2 | 5-SOCH3 | 6-CH3 |
| XX.240 | 3-CH3 | 5-CH3 | 6-SCH2CH2CH=CF2 |
| XX.241 | 3-CH3 | 5-H | 6-SCH2CH2CH=CF2 |
| XX.242 | 3-CH3 | 5-OC4H9 | 6-SO2CH2CH2CH=CF2 |
| XX.243 | 3-CH3 | 5-SCH2CH2CH=CF2 | 6-CH3 |
| XX.244 | 3-CH3 | 5-SCH2CH2CH=CF2 | 6-H |
| XX.245 | 3-H | 5-CH3 | 6-SCH2CH2CH=CF2 |
| XX.246 | 3-H | 5-H | 6-SCH2CH2CH=CF2 |
| XX.247 | 3-H | 5-SCH2CH2CH=CF2 | 6-CH3 |
| XX.248 | 3-H | 5-SCH2CH2CH=CF2 | 6-H |
| XX.249 | 3-H | 5-SOCH2CH2CH=CF2 | 6-CH3 |
| XX.250 | 3-H | 5-SO2CH2CH2CH=CF2 | 6-CH3 |
| XX.251 | 3-SCH2CH2CH=CF2 | —(CH2CH2CH2CH2)— | |
| XX.252 | 3-SOCH2CH2CH=CF2 | —(CH2CH2CH2CH2)— | |
| XX.253 | 3-SO2CH2CH2CH=CF2 | —(CH2CH2CH2CH2)— | |

Examples of compounds of Formula (XXI) according to the invention are set out in Table XXI.

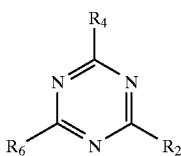

TABLE XXI

| No.   | R2            | R4  | R6  |
|-------|---------------|-----|-----|
| XXI.1 | 2-SCH2CH2CH=CF2 | 4-H | 6-H |

The compounds of formula (I) wherein n is 0 may be prepared by a variety of methods.

They may be prepared, for example, by the reaction of a corresponding thiol compound of formula (XXIII) and an appropriate difluorobut-1-ene alkylating agent of formula (XXIV), where L is a good leaving group. This reaction is preferably conducted in the presence of a mild base such as an alkali metal carbonate, for example sodium or potassium carbonate, in an inert solvent, at a temperature of from 0° C. to 200° C. Conveniently the reaction may be conducted at the reflux temperature of a suitable inert solvent, for example acetone, which has a boiling point within this range.

In formula (XXIV) the leaving group L is preferably a halogen or an ester of sulfonic acid having the formula OSO2Rb, as illustrated by formula (XXV), where Rb is a C1–4 alkyl group or a phenyl group optionally substituted with a C1–4 alkyl group. More preferably, L is bromine as shown in formula (XXVI).

The sulfonic ester of formula (XXV) may be prepared by reaction of 1,4-dibromo-1,1,2-trifluorobutane with the silver salt of the chosen sulfonic acid and debromofluorination of the resulting intermediate, 4-toluenesulfonate ester.

In copending International Patent Application No. PCT/GB94/01570, we disclose a method for preparing the compound of formula (XXVI), namely 4-bromo-1,1-difluorobut-1-ene, in which hydrogen bromide is reacted with commercially available 4-bromo-1,1,2-trifluorobut-1-ene in an inert solvent to give 1,4-dibromo-1,1,2-trifluorobutane. This intermediate can then be treated with a debromofluorinating agent in a suitable solvent, for example acetone or water, to give the compound of formula (XXVI).

It will be appreciated by those skilled in the art that compounds of the Formula (XXIII) may exist in tautomeric equilibrium between the equivalent mercapto and thione forms. For the sake of convenience, these compounds are referred to herein in their mercapto form unless otherwise stated.

Compounds of Formula (XXIII) are commercially available or may be prepared from commercially available precursors by standard procedures well known in the art.

Alternatively, the compounds of formula (I) may be prepared by reacting a corresponding compound of formula (XXVII), where L is again a good leaving group, with a mercapto compound of formula (XXVIII), under conditions well known in the art for such displacement reactions. Preferably, L is halogen or a nitro group. Conveniently the reaction may be carried out using a two phase solvent system, such as water/dichloromethane, in the presence of a phase transfer catalyst, for example tetra-n-butyl ammonium bromide, at ambient-temperature under a nitrogen atmosphere.

The mercapto compound of formula (XXVIII) is conveniently reacted in the form of its S-acetyl or its isothiouronium hydrogen bromide salt, which compounds are readily hydrolysed to the mercapto compound of formula (XXVIII).

The compounds of formula (I) may also be prepared from the corresponding amino compound of formula (XXIX), which can be diazotised, for example with an alkylnitrite, such as tert. butyl nitrite, in the presence of the disulfide of formula (XXX), in a suitable solvent, such as dichloromethane or acetonitrile.

The compounds of formula (I) where n is 1 or 2, may be prepared by oxidising the correspondingly substituted compound of formula (I) when n is 0, using conventional methods, for example by treatment with a suitable oxidising agent in an inert organic solvent. In general, oxidation of a compound of Formula (I) with one equivalent of a suitable oxidising agent provides the corresponding compound wherein n is 1, and oxidation using two equivalents of the oxidising agent provides the corresponding compound wherein n is 2. Suitable oxidising agents include organic and inorganic peroxides such as peroxy carboxylic acids, or their salts, for example, metal-chloroperbenzoic acid, perbenzoic acid, magnesium monoperoxy-phthalic acid or potassium peroxymono-sulfate.

Thus, according to a further aspect of the present invention there is provided a process for the preparation of compounds of formula (I) where n is 1 or 2, which comprises oxidation of the correspondingly substituted compound of formula (I) when n is 0.

As well as the compounds of formula (I) being prepared from the corresponding substituted compounds of formula (XXIII), (XXVII) or (XXIX), it will be appreciated that subsequent functional group transformations may be carried out using known chemistry to obtain the required ring substitution. Examples of such functional group transformations include the reduction of nitro groups to amine groups, halogenation, e.g. chlorination, hydrolysis of an ester to the acid, oxidation of an alcohol to the acid, salt formation.

Various further preferred features and embodiments of the present invention will now be described in further detail with reference to the following illustrative examples in which percentages are by weight and the following abbreviations are used: mp=melting point; bp=boiling point; g=grammes; gc=gas chromatography; NMR=nuclear magnetic resonance; s=singlet; d=doublet; dd=double doublet; t=triplet; q=quartet; m=multiplet; br=broad; M=mole; mM=millimoles; $CDCl_3$=deuteriochloroform. Chemical shifts ($\delta$) are measured in parts per million from tetramethylsilane. $CDCl_3$ was used as solvent for NMR spectra unless otherwise stated. $M^+$=molecular ion as determined by mass spectrometry; FAB=fast atom bombardment; tlc=thin layer chromatography.

The synthesis of a number of intermediate compounds of use in the preparation of compounds according to the invention is given below. Some of these compounds are known in the art.

PREPARATION 1

This illustrates a 3-step preparation of 4-bromo-4,4-difluorobutyl methanesulfonate.

Step 1: 4-bromo-4,4-difluorobutanoic Acid

To a stirred solution of acrylic acid (1.44 g) and acetonitrile (80 cm$^3$) was added sodium dithionite (4.18 g), sodium bicarbonate (2.01 g), water (20 cm$^3$) and finally dibromodifluoromethane (5 cm$^3$). The biphasic mixture was stirred at the ambient temperature with the inorganic salts gradually dissolving. GC analysis after 4 hours indicated complete consumption of acrylic acid. The aqueous phase was saturated with solid sodium chloride. The organic phase was separated, dried over magnesium sulfate, filtered and evaporated under reduced pressure to give a pale yellow oil with a small amount of a white solid. This mixture was taken up in ethyl acetate, filtered and solvent evaporated under reduced pressure to give a pale yellow oil (2.54 g). $^1$H NMR (DMSO-$d_6$): δ 2.45(2H,t); 2.65(H,m).

Step 2: 4-bromo-4,4-difluorobutanol

Under an atmosphere of nitrogen, a solution of lithium aluminium hydride in diethylether (5 cm$^3$, 5 mM) was cooled to 0° C. Maintaining this temperature, 4-bromo-4,4-difluorobutanoic acid (1 g) dissolved in dry diethylether (5 cm$^3$) was added dropwise with stirring. After an hour at 0° C. the reaction mixture was cautiously quenched by the addition of 2M hydrochloric acid. The organic phase was separated, washed with saturated sodium bicarbonate solution, dried over magnesium sulfate, filtered and evaporated under reduced pressure to give a colourless oil (0.57 g). $^1$H NMR: δ 1.82–1.96(2H,m); 2.40–2.60(2H,m); 3.74(2H,t).

Step 3: 4-bromo-4,4-difluorobutyl Methanesulfonate

A stirred solution of 4-bromo-4,4-difluorobutanol (0.57 g) in dry diethylether (5 cm$^3$) was cooled to 0° C. Maintaining this temperature, triethylamine (1.7 cm$^3$) was added. After ten minutes methanesulfonyl chloride (0.3 cm$^3$) was added and the mixture stirred for a further hour at 0° C. The reaction mixture was poured into 2M hydrochloric acid (2 cm$^3$) and diethylether (20 cm$^3$). The organic phase was separated, washed with saturated brine, then passed through a plug of silica gel eluting with further diethylether. The diethylether fractions were evaporated under reduced pressure to give a light yellow oil (0.705 g). $^1$H NMR: δ 2.04–2.18(2H,m); 2.46–2.64(2H,m); 3.04(3H,s); 4.32(2H,t).

PREPARATION 2

This illustrates a 3-step preparation of the 4,4-difluorobut-3-enyl ester of 4-methyl-benzenesulfonic acid from commercially available 4-bromo-1,1,2-trifluorobut-1-ene.

Step 1: Preparation of 1,4-dibromo-1,1,2-trifluorobutane

4-Bromo-1,1,2-trifluorobut-1-ene (Fluorochem Ltd.) (240 g) was washed with water (300 cm$^3$) and then with brine (30 cm$^3$) and dried (MgSO$_4$) before use. Benzoyl peroxide (ca. 0.7 g) was added in one portion and hydrogen bromide gas was bubbled through the mixture at such a rate that the reaction temperature was maintained at 30 to 40° C. After 2 hours, gc of a sample of the reaction mixture showed that little starting material remained. The reaction mixture was washed with water (300 cm$^3$), then with saturated sodium bicarbonate solution and then again with water (300 cm$^3$), dried (MgSO$_4$), and filtered to give a pale yellow oil (296.7 g) identified as 1,4-dibromo-1,1,2-trifluorobutane. The material was shown by gc analysis to be greater than 98% pure. $^1$H NMR: δ 2.38(2H,m); 2.57(2H,m); 4.90(1H,m).

Step 2: Preparation of 4-bromo-3,4,4-trifluorobutyl 4-methyl-benzenesulfonate

The product from Step 1 (1 g) was added dropwise to a stirred suspension of silver tosylate (1.03 g) in acetonitrile (10 cm$^3$) at ambient temperature, protected from the light. The reaction was then heated under reflux for 24 hours after which gc analysis indicated complete consumption of starting material. The reaction mixture was cooled to the ambient temperature and the precipitate was filtered off and washed with ethyl acetate. The filtrate and ethyl acetate washings were combined and washed with water and the aqueous layer extracted with ethyl acetate. The combined ethyl acetate layers were washed with water and brine, dried over magnesium sulfate and evaporated under reduced pressure to give a brown oil (1.21 g). GC analysis showed this material to be >99% pure. $^1$H NMR: δ 2.20(2H,m); 2.46(3H,s); 4.19(2H,m); 4.74(1H,m); 7.38(2H,d); 7.80(2H,d).

Step 3: Preparation of 4,4-difluorobut-3-enyl 4-methyl-benzenesulfonate

To a stirred suspension of powdered zinc (1.41 g) and iodine (one grain, catalytic) in methanol (3 cm$^3$) was added a solution of 4-bromo-3,4,4-difluorobutyl p-tolylsulfonate (0.71 g) in methanol (2 cm$^3$). The reaction mixture was heated under reflux for 2½ hours after which gc analysis indicated complete consumption of starting material. The organic phase was pipetted from the zinc suspension and the zinc was washed with 3 portions of ethyl acetate. The combined ethyl acetate portions were washed with 2M hydrochloric acid, dried over magnesium sulfate and evaporated under reduced pressure to give a brown liquid (0.47 g). GC analysis showed this material to be >99% pure. $^1$H NMR: δ 2.35(2H,m); 2.46(3H,s); 4.01(2H,m); 4.15(1H,m); 7.38(2H,d); 7.79(2H,d).

PREPARATION 3

This illustrates a preparation of 4-bromo-1,1-difluorobut-1-ene from 1,4-dibromo-1,1,2-trifluorobutane.

Zinc powder (0.88 g) was added to a stirred solution of 1,4-dibromo-1,1,2-trifluorobutane (1.38 g) in acetone (6 cm$^3$) containing water (1 drop), under an atmosphere of nitrogen. After 45 minutes, gc analysis showed that a large proportion of the starting material had been consumed. The mixture was then added to more zinc powder (3 g) in acetone containing a trace of water, which had been preheated to 55° C. After a further 20 minutes at this temperature, gc analysis indicated that all of the starting material had been consumed, showing that the de-bromofluorination reaction had initiated. More starting material (12.34 g) was then added to the reaction over a period of 75 minutes while the reaction mixture was kept at 55° C. Heating was then continued for a further 95 minutes. GC analysis of a sample indicated that about 3% of the starting dibromo compound remained unchanged. Further zinc powder (0.16 g) was added and heating continued until gc analysis showed all the starting material had been consumed. The acetone solution was decanted from zinc residues to give a solution of 4-bromo-1,1-difluorobut-1-ene suitable for use in further chemical reactions.

PREPARATION 4

This illustrates a preparation of 4,4-difluorobut-3-enyl thioactetate.

Potassium thioacetate (1.98 g), 4-bromo-1,1-difluorobut-1-ene (3.0 g) and tetra-n-butylammonium bromide (0.3 g, catalyst) were stirred at the ambient temperature under nitrogen for 5 hours and stored for 18 hours. The mixture was distilled using a Kugelrohr apparatus to give 4,4-difluorobut-3-enyl thioacetate as a colourless liquid (1.12 g); $^1$H NMR; δ 2.25(2H,m); 2.30(3H,s); 2.90(2H,t); 4.20(1H, m); (bp 115° C. at 120 mmHg).

PREPARATION 5

This illustrates a preparation of 4,4-difluorobut-3-enylisothiouronium 4-methyl-benzenesulfonate salt.

Thiourea (0.29 g) and 4,4-difluorobut-3-enyl 4-methyl-benzenesulfonate (1 g) were heated together under reflux in ethanol (20 cm$^3$) for 24 hours. The reaction mixture was cooled and the solvent evaporated under reduced pressure to give an oil which slowly crystallised. Trituration with hexane gave (4,4-difluorobut-3-enyl)-thiourea as its 4-methyl-benzenesulfonate salt (1.14 g). MH$^+$(FAB)=167; $^1$H NMR (DMSO-d$_6$): δ 2.48(3H,s); 2.46–2.58(2H,m); 3.42(2H,t); 4.66–4.84(1H,m); 7.32(2H,d); 7.68(2H,d); 9.10–9.40(3H, br).

PREPARATION 6

This illustrates a preparation of 4,4-difluorobut-3-enylisothiouronium hydrobromide.

Thiourea (18.5 g) was added to a solution of 4-bromo-1,1-difluorobut-1-ene (41.5 g) in ethanol (150 cm$^3$) and heated to reflux with stirring for 18 h. The reaction mixture was cooled to ambient temperature and evaporated under reduced pressure. The waxy solid obtained was washed with diethyl ether, filtered, washed with further diethyl ether and sucked to dryness to give the required product as a colourless solid, (57 g). MH$^+$=167; $^1$H NMR(DMSO-d$_6$): δ 2.20 (2H,m); 3.20(2H,t); 4.50(1H,m); 8.95(4H,broad signal).

The N-methyl derivative of the foregoing intermediate was prepared by the above procedure but using N-methyl thiourea in place of thiourea. It had MH$^+$=181; $^1$H NMR (DMSO-d$_6$): δ 2.45–2.55(2H,m); 3.0–3.05(3H,d); 3.4–3.5 (2H,t); 4.30–4.45(1H,m); (m.p. 74–77.2° C.).

PREPARATION 7

This illustrates a preparation of bis-(4,4-difluorobut-3-enyl)disulfide.

A solution of sodium disulfide (previously prepared from sodium sulfide nonahydrate (53 g) and sulfur (7.0 g) in ethanol (250 cm$^3$)) was added to 1-bromo-4,4-difluorobut-3-ene (50 g) in ethanol (100 cm$^3$). The mixture was gradually heated and stirred under reflux for 2 hours, then cooled and evaporated under reduced pressure. The residue was extracted with diethyl ether, the organic phase filtered to remove sodium bromide and the ether evaporated under reduced pressure to give a liquid which was distilled at 16 mm Hg, bp 120° C. to give the bis-(4,4-difluorobut-3-ethyl) disulfide (24 g) as a colourless liquid.

EXAMPLE II.1

This Example illustrates a preparation of 2-(4,4-difluorobut-3-enylthio)furan (Compound II.1).

Butyllithium (6.5 cm$^3$, 2.5M in ether) was added dropwise with stirring to a solution of furan (1 g) in diethyl ether (40 cm$^3$). After 90 minutes, the reaction mixture was heated to reflux for 30 minutes and then cooled to the ambient temperature. Powdered sulfur (0.48 g) was added portionwise with stirring. After 2 hours, 4-bromo-1,1-difluorobut-1-ene (3.0 g) was added and stirring continued at the ambient temperature for 18 hours. The reaction was quenched with water and the product extracted into diethyl ether. The combined organic extracts were dried, filtered and evaporated to give a dark brown liquid. Chromtography on silica (eluant hexane-diethyl ether mixtures) afforded Compound II.1 (0.965 g). $^1$H NMR: δ2.2–2.3 (2H,m); 2.7–2.8 (2H,t); 4.15–4.35 (1H,m); 6.4(1H,dd); 6.53(1H,d); 7.5(1H, d); (oil).

EXAMPLE II.2

This Example illustrates a reparation of 2-(4,4-difluorobut-3-enylthio)-5-methylfuran (Compound II.4).

Butyllithium (5.4 cm$^3$, 2.5M in ether) was added dropwise with stirring to a solution of furan (1 g) in diethyl ether (40 cm$^3$). After 90 minutes, the reaction mixture was heated under reflux for 30 minutes and then cooled to the ambient temperature. Powdered sulfur (0.38 g) was added portionwise with stirring. After 2 hours, 4-bromo-1,1-difluorobut-1-ene (2.05 g) was added and stirring continued for 18 hours. The reaction was quenched with water and the product extracted into diethyl ether. The combined organic extracts were dried, filtered and evaporated. Chromatography on silica (eluant hexane-ether mixture) afforded Compound II.4 (1.25 g). $^1$H NMR: δ2.2–2.3(2H,m); 2.3(3H,s); 2.7–2.77 (2H,t); 4.16–4.34 (1H, m); 5.97(1H,m); 6.43(1H,d); (oil).

EXAMPLE II.3

This Example illustrates a preparation of 3-(4,4-difluorobut-3-ethylthio)-2-methylfuran (Compound II.7).

A solution containing 2-methyl-3-furanthiol (2.0 g), 4-bromo-1,1-difluorobut-1-ene (3.24 g) and potassium carbonate (2.48 g) in acetone (50 cm$^3$) was heated under reflux for 2 hours and then left to stand for 18 hours. The reaction was quenched with water and the product extracted into diethyl ether. The combined organic extracts were dried, filtered and evaporated. Chromatography on silica (eluant 10% ether in hexane) afforded Compound II.7 (2.338 g); M$^+$=204; $^1$H NMR; δ2.1–2.25(2H,m); 2.35(3H,s); 2.65(2H, t); 4.1–4.35(1H,m); 6.3 (1H,d); 7.3(1H, d); (oil).

EXAMPLE II.4

This Examples illustrates a preparation of 2-(4,4-difluorobut-3-enylsulfinyl)furan (Compound II.2).

3-Chloroperbenzoic acid (0.54 g of a 50% of a 50% by weight solid. 1.58 mM) was added portionwise to a solution of Compound II.1 (0.30 g) in dichloromethane (5 cm$^3$) with ice-bath cooling. After stirring for 4 hours, the reaction was partitioned between ethyl acetate and 2M NaOH solution. The organic layer was separated, washed with more 2M NaOH solution, dried over magnesium sulfate, filtered and evaporated to give Compound II.2 (0.210 g). $^1$H NMR: δ2.3–2.5 (2H,m); 3.1–3.4(2H,m); 4.15–4.35(1H,m); 6.5(1H, dd); 7.0(1H,d); 7.7(1H,d); (oil).

The following compounds according to the invention were prepared by the above procedure:
(i) 2-(4,4-difluorobut-3-enylsulfonyl)furan (Compound II.3); $^1$H NMR; δ2.4–2.55(2H,m); 3.25–3.3(2H,t) 4.1–4.3 (1H,m); 6.6(1H,dd); 7.23 (1H,d); 7.67 (1H,d) (oil) from Compound II.1 using 2.1 equivalents of oxidant.
(ii) 2-(4,4-difluorobut-3-enylsulfinyl)-5-methylfuran (Compound II.5); $^1$H NMR: δ2.3–2.45 (5H,m); 3.0–3.15 and 3.3–3.4 (total 2H,m); 4.2–4.3 (1H,m); 6.1 (1H,d); 6.85(1H,d); (oil) from Compound II.4 using 1 equivalent of oxidant.
(iii) 2-(4,4-difluorobut-3-enylsulfonyl)-5-methylfuran (Compound II.6); $^1$H NMR; δ2.4–2.55 (5H,m); 3.2–3.28 (2H,t); 4.15–4.3(1H,m); 6.2(1H,d); 7.1(1H,d); (oil) from Compound II.4 using 2.1 equivalents of oxidant.
(iv) 3-(4,4-difluorobut-3-enylsulfinyl)-2-methylfuran (Compound II.8); $^1$H NMR; δ2.3–2.45 (5H,m); 2.8–2.9 and 3.1–3.2 (total 2H, m); 4.2–4.35 (1H,m); 6.66(1H,d); 7.4(1H,d) from Compound II.4 using 1 equivalent of oxidant.
(v) 3-(4,4-difluorobut-3-enylsulfonyl)-2-methylfuran (Compound II.9); $^1$H NMR; δ2.42–2.52(2H,m); 2.6(3H, s); 3.2–3.28(2H,t) 4.1–4.23 (1H,m); 6.6 (1H,d); 7.36(1H, d) from Compound II.4 using 2.1 equivalents of oxidant.

EXAMPLE III.1

This Example illustrates a preparation of 2-(4,4-difluorobut-3-ethylthio)thiophene (Compound III.1).

A solution containing 2-mercaptothiophene (10 g), 4-bromo-1,1-difluorobut-1-ene (15.47 g) and potassium carbonate (11.8 g) in acetone (250 cm$^3$) was heated under reflux for 2 hours and then left to stand for 18 hours. The reaction was quenched with water and extracted several times with diethyl ether. The combined organic extracts were dried over magnesium sulfate, filtered and evaporated to give an amber oil. Chromatography on silica (eluant 5% ether in hexane) afforded Compound III.1 (9.5 g); M$^+$=206; $^1$H NMR; δ2.2–2.4(2H,m); 2.8(2H,t); 4.1–4.3 (1H,m); 6.95–7.0 (1H, dd); 7.15 (1H,d); 7.35(1H,d); (oil).

The following compound according to the invention was prepared by the above procedure.
(i) 2-(4,4-difluorobut-3-enylthio)benzo[b]thiophene (Compound III.10); $^1$H NMR; δ2.2–2.3(2H,m); 2.7–2.8 (2H,t); 4.15–4.35(1H,m); 6.4(1H,dd); 6.53(1H,d); 7.5 (1H,d), from benzthiophene.

EXAMPLE III.2

This Example illustrates a preparation of 2-(4,4-difluorobut-3-enylthio)-5-formylthiophene (Compound III.4).

Compound III.1 (1.0 g) was added slowly to a solution containing dimethyl formamide (0.48 cm$^3$) and phosphoryl chloride (0.56 cm$^3$). The reaction mixture was heated at 100° C. for 2 hours, cooled in an ice-bath and then neutralised with 2M NaOH solution. The aqueous solution was extracted twice with diethyl ether and the combined organic layers were washed with water and NaHCO$_3$ solution. The organic extracts were dried over magnesium sulfate, filtered and evaporated to give a dark liquid. Filtration through silica (eluant 20% diethyl ether in hexane) afforded Compound III.4 (0.91 g). M$^+$=234; $^1$H NMR; δ2.4(2H,m); 3.0(2H,t); 4.2–4.4(1H,m); 7.1(1H,d); 9.8(1H,s); (oil).

EXAMPLE III.3

This Example illustrates a preparation of 2-(4,4-difluorobut-3-enylthio)-5-hydroxymethylthiophene (Compound III.5).

Sodium borohydride (0.065 g) was added to a solution of Compound III.4 (0.75 g) in ethanol (21 cm$^3$) and water (9 cm$^3$). The reaction mixture was stirred at the ambient temperature for 2 hours, quenched with 2M hydrochloric acid and then partitioned between water and diethyl ether. The organic phase was dried over magnesium sulfate, filtered and evaporated to give a greenish liquid. Chromatography on silica (eluant 20% ethyl acetate in hexane) afforded Compound III.5 (0.44 g). M$^+$=236; $^1$H NMR; δ1.8–2.0(1H, br s); 2.3(2H,m); 2.8(2H,t); 4.1–4.3(1H,m); 4.8(2H,s); 6.8 (1H,d); 7.0(1H,d); (oil).

EXAMPLE III.4

This Example illustrates a preparation of (E)- and (Z)-2-(4,4-difluorobut-3-enylthio)-5-hydroximiinothiophene (Compounds III.6 and III.7).

Hydroxylamine hydrochloride (0.9 g) and sodium hydrogen carbonate (1.09 g) were stirred together in ethanol (15 cm$^3$) and water (15 cm$^3$) for 5 minutes. Compound III.4 (3 g) was added and the reaction mixture was stirred at the ambient temperature for 2 hours and then left to stand for 18 hours. The reaction mixture was partitioned between water and diethyl ether. The organic phase was dried over magnesium sulfate, filtered and evaporated to give an amber liquid (3.4 g). Chromatography on silica (eluant 20% ethyl acetate in hexane) afforded Compounds III.6 (1.5 g) and III.7 (1.3 g). M$^+$=249; $^1$H NMR; δ2.25–2.35 (2H,m); 2.85 (2H,t); 4.14–4.35 (1H,m); 7.05 (2H,m); 7.52(1H,br s); 8.18 (1H,s); (oil) and M$^+$=249; δ2.25–2.38(2H,m); 2.85–2.95 (2H,t); 4.18–4.35(1H,m); 7.08(1H,d); 7.25(1H,d); 7.64(1H, s); (oil).

EXAMPLE III.5

This Example illustrates a preparation of 5-cyano-2-(4,4-difluorobut-3-enylthio)thiophene (Compound III.8).

1,1'-carbonyl-diimidazole (0.326 g) was added to a solution of Compound III.6 (0.5 g) and the reaction mixture was stirred at the ambient temperature for 10 minutes, then heated under reflux for 2 hours and left to stand for 18 hours. A further equivalent of 1,1'-carbonyldiimidazole was added and the reaction mixture heated under reflux for 1 hour. The reaction mixture was filtered through celite and then evaporated to give Compound III.8 (0.28 g). $^1$H NMR; δ2.27–2.38 (2H,m); 2.94(2H,t); 4.15–4.33(1H,m); 7.05(1H,d); 7.5(1H, d); (oil).

EXAMPLE III.6

This Example illustrates a preparation of 5-acetyl-2-(4,4-difluoro-3-enylthio)thiophene (Compound III.9).

A solution of methylmagnesium bromide (1.3 cm$^3$, 3M solution in diethyl ether, 3 equiv.) was added slowly to a solution of Compound III.8 (0.3 g) in tetrahydrofuran (10 cm$^3$). The reaction mixture was stirred at the ambient temperature for 3 hours and then the solvent was evaporated. The residue was partitioned between ammonium hydroxide solution and chloroform. The organic layer was washed with water, dried over Na$_2$SO$_4$ and evaporated. The residue was chromatographed on silica (eluant 10% ethyl acetate in hexane) to give Compound III.9 (0.16 g). $^1$H NMR; δ2.30–2.40(2H,m); 2.50(3H,s); 2.97(2H,t); 4.15–4.33(1H, m); 7.04(1H,d); 7.55(1H,d); (oil).

EXAMPLE III.7

This Example illustrates a preparation of 2-(4,4-difluorobut-3-enylsulfinyl)thiophene (Compound III.2).

Compound III.1 (0.50 g) was stirred at ambient temperature in dichloromethane (5 cm$^3$) and 3-chloro perbenzoic acid (0.834 g of a 50% by weight solid, 1 equiv.) was added. After the indicated consumption of starting material the reaction was quenched by the addition of a saturated aqueous solution of sodium bicarbonate and the product was extracted into dichloromethane. The organic phase was separated, washed with saturated brine and dried over magnesium sulfate. After filtration and concentration by evaporation under reduced pressure, there was obtained a liquid (0.584 g) which was purified by chromatography on silica gel using 20% ethyl acetate in hexane as eluant, and then diethyl ether to elute. Compound III.2 (0.29 g). $^1$H NMR; δ2.3–2.55 (2H, m); 2.9–3.2 (2H, m); 4.2–4.5 (1H, m); 7.15 (1H, m); 7.5 (1H, m); 7.7 (1H, m); (oil).

The following compounds according to the invention were prepared by the above procedure;
(i) 2-(4,4-difluorobut-3-enylsulfonyl)thiophene (Compound III.3). $^1$H NMR; δ2.4–2.6(2H,m); 3.2–3.4(2H,t); 4.1–4.3

(1H, m); 7.15(1H,dd); 7.7–7.8(1H,m); (oil) from Compound III.1 using two equivalents of oxidant.

(ii) 2-(4,4-difluorobut-3-enylsulfinyl)benzo[b]thiophene (Compound III.11). $^1$H NMR: δ2.3–2.4(2H,m); 3.0–3.2 (2H,m); 4.2–4.4(1H,m); 7.45(2H,m); 7.9(2H,m); 7.75 (1H,s) from Compound III.10 using one equivalent of oxidant.

(iii) 2-(4,4-difluorobut-3-enylsulfonyl)benzo[b]thiophene (Compound III.12). $^1$H NMR: δ2.5(2H,m); 3.3(2H,t); 4.2–4.35(1H,m); 7.5(2H,m); 7.9(3H,m) from Compound III.10 using two equivalents of oxidant.

EXAMPLE IV.1

This Example illustrates a preparation of ethyl 5-(4,4-difluorobut-3-enylthio)-3-methylisoxazole- 4-carboxylate (Compound IV.8).

A solution of 4,4-difluorobut-3-enyl thioacetate (2 g) in 50% sodium hydroxide solution (6.7 cm$^3$) was stirred vigorously for 30 minutes. A solution of ethyl 5-chloro-4-methylisoxazole (2.2 g) in dichloromethane (12 cm$^3$) was added followed by tetra-n-butylammonium bromide (catalyst) and the reaction stirred at the ambient temperature under nitrogen. After 3 hours the layers were separated and the organic phase was washed with brine, dried (MgSO$_4$), filtered and evaporated under reduced pressure. The residue was stirred with 880 ammonia resulting in crystallisation. The crystals were isolated by filtration to give Compound IV.8 (2.87 g). $^1$H NMR δ1.35(3H,t); 2.45 (3H,s); 2.50(2H, m); 3.20(2H,t); 4.25(1H,m); 4.30(2H,q); (mp 41–42° C.).

EXAMPLE IV.2

This Example illustrates a preparation of 5(4,4-difluorobut-3-ethylthio)-3-methylisoxazole-4-carboxylic and (Compound IV.9).

A solution of Compound IV.8 (0.5 g) in isopropanol (5 cm$^3$) and 2M NaOH (1 cm$^3$) was stirred for 3 hours. The mixture was then poured into water and washed with ethyl acetate. The aqueous layer was then acidified with 2M HCl and the product extracted into ethyl acetate. This extract was dried (MgSO$_4$), filtered and evaporated under reduced pressure to give Compound IV.9 (0.16 g). M$^+$=249; $^1$H NMR δ2.45(3H,s); 2.50(2H,m); 3.20(2H,t); 4.20–4.40(1H,m); (mp 132–133° C.).

EXAMPLE IV.3

This Example illustrates a preparation of 5-(4,4-difluorobut-3-enylthio)-3-methylisoxazole-4-carboxamide (Compound IV.7).

Triethylamine (0.33 cm$^3$) and ethyl chloroformate (0.24 cm$^3$) were added to Compound IV.9 (0.56 g) in dichloromethane (15 cm$^3$) at 0° C. The reaction was allowed to warm to the ambient temperature and stirred for 2 hours. Ammonia was bubbled through the solution until it was saturated and the reaction was then stirred for a further 1 hour. Aqueous ammonia was added and the product extracted into dichloromethane. The organic phase was washed with water, dried (MgSO$_4$), filtered and evaporated under reduced pressure. Purification by distillation in a kugelrohr apparatus gave Compound IV.7 (0.069 g). $^1$H NMR δ2.45(2H,m); 2.50(3H,s); 3.25(2H,t); 4.25(1H,m); (mp 87° C.).

EXAMPLE IV.4

This Example illustrates a preparation of 3-(5-chlorofur-2-yl)-5-(4,4-difluorobut-3-enylthio)isoxazole (Compound IV.23).

Hydrogen sulfide was bubbled through a stirred solution of potassium methoxide (1.9 g) in ethanol (10 cm$^3$) cooled in an acetone/ice bath. 5-Chloro-3-(5-chlorofur-2-yl) isoxazole (2.2 g) was added and the reaction was then heated under reflux for 1 hour during which time the solvent evaporated. Acetone (10 cm$^3$) and 4-bromo-1,1-difluorobut-1-ene (2 g) were added and the mixture heated under reflux for a further 2 hours. The resulting solution was cooled, poured into diethyl ether and brine and the layers separated. The aqueous layer was extracted with ether. The combined organic phases were washed with brine, dried (MgSO$_4$), filtered and evaporated under reduced pressure to give a black solid. Purification by column chromatography on silica gel using 10% ether in hexane as eluant gave Compound IV.23 (2 g). M$^+$=291; $^1$H NMR δ2.35–2.50(2H,m); 3.10(2H,t); 4.30(1H,m); 6.30(1H,d); 6.43(1H,s); 6.90(1H, d); (m.p. 80–82° C.).

The following compound according to the invention was prepared by the above procedure:

(i) 5-(4,4-difluorobut-3-enylthio)-3-phenylisoxazole (Compound IV.1). M$^+$=267; $^1$H NMR; δ2.43(2H,m); 3.10 (2H,t); 4.28(1H,m); 6.50(1H,s); 7.45(3H,m); 7.78(2H,m); (oil) from 5-chromo-3-phenylisoxazole.

EXAMPLE IV.5

This Example illustrates a preparation of 2-(4,4-difluorobut-3-enylthio)-3-methylisoxazole (Compound IV.10).

To a stirred solution of acetone oxime (0.365 g) in dry tetrahydrofuran (20 cm$^3$) at 0° C. under nitrogen was added n-butyl lithium (4.6 cm$^3$ of a 2.5M solution in hexanes) resulting in formation of a pale yellow precipitate. After stirring at 0° C. for 30 minutes, carbon disulfide (0.3 cm$^3$) was added producing a bright orange solution. After a further 10 minutes, 3M HCl (20 cm$^3$) was added and the reaction was heated under reflux for 3 hours and then cooled. The layers were separated and the aqueous layer was extracted with chloroform. The combined organic layers were dried (MgSO$_4$), filtered and evaporated under reduced pressure to give a brown oil. The oil was then taken up in acetone (11 cm$^3$) and 1-bromo-4,4-difluorobut-3-ene (0.77 g) and potassium carbonate (0,87 g) were added and the reaction heated under reflux for 3.5 hours and then cooled. The mixture was then poured into ethyl acetate and 2M HCl and the layers separated. The aqueous layer was extracted with ethyl acetate and the combined organic phases were dried (MgSO$_4$), filtered and evaporated under reduced pressure to give a brown oil. Purification by column chromatography on silica gel using 1:9 ethyl acetate : hexane as eluant gave 2-(4,4-difluorobut-3-enylthio)-3-methylisoxazole (0.105 g). M$^+$=205; $^1$H NMR; δ2.30(3H,s); 2.40(2H,m); 3.05(2H,t); 4.25(1H,m); 6.00(1H,s); (oil).

EXAMPLE IV.6

This Examples illustrates a preparation of 3-(5-chlorofur-2-yl)-5-(4,4-difluorobut-3-enylsulfonyl)isoxazole (Compound IV.24).

To a stirred solution of Compound IV.23 (2 g) in methanol (40 cm$^3$), cooled in an ice/acetone bath was added magnesium monoperoxyphthalate (9.4 g). After stirring for 30 minutes the cooling bath was removed and the reaction allowed to warm to the ambient temperature and stirred for 1 hour. The mixture was poured into diethyl ether and brine and the layers separated. The combined organic phases were washed with 2M, NaOH, water and brine, dried (MgSO4), filtered and evaporated under reduced pressure to give Compound IV.24 (1.9 g). M⁺=323; ¹H NMR; δ2.50–2.60 (2H,m); 3.40(2H,t); 4.25(1H,m); 6.38(1H,d); 7.05(1H,d); 7.20(1H,s); (mp 86.5–88.5° C.).

The following compounds according to the invention were prepared by the above oxidation procedure:

(i) 5-(4,4-difluorobut-3-enylsulfinyl)-3-phenylisoxazole (Compound IV.2). M⁺=283; ¹H NMR; δ2.53(2H,m); 3.25 (2H,t); 4.29(1H,m); 7.18(1H,s); 7.50(3H,m); 7.80(2H,m); (oil) from Compound IV.1 and one equivalent of oxidant.

(ii) 5-(4,4-difluorobut-3-enylsulfonyl)-3-phenylisoxazole (Compound IV.3). M⁺=299; ¹H NMR; δ2.57(2H,m); 3.43 (2H,t); 4.27(1H,m); 7.2(1H,s); 7.51(3H,m); 7.80(2H,m); (mp 57–58° C.) from Compound IV.1 and two equivalents of oxidant.

(iii) 3-(thien-2-yl)-5-(4,4-enylsulfonyl)isoxazole (Compound IV.26). M⁺=305; ¹H NMR; δ2.50–2.63 (2H, m); 3.41(2H,t); 4.27(1H,m); 7.20(1H,s); 7.14–7.23(1H, m); 7.52(2H,m); (mp 55–57° C.) from 3-(thien-2-yl)-5-(4,4-diflourobut-3-enylthio)isoxazole, Compound IV.25, itself prepared from 5-chloro-3-(thien-2-yl)isoxazole by the procedure of Example IV.4.

EXAMPLE V.1

The Example illustrates a preparation of 3-chloro-4-cyano-5-(4,4-difluorobut-3-enylthio)isothiazole (Compound V.2).

A solution of 4-cyano-3,5-dichloroisothiazole (1 g) in methanol (10 cm³) was added over 15 min to a solution of sodium sulfide nonahydrate (1.3 g) in water (2.6 cm³) and methanol (25 cm³) heated at 50° C. The reaction was stirred for 1 hour and then the solvent was evaporated under reduced pressure to give a yellow solid. This residue was dissolved in acetone (20 cm³), 4-bromo-1,1-difluorobut-1-ene (0.68 g) was added and the reaction was stirred for 12 hours. The resulting mixture was poured into water and the layers separated. The aqueous layer was extracted with ethyl acetate. The combined organic phases were dried MgSO₄), filtered and evaporated under reduced pressure. Purification by column chromatography on silica gel using 1:1 ethyl acetate:hexane as eluant gave Compound V.2. (0.88 g). M⁺=266; ¹H NMR δ2.50(2H,m); 3.20(2H,t); 4.20–4.40(1H, m); (oil).

The following compound according to the invention was prepared by the above procedure but using 2 equivalents of sodium sulfide nonahydrate and 4-bromo-1,1-difluorobut-1-ene.

(i) 3,5-bis-(4,4-difluorobut-3-enylsulfonyl)-4-cyanoisothiazole (Compound V.6) and 3,5-bis-(4,4-difluorobut-3-enylsulfonyl)-4-cyanoisothiazole (Compound V.12). ¹H NMR δ2.40–2.60(4H,m); 3.20(2H, t); 3.30(2H,t); 4.20–4.40(2H,m); (oil).

EXAMPLE V.2

The Example illustrates a preparation of 5-(4,4-difluorobut-3-enylsulfonyl)-4-cyanoisothiazole (Compound V.6) and 3,5-bis-(4,4-difluorobut-3-enylsulfonyl)-4-cyanoisothiazole (Compound V.15).

To a solution of Compound V.12 (0.1 g) in dichloromethane (5 cm³) was added 3-chloroperbenzoic acid (0.42 g) and the reaction mixture was stirred until starting material had disappeared. The reaction mixture was poured into ethyl acetate and water and the layers were separated. The aqueous layer was extracted with ethyl acetate. The combined ethyl acetate phases were washed with sodium hydrogen carbonate, dried (MgSO₄), filtered and evaporated under reduced pressure. The residue was taken up in diethyl ether and triethylamine was added causing the solution to become cloudy. The ether solution was then washed with water, dried (MgSO₄), filtered and evaporated. Purification of the residue by column chromatography on silica gel using 1:1 ethyl acetate:hexane as eluant gave Compound V.15 (0.01 g); M⁺=418; ¹H NMR δ2.60–2.70 (4H,m); 3.60(4H,t); 4.30(2H, m); (oil) and Compound V.6 (0.08 g); M⁺=264; ¹H NMR δ2.60(2H,m); 3.60(2H,t); 4.30(1H,m); 9.40(1H,s); (oil).

EXAMPLE VI.1

Oxazoles substituted with a 4,4-difluorobut-3-enylthio group in the 2, 4 or 5-position may be prepared starting from a correspondingly substituted mercapto-oxazole and an appropriate difluorobut-1-ene alkylating agent. This is illustrated by the following preparation of 2-(4,4-difluorobut-3-enylthio)-5-phenyloxazole (Compound VI.18).

To a solution of 2-mercapto-5-phenyloxazole (0.44 g) in acetone (15 cm³) was added 4,4-difluoro-3-butenyl-4-methyl-benzenesulfonate (0.7 g) and potassium carbonate (0.369 g) and the reaction was heated at reflux for a total of 8 hours after which time some of the starting tosylate remained. Further 2-mercapto-5-phenyloxazole (0.05 g) was added and the heating continued for 5 hours. The reaction mixture was cooled, poured into diethyl ether and water and the layers separated. The aqueous layer was extracted with ether and the combined organic phases were dried (MgSO₄) and evaporated under reduced pressure to give a yellow liquid. Chromatography on silica gel using 5% tert-butyl dimethyl ether in hexane gave Compound VI.18; M⁺=267; ¹H NMR (CDCl₃) δ2.51(2H,m); 3.23(2H,); 4.30(1H,m); 7.23–7.47(4H,m); 7.58(2H,d); (oil).

The following compounds according to the invention were prepared by the above procedure:

(i) 2-(4,4-difluorobut-3-enylthio)-oxazole (Compound VI.1). ¹H NMR (CDCl₃) δ2.45(2H,m); 3.20(2H,t); 4.25 (1H,m); 7.10(1H,s); 7.66(1H,s); (oil) from oxazole-2-thione.

(ii) 2-(4,4-difluorobut-3-enylthio)-4-methyloxazole (Compound VI.6). M⁺205; ¹H NMR δ: 2.04(3H,s); 2.45 (2H,m); 3.18(2H,t); 4.25(1H,m); 7.38(1H,q); (oil) from 2-mercapto-4-methyloxazole.

EXAMPLE VI.2

This Example illustrates a 3-step preparation of methyl 2-(4,4-difluorobut-3-enylthio)-4-methyloxazole-5-carboxylate (Compound VI.32).

Step 1: Methyl 2-amino-4-methyloxazole-5-carboxylate.

Methyl 3-chloroacetoacetate (75 g) and urea (90 g) in methanol (200 cm³) were stirred and heated to reflux for 24 hours. The reaction mixture was cooled to ambient temperature and the precipitate filtered from solution, washed with cold methanol and sucked to dryness. This solid was treated with aqueous 2M sodium hydroxide and the product extracted into ethyl acetate (several portions). Evaporation of solvent under reduced pressure gave a colourless solid (14.5 g) which was recrystallised from acetonitrile, mp 225° C. (dec.) ¹H NMR (DMSO-d₆): δ2.15(3H,s); 3.75(3H,s); 7.4(2H,br).

Step 2: Methyl 2-chloro-4-methyloxazole-5-carboxylate.

The product from Step 1 (1.56 g) was partially dissolved in dry acetonitrile (40 cm³) and added in portions at 8° C. to a stirred mixture of copper (II) chloride (1.61 g) and tertiary butyl nitrite in acetonitrile (dry, 20 cm³) under an atmosphere of nitrogen. The resulting brown solution was stirred at 20° C. for 2 hours and evaporated under reduced pressure.

The residue was treated with aqueous 2M hydrochloric acid, and the product extracted into diethyl ether. The organic phase was dried (MgSO$_4$) and then washed through a short column of silica gel with more ether. The filtrate was evaporated under reduced pressure to give the required intermediate (0.9 g) as a yellow solid. M$^+$+175.

Step 3: Methyl 2-(4,4-difluorobut-3-enylthio)-4-methyloxazole-5-carboxylate

The product from Step 2 (0.176 g) and thiourea (0.084 g) were stirred in ethanol (5 cm$^3$) and heated to reflux under an atmosphere of nitrogen for 5 hours. The reaction was cooled and solvent removed by evaporation under reduced pressure to give a yellow gum which was dissolved in acetone containing 4-bromo-1,1-difluorobut-1,1-difluorobut-1-ene (0.17 g) and potassium carbonate (0.2 g). This mixture was stirred for 1 hour under an atmosphere of nitrogen at ambient temperature and stored for 18 hours. The solvent was evaporated under reduced pressure and the residue treated with water and diethyl ether. The organic phase was separated, dried (MgSO$_4$) and evaporated to give Compound VI.32 (0.095 g); M$^+$=175. $^1$H NMR: δ2.45(5H,m); 3.22(2H, t); 3.90(3H,s); 4.25(1H,m); (oil).

EXAMPLE VI.3

This Example illustrates a preparation of 2-(4,4-difluorobut-3-enylthio)-4-methyloxazole-5-carboxylic acid (Compound VI.37).

Compound VI.32 (0.4 g) was dissolved in propan-2-ol (10 cm$^3$) containing aqueous sodium hydroxide (2 cm$^3$ of 2M solution) and stirred for 5 hours at ambient temperature. The mixture was evaporated under reduced pressure and the residue diluted with water, extracted with ethyl acetate, acidified with dilute hydrochloric acid and re-extracted with ethyl acetate (3×100 cm$^3$). The latter extracts were combined, washed with saturated brine, dried (MgSO$_4$) and evaporated under reduced pressure to give the required product as a colourless solid (0.3 g). M$^+$=249; $^1$H NMR: δ2.5(5H,m); 3.27(2H,t); 4.27(1H,m); 6.5(1H,br s); (mp 66–68° C.). The sodium salt of this compound was prepared by treating a sample (0.7 g) with a solution of sodium methoxide in dry methanol (0.061 g of sodium metal dissolved in methanol (10 cm$^3$)) at ambient temperature. Evaporation of solvent under reduced pressure gave the sodium salt of Compound VI.37 as a colourless solid; M$^+$(FAB)=271; (mp 211–212° C.).

The following compound according to the invention was prepared by the above procedure:
(i) 2-(4,4-difluorobut-3-enylthio)-4-trifluoromethyloxazole-5-carboxylic acid (Compound VI.36). M$^+$=303; $^1$H NMR: δ2.54(2H,m); 3.32(2H,t); 4.28(1H,m) 7.65(1H,br s) from Compound VI.31.

EXAMPLE VI.4

This example illustrates a preparation of 2-(4,4-difluorobut-3-enylthio)-4-trifluoromethyloxazole (Compound VI.4).

2-Amino-4-trifluoromethyloxazole (0.84 g) in dichloromethane (25 cm$^3$) containing bis-(4,4-difluorobut-3-enyl) disulfide (2.71 g) at 0° C. was stirred and treated dropwise with tert. butyl nitrite (0.62 g) under nitrogen. The reaction solution was evaporated under reduced pressure and the residue fractioned at chromatography (silica, eluant hexane) to give Compound VI.4 (0.35 g). M$^+$=259; $^1$H NMR: δ2.50 (2H,m); 3.26(3H,t); 4.28(1H,m); 7.95(1H,q); (oil).

The following compound according to the invention was prepared by the above procedure from the corresponding aminooxazole:

(i) Ethyl 2-(4,4-difluorobut-3-enylthio)-4-trifluoromethyloxazole-5-carboxylate (Compound VI.31). MH$^+$=322; $^1$H NMR: δ1.40(3H,t); 2.52(2H,m); 3,30(2H,m); 4.28(1H,m); 4.43(2H,q); (oil) from ethyl 2-amino-4-trifluoromethyloxazole-5-carboxylate (prepared from ethyl 1,1,1-trifluoromethylacetoacetate and urea in a procedure analogous to Example VI.2).

EXAMPLE VI.5

This Example illustrates a preparation of 2-(4,4-difluorobut-3-enylthio)-5-chlorooxazole (Compound VI.13).

Compound VI.1 (2.0 g) was dissolved in acetonitrile (50 cm$^3$) containing N-chlorosuccinimide (1.50 g) and stirred at ambient temperature for 24 hours. The mixture was evaporated under reduced pressure, extracted with hexane (50 cm$^3$), filtered and the filtrate evaporated under reduced pressure. The residue was fractioned by chromatography (silica; eluant 20% diethyl ether in hexane) to give Compound VI.13 (0.75 g). M$^+$=225; $^1$H NMR: δ2.46(2H,m); 3.16(2H,t); 4.28(1H,m); 6.86(1H,s); (oil).

The following compound according to the invention was prepared from Compound VI.6 by the above procedure:
(i) 2-(4,4-difluorobut-3-enylthio)-4-methyl-5-chlorooxazole (Compound VI.15). M$^+$=239; $^1$H NMR: δ2.05(3H,s); 2.45 (2H,m); 3.15(2H,t); 4.25(1H,m); (oil).

EXAMPLE VI.6

This Example illustrates a preparation of 2-(4,4-difluorobut-3-enylthio)-4-methyloxazole-5-carboxamide (Compound VI.40).

Compound VI.32 (1.5 g) was dissolved in methanol (10 cm$^3$) and treated with aqueous ammonia (35 cm$^3$, density 0.88) an ambient temperature. The mixture was stirred for 5 hours, diluted with brine and the product extracted into ethyl acetate (2×100 cm$^3$). The combined organic phases were washed with brine (4×50 cm$^3$), dried (MgSO$_4$) and evaporated under reduced pressure; the residue was washed with hexane to give Compound VI.40 (1 g). M$^+$=248; $^1$H NMR (DMSO-d$_6$); δ2.50(5H,m); 3.26(2H,t); 3.85(3H,s); 4.28(1H, m); 5.6, 6.0 (2H, br s); (mp 72–73° C.).

EXAMPLE VI.7

This Example illustrates a preparation of 5-cyano-2-(4,4-difluorobut-3-enylthio)-4-methyloxazole (Compound VI.25).

Compound VI.40 (0.64 g) was dissolved in dichloromethane (10 cm$^3$) containing dry pyridine (1 cm$^3$) at ambient temperature and treated with methane sulfonyl chloride (0.5 cm$^3$). The solution was stirred for 5 hours, stored for 72 hours, further methane sulfonyl chloride (0.25 cm$^3$) and pyridine (0.5 cm$^3$) added, stirred for 8 hours, and stored for 48 hours. The mixture was treated with dilute hydrochloric acid, and the product extracted into ethyl acetate. The combined organic phase was washed with brine and dried (MgSO$_4$). After filtration, the solvent was evaporated under reduced pressure and the residue fractionated by chromatography (silica; eluant 10% ethyl acetate in hexane) to give Compound VI.25 (0.46 g). M$^+$=230; $^1$H NMR; δ2.32(3H,s); 2.50(2H,m); 2.58(3H,s); 3.25(2H,t); 3.85(3H, s); 4.28(1H,m); (oil).

EXAMPLE VI.8

This Example illustrates a preparation of N-methylsulfonyl 2-(4,4-difluorobut-3-enylthio)-4-methyl-oxazolecarboxamide (Compound VI.38).

The sodium salt of Compound VI.37 (0.52 g) was stirred in hexane (6.5 cm$^3$) and treated with oxalyl chloride (0.275 g) at ambient temperature. The mixture was stirred for 6 hours, stored for 18 hours and evaporated under reduced pressure. The residue, containing the oxazole carbonyl chloride derivative, was treated with a solution of methane sulfonamide (0.20 g) in dry butan-2-one (5 cm$^3$), heated under reflux with stirring for 8 hours, cooled to ambient temperature and stored for 18 hours. The mixture was evaporated under reduced pressure, the residue dissolved in water, acidified with 2M hydrochloric acid and the product extracted into diethyl ether (2×150 cm$^3$). The ether extracts were combined, washed with aqueous saturated sodium chloride, dried (MgSO$_4$), evaporated under reduced pressure and the residue purified by chromatography, (silica; eluant acetonitrile), to give Compound VI38 (0.20 g). M$^+$=326; $^1$H NMR; δ2.50(5H,m); 3.27(2H,t); 3.40(3H,s); 4.28(1H,m); (mp 60–62° C.).

EXAMPLE VI.9

This Example illustrates a preparation of 2-(4,4-difluorobut-3-enylsulfinyl)-5-phenyloxazole (Compound VI.19).

To a solution of Compound VI.18 (1 g) in dichloromethane (40 cm$^3$) was added 3-chloroperbenzoic acid (1.3 g of a 50% by weight solid, (1 eq) and the reaction was stirred at ambient temperature for 5 hours. The reaction mixture was poured into a mixture of diethyl ether and aqueous sodium bicarbonate and the layers separated. The organic layer was dried (MgSO$_4$) and evaporated under reduced pressure to give a white solid which was purified by chromatography on silica gel, eluting with 1:4 ethyl acetate::hexane to give Compound VI.19 (0.567 g). M$^+$=283; $^1$H NMR; δ250(2H,m); 3.41(2H,t); 4.29(1H,m); 7.27(1H,s); 7.38–7.55 (3H,m); 7.71(2H,d); (oil).

The following compounds were prepared from the corresponding thioethers by the general method described above but using 2 equivalents of 3-chloroperbenzoic acid:
(i) 2-(4,4-difluorobut-3-enylsulfonyl)-4-trifluoromethyloxazole (Compound VI.5). $^1$H NMR: δ2.65(2H,m); 3.58(2H,t); 4.28(1H,m); 8.24(1H,q); (oil).
(ii) 5-chloro-2-(4,4-difluorobut-3-enylsulfonyl)oxazole (Compound VI.14). MNH$_4^+$=275; $^1$H NMR: δ2.60(2H, m); 3.47(2H,t); 4.26(1H,m); 7.18(1H,s); (oil).
(iii) 5-chloro-2-(4,4-difluorobut-3-enylsulfonyl)-4-methyloxazole (Compound VI.16). $^1$H NMR: δ2.25(3H, s); 2.60(2H,m); 3.45(2H,t); 4.26(1H,m); (oil).
(iv) 2-(4,4-difluorobut-3-enylsulfonyl)-5-phenyloxazole (Compound VI.20). M$^+$=299; $^1$H NMR: δ2.62(2H,m); 3.51(2H,t); 4.27(1H,m); 7.26(1H,s); 7.42–7.55(3H,m); 7.69–7.79(2H,d); (mp 55–59° C.).

EXAMPLE VII.1

This Example illustrates a general method for the preparation of thiazoles substituted with a 4,4-difluorobut-3-enylthio group in the 2, 4 or 5-position starting from a correspondingly substituted mercapto thiazole and an appropriate difluorobut-1-ene alkylating agent. This is demonstrated by the following preparation of 2-(4,4-difluorobut-3-enylthio)-5-phenylthiazole (Compound VII.17).

To a solution of 2-mercapto-5-phenylthiazole (0.483 g) in acetone (15 cm$^3$) was added 4,4-difluoro-3-butenyl 4-methyl-benzenesulfonate (0.7 g) and potassium carbonate (0.369 g) and the reaction was heated at reflux for a total of 8 hours after which time some of the starting tosylate remained. Further 2-mercapto-5-phenylthiazole (0.05 g) was added and the heating continued for 5 hours. The reaction mixture was cooled, poured into diethyl ether and water and the layers separated. The aqueous layer was extracted with ether and the combined organic phases were dried (MgSO$_4$) and evaporated under reduced pressure to give a yellow liquid. Chromatography on silica gel using 5% tert-butyl dimethyl ether in hexane gave Compound VII.17 (0.582 g). M$^+$=283; $^1$H NMR: δ2.51(2H,m); 3.31(2H,t); 4.32(1H,m); 7.26(1H,s); 7.30–7.48(3H,m); 7.89(2H,d); (oil).

The following compounds according to the invention were prepared by the above procedure:
(i) 2-(4,4-difluorobut-3-enylthio)-thiazole (Compound VII.1), M$^+$=207; $^1$H NMR; δ2.47(2H,m); 3.26(2H,t); 4.27 (1H,m); 7.22(1H,d); 7.68(1H,d); (oil) from 2-mercaptothiazole.
(ii) 2-(4,4-difluorobut-3-enylthio)-thiazoline (Compound VII.134) M$^+$=209; $^1$H NMR: δ2.40(2H,m); 3.15(2H,t); 3.4(2H,t); 4.18–4.31(1H,m); 4.2(2H,t); (oil) from 2-mercaptothiazole.

EXAMPLE VII.2

This Example illustrates a two-step preparation of 2-(4, 4-difluorobut-3-enylthio)-4-trifluoromethyloxazole (Compound VII.4).

Step 1: Preparation of 2-mercapto-4-trifluoromethyloxazole

1-Bromo-3,3,3-trifluoropropan-2-one (5.0 g) in tert. butanol (20 cm$^3$) was treated with ammonium dithiocarbamate (2.9 g), the mixture stirred at ambient temperature for 18 hours, poured into water, extracted with ethylacetate and the organic phase dried (MgSO$_4$). The solvent was evaporated under reduced pressure and the residue fractionated by chromatography (silica; eluant hexane:ethyl acetate 17:3 to 7:3 by volume) to give a hydrate (2.16 g) of the required mercaptothiazole. A portion (1.0 g) of this material was added to toluene (20 cm$^3$) containing para toluene sulfonic acid (0.005 g, catalyst) and heated under reflux for 4 hours. The water formed during the reaction was removed using a Dean-Stark apparatus. The solution was cooled to ambient temperature, washed with water, dried (MgSO$_4$) and evaporated under reduced pressure to give the required intermediate product (0.37 g); $^1$H NMR: δ7.10(1H,s); 7.80(1H,s).

Step 2: Preparation of Compound VII.4

The product from Step 1 (0.37 g) in acetone (15 cm$^3$) containing anhydrous potassium carbonate (0.3 g) and 4-bromo-1,1-difluorobut-1-ene (0.34 g) were stirred and heated under reflux for 4 hours. The mixture was cooled, poured into water, extracted with ethyl acetate, dried (MgSO$_4$) and evaporated under reduced pressure to give Compound VII.4 (0.30 g). M$^+$=275; $^1$H NMR: δ 2.50(2H, m); 3.32(2H,t);4.28(1H,m);7.60(1H,s); (oil).

The following compounds according to the invention were prepared from the corresponding mercaptothiazoles using Step 2 of the above procedure:
(i) Ethyl 2-(4,4-difluorobut-3-enylthio)thiazole-4-carboxylate (Compound VII.8). $^1$H NMR: δ 1.40(3H,t); 2.48(2H,m); 3.32(2H,t); 4.28(1H,m)); 4.40(2H,q); 8.03 (1H,s); (oil) from ethyl 2-mercaptothiazole-4-carboxylate.
(ii) Methyl 2-(4,4-difluorobut-3-enylthio)-4-methylthiazole-5-carboxylate (Compound VII.41). $^1$H NMR: δ 2.48(2H,m); 2.68(3H,s); 3.26(2H,t); 3.85(3H, s); 4.28(1H,m); (oil) from methyl 2-mercapto-4-methylthiazole-5-carboxylate.
(iii) 2-(4,4-difluorobut-3-enylthio)-5-nitrothiazole (Compound VII.47). M$^+$=252; $^1$H NMR: δ 2.52(2H,m);

3.35(2H,m); 4.27(1H,m); 8.35(1H,s); (oil) from 2-mercapto-5-nitrothiazole (obtained from 2-bromo-5-nitrothiazole and thiourea).

EXAMPLE VII.3

This Example illustrates a three-step preparation of 5-chloro-2-(4,4-difluorobut-3-enylthio)thiazole (Compound VII.24).

Step 1: 2-(4-bromo-3,4,4-trifluorobutylthio)thiazole

2-Mercaptothiazole (11.7 g) in acetone (30 cm$^3$) containing 1,4-dibromo-1,1,2-trifluorobutane (27.0 g) was treated portionwise with anhydrous potassium carbonate (13.8 g) under an atmosphere of nitrogen. The reaction was stirred for 1.5 hours, filtered and the insolubles washed with further acetone (4×25 cm$^3$). The filtrate was evaporated under reduced pressure and the residue fractionated by chromatography (silica, eluant 10% ethyl acetate in hexane) to give 2-(4-bromo-3,4,4-trifluorobutylthio)thiazole (29.5 g). $^1$H NMR: δ 2.2–2.5(2H,m); 3.2–3.6(2H,m); 4.7–5.0(1H,m); 7.23(1H,d); 7.68(1H,d).

Step 2: 2-(4-bromo-3,4,4-trifluorobutylthio)-5-chlorothiazole

The compound from Step 1 (30.6 g) in dichloromethane (130 cm$^3$) was treated at ambient temperature with sulfuryl chloride (9.6 cm$^3$) in dichloromethane (30 cm$^3$) over 1 hour with stirring under an atmosphere of nitrogen. The reaction was stirred for a further 1 hour, poured slowly into water (250 cm$^3$) and stirred for 0.25 hours. The organic phase was separated, the aqueous phase extracted with dichloromethane (2×75 cm$^3$), the combined organic phases washed with aqueous sodium hydrogen carbonate, brine and dried (MgSO$_4$). The solvent was evaporated under reduced pressure and the residue fractionated by chromatography (silica; eluant 5% diethyl ether in hexane) to give 2-(4-bromo-3,4,4-trifluorobutylthio)-5-chlorothiazole (28.0 g); $^1$H NMR: δ 2.20–2.45 (2H,m); 3.25–3.50(2H,m); 4.70–5.0(1H,m); 7.45 (1H,s); (oil).

Step 3: Compound VII.24

Zinc powder (33 g) in water (600 cm$^3$) was stirred with iodine (0.17 g, catalyst), heated to 80° C. and concentrated hydrochloric acid (0.5 cm$^3$) added followed by the compound from Step 2 (125 g) in portions over 1.5 hour under an atmosphere of nitrogen. Further zinc (16.6 g), iodine (0.1 g) and hydrochloric acid (0.6 cm$^3$) were added over 4 hours in portions to complete the reaction. The mixture was cooled to ambient temperature, filtered through keiselghur using dichloromethane as solvent and the filtrate extracted with dichloromethane (5×250 cm$^3$). The combined organic phases were dried (MgSO$_4$), evaporated under reduced pressure and the residue fractionated by chromatography on silica, eluting with hexane to give Compound VII.24 (140 g). M$^+$=241; $^1$H NMR: δ 2.42(2H,m); 3.20(2H,t); 4.25(1H, m); 7.45(1H,s); (oil).

EXAMPLE VII.4

This Example illustrates a preparation of 5-bromo-2-(4,4-difluorobut-3-enylthio)thiazole (Compound VII.14).

2-Amino-5-bromothiazole hydrobromide (11 g) was treated with aqueous sodium hydrogen carbonate, extracted into dichloromethane (2×250 cm$^3$) and dried (MgSO$_4$). The mixture was filtered and the filtrate added to bis-(4,4-difluorobut-3-enyl)disulfide (20 g). Tert. butyl nitrite (9.6 cm$^3$) in dichloromethane (40 cm$^3$) was added dropwise to the stirred solution at ambient temperature under an atmosphere of nitrogen. The reaction was stirred for 18 hours, evaporated onto silica, the residue added to a short column of silica which was eluted with (1) hexane and (2) hexane:diethyl ether, 20:1 by volume to give Compound VII.14 (6.4 g). M$^+$=285; $^1$H NMR: δ 2.46(2H,m); 3.24(3H,t); 4.27(1H,m); 7.54(1H,s); (oil).

EXAMPLE VII.5

This Example illustrates a preparation of 2-(4,4-difluorobut-3-enylthio)-4-methylthiazole-5-sulfonyl fluoride (Compound VII.52) using an alternative diazotisation procedure to that given in Example VII.4.

2-Amino-4-methylthiazole sulfonylfluoride (1.5 g) in acetonitrile (10 cm$^3$) was added dropwise to a stirred mixture of tert. butyl nitrite (1.65 cm$^3$) and bis-(4,4-difluorobut-3-enyl)disulfide (2.25 g) in acetonitrile (50 cm$^3$) at 60° C. under an atmosphere of nitrogen. The mixture was heated for 1 hour, evaporated under reduced pressure and the residue fractionated by chromatography (silica; eluant hexane:ethyl acetate 4:1 by volume) to give Compound VII.52 (1.84 g). M$^+$=303; $^1$H NMR: δ 2.50(2H,m); 2.68(3H,s); 3.32(2H,t); 4.28(1H,m); (oil).

The following compounds according to the invention were prepared from the corresponding aminothiazoles using the above procedure.

(i) 2-(4,4-difluorobut-3-enylthio)-5-methylthiazole (Compound VII.21). M$^+$=221; $^1$H NMR: δ 2.45(5H,m); 3.22(2H,t); 4.26(1H,m); 7.30(1H,s); (oil) from 2-amino-5-methylthiazole.

(ii) 5-chloro-2-(4,4-difluorobut-3-enylthio)thiazole (Compound VII.24). M$^+$=241; $^1$H NMR: δ 2.45(2H,m); 3.22(2H,t); 4.26(1H,m); 7.45(1H,s); (oil) from 2-amino-5-chlorothiazole in an alternative method to that of Example VII.3 above.

(iii) 5-chloro-2-(4,4-difluorobut-3-enylthio)-4-methylthiazole (Compound VII.27). M$^+$=255; $^1$H NMR: δ 2.35(3H,s); 2.42(2H,m); 3.18(2H,t); 4.26(1H, m); (oil) from 2-amino-5-4-methylthiazole.

EXAMPLE VII.6

This Example illustrates a two-step preparation of ethyl 5-bromo-2-(4,4-difluorobut-3-enylthio)thiazole-4-carboxylate (Compound VII.11).

Step 1: Preparation of ethyl 2-amino-5-bromothiazole-4-carboxylate

Ethyl 2-aminothiazole-4-carboxylate (5.0 g) (prepared from ethyl bromopyruvate and thiourea by the procedure described in *J. Med. Chem.*, 1971, 14, 1075 for the corresponding oxazole) in concentrated hydrobromic acid (9 cm$^3$) was stirred at ambient temperature and treated dropwise with bromine (3.2 g), then heated to 60° C. for 2 hours, neutralised with sodium carbonate and the product extracted into ethyl acetate. The organic phase was dried (MgSO$_4$) and evaporated under reduced pressure to give ethyl 2-amino-5-bromothiazole-4-carboxylate (1.54 g). MH$^+$=251; $^1$H NMR: δ 1.40(3H,t); 4.40(21H,t); 5.6(2H,br s).

Step 2: Preparation of Compound VII.11

The product from Step 1 was treated in a diazotisation reaction, as described in Example VII.5 above and gave Compound VII.11; M$^+$=357; $^1$H NMR: δ 1.40(3H,t); 2.50 (2H,m); 3.30(2H,t); 4.30(1H,m); 4.45(2H,q); (oil).

EXAMPLE VII.7

This Example illustrates a three-step preparation of N,N-diethyl 2-(4,4-difluorobut-3-enylthio)-4-methylthiazole-5-sulfonamide (Compound VII.56).

Step 1: N,N-Diethyl 2-acetamido-4-methylthiazole-5-sulfonamide

2-Acetamido-4-methylthiazole-5-sulfonyl chloride (5.2 g) in tetrahydrofuran (100 cm$^3$) was stirred at ambient temperature and treated portionwise with diethylamine (4.5 cm$^3$). The mixture was stirred for 4 hours, evaporated under reduced pressure and the residue extracted into ethyl acetate (200 cm$^3$), washed with water (2×100 cm$^3$), dried (MgSO$_4$) and re-evaporated under reduced pressure to give N,N-diethyl 2-acetamido-4-methylthiazole-5-sulfonamide (4.9 g). $^1$H NMR: δ 1.20(6H,t); 2.28(3H,s); 2.57(3H,s); 3.32(4H, q); 9.7(1H,br s); (solid).

Step 2: N,N-Diethyl 2-amino-4-methylthiazole-5-sulfonamide

The product from Step 1 (2.5 g) was dissolved in methanol (25 cm$^3$) and cooled to 5° C. with stirring under an atmosphere of nitrogen. Sodium methoxide in methanol (2 cm$^3$ of 25% wt./vol. solution) was added dropwise and the mixture allowed to warm to the ambient temperature for 18 hours. The reaction was heated under reflux for 1 hour, cooled, diluted with water (250 cm$^3$), extracted with diethyl ether (2×100 cm$^3$), dried (MgSO$_4$) and evaporated under reduced pressure to give N,N-diethyl 2-amino-4-methylthiazole-5-sulfonamide (0.48 g). M$^+$249; $^1$H NMR: δ 1.20(6H,t); 2.48(3H,s); 3.28(4H,q); 5.25(2H,br s); (solid).

Step 3: Preparation of Compound VII.56

The product from Step 2 was treated in a diazotisation reaction, as described in Example VII.5 above and gave Compound VII.56; M$^+$=356; $^1$H NMR: δ 1.15(6H,t); 2.45 (2H,m); 2.60(3H,s); 3.25(2H,t); 3.26(4H,q); 4.25(1H,m); (oil).

EXAMPLE VII.8

This Example illustrates a preparation of 2-amino-5-(4, 4-difluorobut-3-enylthio)thiazole (Compound VII.128)

4,4-Difluorobut-3-enylisothiouronium hydrobromide (16.87 g) was added to a solution of potassium hydroxide (18.0 g) in ethanol (150 cm$^3$) at ambient temperature and stirred for 0.2 hours under an atmosphere of nitrogen. 2-Amino-5-bromothiazole hydrobromide (17.76 g) in ethanol (150 cm$^3$) was added in portions, the mixture heated to 40° C. for 2 hours, neutralised with hydrochloric acid and evaporated under reduced pressure. The residue was dissolved in 2M hydrochloric acid, extracted with diethy ether, basified with 2M sodium hydroxide and re-extracted with diethyl ether. The latter ether extracts were combined, dried (MgSO$_4$) and evaporated under reduced pressure to give Compound VII.128 (8.0 g). M$^+$=222; $^1$H NMR: δ 2.28(2H, m); 2.67(2H,t); 4.24(1H,m); 5.3(2H,two br s); 7.08(1H,s); (mp 34.6°–35.4° C.).

EXAMPLE VII.9

This Example illustrates a preparation of 5-(4,4-difluorobut-3-enylthio)thiazole (Compound VII.82).

Compound VII.128 (0.30 g) was dissolved in dry tetrahydrofuran (14 cm$^3$) and heated under reflux in an atmosphere of nitrogen. Tert. butyl nitrite (0.52 cm$^3$) in tetrahydrofuran (8 cm$^3$) was added dropwise over 0.25 hours, the mixture heated for 2 hours, further tert. butylnitrite (0.52 cm$^3$) added and heating continued for a further 2 hours. The solution was cooled, evaporated under reduced pressure and the residue fractionated by chromatography (silica; eluant hexane:ethyl acetate 1:1 by volume) to give Compound VII.128 (0.10 g) $^1$H NMR: δ 2.28(2H,m); 2.82(2H,t); 4.24(1H,m); 7.86(1H, s); 8.86(1H,s); (oil).

EXAMPLE VII.10

This Example illustrates a preparation of 2-chloro-5-(4, 4-difluorobut-3-enylthio)thiazole (Compound VII.114).

Compound VII.128 (4.0 g) in acetonitrile (50 cm$^3$) was added at 0° C. to a stirred mixture of copper(II) chloride (5.38 g) and tert. butyl nitrite (3.71 g) in acetonitrile (50 cm$^3$) and allowed to slowly warm to ambient temperature over 18 hours. The solvent was evaporated under reduced pressure, the product dissolved in diethyl ether, filtered and the filtrate re-evaporated to give a yellow-brown liquid which was fractionated by chromatography (silica; eluant hexane:diethyl ether 4:1 by volume) to give Compound VII.114 (2.43 g). M$^+$=241; $^1$H NMR: δ 2.28(2H,m); 2.68 (2H,t); 4.22(1H,m); 7.52(1H,s) (oil).

EXAMPLE VII.11

This Example illustrates a preparation of 2-(4-cyanophenoxy)-5-(4,4-difluorobut-3-enylthio)thiazole (Compound VII.130).

Compound VII.114 (0.483 g), 4-cyanophenol (0.238 g), anhydrous potassium carbonate (0.276 g) and cesium fluoride (0.304 g) in N-methylpyrrolidin-2-one (3 cm$^3$) were stirred together under an atmosphere of nitrogen and heated to 90° C. for 36 hours. The reaction mixture was diluted with water, the product extracted into diethyl ether, dried (MgSO$_4$), evaporated under reduced pressure and the residue fractionated by thick layer chromatography (silica; eluted with hexane:diethyl ether 4:1 by volume) to give Compound VII.130 (0.125 g). M$^+$=324; $^1$H NMR: δ 2.28 (2H,m); 2.80(2H,t); 4.20(1H,m); 7.40(2H,m); 7.75(2H,m); (oil).

EXAMPLE VII.12

This Example illustrates a preparation of ethyl 5-(4,4-difluorobut-3-enylthio)-thiazole-4-carboxylate (Compound VII.98).

Ethyl isocyanoacetate (2.3 g) in dry tetrahydrofuran (15 cm$^3$) was added to a stirred mixture of potassium tert. butoxide (2.24 g) at –40° C. under an atmosphere of nitrogen. After 10 minutes the reaction was cooled to –78° C. and carbon disulfide (1.52 g) in tetrahydrofuran (20 cm$^3$) was added slowly. On complete addition the reaction temperature was allowed to rise to –10° C. and 4,4-difluorobut-3-enyl 4-methyl-benzenesulfonate (5.24 g) in tetrahydrofuran (10 cm$^3$) was added. The mixture was allowed to warm to ambient temperature and was stirred for 24 hours, heated to reflux for 3 hours and cooled to ambient temperature. The reaction mixture was poured into aqueous 2M hydrochloric acid and product was extracted into ethyl acetate. The organic phase was dried (MgSO$_4$) and solvent removed by evaporation under reduced pressure. Column chromatography of the residue on silica gel eluting with 1:1 hexane:ethyl acetate gave Compound VII.98 (3.15 g). $^1$H NMR: δ 1.45 (3H,t); 2.50(2H,m); 3.10(2H,t); 43–4.4(1H,m); 4.50(2H,q); 8.65(1H,.s); (oil).

EXAMPLE VII.13

This example illustrates a preparation of 5-(4,4-difluorobut-3-enylthio)-thiazole-4-carboxamide (Compound VII.94).

Compound VII.98 (0.5 g) in methanol (8 cm³) was stirred with aqueous ammonia (35 cm³; density 0.88) for 4 hours. Compound VII.94 was obtained as a solid which was filtered from solution and suckered to dryness (0.27 g). $^1$H NMR: δ 2.50(2H,m); 3.00(2H,t); 4.30–4.41(1H,m); 5.5 and 7.0(2H, broad); 8.55(1H,s); (solid mp 140°–141° C.).

The following compounds according to the invention were prepared from the corresponding esters using the above procedure:

(i) 2-(4,4-difluorobut-3-enylthio)thiazole-4-carboxamide (Compound VII.7). M$^+$=250; $^1$H NMR: δ 2.50(2H,m); 3.27(2H,t); 4.28(1H,m); 5.9 and 7.1(2H,br,s); 8.03(1H, s); (mp 57°–58° C.) from Compound VII.8.

(ii) 2-(4,4-difluorobut-3-enylthio)-4-methylthiazole-5-carboxamide (Compound VII.36). $^1$H NMR: δ 2.48 (2H,m); 2.66(3H,s) 3.26(2H,t) 3.85(3H,s); 4.28(1H,m); 5.7(2H,br s); (mp 99°–100° C.) from Compound VII.41.

EXAMPLE VII.14

This Example illustrates a preparation of 4-cyano-5-(4,4-difluorobut-3-enylthio)-thiazole (Compound VII.90).

Compound VII.94 (0.27 g) in dry dichloromethane (13 cm³) was treated with pyridine (1 cm³) and methane sulfonyl chloride (0.26 cm³). The mixture was stirred for 5 days, further methane sulfonyl chloride (0.2 cm³) added and again stirred for 2 hours. The reaction was then poured into aqueous 2M hydrochloric acid and the product was extracted into ethyl acetate. The organic phase was dried (MgSO$_4$) and evaporated under reduced pressure. Chromatography of the residue on silica gel gave Compound VII.90 (0.142 g). $^1$H NMR: δ 2.40(2H,m); 3.20(2H,t); 4.30(1H,m); 8.80(1H,s).

The following compounds according to the invention were prepared from the corresponding carboxamides using the above procedure:

(i) 4-cyano-2-)4,4-difluorobut-3-enylthio)thiazole (Compound VII.6). $^1$H NMR: δ 2.50(2H,m); 3.32(2H, t); 4.26(1H,m); 7.86(1H,s); (oil) from Compound VII.7.

(ii) 5-cyano-2-(4,4-difluoro-3-enylthio)-4-methylthiazole (Compound VII.32). $^1$H NMR: δ 2.48(2H,m); 2.58(3H, s) 3.30(2H,t); 3.85(3H,s); 4.28(1H,m); (oil) from Compound VII.36.

EXAMPLE VII.15

This Example illustrates a preparation of 5-bromo-2-(4,4-difluorobut-3-enylthio)thiazole-4-carboxylic acid (Compound VII.13).

Compound VII.11 (0.30 g) in methanol (5 cm³) containing aqueous sodium hydroxide (1.2 cm³ of a 2M solution) was stirred at ambient temperature for 18 hours, poured into water and acidified with 2M hydrochloric acid. The product was extracted into ethyl acetate, dried (MgSO$_4$) and evaporated under reduced pressure to give COMPOUND VII.13 (0.18 g). M$^+$=329; $^1$H NMR: δ 2.48(2H,m); 3.30(2H,t); 4.28(1H,m); 7.0(1H,broad signal); (mp 86.5°–87.5° C.).

The following compounds according to the invention were prepared from the corresponding esters using the above procedure:

(i) 2-(4,4-difluorobut-3-enylthio)thiazole-4-carboxylic acid (Compound VII.10). M$^+$251; $^1$H NMR: δ 2.50(2H, m); 3.35(2H,t); 4.28(1H,m); 8.18(1H,s); (mp 114°–115° C.) from Compound VII.8.

(ii) 2-(4,4-difluorobut-3-enylthio)-4-methylthiazole-5-carboxylic acid (Compound VII.45). M$^+$=265; $^1$H NMR: δ 2.50(2H,m); 2.70(3H,s); 3.27(2H,t); 4.28(1H, m); 9.8(1H,broad signal); (mp 52.0°–53.5° C.) from Compound VII.41.

(iii) 5-(4,4-difluorobut-3-enylthio)thiazole-4-carboxylic acid (Compound VII.102). M$^+$=251; $^1$H NMR: δ 2.50 (2H,m); 3.10(2H,t); 4.28(1H,m); 8.70(1H,s); (mp 128.5° C.) from Compound VII.98.

EXAMPLE VII.16

This Example illustrates methods suitable for the preparation of compounds according to the invention in which the sulfur atom of the 4,4-difluorobut-3-enylthio substituent of the corresponding unoxidised compound is oxidised to sulfoxide (sulfinyl) or sulfone (sulfonyl).

Method A

Using potassium peroxymonosulfate as oxidant
Preparation of 5-chloro-2-(4,4-difluorobut-3-enylsulfonyl) thiazole (Compound VII.26)

A stirred solution of Compound VII.24 (4.83 g) in methanol (50 cm³) at 8° C. was treated dropwise with potassium peroxymonosulfate (27.0 g) in water (100 cm³) with cooling over 0.25 hours, and further methanol (50 cm³) added. The reaction was stirred for 18 hours at ambient temperature, the insolubles filtered from solution, the filtrate extracted with dichloromethane (4×50 cm³) and dried (MgSO$_4$). The solvent was removed under reduced pressure and the residue fractionated by chromatography (silica; eluant hexane:ethyl acetate 4:1 by volume) to give Compound VII.26 (3.91 g). M(NH4)$^4$=291; $^1$H NMR: δ 2.60(2H,m); 3.50(2H,t); 4.25 (1H,m); 7.85(1H,s); (oil).

Method B

Using monomagnesium peroxyphthalic acid
Preparation of 5-bromo-2-(4,4-difluorobut-3-enylsulfinyl) thiazole (Compound VII.15)

Compound VII.14 (1.50 g) was dissolved in dichloromethane (10 cm³) and treated with monomagnesium peroxyphthalic acid hexahydrate (1.6 g, 80% peracid) and water (15 cm³). The mixture was stirred at ambient temperature for 1 hour, diluted with dichloromethane (90 cm³) and the organic phase washed with aqueous sodium hydrogen carbonate and water. The organic phase was dried (MgSO$_4$), evaporated under reduced pressure and the residue fractionated by chromatography (silica; eluant hexane:ethyl acetate 10:1 by volume) to give Compound VII.15 (1.0 g). M(NH4)$^{30}$ =321; $^1$H NMR: δ 2.38 (1H,m); 2.60(1H,m); 3.20(2H,m); 4.20(1H,m); 7.85(1H,s); (oil).

The following compounds according to the invention were prepared from the corresponding thioethers using the above procedure, Method B.

(i) 2-(4,4-difluorobut-3-enylsulfinyl)thiazole (Compound VII.2). MH$^+$=224; $^1$H NMR: δ 2.36(1H,m); 2.50–2.70 (1H,m); 3.20(2H,m); 4.22(1H,m); 7.67(1H,d); 7.98 (1H,d); (oil) from Compound VII.1 and one equivalent of oxidant.

(ii) 2-(4,4-difluorobut-3-enylsulfonyl)thiazole (Compound VII.3). MH$^+$=240; $^1$H NMR: δ 2.55(2H, m); 3.45(2H,t); 4.24(1H,m); 7.78(1H,d); 8.08(1H,d); (oil) from Compound VII.1 and two equivalents of oxidant.

(iii) 5-bromo-2-(4,4-difluorobut-3-enylsulfonyl)thiazole (Compound VII.16). M(NH4)$^+$=335; $^1$H NMR: δ 2.58 (2H,m); 3.46(2H,t); 4.25(1H,m); 7.96(1H,s); (oil) from Compound VII.14 and two equivalents of oxidant.

(iv) 2-(4,4-difluorobut-3-enylsulfinyl)-5-methylthiazole (Compound VII.22). $^1$H NMR: δ 2.38(1H,m); 2.50–265(4H,m); 3.15(1H,m); 4.23(1H,m); 7.60(1H, q); (oil) from Compound VII.21 and one equivalent of oxidant (v) 2-(4,4-difluorobut-3-enylsulfonyl)-5-methylthiazole (Compound VII.23). $^1$H NMR: δ 2.55(2H,m); 2.60(3H, s); 3.45(2H,t); 4.25(1H,m); 7.73(1H,q); (oil) from Compound VII.21 and two equivalents of oxidant.

(vi) 5-chloro-2-(4,4-difluorobut-3-enylsulfinyl)thiazole (Compound VII.25). M(NH4)$^+$=275; $^1$H NMR: δ 2.38 (1H,m); 2.60(1H,m); 3.18(2H,m); 4.25(1H,m); 7.74 (1H,s); (oil) from Compound VII.24 and one equivalent of oxidant.

(vii) 5-(4,4-difluorobut-3-enylsulfinyl)thiazole (Compound VII.83). $^1$H NMR: δ 2.50(2H,m); 3.05(1H, m); 3.20(1H,m); 4.28(1H,m); 8.20(1H,s); 9.12(1H,s); (oil) from Compound VII.82 and one equivalent of oxidant.

(viii) 5-(4,4-difluorobut-3-enylsulfonyl)thiazole (Compound VII.84). $^1$H NMR: δ 2.50(2H,m); 3.30(2H, m); 4.25(1H,m); 8.20(1H,s); 9.12(1H,s); (oil) from Compound VII.82 and two equivalents of oxidant.

(ix) 2-chloro-5-(4,4-difluorobut-3-enylsulfinyl)thiazole (Compound VII.115). $^1$H NMR: δ 2.50(2H,m); 3.05 (1H,m); 3.20(1H,m); 4.28(1H,m); 7.85(1H,s); (oil) from Compound VII.114 and one equivalent of oxidant.

(x) 2-chloro-5-(4,4-difluorobut-3-enylsulfonyl)thiazole (Compound VII.116). $^1$H NMR: δ 2.52(2H,m); 3.30 (2H,m); 4.28(1H,m); 8.08(1H,s); (oil) from Compound VII.114 and two equivalents of oxidant.

Method C

Using 3-chloroperbenzoic acid

The following compounds according to the invention were prepared from the corresponding thioethers using the above procedure, Method B, but with 3-chloroperbenzoic acid in place of monomagnesium peroxyphthalic acid hexahydrate.

(xi) ethyl 2-(4,4-difluorobut-3-enylsulfonyl)thiazole-4-carboxylate (Compound VII.9). M$^+$=311; $^1$H NMR: δ 1.43(3H,t); 2.60(2H,m); 3.56(2H,t); 4.28(1H,m); 4.48 (2H,q); 8.50(1H,s); (mp 64°–65° C.) from Compound VII.8 and two equivalents of oxidant.

(xii) ethyl 5-bromo-2-(4,4-difluorobut-3-enylsulfonyl) thiazole-4-carboxylate (Compound VII.12). M$^+$=389; $^1$H NMR: δ 1.43(3H,t); 2.60(2H,m); 3.56(2H,t); 4.28 (1H,m); 4.48(2H,q); (mp 72°–73° C.) from Compound VII.11 and two equivalents of oxidant.

(xiii) 5-chloro-2-(4,4-difluorobut-3-enylsulfonyl)-4-methylthiazole (Compound VII.28). $^1$H NMR: δ 2.55 (2H,m); 2.45(3H,s); 3.40(2H,t); 4.25(1H,m); (oil) from Compound VII.27 and two equivalents of oxidant.

(xiv) methyl 2-(4,4-difluorobut-3-enylsulfonyl)-4-methylthiazole-5-carboxylate (Compound VII.43). $^1$H NMR: δ 2.60(2H,m); 2.85(3H,s); 3.50(2H,t); 3.95(3H, s); 4.25(1H,m); (oil) from Compound VII.41 and two equivalents of oxidant.

(xv) 2-(4,4-difluorobut-3-enylsulfonyl)-4-methylthiazole-5-sulfonyl fluoride (Compound VII.53). $^1$H NMR: δ 2.60(2H,m); 2.85(3H,s); 3.55(2H, t); 4.28(1H,m); (mp 67° C.) from Compound VII.52 and two equivalents of oxidant.

EXAMPLE VIII.1

This Example illustrates a preparation of 2-(4,4-difluorobut-3-enylthio)-1-methylimidazole (Compound VIII.5).

To a solution of 2-mercapto-1-methylimidazole (9.78 g) in acetone (300 cm$^3$) was added potassium carbonate (14.2 g) and 4-bromo-1,1-difluorobut-1-ene (16.12 g) as a solution in acetone (100 cm$^3$). The mixture was heated at reflux for 18 hours and allowed to cool. Inorganic solids were removed by filtering the reaction mixture through a plug of sorbsil-C30 silica, washing with ethyl acetate. The filtrate was evaporated under reduced pressure to give crude Compound VIII.5 (17.8 g), which was suitable for further reaction (see Example VIII.7). A portion 1 g) was purified by chromatography on sorbsil C-30, eluting with ethyl acetate:hexane 3:7, and gave pure Compound VIII.5 (0.776 g). $^1$H NMR: δ 2.3–2.4(2H,m); 3.05–3.15(2H,t); 3.60(3H,s); 4.15–4.35(1H, m); 6.95(1H,s); 7.05(1H,s); (oil).

The following compounds according to the invention were prepared by the above procedure, using the appropriate mercapto imidazole:

(i) 2-(4,4-difluorobut-3-enylthio)-1-phenylimidazole (Compound VIII.3). M$^+$=266; $^1$H NMR: δ 2.3–2.4(2H, m); 3.1–3,15(2H,t); 4.1–4.25(1H,m); 7.1–7.2(2H,m); 7.3–7.55(5H,m); (oil).

(ii) 2-(4,4-difluorobut-3-enylthio)-1-ethylimidazole (Compound VIII.10). M$^+$=218; $^1$H NMR: δ 1.4(3H,t); 2.3–2.4(2H,m); 3.15(2H,t); 4.0(2H,q); 4.2–4.35(1H, m); 6.95(1H,s); 7.1(1H,s); (oil).

(iii) 2-(4,4-difluorobut-3-enylthio)-4-ethyl-5-methylimidazole (Compound VIII.27). M$^+$=232; $^1$H NMR: δ 1.15(3H,t); 2.15(3H,s); 2.35–2.45(2H,m); 2.5–2.6(2H,q); 2.95(2H,t); 4.1–4.3(1H,m); (m.p. 54°–56° C.).

(iv) 2-(4,4-difluorobut-3-enylthio)-4-methylimidazole (Compound VIII.58). M$^+$=204; $^1$H NMR: δ 2.25–2.35 (5H,m); 3.0(2H,t); 4.15–4.3(1H,m); 6.75(1H,s); (oil).

(v) 2-(4,4-difluorobut-3-enylthio)-4-ethoxycarbonylimidazole (Compound VIII.64). M$^+$=262; $^1$H NMR: δ 1.3–1.35(3H,t); 2.25–2.35(2H, m); 3.05–3.15(2H,t); 4.1–4.25(1H,m); 4.3–4.4(2H,q); 7.8(1H,br s); (mp 57.8°–61° C.).

(vi) 3-(4,4-difluorobut-3-enylthio)imidazo[1,5a]-pyridine (Compound VIII.151). $^1$H NMR: δ 2.30 (2H,m); 3.00 (2H,t); 4.20(1H,m); 6.65(1H,m); 6.80(1H,m); 7.45(1H, dt); 7.55(1H,s); 8.15(1H,dd); (oil) from 2,3-dihydroimidazo-[1,5a]-pyridine-3-thione.

EXAMPLE VIII.2

This Example illustrates a preparation of 2-(4,4-difluorobut-3-enylthio)-imidazole (Compound VIII.1) and 1-(4,4-difluorobut-3-enyl)-2-(4,4-difluorobut-3-enylthio) imidazole (Compound VIII.8) as a mixture of products separable by chromatography.

To a solution of 2-mercapto-imidazole (10.01 g) in acetone (400 cm$^3$) was added potassium carbonate (20.73 g) and 4-bromo-1,1-difluorobut-1-ene (18.79 g). The mixture was heated at reflux for 18 hours and allowed to cool. Inorganic solids were removed by filtering the reaction mixture through a plug of sorbsil-C30 silica, washing with ethyl acetate. The filtrate was evaporated under reduced pressure to give a pale brown oil (19.2 g) which was chromatographed on silica, eluting with 15% ethyl acetate in hexane, progressing to 50% ethyl acetate in hexane. Two main fractions were obtained, the first of which (7.4 g) was shown by tlc to contain two products. The second fraction (10.75 g) obtained as a white solid, was shown to be pure Compound VIII.1. The first fraction was subjected to further chromatography as before to give Compound VIII.8 (1.61 g); M$^+$=280; $^1$H NMR: δ 2.3–2.45(4H,m); 3.1–3.15(2H,t); 3.9–4.0(2H,t); 4.05–4.3(2H,m); 6.95(1H,s); 7.05(1H,s); (oil) and Compound VIII.1 (5.31 g). This sample of Compound VIII.1 was recrystallised from ethyl acetate and hexane to provide 4.2 g which had M$^+$=190; $^1$H NMR: δ 2.3–2.4(2H,m); 3.0–3.1(2H,t); 4.15–4.3(1H,m); 7.0–7.1(2H, br s); 9.2(1H,br s); (m.p. 58.6°–59.6° C.).

EXAMPLE VIII.3

This Example illustrates a preparation of 2-(4,4-difluorobut-3-enylthio)-4-phenylimidazole (Compound VIII.19).

Phenacyl bromide (1.611 g) in chloroform (7 cm$^3$) was added to 4,4-difluorobut-3-enylisothiouronium hydrobromide (2 g) in 84% ethanol/water (20 cm$^3$) and sodium bicarbonate (2.72 g) was slowly added with stirring. The resultant yellow suspension was heated under reflux for 3 hours. The mixture was cooled and solvent was removed by evaporation under reduced pressure. The residue was washed twice with warm water (2×20 cm$^3$) which was decanted off to remove inorganic material. The crude product so obtained was purified by chromatography on silica, eluting with 20% ethyl acetate in hexane, and product-containing fractions were recolumned using 5% ethyl acetate in toluene. This gave Compound VIII.19 (0.78 g); M$^+$=266; $^1$H NMR: δ 2.3–2.4(2H,m); 3.05–3.1(2H,t); 4.15–4.3(1H,m); 7.2–7.4(4H,m); 7.6–7.75(2H,br s) free of a byproduct, the corresponding N-jphenacyl derivative.

The following compounds according to the invention were prepared by the above procedure:

(i) 2-(4,4-difluorobut-3-enylthio)-1-methyl-4-phenylimidazole (Compound VIII.22). M$^+$=280; $^1$H NMR: δ 2.35–2.45(2H,m); 3.10–3.18(2H,t); 3.65(3H, s); 4.19–4.35(1H,m); 7.2–7.25(2H,m); 7.33–7.38(2H, t); 7.72–7.78(2H,d) (oil) using N-methyl 4,4-difluorobut-3-enylisothiouronium hydrobromide.

(ii) 2-(4,4-difluorobut-3-enylthio)-5-ethyl-4-methoxycarbonyl-1-methylimidazole (Compound VIII.68). M$^+$=290; $^1$H NMR: δ 1.2–1.25(3H,t); 2.35–2.45(2H,m); 2.8–2.9(2H,q); 3.2–3.25(2H,t); 378 (3H,s); 3.85(3H,s); 4.16–4.32(1H,m); (oil) using N-methyl 4,4-difluorobut-3-enylisothiouronium hydrobromide and methyl 2-bromo-3-oxopentanoate.

EXAMPLE VIII.4

This Example illustrates a preparation of 2-(4,4-difluorobut-3-enylthio)-4,5-dimethylimidazole (Compound VIII.29).

Potassium carbonate (18.9 g) and 4,4-difluorobut-3-enylisothiouronium hydrobromide (16.9 g) were added to a solution of 3-bromobutan-2-one (10.32 g) in dimethyl formamide (100 cm$^3$) and the mixture was stirred at 60° C. for 90 minutes, then at 80° C. for 30 minutes. The resulting mixture was cooled, water (100 cm$^3$) added, and the product extracted into diethyl ether. The combined organic phases were washed with water and brine and dried (MgSO$_4$). Concentration by evaporation under reduced pressure gave a pale orange liquid (12.2 g), which was purified by chromatography on sorbsil C30 silica, eluting with 30% ethyl acetate in hexane. Three components were obtained. The first eluted was identified as 3-(4,4-difluorobut-3-enylthio) butan-2-one (0.68 g); M$^+$=194; $^1$H NMR: δ 1.4(3H,d); 2.15–2.3(5H,m); 2.45(2H,t); 3.3–3.4(1H,q); 4.1–4.35(1H, m). The second compound eluted was the desired Compound VIII.29 (4.1 g); M$^+$=218; $^1$H NMR: δ 2.15(6H,s) 2.25–2.35(2H,m); 2.9–3.0(2H,t); 4.15–4.3(1H,m); (mp 81.4°–84.4° C.). The third compound eluted was identified as the product of a further N-alkylation of Compound VIII.29 with additional 3-bromobutan-2-one, namely N-(1-methylpropan-2-one) 2-(4,4-difluorobut-3-enylthio)-4,5-dimethylimidazole (1.11 g); M$^+$=217; $^1$H NMR: δ 1.55(3H, s); 2.0(3H,s); 2.05(3H,s); 2.15(3H,s); 2.3–2.4(2H,m); 3.0–3.05(2H,t); 4.15–4.35(1H,m); 5.0–5.1(1H,m); (oil).

EXAMPLE VIII.5

This Example illustrates a preparation of 2-(4,4-difluorobut-3-enylthio)-1-propylimidazole (Compound VIII.12) from the corresponding N-H imidazole, Compound VIII.1, by alkylation using propyl iodide.

Compound VIII.1 (2 g) was added in portions (effervescence) to a suspension of sodium hydride (0.736 g of a 60% solid in oil) in dimethyl formamide (20 cm$^3$) under a nitrogen atmosphere. After stirring the mixture for 30 minutes, n-propyl iodide (2.68 g) was added and the reaction mixture was stirred at the ambient temperature for 18 hours. Water and diethyl ether were then added and the product extracted into ether. The combined organic phases were washed with water and saturated brine and dried (MgSO$_4$). After filtration, the solvent was removed by evaporation under reduced pressure to give crude product (2.7 g) which was purified by chromatography on sorbsil C-30, eluting with ethyl acetate:hexane 3:7 and gave Compound VIII.12 (2.15 g); M$^+$=232; $^1$H NMR: δ 0.9–0.95(3H,t); 1.75–1.85 (2H,m); 2.3–2.45(2H,m); 3.1–3.15(2H,t); 3.85–3.95(2H,t); 4.15–4.35(1H,m); 6.9(1H,s); 7.1(1H,s); (oil).

The following compounds according to the invention were prepared by the above procedure, using the appropriate alkylating agent and starting N-H imidazole:

(i) 2-(4,4-difluorobut-3-enylthio)-1-(1-methylethyl)-imidazole (Compound VIII.14). M$^+$=232; $^1$H NMR: δ 1.4(6H,d); 2.3–2.4(2H,m); 3.1–3.15(2H,t); 4.15–4.3 (1H,m); 4.5–4.6(1H,m); 7.0(1H,s); 7.1(1H,s); (oil) from Compound VIII.1.

(ii) 2-(4,4-difluorobut-3-enylthio)-1,4,5-trimethylimidazole (Compound VIII.31). $^1$H NMR: δ 2.15(6H,two s); 2.25–2.35(2H,m); 2.95(2H,t); 3.5(3H, s); 4.15–4.3(1H,m); (oil) from Compound VIII.29.

(iii) 1-ethyl-2-(4,4-difluorobut-3-enylthio)-4,5-dimethylimidazole (Compound VIII.33). $^1$H NMR: δ 1.25(3H,t); 2.15(6H,br s); 2.3–2.4(2H,m); 3.0(2H,t); 3.9–3.95(2H,q); 4.15–4.3(1H,m); (oil) from Compound VIII.29.

(iv) A mixture of 2-(4,4-difluorobut-3-enylthio)-1,5-dimethylimidazole (Compound VIII.35) and 2-(4,4-difluorobut-3-enylthio)-1,4-dimethylimidazole (Compound VIII.60); $^1$H NMR: δ 2.15(3H,s); 2.3–2.4 (2H,m); 3.0–3.05)2H,t); 3.5 and 3.55(3H,two s); 4.15–4.3(1H,m); 6.65 and 6.80(1H,two s) from Compound VIII.58.

(v) A mixture of 2-(4,4-difluorobut-3-enylthio)-5-methyl-1-(1-methylethyl)-imidazole (Compound VIII.37) and 2-(4,4-difluorobut-3-enylthio)-4-methyl-1-(1-methylethyl)-imidazole (Compound VIII.62); shown to be mainly the latter isomer, $^1$H NMR: δ 1.35(6H,d); 2.2(3H,s); 2.3–2.4(2H,m); 3.05(2H,t); 4.15–4.3(1H,m); 4.5–4.6(1H,m); 6.70(1H,s) from Compound VIII.58.

(vi) 2-(4,4-difluorobut-3-enylthio)-5-ethoxycarbonyl-1-methylimidazole (Compound VIII.52). M$^+$=276; $^1$H NMR: δ 1.32–140(3H,t); 2.37–2.47(2H,m); 3.2–3.3 (2H,t); 3.82(3H,s); 4.17–4.32(1H,m); 4.25–4.35(2H,q);

7.7(1H,s); (oil) from Compound VIII.64. This reaction produced a chromatographically separable mixture of Compound VIII.52 and VIII.65, the former eluting first.

(vii) 2-(4,4-difluorobut-3-enylthio)-4-ethoxycarbonyl-1-methylimidazole (Compound VIII.65). M$^+$=276; $^1$H NMR: δ 1.35–1.40(3H,t); 2.35–2.42(2H,m); 3.20–3.27 (2H,t); 3.63(3H,s); 4.15–4.30(1H,m); 4.3–4.4(2H,q); 7.60(1H,s); (oil) from Compound VIII.64.

EXAMPLE VIII.6

This example illustrates a preparation of 2-(4,4-difluorobut-3-enylthio)-N-(methane sulfonyl)imidazole (Compound VIII.18).

A solution of Compound VIII.1 (0.49 g) in dry tetrahydrofuran (3 cm$^3$) was added dropwise to a suspension of sodium hydride (55% in oil, 0.12 g, washed with hexane prior to use) in dry tetrahydrofuran (5 cm$^3$) cooled in a cold water bath. The reaction mixture was allowed to stir at the ambient temperature for 2 hours and then methanesulfonyl-chloride (0.3 g) was added and the reaction stirred for a further 16 hours. The reaction mixture was poured into ethyl acetate/water and the layers separated. The aqueous layer was extracted with ethyl acetate and the combined organic phases were dried (MgSO$_4$), filtered and evaporated under reduced pressure to give a yellow oil. Purification by column chromatography on silica gel using 3:7 ethyl acetate:hexane gave Compound VIII.18 (0.31 g). $^1$H NMR: δ 2.40–2.50 (2H,m); 3.30 (2H,t); 3.30(3H,s); 4.25(1H,m); 7.05(1H,d); 7.35(1H,d); (oil).

EXAMPLE VIII.7

This Example illustrates a method suitable for the preparation of compounds according to the invention in which the sulfur atom of the 4,4-difluorobut-3-enylthio substituent of the corresponding unoxidised compound is oxidised to sulfoxide (sulfinyl) or sulfone (sulfonyl).

Preparation of Compound VIII.7 from Compound VIII.5

Compound VIII.5 (18.1 g) was cooled to 0° C. in dichloromethane (400 cm$^3$) and 3-chloroperbenzoic acid (61.2 g of water-wet solid, 2 equiv.) was added. The mixture was stirred at the ambient temperature for 18 hours and then poured into saturated aqueous sodium bicarbonate. The product was extracted into dichloromethane, the organic phase washed with water and saturated brine and dried (MgSO$_4$). Evaporation of solvent under reduced pressure gave crude Compound VIII.7 which was chromatographed on silica, eluting with 15% ethyl acetate in hexane, progressing to 50% ethyl acetate in hexane, to give pure Compound VIII.7. $^1$H NMR: δ 2.55–2.6(2H,m); 3.5–3.55 (2H,t); 4.0(3H,s); 4.15–4.3(1H,m); 7.0(1H,s); 7.15(1H,s); (oil).

The following compounds according to the invention were prepared by the above procedure of Example VIII., using two equivalents of oxidant unless otherwise specified, with the appropriate starting thioether:

(i) 2-(4,4-diflurobut-3-enylsulfonyl)-imidazole (Compound VIII.2). MH$^+$=223; $^1$H NMR: δ 2.4–2.6 (2H,m); 3.4–3.45(2H,t); 4.1–4.3(1H,m); 7.3–7.4(3H,br s); (white solid, m.p. 113°–114° C.).

(ii) 2-(4,4-difluorobut-3-enylsulfonyl)-1-phenylimidazole (Compound VIII.4). M$^+$=298; $^1$H NMR: δ 2.45–2.55 (2H,m); 3.45–3.55(2H,t); 4.15–4.3(1H,m); 7.2(1H,d); 7.25(1H,d); 7.45–7.55(5H,m); (oil).

(iii) 1-(4,4-difluorobut-3-enyl)-2-(4,4-difluorobut-3-enylsulfonyl)-imidazole (Compound VIII.9). M$^+$=312; $^1$H NMR: δ 2.5–2.65(4H,m); 3.5–3.6(2H,t); 4.1–4.35 (2H,m); 4.4–4.45(2H,t); 7.05(1H,s); 7.15(1H,s); (oil).

(iv) 2-(4,4-difluorobut-3-enylsulfonyl)-1-ethylimidazole (Compound VIII.11). M$^+$=250; $^1$H NMR: δ 1.5(3H,t); 2.5–2.65(2H,m); 3.5–3.6(2H,t); 4.15–4.35(1H,m); 4.4–4.45(2H,q); 7.05(1H,s); 7.15(1H,s); (oil).

(v) 2-(4,4-difluorobut-3-enylsulfonyl)-1-propylimidazole (Compound VIII.13). MH$^+$=265; $^1$H NMR: δ 0.9–1.0 (3H,t); 1.8–2.0(2H,m); 2.5–2.6(2H,m); 3.5–3.6(2H,t); 4.15–4.35(3H,m); 7.05(1H,s); (oil).

(vi) 2-(4,4-difluorobut-3-enylsulfonyl)-1-(1-methylethyl)-imidazole (Compound VIII.15). M$^+$=264; $^1$H NMR: δ 1.5(6H,d); 2.55–2.65(2H,m); 3.5–3.6(2H, m); 4.15–4.35(1H,m); 5.15–5.35(1H,m); 7.15(2H,br); (oil).

(vii) 2-(4,4-difluorobut-3-enylsulfinyl)-4-phenylimidazole (Compound VIII.20). M$^+$=282; $^1$H NMR: δ 2.35–2.65(2H,m); 3.25–3.4(2H,t); 4.15–4.3 (1H,m); 7.25–7.5(4H,m); 7.6–7.8(2H,m); (oil) using 1.5 equivalents of oxidant.

(viii) 2-(4,4-difluorobut-3-enylsulfonyl)-4-phenylimidazole (Compound VIII.21). M$^+$=298; $^1$H NMR: δ 2.45–2.6(2H,m); 3.4–3.5(2H,t); 4.1–4.28(1H, m); 7.3–7.55(4H,m); 7.7–7.75(2H,d); (m.p. 109.6°–110.4° C.) using 1.5 equivalents of oxidant.

(ix) 2-(4,4-difluorobut-3-enylsulfinyl)-1-methyl-4-phenylimidazole (Compound VIII.23). M$^+$=296; $^1$H NMR: δ 2.5–2.65(2H,m); 3.4–3.65(2H,m); 4.0(3H,s); 4.25–4.4(1H,m); 7.25–7.45(4H,m); 7.7–7.75(2H,dd); (m.p. 106°–106.6° C.) using 1.5 equivalents of oxidant.

(x) 2-(4,4-difluorobut-3-enylsulfonyl)-1-methyl-4-phenylimidazole (Compound VIII.24). M$^+$=312; $^1$H NMR: δ2.6–2.7(2H,m); 3.58–3.65(2H,t); 4.02(3H,s); 4.2–4.35(1H,m); 7.25–7.42(4H,m); 7.7–7.75(2H,dd); (m.p. 78.6–79.6° C.) using 1.5 equivalents of oxidant.

(xi) 2-(4,4-difluorobut-3-enylsulfonyl)-4-ethyl-5-methylimidazole (compound VIII.28). M$^+$=264; $^1$H NMR: δ1.15–1.3(3H,q); 2.25(3H,two s (tautomers)); 2.45–2.7(4H,m); 3.35–3.45(2H,t); 4.1–4.3(1H,m); 11.3 (1H,br s); (oil).

(xii) 2-(4,4-difluorobut-3-enylsulfonyl)-4,5-dimethylimidazole (Compound VIII.30). M$^+$=250; $^1$H NMR: δ2.25(6H,two s); 2.45–2.55(2H,m); 3.35(2H,t); 4.1–4.25(1H,m); 10.3–10.6(1H,br s); (mp 113.4–114.6° C.).

(xiii) 2-(4,4-difluorobut-3-enylsulfonyl)-1,4,5-trimethylimidazole (Compound VIII.32). M$^+$=264; $^1$H NMR: δ2.2(6H,br s); 2.5–2.6(2H,m); 3.4–3.5(2H,t); 3.85 (3H,s); 4.15–4.3(1H,m); (oil).

(xiv) 1-ethyl-2-(4,4-difluorobut-3-enylsulfonyl)-4,5-dimethylimidazole (Compound VIII.34). M$^+$=278; $^1$H NMR: δ1.4(3H,t); 2.15(6H,br s); 2.5–2.6(2H,m); 3.5(2H, t); 4.15–4.3(1H,m); (oil).

(xv) A mixture of 2-(4,4-difluorobut-3-enylsulfonyl)-1,5-dimethylimidazole (Compound VIII.36) and 2-(4,4-difluorobut-3-enylsulfonyl)-1,4-dimethylimidazole (Compound VIII.61); $^1$H NMR: δ2.20(3H,s); 2.25(3H,s); 2.5–2.6(4H,m); 3.45–3.55(4H,m); 3.85(3H,s); 3.95(3H, s); 4.15–4.3(2H,m); 6.75(1H,s); 6.95(1H,s); from the mixture of Compounds VIII.35 and VIII.60 prepared in Example VIII.5(iv) above.

(xvi) An 18:82 mixture of 2-(4,4-difluorobut-3-enylsulfonyl)-5-methyl-1-(1-methylethyl)-imidazole (Compound VIII.38); $^1$H NMR: δ1.55(6H,d); 2.4(3H,s);

2.55–2.65(2H,m); 3.6(2H,t); 4.15–4.35(1H,m); 5.15–5.30 (1H,m); 6.85(1H,s); and 2-(4,4-difluorobut-3-enylsulfonyl)-4-methyl-1-(1-methylethyl)-imidazole (Compound VIII.63); $^1$H NMR: δ1.45(6H,d); 2.25(3H,s); 2.55–2.65(2H,m); 3.55(2H,t); 4.15–4.35(1H,m); 5.15–5.30 (1H,m); 6.90(1H,s); from the mixture of Compounds VIII.37 and VIII.62 prepared in Example VIII.5 (v) above.

(xvii) 2-(4,4-difluorobut-3-enylsulfonyl)-5-ethoxycarbonyl-1-methylimidazole (Compound VIII.53). M$^+$=308: $^1$H NMR: δ1.37–1.42(3H,t); 2.55–2.67(2H,m); 3.6–3.65(2H, t); 4.2–4.35 (1H,m); 4.25(3H,s); 4.32–4.4(2H,q); 7.7(1H, s); (oil).

(xviii) 2-(4,4-difluorobut-3-enylsulfonyl)-4-methylimidazole (Compound VIII.59). M$^+$=236; $^1$H NMR: δ2.3–2.4(3H,br); 2.45–2.55(2H,m); 3.4(2H,t); 4.2–4.4(1H,m); 7.0(1H,br); (oil).

(xix) 2-(4,4-difluorobut-3-enylsulfonyl)-4-ethoxycarbonyl-1-methylimidazole (Compound VIII.66). M$^+$=292; $^1$H NMR: δ1.35–1.4(3H,t); 2.49–2.7(2H,m); 3.35–3.6(2H, m); 4.02(3H,s); 4.2–4.38(1H,m); 4.35–4.42(2H,q); 7.67 (1H,s); (oil) using 1.5 equivalents of oxidant.

(xx) 2-(4,4-difluorobut-3-enylsulfonyl)-4-ethoxycarbonyl-1-methylimidazole (Compound VIII.67). M$^+$=308; $^1$H NMR: δ1.35–1.4(3H,t); 2.55–2.65(2H,m); 3.65–3.70(2H, t); 4.02(3H,s); 4.2–4.38(1H,m); 4.35–4.42(2H,q); 7.65 (1H,s); (oil) using 1.5 equivalents of oxidant.

(xxi) 3-(4,4-difluorobut-3-enylsulfonyl)imidazo-[1,5a]-pyridine (Compound VIII.152). M$^+$=272; $^1$H NMR: δ2.50 (2H,m); 3.50(2H,t); 4.15(1H,m); 6.90(1H,m); 7.10(1H, m); 7.20(1H,s); 7.65(1H,m); 8.95(1H,dd); (oil).

EXAMPLE IX.1

This Example illustrates a preparation of 5-(4,4-difluorobut-3-enylthio)-1,3-dimethyl-4-nitropyrazole (Compound IX.82).

4,4-Difluorobut-3-enylisothiouronium hydrobromide (2.46 g) was stirred at ambient temperature with aqueous sodium hydroxide (1.2 g in 12 cm$^3$ water) for 0.3 hours. 5-Chloro-1,3-dimethyl-4-nitropyrazole (1.76 g) in dichloromethane (12 cm$^3$) containing tetra-n-butyl ammonium bromide (0.01 g; catalyst) was added at ambient temperature and the reaction mixture stirred for 18 hours under an atmosphere of nitrogen. The reaction was diluted with water (100 cm$^3$) and the product extracted indo dichloromethane (100 cm$^3$). The organic phases were combined, washed with water, dried (MgSO$_4$) and evaporated under reduced pressure to give a pale yellow liquid (2.6 g). A sample (0.9 g) was fractionated using chromatography (silica; hexane:ethyl acetate 10:1 by volume) to give compound IX.82 (0.78 g). M$^+$=263; $^1$H NMR: δ2.25(2H,m); 2.55(3H,s); 3.08(2H,t); 3.94(3H,s); 4.20(1H,m); (oil).

EXAMPLE IX.2

This example illustrates a preparation of 5-(4,4-difluorobut-3-enylsulfonyl)-1,3-dimethyl-4-nitropyrazole (Compound IX.84).

3-Chloroperbenzoic acid (1.74 g, of 50% by weight solid) was added to a solution of Compound IX.82 (0.526 g) in dichloromethane (10 cm$^3$) and the reaction was stirred at ambient temperature for 3 days. The reaction was diluted with dichloromethane (100 cm$^3$), washed with aqueous sodium hydrogen carbonate and then water, dried (MgSO$_4$) and evaporated under reduced pressure to give an oil solid. The crude product was fractionated using chromatography to give compound IX.84 (0.15 g). $^1$H NMR: δ2.52(3H,m); 2.60(2H,m); 3.74(2H,t); 4.20(3H,s); 4.25(1H,m); (gum).

EXAMPLE IX.3

This Example illustrates a 3-step preparation of 5-4,4-difluorobut-3-enylthio)-1,3-dimethyl-4-iodopyrazole (Compound IX.61)

Step 1: Preparation of 4-amino-5-(4,4-difluorobut-3-enylthio)-1,3-dimethylpyrazole Compound IX.82 (1.0 g) was dissolved in propan-2-ol (10 cm$^3$) containing water (2 cm$^3$) and concentrated hydrochloric acid (catalyst, 0.1 cm$^3$) and treated with reduced iron powder (1.0 g). The mixture was stirred and heated under reflux for 3 hours, cooled, neutralised with solid sodium hydrogen carbonate and filtered through keiselgel. The insolubles were washed with propan-2-ol, and the filtrate evaporated under reduced pressure to give the amino pyrazole intermediate as a red-brown oil, (1.0 g). M$^+$=233.

Step 2:

The produce from Step 1 (4.6 g) was dissolved in dichloromethane (25 cm$^3$) and added to a stirred solution of boron trifluoride diethyl etherate (4.26 g) in dry dichloromethane (25 cm$^3$) at −15° C. Tert. butyl nitrite in dichloromethane (10 cm$^3$) was added dropwise to the mixture. The reaction was allowed to warm to 5° C. for 0.3 hours, diluted with hexane and the required diazonium tetrafluoroborate salt was filtered from solution as a brown solid (6.7 g).

Step 3: Compound IX.61

The product from Step 1 (1.33 g) was added in portions to a stirred solution of potassium iodide (1.7 g) in water (5 cm$^3$) at 35° C. The reaction mixture evolved gas during the process and gave a red-brown oil. After 1 hour at 35° C. the mixture was cooled, diluted with water, extracted with diethyl ether (100 cm$^3$), the organic phase washed successively with aqueous sodium metabisulfite then water and dried (MgSO$_4$). The solvent was removed under reduced pressure and the residual oil fractionated by chromatography (silica; hexane:ethyl acetate 10:1 by volume) to give Copound IX.61 as a brown oil (0.2 g). M$^+$=344.

EXAMPLE IX.4

The Example illustrates a preparation of 5-(4,4-difluorobut-3-enylthio)-1,3-dimethyl-pyrazole (Compound IX.55).

The diazonium salt from Example IX.3, Step 2 (2.0 g) was stirred in methanol (20 cm$^3$) at 0° C. and sodium borohydride (powder, 0.25 g) was added in portions. Gas was evolved and the solution changed from colourless to orange-brown. The mixture was allowed to warm to 15° C. over 0.5 hours, stored at ambient temperature for 18 hours, diluted with water, extracted with diethyl ether, dried (MgSO$_4$) and evaporated under reduced pressure to give a red-brown liquid. The liquid was fractionated using chromatography (silica; hexane:diethyl ether 1:1 by volume) to give Compound IX.55 (0.42 g). M$^+$=218; $^1$H NMR: δ2.20–2.30(5H, m); 274(2H,m); 3.75(3H,s); 4.23(2H,m); 6.12(1H,s); (oil).

EXAMPLE IX.5

This Example illustrates a preparation of ethyl 5-(4,4-difluorobut-3-enylthio)-1-methylpyrazol-4-yl carboxylate (Compound IX.34).

Bis-(4,4-difluorobut-3-enyl)disulfide (2.90 g) and tert. butyl nitrite (1.22 g) in acetonitrile (40 cm$^3$) were heated to 60° C. under an atmosphere of nitrogen. To the stirred solution was added dropwise ethyl 5-amino-1-methylpyrazol-4-yl carboxylate (1.00 g) in acetonitrile (10 cm$^3$). On complete addition the reaction solution was heated for 2 hours at 60° C., evaporated under reduced pressure and fractionated by chromatography (silica; hexane:diethyl ether, 5:1 by volume) to give Compound IX.34 (yield 42%). M$^+$=276; $^1$H NMR: δ1.38(3H,t); 2.20(2H,m); 3.05(2H,t); 3.97(3H,s); 4.25(1H,m); 4.34(2H,q); 7.98(1H,s); (oil).

The following compounds according to the invention were prepared using the above procedure and the appropriate amino-pyrazole:

(i) 4-bromo-5-(4,4-difluorobut-3-enylthio)-1-methylpyrazole (Compound IX.31). M$^+$=282; $^1$H NMR: δ2.32(2H,m); 2.95(2H,t); 3.88(3H,s); 4.30(1H,m); 7.38 (1H,s); (oil).

(ii) 4-cyano-5-(4,4-difluorobut-3-enylthio)-1,3-dimethylpyrazole (Compound IX.75). $^1$H NMR: δ1.38 (3H,t); 2.20(2H,m); 2.38(3H,s); 3.02(2H,t); 3.97(3H,s); 4.25(1H,m); (oil).

(iii) ethyl 5-(4,4-difluorobut-3-enylthio)-1-phenylpyrazol-4-yl carboxylate (Compound IX.124). M$^+$=338; $^1$H NMR: δ1.40(3H,t); 2.05(2H,m); 2.88(2H,t); 3.97(1H,m); 4.37 (2H,q); 7.50(5H,m); 8.16(1H,s); (oil).

EXAMPLE IX.6

This example illustreates a preparationh of 4-cyano-5-(4,4-difluorobut-3-enylthio)-1,3-dimethylpyrazole (Compound IX.75).

Compound IX.73 (1.32 g) in dichloromethane (120 cm$^3$) was treated at ambient temperature with 3-chloroperbenzoic acid (3.94 g containing 50% peracid). The mixture was stirred for 18 hours, diluted with further dichloromethane and washed successively with aqueous solutions of sodium carbonate, sodium metabisulfite. Further washing with water, sodium carbonate, and water were performed before the organic phase was dried (MgSO$_4$). The solvent was evaporated under reduced pressure and the residue fractionated by chromatography (silica; hexane:diethyl ether 1:1 by volume) to give Compound IX.75 (0.47 g). M$^+$=275; $^1$H NMR: δ2.42(3H,s); 2.30(2H,m); 2.58(3H,s); 3.38(2H,t); 4.14(3H,s); 4.36(1H,m); (mp 78–81° C.).

The following compounds according to the invention were prepared by using the above procedure and the appropriate pyrazole:

(i) 4-bromo 5-(4,4-difluorobut-3-enylthio)-1-methylpyrazole (Compound IX.33). $^1$H NMR: δ2.54(2H, m); 3.35(2H,t); 4.00(3H,s); 4.27(1H,m); 7.55(1H,s); (mp 42.6–43.6° c.) from Compound IX.31.

(ii) ethyl 5-(4,4-difluorobut-3-enylsulfonyl)-1-methylpyrazole-4-carboxylate (Compound IX.36). $^1$H NMR: δ1.38(3H,t); 2.50(2H,m); 3.78(2H,t); 4.15–4.30 (1H,m); 4.36(2H,q); 7.95(1H,s); (oil) from Compound IX.34.

(iii) ethyl 5-(4,4-difluorobut-3-enylsulfonyl)-1-phenylpyrazole-4-carboxylate (Compound IX.126). $^1$H NMR: δ1.42(3H,t); 2.45(2H,m); 3.72(2H,t); 4.18(1H,m); 4.40(2H,q); 7.35–7.55(5H,m); 8.13(1H,s); (mp 62.5–63.0° C.) from Compound IX.124.

EXAMPLE IX.7

This Example illustraes a preparation of 5-(4,4-difluorobut-3-enylthio)-1-methylpyrazole-4-carboxylic acid (Compound IX.40) and propan-2-yl 5-(4,4-difluorobut-3-enylthio)-1-methylpyrazole-4-carboxylate (Compound IX.37).

Compound IX.34 (1.5 g) was dissolved in propan-2-ol (40 cm$^3$) and treated with 2M aqueous sodium hydroxide (8 cm$^3$) and stirred at ambient temperature for 18 hours. The mixture was diluted with water (100 cm$^3$), acidified with 2M aqueous hydrochloric acid and extracted with ethyl acetate (3×50 cm$^3$). The combined organic phase was dried (MgSO$_4$) and evaporated under reduced pressure to give a yellow oil which solidified on treatment with hexane/diethyl ether. The solid was filtered from solution, washed with hexane and sucked to dryness to give Compound IX.40 (0.76 g). $^1$H NMR: δ2.24(2H,m); 3.06(2H,t); 4.00(3H,s); 4.20(1H,m); 8.08(1H,s); (mp 59.4–60.0° C.).

The hexane/diethyl ether filtrate was evaporated under reduced pressure and the oil (containing (Compound IX.37 with about 10% of the ethyl ester starting material from step 1) was treated with propan-2-ol (20 cm$^3$) containing sodium methoxide (transesterification catalyst, 10 mg) and the mixture heated under reflux for 5 hours. The reaction was cooled, diluted with water, and product extracted into diethyl ether. The orgnaic phase was dried (MgSO$_4$) and evaporated under reduced pressure to give Compound IX.37 (0.1 g). MH$^+$=291; $^1$H NMR: δ1.35(6H,d); 2.22(2H,m); 3.05(2H,t); 3.97(3H,s); 4.20(1H,m); 5.20(1H, septuplet); 7.95(1H,s); (oil).

EXAMPLE IX.8

This example illustrates a preparaton of 5-(4,4-difluorobut-3-enylsulfonyl)-1-methylpyrazole-4-carboxylic acid (Compound IX.42).

Compound IX.36 (0.83 g) was dissolved in ethanol (35cm$^3$) and treated with lithium hydroxide monohydrate (0.34 g) in water (7 cm$^3$) at ambient temperature. The reaction mixture was stirred for 18 hours, the ethanol evaporated under reduced pressure, the aqueous phase acidified with 2M hydrochloric acid, and product extract into ethyl acetate. The organic phase was dried (MgSO$_4$) and solvent was removed under reduced pressure to give a gum which was triturated with diethyl ether/hexane, giving Compound IX.42 (0.43 g). M(NH4)$^+$=298; $^1$H NMR: δ2.52(2H, m); 3.72(2H,t); 4.10–4.30(3H,m); 8.05(1H,s); (mp 118.4–122.0° C.).

EXAMPLE X.1

This Example illustrates two related syntheses of mercapto-1,2,4-oxadiazoles required as intermediates for preparation of compounds of the invention. A general method for synthesis of 5-mercapto-1,2,4-oxadiazoles is by cyclisation of an amidoxime and an activated thiocarbonyl compound such as thiophosgene or 1,1-thiocarbonyldiimidazole. Use of the first of these reagents is illustrated by the prepration of 5-mercapto-3-phenyl-1,2,4-oxadiazole.

Benzonitrile (15 g), hydroxylamine hydrochloride (10 g), potassium carbonate (10 g), ethanol (150 cm$^3$) and water (15 cm$^3$) were heated to gether at reflux for 6 hours and then allowed to cool overnight. The reaction mixture was filtered and the solid residue washed with ethanol. The filtrate and washings were combined and evaporated and the resultant brown residue partitioned between ethyl acetate and water. The organic phase was separated, washed with brine and dried (MgSO$_4$). Evaporation gave a brown oil which crystallised on addition of ethyl acetate and hexane to give a grey solid (10.3 g). The solid (4.4 g) was stirred in ether (50 cm$^3$) and thiophosgene (0.55 cm$^3$) was added causing a thick white precipitate to form. The reaction was heated at reflux for 1 hour and then allowed to cool. A solution of sodium hydroxide in water (50 cm$^3$) was then added and the reaction heated for a further 4 hours, then allowed to cool to leave a yellow biphasic reaction mixture. The organic phase was separated and the aqueous layer was extracted twice with ether. The aqueous layer was acidified to pH 1 causing formation of a yellow ppt. The aqueous layer was extracted with ethyl acetate and the combined ethyl acetate layers were dried ($MgSO_4$) and evaporated to give 5-mercapto-3-phenyl-1,2,4-oxadiazole as an orange-brown solid (0.554 g), which was used without further purification. $^1$H NMR: δ7.45–7.63(3H,m); 7.70–7.90(2H,m).

Use of the alternative reagent, 1,1-thiocarbonyldiimidazole, is illustrated by the preparation of 5-mercapto-3-methoxymethyl-1,2,4-oxadiazole.

Methoxyacetonitrile (7.1 g), hydroxylamine hydrochloride (7 g), potassium carbonate (13.8 g), ethanol (90 cm$^3$) and water (9 cm$^3$) were heated together at 50° C. for 9 hours and then allowed to cool. The reaction mixture was filtered and the white solid residue washed with ethyl acetate. The filtrate and washings were combined and evaporated and the resultant residue dissolved in dichloromethane. Insoluble material was removed by filtration and the filtrate evaporated to give a viscous oil (9.2 g). The oil was added to toluene (60 cm$^3$) and dry dimethylformamide (4 cm$^3$) containing 1,1-thiocarbonyldiimidazole (5.655 g) and the mixture was stirred at the ambient temperature for 2 hours. After standing for a further 60 hours the beige solid which had formed was recovered by filtration (5.2 g obtainedk) and shown by NMR to be the uncyclised product of reaction between the hydroxy group of the amidoxime and the thiocarbonyl group. A portion of the solid (2 g) was added to a suspension of sodium hydride (0.33 g) in dry dimethylformamide (30 cm$^3$) (frothing) and the mixture was stirred at the ambient temperature for 5 hours and left to stand for 18 hours. The reaction product was poured into water and the product extracted into ethyl acetate. The combined organic phases were sepaerated, dried ($MgSO_4$) and evaporated under reduced pressure, finally at high vacuum to remove traces of dimethylformamide. The crude 5-mercapto-3-methoxymethyl-1,2,4-oxadiazole had $^1$H NMR: δ3.2(3H,s); 4.10(2H,s); 6.92–6.98(1H,br s) and was used without further purification.

EXAMPLE X.2

This Example illustraets a general process for the preparation of 5-(4,4-difluorobut-3-enylthio)-3-substituted-1,2,4-oxadiazoles using the corresponding 5-mercapto intermediate prepared for example as above. This is illustrated by the following preparation of 5-(4,4-difluorobut-3-enylthio)-3-methoxymethyl-1,2,4-oxadiazole, Compound X.26.

To a solution of 5-mercapto-3-methoxymethyl-1,2,4-oxadiazole (2.78 g) in acetone (150 cm$^3$) was added 4-bromo-1,1-difluorobut-1-ene (4.87 g) and potassium carbonate (3.15 g) and the mixture heated under reflux for 18 hours. Gc indicated that reaction was complete. Inorganic solids were removed by filtering the reaction mixture through a plug of sorbsil-C30 silica, washing with acetone. The filtrate was evaporated under reduced pressure and the yellow oily residue was chromatographed on sorbsil-C30, eluting with 5% ethyl acetate in hexane, to give Compound X.26 (1.6 g) $^1$H NMR: δ2.47–2.58(2H,m); 3.28–3.35(2H,t); 3.49(3H,s); 4.18–4.36(1H,m); 4.54(2H,s); (oil).

The following compounds according to the invention were prepared using the above procedure and the appropriate intermediates indicated:
(i) 5-(4,4-difluorobut-3-enylthio)-3-methoxymethyl-1,2,4-oxadiazole (Compound X.32). $^1$H NMR: δ2.37(3H,s); 2.45–2.55(2H,m); 3.22–3.30(2H,t); 4.16–4.35(1H,m); (oil) from 5-mercapto-3-methyl-1,2,4-oxadiazole.
(ii) 5-(4,4-difluorobut-3-enylthio)-3-phenyl-1,2,4-oxadiazole (Compound X.1). M$^+$=268; $^1$H NMR: δ2.58 (2H,m); 3.35(2H,t); 4.31(1H,m); 7.47–7.56(3H,m); 8.07(2H,d); (oil) from 5-mercapto-3-phenyl-1,2,4-oxadiazole.

EXAMPLE X.3

This Example illustrates a preparation of 5-(4,4-difluorobut-3-enylthio)-3-methoxymethyl-1,2,4-oxadiazole (Compound X.27) from Compound X.26.

Compound X.26 (0.6 g) was cooled to 0° C. in dichloromethane (50 cm$^3$) and 3-chloroperbenzoic acid (2.19 g, 2.5 equiv.) was added over a period of five minutes. The mixture was stirred at the ambient temperature for 1 hour and stood for 40 hours. The reaction mixture was poured into saturated aqueous sodium bicarbonate and the product was extracted into dichloromethane. The organic layer was washed with saturated aqueous sodium bicarbonate, water and saturated brine and dried ($MgSO_4$). Evaporation of solvent under reduced pressure gave a light brown solid which was chromatographed on silica, eluting with 10% ethyl acetate in hexane, progressing to 20% ethyl acetate in hexane, to give Compound X.27 having $^1$H NMR: δ2.6–2.71 (2H,m); 3.51(3H,s); 3.58–3.65(2H,t); 4.21–4.37(1H,m); 4.69(2H,s); (oil). This material was found to be unstable and on standing for 60 hours as the ambient temperature had hydrolysed appreciably.

EXAMPLE XI.1A

This Example illustrates a general procedures for the preparation of 5-chloro-3-substituted-1,2,4-thiadiazoles as demonstrated by the following preparation of 5-chloro-3-chloromethyl-1,2,4-thiadiazole from chloroacetamidine hydrochloride.

A suspension of chloroacetamidine hydrochloride (12.9 g) in dichloromethane (100 cm$^3$) was cooled to –5° C. and perchloromethyl mercaptan (20.44 g) was added. Sodium hydroxide in water (20 g in 30 cm$^3$) was added dropwise (exotherm), maintaining the temperature of the reaction mixture below 5° C. After the addition was complete, the reaction was allowed to warm to the ambient temperature and stirred overnight. The mixture was diluted with water and dichloromethane and the whole filtered through a pad of celite to remove insoluble material. The organic phase was separated, washed with saturated brine and dried over magnesium sulfate. The solution of product was then filtered and evaporated under reduced pressure to give a brown oil (9.72 g) which was used without further purification. M$^+$=168; $^1$H NMR: δ4.75(s).

The following intermediate compounds were prepared according to the procedure of Example XI.1A. The starting materials were known compounds.
(i) 5-chloro-3-trifluoromethyl-1,2,4-thiadiazole. M$^+$=188 (bp 50° C. at 12 mm Hg).
(ii) 5-chloro-3-methylmercapto-1,2,4-thiadiazole. M$^+$=166.
(iii) 5-chloro-3-methoxy-1,2,4-thiadiazole. M$^+$=150.
(iv) 5-chloro-3-(2-pyrazinyl)-1,2,4-thiadiazole. M$^+$=198.
A related procedure was used to prepare Compound XI.102 of the invention, as follows.

Preparation of 5-chloro-3-(4,4-difluorobut-3-enylthio)-1,2,4-thiadiazole

A suspension of 4,4-difluorobut-3-enylisothiouronium hydrobromide (8.68 g) in water (200 cm$^3$) containing sodium lauryl sulfate (0.1 g, catalytic) and perchloromethyl mercaptan (7.17 g) was cooled to 0° C. and sodium hydroxide in water (5.6 g in 200 cm$^3$) was added dropwise, maintaining the temperature of the reaction mixture below 5° C. After the addition was complete, the rection was allowed to warm to the ambient temperature and stirred overnight. The mixture was extracted twice with ethyl acetate, the organic phase was separated, washed with saturated brine and dried (MgSO$_4$). The solution of product was then filtered and evaporated under reduced pressure to give a brown oil (8.2 g) which was chromatographed on silica gel (Sorbsil C30) using 3% ethyl acetate in hexane as eluant to give Compound XI.102 (2.82 g). M$^+$=242; $^1$H NMR: δ2.4–2.6(2H,m); 3.2–3.3(3H,t); 4.2–4.4 (1H,m); (oil).

EXAMPLE XI.1B

A general procedure for the preparation of 5-[(4-methylphenyl)-sulfonyl]-3-substituted-1,2,4-thiadiazoles is illustrated by the following two-step preparation of 3-methoxymethyl-5-[(4-methylphenyl)-sulfonyl]-1,2,4-thiadiazole from methoxyacetamide.

Step 1: Preparation of 5-methoxymethyl-1,3,4-oxathiazol-2-one

Chlorocarbonylsulfenyl chloride (7.35 g) was added to a suspension of methoxyacetamide (5 g) in toluene (30 cm$^3$). The reaction mixture was stirred and heated at 90–100° C. for 5 hours, then cooled. The solvent was removed by evaporation under reduced pressure to give a brown gum (6.6 g). M$^+$=147; $^1$H NMR (DMSO-d$_6$): δ3.30(3H,s); 4.30 (2H,s) which was used in the next step without further purification.

Step 2: Preparaton of 3-methoxymethyl-5[(4-methylphenyl)-sulfonyl]-1,2,4-thiadiazole 4-Methylbenzenesulfonyl cyanide (16.26 g) was added to an emulsion of 5-methoxymethyl-1,3,4-oxathiazol-2-one (6.6 g) in dodecane (60 cm$^3$). The reaction mixture was stirred and heated at 150° C. for 18 hours, then cooled. Water was added and the product extracted into ethyl acetate. The combined organic phases were dried (MgSO$_4$) and ethyl acetate was removed by evaporation under reduced pressure. The residue separated into a brown liquid and a clear dodecane layer which was removed and discarded. Chromatography of the brown liquid on silica gel (Sorbsil C30) using 3:7 ethyl acetate:hexane as eluant give a pale orange oil which solidified on standing (6.94 g). M$^+$=284; $^1$H NMR: δ2.40(3H,s); 3.45(3H,s); 4.7(2H,s); 7.4(2H,d); 8.0(2H,d); (mp 43.4–45.4° C.).

The following itnermediate compounds were prepared according to the two-step procedure of Example XI.1B. The starting materials were known compounds.
(i) 3-ethyl-5-[(4-methylphenyl)-sulfonyl]-1,2,4-thiadiazole. M$^+$=268; $^1$H NMR: δ1.3–1.4 (3H,t); 2.45(3H,s); 2.95–3.05(2H,q); 7.4(2H,m); 8.0(2H,m) from propionamide.
(ii) 3-(E-prop-1-enyl)-5-[(4-methylphenyl)-sulfonyl]-1,2,4-thiadiazole. M$^+$=280; $^1$H NMR: δ1.95(3H,dd); 2.45(3H, s); 6.5–6.6(1H,m); 7.0–7.1(1H,m); 7.4(2H,m); 8.0(2H,m) from crotonamide.

EXAMPLE XI.2

This example illustrates a process for the preparation of 5-(4,4-difluorobut-3-enylthio)-3-substituted-1,2,4-thiadiazoles using either the corresponding 5-chloro or 5-[(4-methylphenyl)-sulfonyl]-1,2,4-thiadiazole intermediate prepared as above. The general procedure is illustrated by the following preparation of 5-(4,4-difluorobut-3-enylthio)-3-methoxymethyl-1,2,4-thiadiazole (Compound XI.34).

Sodium hydroxide in water (0.845 g in 10 cm$^3$) was added to 4,4-difluorobut-3-enylisothiouronium hydrobromide (1.75 g) and the mixture stirred at ambient temperature for 20 minutes. A solution of 3-methoxymethyl-5-[(4-methylphenyl)-sulfonyl]-1,2,4-thiadiazole (2.01 g) in dichloromethane (10 cm$^3$) and tetrabutylammonium bromide (0.1 g, catalyst) were added and the mixture was stirred for 20 minutes. Tlc showed that the product had formed. The mixture was diluted with more dichloromethane (10 cm$^3$) and the organic phase was separated, washed with saturated brine, dried (MgSO$_4$), filtered and evaporated under reduced pressure to give an orange-yellow liquid. Chromatography of the crude product on silica gel (Sorbsil C30) using 1:4 ethyl acetate:hexane as eluant give Compound XI.34 (1.67 g). M$^+$=252; $^1$H NMR: δ2.45–2.55(2H,m); 3.25–3.35(2H,t); 3.5(3H,s); 4.15–4.35(1H,m); 4.65(2H,s); (oil).

The following compounds according to the invention were prepared using the above procedure but with the appropriate intermediates.
(i) 5-(4,4-difluorobut-3-enylthio)-3-trifluoromethyl-1,2,4-thiadiazole (Compound XI.9). M$^+$=276; $^1$H NMR: δ2.5–2.6(2H,m); 3.3–3.4(2H,t); 4.2–4.4(1H,m); (oil).
(ii) 5-(4,4-difluorobut-3-enylthio)-3-(E-prop-1-enyl)-1,2,4-thiadiazole (Compound XI.11). M$^+$=248; $^1$H NMR: δ1.95 (3H,dd); 2.5–2.6(2H,m); 3.3(2H,t); 4.2–4.4(1H,m); 6.45–6.55 (1H,m); 6.9–7.1(1H,m); (oil).
(iii) 3-ethyl-5-(4,4-difluorobut-3-enylthio)-1,2,4-thiadiazole (Compound XI.23). M$^+$=236; $^1$H NMR: δ1.3–1.4(3H,t); 2.45–2.55(2H,m); 2.9–3.0(2H,q); 3.3(2H,t); 4.2–4.4(1H, m); (oil).
(iv) 3-chloromethyl-5-(4,4-difluorobut-3-enylthio)-1,2,4-thiadiazole (Compound XI.25). M$^+$=256; $^1$H NMR: δ2.45–2.55(2H,m); 3.35(2H,t); 4.2–4.35(1H,m); 4.7(2H, s); (oil). Two further products were produced in this reaction, which were separated during the chromatography and characterised. These were 3-((4,4-difluorobut-3-enylthiomethyl)-5-((4,4-difluorobut-3-enylthio)-1,2,4-thiadiazole (Compound XI.38). M$^+$=344; $^1$H NMR: δ2.25–2.35(2H,m); 2.45–2.55(2H,m); 2.65(2H,t); 3.3(2H, t); 3.9(2H,s); 4.15–4.35 (2H,m); (oil) and 5-chloro-3-(4, 4-difluorobut-3-enylthiomethyl)-1,2,4-thiadiazole. M$^+$=256; $^1$H NMR: δ2.2–2.3(2H,m); 2.65(2H,t); 3.9(2H, ds); 4.1–4.3(1H,m); (oil)
(v) 5-(4,4-difluorobut-3-enylthio)-3-methoxy-1,2,4-thiadiazole (Compound XI.87). M$^+$=238; $^1$H NMR: δ2.45–2.55(2H,m); 3.3(2H,t); 4.1(3H,s); 4.2–4.35(1H,m); (oil)
(vi) 3,5-bis-((4,4-difluorobut-3-enylthio)-1,2,4-thiadiazole (Compound XI.109). M$^+$=330; $^1$H NMR: δ2.45–2.6(4H, m); 3.2–3.35(4H,m); 4.2–4.4(2H,m); (oil) from Compound XI.102.
(vii) 5-(4,4-difluorobut-3-enylthio)-3-(2-pyrazinyl)-1,2,4-thiadiazole (Compound XI.125). M$^+$=286; $^1$H NMR: δ2.55–2.65(2H,m); 3.35–3.45(2H,t); 4.25–4.40(1H,m); 8.65(1H,d); 8.75(1H,dd); 9.55(1H,d); (oil)

EXAMPLE XI.3

This Example illustrates the preparation of 3-butoxymethyl-5-(4,4-difluorobut-3-enylthio)-1,2,4-thiadiazole (Compound XI.30).

Potassium carbonate (0.444 g) and n-butanol (0.397 g) were added to a solution of Compound XI.25 (0.275 g) in dimethylformamide (2 cm$^3$) and the mixture was stirred at ambient temperature for 18 hours. Tlc indicated that Compound XI.25 was still present in the mixture, so sodium hydride (0.1 g) and n-butanol (0.4 g) were added and stirring continued for a further 24 hours. Water was added and the product was extracted into diethyl ether. The organic phase was dried (MgSO$_4$), filtered and evaporated under reduced pressure to give an oil (0.442 g) which was purified by chromatography on silica gel (Sorbsil C30) using 10% ethyl acetate in hexane as eluant to give Compound XI.30 (0.131 g). M$^+$=294; $^1$H NMR: δ0.95–1.0(3H,t); 1.4–1.55(2H,m); 1.75–1.9(2H,m); 2.25–2.45(2H,m); 2.6–2.7(2H,t); 3.75(2H, s); 4.15–4.3(1H,m); 4.4–4.5(2H,t); (oil).

The following compound according to the invention was prepared using the above procedure, with n-propanol in place of n-butanol.

(i) 5-(4,4-difluorobut-3-enylthio)-3-propoxymethyl-1,2,4-thiadiazole (Compound XI.31). M$^+$=280; $^1$H NMR: δ1.0–1.1(3H,t); 1.8–1.95(2H,m); 2.25–2.35(2H,m); 2.6–2.7(2H,t); 3.75(2H,s); 4.15–4.4(1H,m); 4.4–4.45(2H, t); (oil).

EXAMPLE XI.4

This Example illustrates a two step process for the preparation of 5-(4,4-difluorobut-3-enylthio)-3-methyl-1,2,4-thiadiazole (Compound XI.40).

Step 1: Preparation of 3-methyl-1,2,4-thiadiazole-5(4H)-thione

To a solution of acetamidine (5 g) in methanol (100 cm$^3$) was added carbon disulfide (4 g), sulfur (1.7 g), and sodium methoxide (5.7 g) and the mixture was heated udner reflux for 6 hours. The mixture was cooled, filtered through hi-flow filter aid to remove excess sulfur and the filtrate was partitioned between water and ethyl acetate. The ethyl acetate was evaporated to give a brown solid and on acidification of the aqueous layer a red solid was formed and filtered off. Both the solids obtained from the filtrate appeared to be a mixture of 3-methyl-1,2,4-thiadiazole-5 (4H)-thione and sulfur. These two solids were combined and used in the next step.

Step 2: Preparation of Compound XI.40

To a solution of 3-methyl-1,2,4-thiadiazole-5(4H)-thione (1.2 g) in acetone (100 cm$^3$) was added 4,4-difluorobut-3-enyl 4-methylbenzenesulfonate (2.4 g) and potassium carbonate (1.2 g) and the mixture was refluxed for 4 hours after which tlc indicated complete consumption of starting material. The reaction was poured into ethyl acetate and water and the layers separated. The aqueous layer was extracted with ethyl acetate and the combined organic layers were dried (MgSO$_4$). The solution of product was then filtered and evaporated under reduced pressure to give a brown oil which was purified by flash chromatography (silica, 7% ethyl acetate in hexane) to give 5-((4,4-difluorobut-3-enylthio)-3-methyl-1,2,4-thiadiazole as a brown oil (0.645 g). M$^+$=222; $^1$H NMR: δ2.56(2H, br q); 2.63 (3H,s); 3.30 (2H,t); 4.30(1H,m).

The following compound according to the invention was prepared using the above procedure but with 3-phenyl-1,2, 4-thiadiazole-5(4H)-thione as starting material.

(i) 5-((4,4-difluorobut-3-enylthio)-3-phenyl-1,2,4-thiadiazole (Compound XI.5). $^1$H NMR: δ2.53(2H,q); 3.30(2H,t); 4.24(1H,m); 7.38(3H,m); 8.2(2H,m).

EXAMPLE XI.5

This Example illustrates the preparation of 3-(4,4-difluorobut-3-enylthio)-5-methoxy-1,2,4-thiadiazole (Compound XI.108).

Sodium hydroxide (0.182 g) was added to a solution of Compound XI.102 (1 g) in methanol (5 cm$^3$) and the mixture stirred at the ambient temperature for 45 minutes, when tlc indicated consumption of starting material. Water and diethyl ether were added to the mixture and the product was extraced into diethyl ether. The organic phase was dried (MgSO$_4$), filtered and evaporated under reduced pressure to give a yellow oil (0.9 g). Purification by flash chromatography (silica, 5% ethyl acetate in hexane) gave Compound XI.108 (0.78 g). M$^+$=238; $^1$H NMR: δ2.4–2.5(2H,m); 3.2 (2H,t); 4.15(3H,s); 4.2–4.35 (1H,m); (oil).

EXAMPLE XI.6

This Example illustrates the preparation of 5-(4,4-difluorobut-3-enylthio)-3-methylthio-1,2,4-thiadiazole (Compound XI.110).

Sodium sulfide nonahydrate (0.555 g) was added to 5-chloro-3-methylthio-1,2,4-thiadiazole (1.5 g) in ethanol (10 cm$^3$) and the mixture stirred and heated under reflux for 18 hours. The reaction mixture was cooled and solvent removed by evaporation under reduced pressure to give a yellow solid (1.76 g) which was dissolved in actetone (30 cm$^3$). Potassium carbonate (2.22 g) and 4-bromo-1,1-difluorobut-1-ene (1.83 g) were added and the mixture stirred and heated under reflux for 18 hours. The reaction mixture was cooled, filtered through hi-flo filter aid to remove inorganic material, washing with ethyl acetate, and solvent removed by evaporation under reduced pressure to give a brown gum which was purified by chromatography on silica gel (Sorbsil C30) using 5% ethyl acetate in hexane as eluane to give Compound XI.110 (0.392 g). M$^+$=254; $^1$H NMR: δ2.45–2.55(2H,m); 2.65(3H,s); 3.25–3.35 (2H,t); 4.2–4.4(1H,m); (oil).

EXAMPLE XI.7

This Example illustrates the preparation of 5-(4,4-difluorobut-3-enylthio)-3-(3-nitrophenyl)-1,2,4-thiadiazole (Compound XI.127).

Hydrogen sulfide gas was bubbled for 40 minutes through a stirred mixture of potassium methoxide (2.2 g) and absolute ethanol (25 cm$^3$), cooled at ~–10° C. The flask was removed from the cooling bath, 5-chloro-3-(3-nitrophenyl)-1,2,4-thiadiazole (3 g) was added, and the mixture was heated under reflux for 1 hour. The reaction was cooled and poured into ether and the resulting precipitate was filtered off. The filtrate, containing 5-mercapto-3-(3-nitrophenyl)-1, 2,4-thiadiazole, was then placed in a flask and 4,4-difluorobut-3-enyl 4-methylbenzenesulfonate (1.5 g) and ~1 g of potassium carbonate were added and the mixture was heated under reflux for 3 hours after which gc indicated virtually complete consumption of tosylate. The reaction was poured into ethyl acetate and water and the layers separated. The aqueous layer was extracted with ethyl acetate and the combined organic layers were dried (MgSO$_4$). Evaporation under reduced pressure gave a brown liquid which was purified by flash chromatography (silica; eluant 5% ethyl acetate in hexane) to give Compound XI.127 (0.901 g). M$^+$=329; $^1$H NMR: δ2.60(2H,broad q) 3.44(2H,t); 4.34(1H,m); 7.65(1H,t); 8.32(1H,dd); 8.6(1H,d); 9.1(1H,d) (oil).

EXAMPLE XI.8

This Example illustrates a method suitable for the preparation of compounds according to the invention in which the sulfur atom of the 4,4-difluorobut-3-enylthio substituent of the corresponding unoxidised compound (prepared according to the procedures of the preceding Examples) is oxidised to sulfoxide (sulfinyl) or sulfone (sulfonyl).

Preparation of Compounds XI.35 and XI.36 from Compound XI.34.

Compound XI.34 (0.85 g) was stirred at ambient temperature in dichloromethane (10 cm$^3$) and 3-chloro perbenzoic acid (0.814 g, 1.4 equiv.) was added. After three and a half hours, tlc indicated consumption of starting material, with the formation of two products. The reaction was quenched by the addition of a saturated aqueous solution of sodium bicarbonate and the products were extracted into dichloromethane. The organic phase was separated, washed with saturated brine and dried over magnesium sulfate. After filtration and concentration by evaporation under reduced pressure, there was obtained a white solid (1.2 g) which was purified by chromatography on silica gel using 3:7 ethyl acetate:hexane as eluant to give first 5-[(4,4-difluorobut-3-enyl)sulfonyl]-3-methoxymethyl-1,2,4-thiadiazole (Compound XI.36) (0.298 g). M$^+$=284; $^1$H NMR: δ2.55–2.65(2H,m); 3.55(3H,s); 3.5–3.6(2H,t); 4.2–4.35(1H, m); 4.80(2H,s); (oil). Further elution gave 5-[(4,4-difluorobut-3-enyl) sulfinyl]-3-methoxymethyl-1,2,4-thiadiazole (Compound XI.35) (0.402 g). M$^+$=268; $^1$H NMR: δ2.3–2.75(2H,m); 3.15–3.4(2H,m); 3.55(3H,s); 4.15–4.35(1H,m); 4.75(2H,s); (oil).

The following compound according to the invention was prepared by the above procedure, using two equivalents of oxidant.

(i) 5-[(4,4-difluorobut-3-enyl)sulfonyl]-3-ethyl-1,2,4-thiadiazole (Compound XI.24) M$^+$=268; $^1$H NMR: δ1.4–1.5(3H,t); 2.55–2.65(2H,m); 3.05–3.15(2H,q); 3.5–3.55(2H,t); 4.2–4.4(1H,m); (oil).

EXAMPLE XII.1

Methods for synthesis of the mercapto 1,3,4-oxadiazoles used as intermediates in preparing compounds according to the invention are well known in the art. Two representataive methods are illustrated below.

Method A—Preparation of 2-mercapto-5-methyl-1,3,4-oxadiazole.

To a solution of acetic hydrazide (5 g) in ethanol (10 cm$^3$) was added carbon disulfide (7.7 g) followed by a solution of potassium hydroxide in ethanol (5.7 g in 20 cm$^3$) which caused a white precipitate to form. The reaction was then stirred at ambient temperature for 2 hours and left to stand overnight. The reaction was filtered to give a white solid (11 g). This salt (5 g) was taken up in pyridine (10 cm$^3$) and the mixture heated under reflux for a total of 14 hours. After cooling, the reaction was acidified and extracted twice with diethyl ether. The ether layer was dried over magnesium sulfate, filtered and evaporated under reduced pressure to give an orange solid. This was recrystallised from ethyl acetate to give 2-mercapto-5-methyl-1,3,4-oxadiazole (0.655 g). M$^+$=116; $^1$H NMR: δ2.43 (3H,s); 10.9(1H,br s).

Method B—Preparation of 5-(4-methoxybenzyl)-1,3,4-oxadiazole-2(3H)-thione.

Step 1: Preparation of (4-methoxyphenyl)acetic acid hydrazide.

Hydrazine hydrate (4.7 cm$^3$) was added dropwise to ethyl (4-methoxyphenyl)acetate (3.73 g) and then methanol (20 cm$^3$) was added to form a homogeneous reaction mixture. This mixture was stirred for 18 hours at ambient temperature during which time a white precipitate formed. The precipitate was isolated by filtration and washed with methanol and water, then air-dried to give (4-methoxyphenyl)acetic acid hydrazide (2g). M$^+$=180; $^1$H NMR: δ 3.50(2H,s); 380(3H,s); 3.85(2H,br s); 6.70(1H,br s); 6.90(2H,d); 7.20(2H,d); (solid).

The following intermediate compounds were made by the above methods:

(i) 2-methylpropanoic acid hydrazide. M$^+$=102; (solid).
(ii) cyclopropylacetic acid hydrazide. M$^+$=100; (solid).
(iii) butanoic acid hydrazide. $^1$H NMR: δ 0.95(3H,t); 1.60–1.75(2H,m); 2.15(2H,t); 3.90(2H,br s); 6.95(1H,br s); (solid).
(iv) propanoic acid hydrazide. M$^+$=88; (solid).
(v) pentanoic acid hydrazide. $^1$H NMR: δ 0.90(3H,t); 1.30–1.40(2H,m); 1.60–1.70(2H,m); 2.20(2H,t); 3.90(2H, br s); 6.80(1H,br s); (solid).
(vi) hexanoic acid hydrazide. $^1$H NMR: δ 0.90(3H,t); 1.20–135(4H,m); 1.60–1.70(2H,m); 2.15(2H,t); 3.90(2H, br s); 6.70(1H,br s); (solid).
(vii) (4-nitrophenyl)acetic acid hydrazide. $^1$H NMR: δ (DMSO-d$_6$) 3.50(2H, s); 7.50(2H,d); 8.10(2H,d); (solid).
(viii) (2,6-difluorophenyl)acetic acid hydrazide. M$^+$=186; $^1$H NMR: δ 3.60(2H,s); 6.90–7.00(2H,m); 7.20–7.30(1H, m); (solid).
(ix) 2-methylbenzoic acid hydrazide. M$^+$=150; $^1$H NMR: δ 2.45(3H,s); 4.10(2H,br s); 7.00(1H,br s); 7.20–7.40(4H, m); (solid).

Step 2: Preparation of 5-(4-methoxybenzyl)-1,3,4-oxadiazole-2(3H)-thione.

A solution of potassium hydroxide (0.7 g) in water (2 cm$^3$) was added to a stirred solution of (4-methoxyphenyl) acetic acid hydrazide (1.99 g) in ethanol (30 cm$^3$). carbon disulfide (0.7 cm$^3$) was added and the reaction was heated to reflux for 6 hours and then left to cool. The reaction mixture was evaporated to dryness under reduced pressure and the solid residue dissolved in water. The pH was adjusted to 1 with concentrated hydrochloric acid, resulting in formation of a white precipitate. The precipitate was isolated by filtration, washed with water and ether and air dried to give 5-(4-methoxybenzyl)-1,3,4-oxadiazole-2(3H)-thione (1.96 g). M$^+$=222; $^1$H NMR: δ 3.80(3H,s); 3.95(2H,s); 6.90(2H, d); 7.20(2H,d); (solid).

The following compounds were prepared by the above method, using the appropriate intermediate (either known compounds or as prepared in Step 1):

(i) 1,3,4-thiadiazole-2(3H)-thione-5-carboxamide. M$^+$=145; (solid).
(ii) 5-thienyl-1,3,4-thiadiazole-2(3H)-thione. M$^+$=184; (solid).
(iii) 5-isopropyl-1,3,4-thiadiazole-2(3H)-thione. M$^+$=144; (gum).
(iv) 5-cyclopropyl-1,3,4-thiadiazole-2(3H)-thione. M$^+$=142; (gum).
(v) 5-propyl-1,3,4-thiadiazole-2(3H)-thione. M$^+$=144; (oil).
(vi) 5-ethyl-1,3,4-thiadiazole-2(3H)-thione. M$^+$=130; (oil).
(vii) 5-(4-pyridyl)-1,3,4-thiadiazole-2(3H)-thione. M$^+$=179; $^1$H NMR: δ 7.75(2H,d); 8.75(2H,d); (solid).
(viii) 5-butyl-1,3,4-thiadiazole-2(3H)-thione. $^1$H NMR: δ 0.95(3H,t); 1.35–1.50(2H,m); 1.65–1.75(2H,m); 2.70(2H, t); 2.90(1H,br s); (oil).
(ix) 5-pentyl-1,3,4-thiadiazole-2(3H)-thione. $^1$H NMR: δ 0.90(3H,t); 1.25–1.45(4H,m); 1.75(2H,m); 2.70(2H, m); (oil).
(x) 5-(4-nitrobenzyl)-1,3,4-thiadiazole-2(3H)-thione. M$^+$=237; $^1$H NMR: δ 4.20(2H,s); 7.50(2H,d); 8.25(2H,d); (solid).
(xi) 5-(2,6-difluorobenzyl)-1,3,4-thiadiazole-2(3H)-thione. $^1$H NMR: δ 4.10(2H,s); 6.90–7.00(2H,m); 7.25–7.40(1H, m); (solid).
(xii) 5-(4-methoxyphenyl)-1,3,4-thiadiazole-2(3H)-thione. $^1$H NMR: δ 3.80(3H,s); 7.10(2H,d); 7.75(2H,d); (solid).
(xiii) 5-(2-methylphenyl)-1,3,4-thiadiazole-2(3H)-thione. $^1$H NMR: δ (DMSO-d$_6$) 2.50(3H,s); 7.30–7.40(2H,m); 7.40–7.50(1H,m); 7.55(1H,br d); (solid).
(xiv) 5-(2-methoxyphenyl)-1,3,4-thiadiazole-2(3H)-thione. M$^+$=208; (solid).

(xv) 5-(4-nitrophenyl-1,3,4-thiadiazole-2(3H)-thione. $M^+$=223; $^1$H NMR: δ 8.05(2H,d); 8.30(2H,d); (solid).

(xvi) 5-benzyl-1,3,4-oxadiazole-2(3H)-thione. $^1$H NMR: δ 4.00(2H,s); 7.25–7.40(5H,m); (solid).

EXAMPLE XII.2

This Example illustrates a preparation of 2-(4,4-difluorobut-3-enylthio)-5-phenyl-1,3,4-oxadiazole (Compound XII.3).

To a solution of 2-mercapto-5-phenyl-1,3,4-oxadiazole (0.499 g) in acetone (15 cm$^3$) was added potassium carbonate (0.387 g) and 4,4-difluorobut-3-enyl 4-methylbenzenesulfonate (0.7 g) and the mixture was heated under reflux for 1.5 hours after which time all starting material had been consumed. The reaction was poured into diethyl ether and water and the layers separated. The aqueous layer was extracted with ether and the combined organic layers were washed with water and dried (MgSO$_4$). Evaporation of solvent under reduced pressure gave a pale yellow liquid which was purified by flash chromatography to give Compound XII.3 as a colourless oil that solidified on standing (0.293 g). $M^+$=268; $^1$H NMR: δ 2.58(2H,m); 3.32(2H,t); 4.31(1H,m); 7.45–7.57(3H,m); 8.01(2H,d); (mp 38–40° C.).

The following compounds according to the invention were prepared from the appropriate intermediate (either known compounds or prepared as in Example XII.1) using the above method but with 4-bromo-1,1-difluorobut-1-ene as alkylating agent instead of 4,4-difluorobut-3-enyl 4-methyl-benzenesulfonate.

(i) 5-cyclopropyl-2-(4,4-difluorobut-3-enylthio)-1,3,4-oxadiazole (Compound XII.1). $^1$H NMR: δ 1.10–1.15(4H, m); 2.10–2.20(1H,m); 2.45–2.55(2H,m); 3.20(2H,t); 4.30 (1H,m); (oil).

(ii) 2-(4,4-difluorobut-3-enylthio)-5-isopropyl-1,3,4-oxadiazole (Compound XII.8). $M^+$=234; $^1$H NMR: δ 1.19(6H,d); 2.50–2.60(2H,m); 3.15(1H,septet); 3.30(2H, t); 4.30(1H,m); (oil).

(iii) 5-(2,6-difluorobenzyl)-2-(4,4-difluorobut-3-enylthio)-1,3,4-oxadiazole (Compound XII.11). $^1$H NMR: δ 2.45–2.55(2H,m); 3.25(2H,t); 4.20(2H,s); 4.25(1H,m); 6.90–7.00(2H,m); 7.25–7.35(1H,m); (oil).

(iv) 2-(4,4-difluorobut-3-enylthio)-5-(4-nitrobenzyl)-1,3,4-oxadiazole (Compound XII.12). $^1$H NMR: δ 2.50–2.60 (2H,m); 3.30(2H,t); 4.20(1H,m); 4.30(2H,s); 7.50(2H,d); 8.20(2H,d); (oil).

(v) 2-(4,4-difluorobut-3-enylthio)-5-isobutyl-1,3,4-oxadiazole (Compound XII.23). $^1$H NMR: δ 1.00(6H,d); 2.10–2.20(1H,m); 2.50–2.60(2H,m); 2.70(2H,d); 3.25 (2H,t); 4.30(1H,m); (oil).

(vi) 2-(4,4-difluorobut-3-enylthio)-5-pentyl-1,3,4-oxadiazole (Compound XII.25). $^1$H NMR: δ 0.90(3H,t); 1.30–1.40(4H,m); 1.70–1.80(2H,m); 2.50–2.55(2H,m); 2.80(2H,t); 3.25(2H,t); 4.30(1H,m); (oil).

(vii) 5-butyl-2-(4,4-difluorobut-3-enylthio)-1,3,4-oxadiazole (Compound XII.28). $^1$H NMR: δ 0.95(3H,t); 1.35–1.50(2H,m); 1.70–1.80(2H,m); 2.50–2.60(2H,m); 2.80(2H,t); 3.25(2H,t); 4.30(1H,m); (oil).

(viii) 2(4,4-difluorobut-3-enylthio)-5-propyl-1,3,4-oxadiazole (Compound XII.31). $^1$H NMR: δ 1.00(3H,t); 1.75–1.90(2H,m); 2.50–2.60(2H,m); 2.80(2H,t); 3.25(2H, t); 4.30(1H,m); (oil).

(ix) 2-(4,4-difluorobut-3-enylthio)-5-ethyl-1,3,4-oxadiazole (Compound XII.35). $^1$H NMR: δ 1.40(3H,t); 2.50–2.60 (2H,m); 2.85(2H,t); 3.25(2H,t); 4.30(1H,m); (oil).

(x) 2-(4,4-difluorobut-3-enylthio)-5-methyl-1,3,4-oxadiazole (Compound XII.49). $M^+$=206; $^1$H NMR: δ 2.51(2H,m); 2.73(3H,s); 3.27(2H,t); 4.25(1H,m); (oil).

(xi) 2-(4,4-difluorobut-3-enylthio)-1,3,4-oxadiazole-5-carboxamide (Compound XII.55). $M^+$=235; $^1$H NMR: δ 2.50–2.60(2H,m); 3.35(2H,t); 4.30(1H,m); (mp 113° C.).

(xii) 2-(4,4-difluorobut-3-enylthio)-5-(2-methylphenyl)-1,3,4-oxadiazole (Compound XII.128). $^1$H NMR: δ 2.55–2.65(2H,m); 2.70(3H,s); 3.35(2H,t); 4.30(1H,m); 7.30–7.45(3H,m); 7.90(1H,d); (oil).

(xiii) 2-(4,4-difluorobut-3-enylthio)-5-(2-furyl)-1,3,4-oxadiazole (Compound XII.131). $M^+$=258; $^1$H NMR: δ 2.50–2.60(2H,m); 3.35(2H,t); 4.30(1H,m); 6.60(1H,m); 7.10(1H,d); 7.60(1H,d); (oil).

(xiv) 2-(4,4-difluorobut-3-enylthio)-5-(2-methoxyphenyl)-1,3,4-oxadiazole (Compound XII.132). $^1$H NMR: δ 2.50–2.60(2H,m); 3.30(2H,t); 3.95(3H,s); 4.30(1H,m); 7.10(2H,m); 7.50(1H,dt); 7.90(1H,dd); (mp 35–37° C.).

(xv) 2-(4,4-difluorobut-3-enylthio)-5-(2-thienyl)-1,3,4-oxadiazole (Compound XII.133). $M^+$=274; $^1$H NMR: δ 2.50–2.60(2H,m); 3.30(2H,t); 4.30(1H,m); 7.10–7.20(1H, m); 7.55(1H,d); 7.70(1H,d); (oil).

(xvi) 2-(4,4-difluorobut-3-enylthio)-5-(3-furyl)-1,3,4-oxadiazole (Compound XII.134). $^1$H NMR: δ 2.50–2.60 (2H,m); 3.30(2H,t); 4.30(1H,m); 6.90(1H,m); 7.50–7.55 (1H,m); 8.05(1H,br s); (oil).

(xvii) 2-(4,4-difluorobut-3-enylthio)-5-(4-methoxyphenyl)-1,3,4-oxadiazole (Compound XII.144). $^1$H NMR: δ 2.50–2.60(2H,m); 3.30(2H,t); 3.90(3H,s); 4.30(1H,m); 7.00(2H,d); 8.00(2H,d); (oil).

(xviii) 2-(4,4-difluorobut-3-enylthio)-5-(4-pyridyl)-1,3,4-oxadiazole (Compound XII.148). $M^+$=269; $^1$H NMR: δ 2.50–2.65(2H,m); 3.40(2H,t); 4.30(1H,m); 7.90(2H,d); 8.80(2H,d); (oil).

EXAMPLE XII.3

This Example illustrates a preparation of 2-(4,4-difluorobut-3-enylsulfinyl)-5-phenyl-1,3,4-oxadiazole (Compound XII.4).

To a solution of Compound XII.3 (1 g) in dry dichloromethane stirring at 0° C. was added 3-chloroperbenzoic acid (1.3 g of a 50% by weight solid, 1 equivalent). The reaction was allowed to warm to ambient temperature, stirred for 3 hours and left overnight. Tlc indicated complete consumption of starting material. The reaction mixture was filtered and the filtrate partitioned between dichloromethane and sodium bicarbonate solution. The aqueous layer was extracted with dichloromethane and the combined organic phases were dried over magnesium sulfate. Evaporation of solvent under reduced pressure gave a yellow oil which was purified by flash chromatography on silica gel, eluting with 25% ethyl acetate in hexane to give Compound XII.4 (0.474 g). $M^+$=284; $^1$H NMR: δ 2.67(2H,m); 3.52(2H,m); 4.32(1H, m); 7.50(3H,m); 8.12(2H,d); (oil).

The following compounds according to the invention were prepared from the appropriate thioether using the above method (i) 2-(4,4-difluorobut-3-enylsulfinyl)-5-(4-methoxybenzyl)-1,3,4-oxadiazole (Compound XII.14). $^1$H NMR: δ 2.45–2.70(2H,m); 3.30–3.50(2H,m); 3.80(3H,s); 4.25 (1H,m); 4.25(2H,s); 6.90(2H,d); 7.25(2H,d); (oil).

(ii) 2-(4,4-difluorobut-3-enylsulfinyl)-5-pentyl-1,3,4-oxadiazole (Compound XII.26). $^1$H NMR: δ 0.95(3H,t); 1.30–1.40(4H,m); 1.80–1.90(2H,m); 2.50–2.75(2H,m); 2.95(2H,t); 3.35–3.55(2H,m); 4.30(1H,m); (oil).

(iii) 5-butyl -2-(4,4-difluorobut-3-enylsulfinyl)-1,3,4-oxadiazole (Compound XII.29). $^1$H NMR: δ 1.00(3H,t); 1.40–1.50(2H,m); 1.80–1.90(2H,m); 2.50–2.75(2H,m); 3.00(2H,t); 3.35–3.55(2H,m); 4.30(1H,m); (oil).

(iv) 2-(4,4-difluorobut-3-enylsulfinyl)-5-propyl-1,3,4-oxadiazole (Compound XII.32). $^1$H NMR: δ 1.05(3H,t);

1.80–1.95(2H,m); 2.50–2.75(2H,m); 2.95(2H,t); 3.35–3.55(2H,m); 4.30(1H,m); (oil).

(v) 2-(4,4-difluorobut-3-enylsulfinyl)-5-(2-methylphenyl)-1,3,4-oxadiazole (Compound XII.129). $^1$H NMR: δ 2.55–2.80(2H,m); 2.70(3H,s); 3.40–3.60(2H,m); 4.30 (1H,m), 7.30–7.40(1H,m); 7.45–7.50(1H,m); 8.00(1H,d); (oil).

(vi) 2-(4,4-difluorobut-3-enylsulfinyl)-5-(4-nitrophenyl)-1,3,4-oxadiazole (Compound XII.142). $^1$H NMR: δ 2.55–2.80(2H,m); 3.45–3.70(2H,m); 4.35(1H,m); 8.35 (2H,d); 8.45(2H,d); (oil).

(vii) 2-(4,4-difluorobut-3-enylsulfinyl)-5-(4-methoxyphenyl)-1,3,4-oxadiazole (Compound XII.145). $^1$H NMR: δ 2.50–2.80(2H,m); 3.40–3.60(2H,m); 3.90 (3H,s); 4.30(1H,m); 7.05(2H,d); 8.05(2H,d); (oil).

The following compounds according to the invention were prepared from the appropriate thioether using the general method described above but with 2 equivalents of 3-chloroperbenzoic acid as oxidant.

(viii) 2-(4,4-difluorobut-3-enylsulfonyl)-5-phenyl-1,3,4-oxadiazole (Compound XII.5). M$^+$=300; $^1$H NMR: δ 2.71(2H,m); 3.67(2H,m); 4.33(1H,m); 7.52–7.70(3H,m); 8.25(2H,d); (mp 104–106° C.).

(ix) 2-(4,4-difluorobut-3-enylsulfonyl)-5-isopropyl-1,3,4-oxadiazole (Compound XII.9). $^1$H NMR: δ 1.50(6H,d); 2.60–2.70(2H,m); 3.20–3.40(1H,m); 3.60(2H,t); 4.30(1H, m); (gum).

(x) 2-(4,4-difluorobut-3-enylsulfonyl)-5-(4-nitrobenzyl)-1,3,4-oxadiazole (Compound XII.13). $^1$H NMR: δ 2.60–2.70(2H,m); 3.60(2H,t); 4.30(1H,m); 4.40(2H,s); 7.55(2H,d); 8.25(2H,d); (oil).

(xi) 2-(4,4-difluorobut-3-enylsulfonyl)-5-(4-methoxybenzyl)-1,3,4-oxadiazole (Compound XII.15). $^1$H NMR: δ 2.60–2.70(2H,m); 3.65(2H,t); 3.80(3H,s); 4.20(1H,m); 4.25(2H,s); 6.90(2H,d); 7.25(2H,d); (mp 60–63° C.).

(xii) 5-benzyl-2(4,4,-difluorobut-3-enylsulfonyl)-1,3,4-oxadiazole (Compound XII.19). $^1$H NMR: δ 2.60(2H,m); 3.60(2H,t); 4.25(1H,m); 4.30(2H,s); 7.25–7.40(5H,m); (oil).

(xiii) 2-(4,4-difluorobut-3-enylsulfonyl)-5-pentyl-1,3,4-oxadiazole (Compound XII.27). $^1$H NMR: δ 0.95(3H,t); 1.30–1.45(4H,m); 1.80–1.90(2H,m); 2.60–2.70(2H,m); 3.00(2H,t); 3.60(2H,t); 4.30(1H,m); (oil).

(xiv) 5-butyl-2-(4,4-difluorobut-3-enylsulfonyl)-1,3,4-oxadiazole (Compound XII.30). $^1$H NMR: δ 1.00(3H,t); 1.40–1.50(2H,m); 1.80–1.90(2H,m); 2.60–2.70(2H,m); 3.00(2H,t); 3.60(2H,t); 4.30(1H,m); (oil).

(xv) 2-(4,4-difluorobut-3-enylsulfonyl]-5-propyl-1,3,4-oxadiazole (Compound XII.33). $^1$H NMR: δ 1.10(3H,t); 1.85–2.00(2H,m); 2.60–2.70(2H,m); 2.95(2H,t); 3.60(2H, t); 4.30(1H,m); (oil).

(xvi) 2-(4,4-difluorobut-3-enylsulfonyl)-5-methyl-1,3,4-oxadiazole (Compound XII.51). $^1$H NMR: δ 2.20–2.30 (2H,m); 2.30(3H,s); 3.60(2H,t); 4.30(1H,m); (oil).

(xvii) 2-(4,4-difluorobut-3-enylsulfonyl)-5-(2-methylphenyl-1,3,4-oxadiazole (Compound XII.130). $^1$H NMR: δ 2.70–2.80(2H,m); 2.75(3H,s); 3.70(2H,t); 4.30 (1H,m); 7.40(1H,d); 7.50(1H,d); 8.00(1H,d); (mp 90–93° C.).

(xviii) 2-(4,4-difluorobut-3-enylsulfonyl)-5-(4-nitrophenyl)-1,3,4-oxadiazole (Compound XII.143). M$^+$=345; $^1$H NMR δ 2.70–2.80(2H,m); 3.70(2H,t); 4.35 (1H,m); 8.35(2H,d); 8.45(2H,d); (oil).

(xix) 2-(4,4-difluorobut-3-enylsulfonyl)-5-(4-methoxyphenyl)-1,3,4-oxadiazole (Compound XII.146). $^1$H NMR: δ 2.70–2.80(2H,m); 3.65(2H,t); 3.90(3H,s); 4.30(1H,m); 7.05(2H,d); 8.10(2H,d); (mp 60° C.).

EXAMPLE XIII.1

This example illustrates a general procedure for the preparation of 2-(4,4-difluorobut-3-enylthio)-5-substituted-1,3,4-thiadiazoles from the corresponding thiadiazole-2 (3H)-thione, compounds which are well known in the art. The process is illustrated by the preparation of 2-(4,4-difluorobut-3-enylthio)-5-methylamino-1,3,4-thiadiazole (Compound XIII.70) from the corresponding thione and 4,4-difluorobut-3-enyl 4-methyl-benzenesulfonate. Other alkylating agents, for example 4-bromo-1,1-difluorobut-1-ene may also be used.

Preparation of Compound XIII.70

To a solution of 5-methylamino-1,3,4-thiadiazole-2(3H)-thione (0.393 g) in acetone (10 cm$^3$) was added potassium carbonate (0.369 g) and 4,4-difluorobut-3-enyl 4-methylbenzenesulfonate (0.7 g) and the mixture was heated under reflux for 3 hours after which gc analysis indicated complete consumption of starting material. The reaction mixture was filtered through hi-flo filter aid and the pad washed thoroughly with diethyl ether. The filtrate was poured into ether and water and the layers were separated. The aqueous layer was extracted twice with ether and the combined organic phases were dried (MgSO$_4$). Evaporation of solvent under reduced pressure gave a brown oil which was purified by flash chromatography on silica gel, eluting with 1:1 ethyl acetate:hexane to give Compound XIII.70 (0.273 g) M$^+$=237; $^1$H NMR: δ 2.43(2H,m); 3.04(3H,s); 3.15(2H,t); 4.29(1H,m); 5.36(1H,br, s); (mp 52.5–53.5° C.).

The following compounds according to the invention were prepared by the above general method using the appropriate mercapto thiadiazoles and in some cases 4-bromo-1,1-difluorobut-1-ene as alkylating agent.

(i) 5-cyclopropyl-2-(4,4-difluorobut-3-enylthio)-1,3,4-thiadiazole (Compound XIII.6). M$^+$=248; $^1$H NMR: δ 1.10–1.30(4H,m); 2.30–2.40(1H,m); 2.45–2.55(2H,m); 3.30(2H,t); 4.30(1H,m); (oil).

(ii) 2-(4,4-difluorobut-3-enylthio)-5-phenyl-1,3,4-thiadiazole (Compound XIII.9). M$^+$=284; $^1$H NMR: δ 2.50–2.65(2H,m); 3.40(2H,t); 4.50(1H,m); 7.40–7.50(3H,m); 7.85–7.95(2H,m); (mp 39° C.).

(iii) 2-(4,4-difluorobut-3-enylthio)-5-isopropyl-1,3,4-thiadiazole (Compound XIII.16). M$^+$=250; $^1$H NMR: δ 1.40(3H,s); 1.45(3H,s); 2.45–2.60(2H,m); 3.35(2H,t); 3.35–3.50(1H,m); 4.30 (1H,m); (oil).

(iv) 5-benzyl-2-(4,4-difluorobut-3-enylthio)-1,3,4-thiadiazole (Compound XIII.20). M$^+$=298; $^1$H NMR: δ 2.45–2.55(2H,m); 3.30(2H,t); 4.30(1H,m); 4.40(2H,s); 7.25–7.40(5H,m); (oil).

(v) 2-(4,4-difluorobut-3-enylthio)-5-methyl-1,3,4-thiadiazole (Compound XIII.40). M$^+$=222; $^1$H NMR: δ 2.50(2H,m); 2.73(3H,s); 3.35(2H,t); 4.29(1H,m); (oil).

(vi) 2-(4,4-difluorobut-3-enylthio)-1,3,4-thiadiazole-5-carboxamide (Compound XIII.45). M$^+$=151; $^1$H NMR: δ 2.50–2.60(2H,m); 3.45(2H,t); 4.30(1H,m); 6.80(1H,br s); 7.15(1H,br s); (mp 168° C.).

(vii) 2-(4,4-difluorobut-3-enylthio)-1,3,4-thiadiazole (Compound XIII.63). M$^+$=208; $^1$H NMR: δ 2.54(2H,m); 3.43(2H,t); 4.30(1H,m); 9.03(1H,s); (oil).

(viii) 5-amino-2-(4,4-difluorobut-3-enylthio)-1,3,4-thiadiazole (Compound XIII.69). M$^+$=223; $^1$H NMR: δ 2.45(2H,m); 3.20(2H,t); 4.30(1H,m); 5.20(2H,br, s); (mp 138° C.).

(ix) 2-(4,4-difluorobut-3-enylthio)-5-(3-trifluoromethylbenzylthio)-1,3,4-thiadiazole (Compound XIII.110). M$^+$=304; $^1$H NMR: δ 2.51(2H,m); 3.31(2H,t); 4.27(1H,m); 4.56(2H,s); 7.42–7.70(4H,m); (oil).

(x) 5-cyclopropylmethylthio-2-(4,4-difluorobut-3-enylthio)-1,3,4-thiadiazole (Compound XIII.114). $M^+$=294; $^1$H NMR: δ 0.35(2H,m); 0.65(2H,m); 1.25(1H,m); 2.50(2H, m); 3.25(2H,d); 3.30(2H,t); 4.25(1H,m); (oil).

(xi) 2,5-bis-(4,4-difluorobut-3-enylthio)-1,3,4-thiadiazole (Compound XIII.117). $M^+$=330; $^1$H NMR: δ 2.51(4H,m); 3.32(4H,t); 4.29(2H,m); (oil).

(xii) 2-(4,4-difluorobut-3-enylthio)-5-methylthio-1,3,4-thiadiazole (Compound XIII.119). $M^+$=254; $^1$H NMR: δ 2.51(2H,m); 2.77(3H,s); 3.31(2H,t); 4.20(1H,m); (oil).

(xiii) 2-(4,4-difluorobut-3-enylthio)-5-(sulfonamidophenyl)-1,3,4-thiadiazole (Compound XIII.143). $M^+$=363; $^1$H NMR: δ 2.55 . 2.65(2H,m); 3.50 (2H,t); 4.30(1H,m); 4.95(2H,br s); 8.05(4H,m); (mp 154° C.).

EXAMPLE XIII.2

This Example illustrates a general procedure for the preparation of 2-(4,4-difluorobut-3-enylthio)-5-substituted-1,3,4-thiadiazoles from 2-amino-5-substituted thiadiazoles. The process is illustrated by the preparation of 2-(4,4-difluorobut-3-enylthio)-5-ethyl-1,3,4-thiadiazole (Compound XIII.27) from 2-amino-5-ethyl-1,3,4-thiadiazole.

Preparation of Compound XIII.27

A solution of 2-amino-5-ethyl-1,3,4-thiadiazole (0.786 g) and di-4,4-difluorobut-3-enyl disulfide (1.5 g) in dichloromethane (25 cm$^3$) was stirred and cooled in an ice-water bath. Tert. butyl nitrite (1.2 g) was added, the cold bath removed and the reaction heated under reflux for 1.3 hours. The mixture was then poured into diethyl ether/water and the layers separated. The aqueous layer was extracted with ether and the combined organic phases were dried (MgSO$_4$), filtered and evaporated under reduced pressure to give a brown oil. Purification by column chromatography on silica gel using 1:9 and 2:8 ethyl acetate:hexane as eluant gave Compound XIII.27 (0.959 g). $M^+$=236; $^1$H NMR: δ 1.40 (3H,t); 2.45–2.60(2H,m); 3.10(2H,q); 3.35(2H,t); 4.30(1H, m); (oil).

The following compounds according to the invention were prepared by the above procedure, using the appropriate intermediates:

(i) 5-bromo-2-(4,4-difluorobut-3-enylthio)-1,3,4-thiadiazole (Compound XIII.1). $M^+$=286; $^1$H NMR: δ 2.45–2.60(2H, m); 3.40(2H,t); 4.30(1H,m); (oil).

(ii) 2-(4,4-difluorobut-3-enylthio)-5-tert.-butyl-1,3,4-thiadiazole (Compound XIII.3). $M^+$=264; $^1$H NMR: δ 1.48(9H,s); 2.45–2.60(2H,m); 3.35(2H,t); 4.30(1H,m); (oil).

(iii) 2-(4,4-difluorobut-3-enylthio)-5-trifluoromethyl-1,3,4-thiadiazole (Compound XIII.14). $M^+$=276; $^1$H NMR: δ 2.50–2.60(2H,m); 3.45(2H,t); 4.30(1H,m); (oil).

EXAMPLE XIII.3

This Example illustrates a preparation of 2,5-bis-(4,4-difluorobut-3-enylsulfinyl)-1,3,4-thiadiazole (Compound XIII.133) using 3-chloroperbenzoic acid as the oxidant.

A solution of Compound XIII.117 (0.49 g) in dichloromethane (30 cm$^3$) was cooled in a methanol ice bath to ~-10° C., 3-chloroperbenzoic acid (1 g of a 50% by weight solid, 2 equivalents) was added and the reaction was allowed to stir and gradually warm to the ambient temperature, then stirred for 7 hours and left to stand for 18 hours. The mixture was then poured into sodium bicarbonate solution and the product extracted into diethyl ether. The combined organic phases were washed with sodium bicarbonate solution and dried (MgSO$_4$). Evaporation of solvent under reduced pressure gave a pale yellow liquid which was purified by flash chromatography on silica gel, eluting with 30% ethyl acetate in hexane to give Compound XIII.133 (0.168 g). $M^+$=362; $^1$H NMR: δ 2.58(4H,m); 3.36(4H,m); 4.26(2H,m). (mp 46–48° C.).

The following compounds according to the invention were prepared by the above general procedure, using the appropriate number of equivalents of 3-chloroperbenzoic acid as oxidant.

(i) 2-(4,4-difluorobut-3-enylsulfinyl)-5-phenyl-1,3,4-thiadiazole (Compound XIII.10). $M^+$=300; $^1$H NMR: δ 2.40–2.80(2H,m); 3.30–3.40(2H,m); 4.30(1H,m); 7.45–7.60(3H,m); 7.95–8.00(2H,m); (mp 67° C.).

(ii) 2-(4,4-difluorobut-3-enylsulfonyl)-5-phenyl-1,3,4-thiadiazole (Compound XIII.11). $M^+$=316; $^1$H NMR: δ 2.60–2.75(2H,m); 3.65(2H,t); 4.30(1H,m); 7.45–7.65(3H, m); 7.95–8.05(2H,m); (mp 80° C.).

(iii) 2-(4,4-difluorobut-3-enylsulfinyl)-5-methyl-1,3,4-thiadiazole (Compound XIII.41). $M^+$=238; $^1$H NMR: δ 2.35–2.55(1H,m); 2.55–2.75(1H,m); 2.90(3H,s); 3.20–3.40(2H,m); 4.30(1H,m); (oil).

(iv) 2-(4,4-difluorobut-3-enylsulfonyl)-5-methyl-1,3,4-thiadiazole (Compound XIII.42). $M^+$=255; $^1$NMR: δ 2.55–2.70(2H,m); 2.95(3H,s); 3.60(2H,t); 4.30(1H,m); (oil).

(v) 2-(4,4-difluorobut-3-enylsulfinyl)-1,3,4-thiadiazole (Compound XIII.64). $M^+$=225; $^1$H NMR: δ 2.35–2.50 (1H,m); 2.60–2.75(1H,m); 3.25–3.45(2H,m); 4.30(1H, m); 9.35(1H,s); (oil).

(vi) 2-(4,4-difluorobut-3-enylsulfonyl)-1,3,4-thiadiazole (Compound XIII.65). $MH^+$=241; $^1$H NMR: δ 2.60–2.70 (2H,m); 3.70(2H,t); 4.30(1H,m); 9.40(1H,s); (oil).

(vii) 2,5-bis-(4,4-difluorobut-3-enylsulfonyl)-1,3,4-thiadiazole (Compound XIII.124). $M^+$=394; $^1$H NMR: δ 2.69(4H,m); 3.70(4H,t); 4.30(2H,m); (mp 88–91° C.).

(viii) 2-(4,4-difluorobut-3-enylsulfonyl)-5-(4,4-difluorobut-3-enylsulfinyl)-1,3,4-thiadiazole (Compound XIII.134). $M^+$=378; $^1$H NMR: δ 2.38–2.55(1H,m); 2.60–2.79(3H, m); 3.38(2H,m); 3.62–3.74(2H,m); 4.19–4.39(2H,m); (mp 45–47° C.).

The following compounds according to the invention were prepared by the above general procedure but using the appropriate number of equivalents of magnesium monoperoxyphthalate as oxidant.

(ix) 5-bromo-2-(4,4-difluorobut-3-enylsulfonyl)-1,3,4-thiadiazole (Compound XIII.2). $MH^+$=319; $^1$H NMR: δ 2.60–2.70(2H,m); 3.65(2H,t); 4.30(1H,m); (oil).

(x) 2-(4,4-difluorobut-3-enylsulfonyl)-5-tert.-butyl-1,3,4-thiadiazole (Compound XIII.4). $MH^+$=297; $^1$H NMR: δ 1.55(9H,s); 2.60–2.70(2H,m); 3.65(2H,t); 4.30(1H,m); (mp 37° C.).

(xi) 5-cyclopropyl-2-(4,4-difluorobut-3-enylsulfonyl)-1,3,4-thiadiazole (Compound XIII.7). $MH^+$=281; $^1$H NMR: δ 1.25–1.45(4H,m); 2.40–2.55(1H,m); 2.55–2.65(2H,m); 3.60(2H,t); 4.30(1H,m); (gum).

(xii) 2-(4,4-difluorobut-3-enylsulfonyl)-5-trifluoromethyl-1,3,4-thiadiazole (Compound XIII.15). $M-SO_2H^+$=243; $^1$H NMR: δ 2.60–2.75(2H,m); 3.75(2H,t); 4.20–4.40(1H, m); (gum).

(xiii) 2-(4,4-difluorobut-3-enylsulfonyl)-5-isopropyl-1,3,4-thiadiazole (Compound XIII.17). $M^+$=283; $^1$H NMR: δ 1.50(3H,s); 1.55(3H,s); 2.60–2.70(2H,m); 3.50–3.70(3H, m); 4.30(1H,m); (mp 43° C.).

(xiv) 2-(4,4-difluorobut-3-enylsulfinyl)-5-ethyl-1,3,4-thiadiazole (Compound XIII.28). $^1$H NMR: δ 1.50(3H,t);

2.40–2.50(1H,m); 2.60–2.70(1H,m); 3.20(2H,q); 3.25–3.35(2H,m); 4.25(1H,m); (gum).

(xv) 2-(4,4-difluorobut-3-enylsulfonyl)-5-ethyl-1,3,4-thiadiazole (Compound XIII.29). $M^+$=269; $^1$H NMR: δ 1.50(3H,t); 2.60–2.70(2H,m); 3.20(2H,q); 3.65(2H,t); 4.30(1H,m); (gum).

EXAMPLE XIII.4

This Example illustrates a preparation of 2-(4,4-difluorobut-3-enylthio)-5-methoxy-1,3,4-thiadiazole (Compound XIII.101) from Compound XIII.1.

To a stirred suspension of sodium hydride (0.030 g) in toluene (3 cm$^3$) was added methanol (0.022 g), resulting in effervescence. After stirring for 10 minutes, Compound XIII.1 (0.20 g) was added and the reaction was stirred at the ambient temperature for 18 hours. The reaction was analysed by gc and further portions of sodium hydride and methanol added until complete loss of starting material was observed. The reaction was poured into water and the layers separated. The product was extracted into diethyl ether and the combined organic phases were dried (MgSO$_4$) filtered and evaporated under reduced pressure to give a pale yellow oil. Purification by column chromatography on silica gel using 3:17 ether:hexane as the eluant gave Compound XIII.101 (0.069 g). $M^+$=238; $^1$H NMR: δ 2.40–2.55(2H,m); 3.25(2H,t); 4.20(3H,s); 4.30(1H,m); (oil).

EXAMPLE XIV.1

This Example illustrates the preparation of 5-(4,4-difluorobut-3-enylthio)-1-methyltetrazole (Compound XIV.1).

The sodium salt of 5-mercapto-1-methyltetrazole was alkylated with 4-bromo-1,1-difluorobut-1-ene using the procedure of Example XIII.1 to give Compound XIV.1. $M^+$=206; $^1$H NMR: δ 2.53(2H,m); 3.38(2H,t); 3.92(3H,s); 4.28(1H,m); (oil).

EXAMPLE XV.1

This example illustrates a preparation of 1-(4,4-difluorobut-3-enylthio)-4-nitrobenzene (Compound XV.1).

4-Nitro-thiophenol (0.5 g), potassium carbonate (0.448 g), 4,4-difluorobut-3-enyl 4-methyl-benzenesulfonate (0.846 g) and potassium iodide (0.388 g) were heated and stirred under reflux in acetone (15 cm$^3$) for a total of 6 hours after which none of the starting tosylate was detectable by tlc. The reaction mixture was poured into water and extracted with 3 portions of ethyl acetate. The combined organic phases were washed 3 times with 2M NaOH, and saturated aqueous brine and then dried (MgSO$_4$). Removal of solvent by evaporation under reduced pressure gave a dark yellow oil which was purified by flash chromatography on silica gel using 5% ethyl acetate in hexane as eluant to give Compound XV.1 (0.474 g). $M^+$=245; $^1$H NMR: δ 2.42(2H,m); 3.09(2H,t); 4.30(1H,m); 7.35(2H,d); 8.14(2H,d); (oil).

EXAMPLE XVI.1

This Example illustrates a preparation of 2-chloro-4-(4,4-difluorobut-3-enylthio)pyridine (Compound XVI.1).

Tert-butyl nitrite (0.442 g) in dichloromethane (20 cm$^3$) was added dropwise to a solution of 4-amino-2-chloropyridine and bis-(4,4-difluorobut-3-enyl)disulfide (1.9 g) in dichloromethane (20 cm$^3$) while stirring the mixture at 0° C. The reaction mixture was stirred for 4 hours and then allowed to stand at the ambient temperature for 18 hours. Water was added and the product extracted into ethyl acetate. The combined organic phases were washed with saturated brine, dried (MgSO$_4$), filtered and evaporated under reduced pressure to give an orange-brown gum. Chromatography on sorbsil-C30 using 4% ethyl acetate in hexane as eluant gave Compound XVI.1 (0.134 g). $M^+$=235; $^1$H NMR: δ 2.35–2.46(2H,m); 2.98–3.7(2H,t); 4.18(1H,m); 7.02(1H,d); 7.11(1H,d); 8.14–8.21(1H,d); (oil).

EXAMPLE XVI.2

This Example illustrates a 2-step preparation of 4-(4,4-difluorobut-3-enylthio)-2,3,5,6-tetrafluoropyridine (Compound XVI.2).

Step 1: Preparation of the sodium salt of 2,3,5,6-tetrafluoropyridine-4-thiol

4-Chloro-2,3,5,6-tetrafluoropyridine (2 g) and sodium hydrosulfide dihydrate were stirred and heated under reflux in iso-propanol (40 cm$^3$) for 3 hours. The mixture was then stirred at the ambient temperature for 18 hours. The precipitated solid was removed by filtration, washed with diethyl ether and discarded. The combined organic solutions were evaporated under reduced pressure to give 2,3,5,6-tetrafluoropyridine-4-thiol as its sodium salt (2.21 g), which was used without further purification in the second step.

Step 2: Preparation of (Compound XVI.2)

The intermediate from step 2 (1.7 g), 4-bromo-1,1,-difluorobut-1-ene (1.99 g), and potassium carbonate (1.53 g), were stirred and heated under reflux in acetone (30 cm$^3$) for 18 hours. The inorganic precipitate was removed by filtration and the filtrate evaporated under reduced pressure to give a dark brown oil. Chromatography on sorbsil-C30 using hexane as eluant gave Compound XVI.2 (1.82 g). $M^+$=273; $^1$H NMR: δ 2.3–2.42(2H,m); 3.15–3.25(2H,t); 4.15–4.34(1H,m); (oil).

The following compounds according to the invention were prepared using the procedure of Step 2 above. The alkylating agent was 4-bromo-1,1,-difluorobut-1-ene or 4,4-difluorobut-3-enyl 4-methyl-benzenesulfonate.

(i) 4-(4,4-difluorobut-3-enylthio)-pyridine (Compound XVI.5). $M^+$=201; $^1$H NMR: δ 2.40(2H,m); 3.04(2H,t); 4.30(1H,m); 7.11(2H,d); 8.41(2H,d); (oil) from 4-mercaptopyridine.

(ii) 4,4-difluorobut-3-enyl 2-(4,4-difluorobut-3-enylthio) pyridine-3-carboxylate (Compound XVI.10). $M^+$=335; $^1$H NMR: δ 2.43(4H,m); 3.22(2H,t); 4.29(2H,m); 4.36 (2H,t); 7.09(1H,dd); 8.20(1H,dd); 8.57(1H,dd); (oil) from 2-mercaptopyridine-3-carboxylic acid. Potassium iodide was used to convert two equivalents of 4,4-difluorobut-3-enyl 4-methyl-benzenesulfonate to the more reactive 4-iodo-1,1-difluorobut-1-ene in situ in this reaction.

(iii) 2-(4,4-difluorobut-3-enylthio)-5-trifluoromethylpyridine (Compound XVI.11). $^1$H NMR: δ 2.40(2H,m); 3.25(2H,t); 4.25(1H,m); 7.25(1H,dd); 7.45 (1H,dd); 8.40(1H,d); (oil) from 2-mercapto-5-trifluoromethylpyridine.

(iv) 2-(4,4-difluorobut-3-enylthio)pyridine (Compound XVI.19). $M^+$=201; $^1$H NMR: δ 2.40(2H,m); 3.20(2H,t); 4.30(1H,m); 6.90(1H,dd); 7.20(1H,dd); 7.45(1H,td); 8.40 (1H,dd); (oil).

(v) 2-(4,4-difluorobut-3-enylthio)-5-nitropyridine (Compound XVI.21). $M^+$=246; $^1$H NMR: δ 2.45(2H,m); 3.30(2H,t); 4.28(1H,m); 7.30(1H,d); 8.23(1H,dd); 9.25 (1H,d); (oil) from 2-mercapto-5-nitropyridine.

EXAMPLE XVI.3

This Example gives a general procedure for the preparation of 2-(4,4-difluorobut-3-enylthio)-5-substitutedpyridines from 2-chloro-5-substituted-pyridines. The method is illustrated by the preparation of 5-chloro-2-(4,4-difluorobut-3-enylthio)pyridine (Compound XVI.13) from 2,5-dichloropyridine.

Sodium hydrosulfide dihydrate (0.672 g) was added to a solution of 2,5-dichloropyridine (1.48 g) in dimethylformamide (20 cm3), causing the mixture to go blue and then green on heating to 100° C. The reaction was heated for 7 hours and then 4-bromo-1,1-difluorobut-1-ene (1.71 g) and potassium carbonate (1.38 g) were added. The reaction was heated for 2 hours then allowed to cool. The reaction mixture was poured into diethyl ether and 2M HCl and the layers separated. The aqueous layer was extracted with ether. The combined organic phases were then washed with 2M HCl, water and brine (alternately 3 times each), dried (MgSO$_4$), filtered and evaporated under reduced pressure to give a brown oil. Column chromatography on silica gel using 2% diethyl ether in hexane as eluant gave Compound XVI.13 (0.805 g). M$^+$=235; $^1$H NMR: δ 2.40(2H,m); 3.20(2H,t); 4.25(1H,m); 7.15(1H,dd); 7.45(1H,dd); 8.40(1H,d); (oil).

The following compound according to the invention was prepared using the above procedure:
(i) 5-cyano-2-(4,4-difluorobut-3-enylthio)pyridine (Compound XVI.15). $^1$H NMR: δ 2.40(2H,m); 3.25(2H, t); 4.25(1H,m); 7.25(1H,dd); 7.70(1H,dd); 8.65(1H,d); (mp 34° C.).

EXAMPLE XVI.4

This Example gives a general procedure for the preparation of 2-(4,4-difluorobut-3-enylthio)-3-substituted-pyridines from 2-chloro-3-substituted-pyridines and 4,4-difluorobut-3-enylisothiouronium hydrobromide. The method is illustrated by the preparation of 2-(4,4-difluorobut-3-enylthio)-3-nitropyridine (Compound XVI.24) from 2-chloro-3-nitropyridine.

4,4-Difluorobut-3-enylisothiouronium hydrobromide (1.24 g) was added to a solution of sodium hydroxide (0.6 g) in water (10 cm$^3$) and the reaction was stirred vigorously at the ambient temperature for 20 minutes. A solution of 2-chloro-3-nitropyridine (0.795 g) in dichloromethane (10 cm$^3$) was added to the reaction followed by tetra-n-butylammonium bromide (catalytic). The reaction was stirred vigorously for 3 hours. The mixture was diluted with dichloromethane and the layers separated. The organic layer was washed with brine, dried (MgSO$_4$), filtered, and evaporated under reduced pressure to give a yellow oil. Column chromatography on silica gel using 15% diethyl ether in hexane as eluant gave Compound XVI.24 (0.847 g). M$^+$=246; $^1$H NMR: δ 2.40(2H,m); 3.25(2H,t); 4.30(1H,m); 7.20(1H,dd); 8.50(1H,dd); 8.70(1H,dd); (oil).

The following compound according to the invention was prepared using the above procedure:
(i) 3-cyano-2-(4,4-difluorobut-3-enylthio)pyridine (Compound XVI.8). M$^+$=226; $^1$H NMR: δ 2.40(2H,m); 3.30(2H,t); 4.25(1H,m); 7.10(1H,dd); 7.80(1H,dd); 8.55 (1H,dd); (oil).

EXAMPLE XVI.5

This Example illustrates a method suitable for the preparation of compounds according to the invention in which the sulfur atom of the 4,4-difluorobut-3-enylthio substituent of the corresponding unoxidised compound (prepared according to the procedures of the preceding Examples) is oxidised to sulfoxide (sulfinyl) or sulfone (sulfonyl).

Preparation of Compound XVI.3 from Compound XVI.2 using one equivalent of oxidant Compound XVI.2 (0.818 g) was cooled to 0° C. in dichloromethane (30 cm$^3$) and 3-chloroperbenzoic acid (0.99 g) was added over a period of five minutes. The mixture was stirred at the ambient temperature for 6 hour and stood for 40 hours. The reaction mixture was poured into saturated aqueous sodium bicarbonate and the product was extracted into dichloromethane. The organic layer was washed with water and dried (MgSO$_4$). Evaporation of solvent under reduced pressure gave a yellow oil which was chromatographed on sorbsil-C30, eluting with 15% ethyl acetate in hexane to give 4-(4,4-difluorobut-3-enylsulfinyl)-2,3,5,6-tetrafluoropyridine (0.711 g). $^1$H NMR: δ 2.45–2.8 (2H,m); 3.15–3.3(1H,m); 3.5–3.65(1H,m); 4.2–4.4(1H,m); (oil).

Preparation of 5-cyano-2-(4,4-difluorobut-3-enylsulfonyl)pyridine (Compound XVI.16) from Compound XVI.15 using two equivalents of oxidant 3-Chloroperbenzoic acid (3.14 g of a 50% solid) was added portionwise to a stirred solution of Compound XVI.15 (1.03 g) in dichloromethane (30 cm$^3$) at 0° C. The reaction was then allowed to warm to the ambient temperature and stirred for 4 hours. The mixture was poured into 2M aqueous sodium hydroxide and the layers separated. The aqueous layer was extracted with dichloromethane and the combined organic layers were dried over magnesium sulfate, filtered and evaporated under reduced pressure to give a yellow oil which crystallised on standing. Column chromatography on silica gel using 3:7 ethyl acetate:hexane as eluant gave Compound XVI.16 (0.785 g). $^1$H NMR: δ 2.40(2H,m); 3.25(2H,t); 4.25(1H,m); 7.25(1H,dd); 7.70(1H, dd); 8.65(1H,dd); (mp 34° C.).

The following compounds according to the invention were prepared using the above procedure:
(i) 4-(4,4-difluorobut-3-enylsulfonyl)pyridine (Compound XVI.6). $^1$H NMR: δ 2.50(2H,m); 3.20(2H,t); 4.25(1H,m); 7.80(2H,d); 8.95(2H,d); (oil).
(ii) 2-(4,4-difluorobut-3-enylsulfonyl)-5-trifluoromethylpyridine (Compound XVI.12). $^1$H NMR: δ 2.50(2H,m); 3.50(2H,t); 4.25(1H,m); 8.25(2H,d); 9.00 (1H,br s); (mp 60° C.).
(iii) 2-(4,4-difluorobut-3-enylsulfonyl)pyridine (Compound XVI.20). $^1$H NMR: δ 2.50(2H,m); 3.50(2H,t); 4.25(1H, m); 7.55–7.50(1H,m); 8.00(1H,dt); 8.10(1H,d); 8.75(1H, d); (oil).

EXAMPLE XVII.1

This Example illustrates a 2-step preparation of 3-(4,4-difluorobut-3-enylthio)-6-methylpyridazine (Compound XVII.1).

Step 1: Preparation of 3-mercapto-6-methylpyridazine

3-Chloro-6-methylpyridazine (5 g) and thiourea (2.96 g) were stirred together and heated under reflux in ethanol (50 cm$^3$) for 7.5 hours. The reaction was cooled and allowed to stand for 18 hours. The solid precipitate which had formed was filtered off and washed with diethyl ether to give 3-mercapto-6-methylpyridazine (2.3 g), which was used in the next step without further purification. $^1$H NMR: δ 2.40(3H,s); 7.30(1H,d); 7.63(1H,d); 14.5–14.7(1H,br s).

Step 2: Preparation of Compound XVII.1

A mixture of the product from Step 1 (0.337 g), 4,4-difluorobut-3-enyl 4-methylbenzenesulfonate (0.70 g), potassium iodide (0.444 g) and potassium carbonate (0.369 g) were stirred together and heated under reflux in acetone (20 cm$^3$) for 11 hours. Inorganic solids were removed by filtration and the filtrate evaporated under reduced pressure to give a brown oil. Chromatography on silica gel using 1:4 ethyl acetate:hexane as eluant gave Compound XVII.1 (0.15 g). M$^+$=216; $^1$H NMR: δ 2.48(2H,m); 2.62(3H,s); 3.36(2H, t); 4.20–4.40(1H,m); 7.10(1H,d); 7.21(1H,d); (oil).

The following compounds according to the invention and the corresponding intermediate compounds were prepared using the procedure of Steps 1 and 2 above.
(i) 3-(4,4-difluorobut-3-enylthio)-6-chloropyridazine (Compound XVII.2). M$^+$32 236; $^1$H NMR: δ 2.50(2H,m); 3.39(2H,t); 4.20–4.40(1H,m); 7.27(2H,s); (oil) from 3,6-dichloropyridazine.
(ii) 3-(4,4-difluorobut-3-enylthio)-6-methoxypyridazine (Compound XVII.3). M$^+$=232; $^1$H NMR: δ 2.47(2H,m); 3.31(2H,t); 4.09(3H,s); 4.20–4.40(1H,m); 6.83(1H,d); 7.20(1H,d); (solid mp 39.3–40.1° C.) from 3-chloro-6-methoxypyridazine.
(iii) 3-(4,4-difluorobut-3-enylthio)-6-phenylpyridazine (Compound XVII.4). M$^+$=278; $^1$H NMR: δ 2.54(2H,m); 3.46(2H,t); 4.25–4.42(1H,m); 7.39(1H,d); 7.51(3H,m); 7.69(1H,d); 8.05(2H,m); (solid mp 91.7–92.1° C.) from 3-chloro-6-phenylpyridazine.
(iv) 1-(4,4-difluorobut-3-enylthio)-phthalazine (Compound XVII.7). M$^+$=252; $^1$H NMR (CDCl$_3$); δ 2.59(2H,m); 3.55(2H,t); 4.28–4.45(1H,m); 7.89(3H,m); 8.12(1H,m); 9.25(1H,s); (oil) from 1(2H)-phthalazinthione using the procedure of Step 2 above.

EXAMPLE XVII.2

This Example illustrates a preparation of Compounds XVII.5 and XVII.6 from Compound XVII.4.

Compound XVII.4 (0.5 g) was stirred at ambient temperature in iso-propanol (20 cm$^3$) and magnesium monoperoxyphthalic acid hexahydrate (0.89 g in 10 cm$^3$ water) was added. The mixture was stirred at the ambient temperature for 20 hours. The solid which had precipitated was filtered off and washed with water. The filtrate was pored into a saturated aqueous solution of sodium bicarbonate and further product was extracted into ethyl acetate. The combined organic layers were washed with saturated brine and dried (MgSO$_4$). Evaporation of solvent under reduced pressure gave an off-white solid which was combined with the material first precipitated and chromatographed on silica gel, eluting with 30% ethyl acetate in hexane. The first product recovered was 3-(4,4-difluorobut-3-enylsufonyl)-6-phenylpyridazine (Compound XVII.6) (0.2 g) M$^+$=310; $^1$H NMR: δ2.60(2H,m); 3.75(2H,t); 4.20–4.40(1H,m); 7.60(3H, m); 8.11(1H,d); 8.15(2H,m); 8.22(1H,d); (solid mp 141.7–144.3° C.). Further elution gave 3-(4,4-difluorobut-3-enylsufinyl)-6-phenylpyridazine (Compound XVII.5) (0.25 g), M$^+$=294; $^1$H NMR: δ 2.40 and 2.65(2H,m); 3.20–3.40(2H,m); 4.18–4.32(1H,m); 7.59(3H,m); 8.11(1H, d); 8.15(2H,m); 8.21(1H,d); (mp 133–134° C.).

EXAMPLE XVIII.1

This Example illustrates a 3-step preparation of 2-(4,4-difluorobut-3-enylthio)quinoxaline (Compound XVIII.1)
Step 1: Preparation of quinoxalin-2-thione
2-Quinoxalinol (10 g), phosphorous pentasulfide (16.72 g) and pyridine (200 cm$^3$) were stirred together and heated under reflux for 7 hours. The reaction mixture was allowed to cool and most of the pyridine was removed by evaporation under reduced pressure. The residue was partitioned between ethyl acetate and water and the organic layer was separated. The aqueous layer was extracted with three further portions of ethyl acetate and the combined organic phases were washed with saturated aqueous brine, dried (MgSO$_4$) and evaporated under reduced pressure to give a brown oily solid which was triturated with hot ethyl acetate-:hexane (1:1) to dissolve the produce and leave an insoluble residue. The solvent was removed under reduced pressure and gave an orange solid, part of which was used without further purification in Step 2.
Step 2: Preparation of 2-(4-bromo-4,4-difluorobutylthio)-quinoxaline
A mixture of the product from Step 1 (1 g), 4-bromo-4, 4-difluorobutyl methanesulfonate (1.65 g) and potassium carbonate (0.852 g) were stirred together in acetone (30 cm$^3$) at ambient temperature for 7 hours. Inorganic solids were removed by filtration and the filtrate evaporated under reduced pressure to give a brown oil. Chromatography on silica gel using 1:4 ethyl acetate:hexane as eluant gave 2-(4-bromo-4,4-difluorobutylthio)-quinoxaline (1.375 g). M$^+$=332; $^1$H NMR: δ 2.19(2H,m); 2.50–2.70(2H,m); 3.43 (2H,t); 7.60–7.73(2H,m); 7.93(1H,dd); 8.03(1H,dd); 8.60 (1H,s); (oil).
Step 3: Preparation of Compound XVIII.1
1,8-Diazabicyclo[5.4.0] undec-7-ene (DBU) (1.14 cm$^3$) and the product from step 2 (1.275 g) were stirred in toluene (30 cm$^3$) and heated under reflux for 5 hours. The mixture was cooled, then excess ethyl acetate and 2M aqueous hydrochloric acid were added and the organic phase separated. The aqueous phase was extracted with ethyl acetate and the combined organic phases were washed with saturated brine, dried (MgSO$_4$), filtered and evaporated under reduced pressure to give a brown oil. Chromatography on silica gel using 1:4 ethyl acetate:hexane as eluant gave Compound XVIII.1 (0.65 g). M$^+$=252; $^1$H NMR: δ 2.51(2H, m); 3.39(2H,t); 4.03–4.40(1H,m); 7.60–7.75(2H,m); 7.90 (1H,dd); 8.03(1H,dd); 8.60(1H,s); (oil).

The following compound according to the invention and the corresponding intermediate compound were prepared using the procedure of Steps 2 and 3 above:
(i) 6-chloro-2-(4,4-difluorobut-3-enylthio)-quinoxaline (Compound XVIII.4). M$^+$=286; $^1$H NMR: δ 2.50(2H,m); 3.35(2H,t); 4.20–4.40(1H,m); 7.65(1H,dd); 7.86(1H,d); 8.01(1H,d); 8.59(1H,s); (oil), from 6-chloroquinoxalin-2-thione via 2-(4-bromo-4,4-difluorobutylthio)-6-chloroquinoxaline. $^1$H NMR: δ 2.08–2.21(2H,m); 2.48–2.68(2H,m); 3.40(2H,t); 7.65(1H,dd); 7.88(1H,d); 8.00(1H,d); 8.60(1H,s); (oil).

EXAMPLE XVIII.2

This Example illustrates a 2-step preparation of 2-(4,4-difluorobut-3-enylthio)-pyrazine (Compound XVIII.7)
Step 1: Preparation of 2-mercaptopyrazine
2-Chloropyrazine (5 g) and thiourea (3.32 g) were heated under reflux in ethanol (50 cm$^3$) for 8 hours. The reaction mixture was cooled and the ethanol was removed by evaporation under reduced pressure to give a brown gum (8.31 g) which was stirred with 2M aqueous sodium hydroxide (50 cm$^3$) for 16 hours. The solid which precipitated was filtered off and washed with water and acetone and vacuum dried. This gave a yellow solid (0.72 g); $^1$H NMR (DMSO-d$_6$): δ 7.69(1H,d); 7.89(1H,d); 8.6(1H,s), which was used in the second step without further purification.
Step 2: Preparation of Compound XVIII.7
The produce from Step 1 (0.213 g), 4,4-difluorobut-3-enyl 4-methyl-benzenesulfonate (0.5 g), potassium carbonate (0.263 g) and potassium iodide (0.317 g) were mixed in acetone (10 cm$^3$) and heated under reflux for 9 hours then allowed to cool over a weekend. The precipitate formed was removed by filtration and the filtrate evaporated under reduced pressure to give a brown oil. Chromatography on silica gel using 1:4 ethyl acetate:hexane as eluant gave Compound XVIII.7 (0.3 g) M$^{30}$=202; $^1$H NMR: δ 2.40(2H, m); 3.21(2H,t); 4.20–4.40(1H,m); 8.20(1H,d); 8.38(1H,t); 8.48(1H,s); (oil).

EXAMPLE XVIII.3

This Example illustrates a 2-step preparation of 3-chloro-2-(4,4-difluorobut-3-enylthio)-pyrazine (Compound XVIII.10).

Step 1: Preparation of 2-chloro-3-mercaptopyrazine and 2,3-dimercaptopyrazine 2,3-Dichloropyrazine (1 g) and sodium hydrosulfide dihydrate (2.5 g) were combined in isopropanol (20 cm$^3$) and the mixture heated under reflux for 1 hour. The reaction was cooled and allowed to stand for 36 hours. The yellow solid which precipitated was recovered by filtration, washed with diethyl ether and dried under vacuum. The filtrate was discarded. The solid was dissolved in hot ethanol and on cooling a small amount of sodium hydrosulfide precipitated and was removed by filtration. The remaining ethanol solution was diluted with diethyl ether whereupon a yellow solid (0.3 g) precipitated. This was identified as the bis-sodium salt of 2,3-dimercaptopyrazine, MH$^+$(FAB)=188; $^1$H NMR (DMSO-d$_6$): δ 7.35(1H,d); 7.50(1H,d). Evaporation of the mother liquors gave a yellow solid (0.8 g), identified as the sodium salt of 2-chloro-3-mercaptopyrazine, M$^+$(FAB)= 145; $^1$H NMR (DMSO-d$_6$): δ 7.35(1H,d); 7.80(1H,d)

Step 2: Preparation of 3-chloro-2-(4,4-difluorobut-3-enylthio)-pyrazine

The mono-thiolate product from Step 1 (0.8 g), 4,4-difluorobut-3-enyl 4-methylbenzenesulfonate (1.24 g) and potassium carbonate (0.655 g) were mixed in acetone (25 cm$^3$) containing dimethyl formamide (5 cm$^3$) and heated under reflux for 15 hours then allowed to cool. The precipitate was removed by filtration and the filtrate evaporated under reduced pressure to give a brown oil. Chromatography on silica gel using a 95:5 mixture of hexane:ethyl acetate as eluant gave Compound XVIII.10 (0.45 g). M$^+$=236; $^1$H NMR: δ 2.41(2H,m); 3.20(2H,t); 4.20–4.40(1H,m); 8.05 (1H,d); 8.30(1H,d) (oil). This contained (gc) 5% of Compound XVIII.13 as an impurity.

Compound XVIII.13 was obtained pure in its own right by treatment of the bis-thiolated product from Step 1 of the above example with two equivalents of 4,4-difluorobut-3-enyl 4-methyl-benzenesulfonate under the same conditions as Step 2 of this Example. Chromatography on silica gel using a 4:1 mixture of hexane:ethyl acetate as eluant gave 2,3-bis-(4,4-difluorobut-3-enylthio)-pyrazine. M$^+$=324, $^1$H NMR: δ 2.40(4H,m); 3.22(4H,t); 4.20–4.40(2H,m); 8.07 (2H,s) (oil).

The following compound according to the invention was prepared using the above procedure:

(i) 6-chloro-2-(4,4-difluorobut-3-enylthio)-pyrazine (Compound XVIII.14). M$^+$=236; $^1$H NMR: δ 2.42(2H,m); 3.21(2H,t); 4.20–4.40(1H,m); 8.20(1H,s); 8.35(1H,s) (oil) from 2,6-dichloropyrazine.

EXAMPLE XVIII.4

This Example illustrates a preparation of Compounds XVIII.2 and XVIII.3 from Compound XVIII.1.

Compound XVIII.1 (0.25 g) was stirred at ambient temperature in ethanol (10 cm$^3$) and magnesium monoperoxyphthalic acid hexahydrate (0.589 g in 5 cm$^3$ water) was added over a period of five minutes. After 30 minutes, the mixture was heated to 70° C. for 1 hour. The reaction mixture was cooled, poured into saturated aqueous sodium bicarbonate and the products were extracted into ethyl acetate. The organic layer was washed with water and dried (MgSO$_4$). Evaporation of solvent under reduced pressure gave an off-white solid (0.15 g) which was chromatographed on silica gel, eluting with 10% ethyl acetate in hexane. The main product recovered was 2-(4,4-difluorobut-3-enylsulfonyl)-quinoxaline (Compound XVIII.3) (0.1 g) mp 86.5–87.5° C. M$^+$=284; $^1$H NMR: δ 2.61(2H,m); 3.62(2H,t); 4.20–4.40(1H,m); 8.00(2H,m); 8.25(2H,m); 9.51(1H,s). Tlc indicated the presence of a lower rf material, 2-(4,4-difluorobut-3-enylsulfinyl)-quinoxaline (Compound XVIII.2) in the crude reaction product but this was not isolated pure.

The following compounds according to the invention were prepared by the above procedure:

(i) 6-chloro-2-(4,4-difluorobut-3-enylsulfinyl)-pyrazine (Compound XVIII.15). M$^+$=253; $^1$H NMR: δ 2.30–2.70 (2H,m); 3.00–3.30(2H,m); 4.19–4.35(1H,m); 8.70(1H,s); 9,10(1H,s) (oil) from Compound XVIII.14.

(ii) 6-chloro-2-(4,4-difluorobut-3-enylsulfonyl)-pyrazine (Compound XVIII.16). M$^+$=268; $^1$H NMR: δ 2.55(2H,m); 3.50(2H,t); 4.20–4.35(1H,m); 8.90(1H,s); 9.19(1H,s) (oil) from Compound XVIII.14.

EXAMPLE VIII.1

This Example illustrates a 3-step preparation of 4-(4,4-difluorobut-3-enylthio]-1,2,3-benzotriazine (Compound XIX.1).

Step 1: Preparation of 4-mercapto-1,2,3-benzotriazine

2-Aminobenzonitrile (5 g) was stirred in pyridine (30 cm$^3$), triethylamine (6 cm$^3$) was added and hydrogen sulfide gas was bubbled into the reaction over 4 hours. The mixture was then poured into water (20 cm$^3$) and the oil which separated out on shaking was separated off, and dried by azeotroping with ethanol and toluene. This gave a yellow solid (2-aminothiobenzamide, 3 g) which was stirred in 2M hydrochloric acid (30 cm$^3$) at 0° C. Sodium nitrite (1.65 g) in water (10 cm$^3$) was added dropwise and the reaction mixture was stirred cold for 1 hour, then allowed to warm to the ambient temperature and stirred for a further 1 hour. The solid which was produced was filtered off, washed with water and dried by washing with diethyl ether, to give a brown solid (2.15 g).

Step 2: Preparation of 4-(4,4-difluorobut-3-enylthio)-1,2,3-benzotriazine

The product of Step 1 (1 g) 4-bromo-4,4-difluorobutyl methanesulfonate (1.65 g) and potassium carbonate (0.852 g) were stirred together in acetone (30 cm$^3$) at ambient temperature for 36 hours. Inorganic solids were removed by filtration and the filtrate evaporated under reduced pressure to give a brown oil. Chromatography on silica gel using 1:4 ethyl acetate:hexane as eluant gave two yellow oils (ea 0.5 g). The first-eluted oil was identified as N-alkylated material and the second was the desired S-alkyated intermediate 4-(4-bromo-4,4-difluorobutylthio)-1,2,3-benzotriazine. $^1$H NMR: δ 2.18–2.31(2H,m); 2.58–2.71(2H,m); 3.63(2H,t); 7.95(1H,t); 8.09(2H,m); 8.40(1H,d).

Step 3: Preparation of Compound XIX.1

1.8-Diazabicyclo[5.4.0] undec-7-ene (DBU) (0.45 cm$^3$) and the product from step 2 (0.5 g) were stirred in toluene (15 cm$^3$) and heated under reflux for 6 hours. The mixture was cooled, then excess ethyl acetate and 2M aqueous hydrochloric acid were added and the organic phase separated. The aqueous phase was extracted with ethyl acetate and the combined organic phases were washed with saturated brine, dried over anhydrous magnesium sulfate, filtered and evaporated under reduced pressure to give a yellow oil. Chromatography on silica gel using 1:4 ethyl acetate:hexane as eluant gave Compound XIX.1 (0.25 g) MH$^+$=2.54; $^1$H NMR: δ 2.60(2H,m); 3.60(2H,t); 4.30–4.40 (1H,m); 7.93(1H,t); 8.09(2H,m); 8.39(1H,d); (oil)

EXAMPLE XX.1

Two methods (A and B) of preparing mercapto-1,2,4-triazines required as intermediates for preparation of compounds of the invention are described below.

METHOD A

A general synthesis of 3-mercapto-1,2,4-triazines is by reaction between thiosemicarbazide and a 1,2 di-carbonyl compound. This is illustrated by the preparation of 3-mercapto-5-methyl-1,2,4-triazine.

A solution of sodium bicarbonate (8 g) in water (100 cm$^3$) was added to a suspension of thiosemicarbazide (8 g) in water (100 cm$^3$). The resulting solution was cooled below 5° C. and pyruvic aldehyde (40% weight solution in water, (20 cm$^3$)) was added. The solution was kept at 5° C. for 18 hours, then washed with chloroform (10×50 cm$^3$). The pH of the aqueous layer was adjusted to 2 with concentrated hydrochloric acid. The resulting precipitate was filtered off, washed with copious amounts of water and dried, giving an orange solid (4.036 g). The 3-mercapto-5-methyl-1,2,4-triazine was used without further purification in subsequent steps.

The following intermediate mercaptotriazines were prepared following the above procedure. In some cases, ethanol was used as solvent in place of water. The starting materials were commercially available.

(i) 3-mercapto-1,2,4-triazine from glyoxal.
(ii) 3-mercapto-5-propyl-6-methyl-1,2,4-triazine from hexane-2,3-dione. $^1$H NMR: δ 0.98(3H,t); 1.54–1.68(2H, m); 2.08(3H,s); 3.04(2H,t); 8.2(1H,br s).
(iii) 3-mercapto-5-phenyl-6-methyl-1,2,4-triazine from 1-phenylpropane-1,2-dione.

METHOD B

An alternative method for preparing mercapto-1,2,4-triazines comprises treatment of a corresponding hydroxy-triazine (which may exist in various tautomeric forms) with a thiolating reagent such as phosphorous pentasulfide. This following illustrates the preparation of 1,2,4-triazine-3,5 (2H,4H)-dithione from 1,2,4-triazine-3,5(2H,4H)-dione (6-azauracil).

6-Azauracil (2 g), phosphorous pentasulfide (15.72 g) and pyridine 50 cm$^3$ were stirred together and heated under reflux for 56 hours. The reaction mixture was allowed to cool and most of the pyridine was removed by evaporation under reduced pressure. The residue was agitated with diethyl ether and water and the organic layer was separated. The aqueous layer was extracted with three further portions of diethyl ether and the combined organic phases were washed with saturated aqueous brine, dried (MgSO$_4$) and evaporated under reduced pressure to give a brown oil which was chromatographed on silica gel, using 1:5 ethyl acetate-:hexane as eluant. This gave an orange solid (1 g) which was used without further purification. $^1$H NMR (DMSO-d$_6$): δ 7.95(1H,s); 13.8–14.1(1H,br s); 14.3–14.6(1H,br s)

3-Mercapto-1,2,4-benzotriazine was prepared from 3-hydroxy-1,2,4-benzotriazine and 6-methyl-1,2,3-triazine-5-(4H)-thione from 6-methyl-1,2,3-triazine-5-(4H)-one following essentially the above procedure.

EXAMPLE XX.2

This Example illustrates the preparation of compounds according to the invention which contain a 1,2,3-triazine substituted with a 4,4-difluorobut-3-enylthio group in the 3, 5 or 6-position, starting from a correspondingly substituted mercaptotriazine and an appropriate difluorobut-1-ene alkylating agent. This is demonstrated by the following preparation of 3-(4,4-difluorobut-3-enylthio)-5-hydroxy-1,2,4-triazine (Compound XX.227) from 6-aza-2-thiouracil and 4,4-difluorobut-3-enyl 4-methyl-benzenesulfonate.

4,4-Difluorobut-3-enyl 4-methyl-benzenesulfonate (1.5 g) and potassium iodide (0.95 g) were stirred in ethanol (5 cm$^3$) and heated under reflux for three hours then allowed to cool. This part of the procedure converts the starting material to the more chemically reactive and thio-selective alkylating agent, 4-iodo-1,1-difluorobut-1-ene. 6-Aza-2-thiouracil (0.744 g) was added as a solution in 1M aqueous sodium hydroxide (5.73 cm$^3$) and the reaction mixture stirred at ambient temperature for 70 hours. The reaction was worked up by addition of an excess of 1M aqueous sodium hydroxide and ethyl acetate. The ethyl acetate layer was separated and the aqueous layer was washed with more ethyl acetate. These extracts were discarded. The aqueous layer was then acidified to pH4 with 2M aqueous hydrochloric acid. The product was extracted into ethyl acetate (3 portions) and these combined organic layers were washed with water and saturated aqueous brine and dried (MgSO$_4$). The product was recovered from the solution by evaporation under reduced pressure to give a cream solid (0.659 g). A portion was redissolved in hot ethyl acetate and some insoluble material removed by filtration. Compound XX.227 recovered from solution by evaporation had mp 102°–103° C. M$^+$=219; $^1$H NMR (DMSO-d$_6$): δ 2.41(2H,m); 3.25(2H, t); 4.55–4.75(1H,m); 7.69 and 7.79(total 1H,ea s, tautomeric protons)

Compound XX.247 was prepared using a related procedure, as follows.

6-Methyl-1,2,3-triazine-5(4H)-thione (0.5 g), 4-bromo-1, 1-difluorobut-1-ene (0.673 g) and potassium carbonate (0.543 g) were stirred together in acetone (5 cm$^3$) for 60 hours at the ambient temperature. Then inorganic material was filtered off and washed with acetone. Solvent was removed from the combined acetone solutions by evaporation under reduced pressure and the residual brown gum was chromatographed on silica, eluting with 20% ethyl acetate in hexane, to give 5-(4,4-difluorobut-3-enylthio)-6-methyl-1, 2,4-triazine (Compound XX.247) (0.075 g). M$^+$=217; $^1$H NMR: δ 2.45(2H,m); 2.60(3H,s); 3.29(2H,t); 4.20–4.40(1H, m); 9.11(1H,s); (oil).

EXAMPLE XX.3

When the mercaptotriazine is fully soluble in acetone and carries no other potentially interfering nucleophilic groups a procedure alternative to that of Example XX.2 may be used.

This is illustrated by the following preparation of 3,5-bis-(4,4-difluorobut-3-enylthio)-1,2,4-triazine (Compound XX.231) from 1,2,4-triazine-3,5-(2H,4H)-dithione and 4,4-difluoro-3-butenyl 4-methyl-benzenesulfonate.

1,2,4-Triazine-3,5(2H,4H)-dithione (1 g), 4,4-difluorobut-3-enyl 4-methyl-benzenesulfonate (3.6 g), potassium iodide (1.14 g) and potassium carbonate (0.952 g) were stirred and heated under reflux in acetone (20 cm$^3$) for 7 hours. The solution was cooled and filtered to remove solids. The filtrate and further acetone washings of the solids were combined and evaporated under reduced pressure to give a brown oil. Chromatography on silica gel using 15:85 ethyl acetate:hexane as eluant gave Compound XX.231 (1 g) as an orange oil. M$^+$=325; $^1$H NMR: δ 2.40–2.55(4H,m); 3.25(4H,m); ;4.15–4.40(2H,m); 8.70(1H,s).

EXAMPLE XX.4

This Example illustrates a general procedure for the two-step preparation of compounds according to the invention by reaction of a mercapto-substituted 1,2,4-triazine with 4-bromo-4,4-difluorobutyl methanesulfonate followed by dehydrobromination of the resulting intermediate as demonstrated by the following preparation of 3-(4,4-difluorobut-3-enylthio)-5-phenyl-6-methyl-1,2,4-triazine (Compound XX.4).

Step 1: 3-(4-bromo-4,4-difluorobutylthio)-5-phenyl-6-methyl-1,2,4-triazine.

A mixture of 4-bromo-4,4-difluorobutyl methanesulfonate (0.7 g), 3-mercapto-5-phenyl-6-methyl-1,2,4-triazine (0.5 g) and potassium carbonate (0.7 g) were stirred together and heated under reflux in acetone (40 cm$^3$) for 14 hours. Inorganic solids were removed by filtration and the filtrate evaporated under reduced pressure to give a brown oil (1.058 g). Chromatography on silica gel using 1:4 ethyl acetate:hexane as eluant gave an orange oil (0.576 g). This was stirred and heated under reflux in trifluoroacetic acid (3 cm$^3$) for 6 hours to re-cyclise some material which had undergone partial hydrolysis and ring opening. Product was recovered by evaporation of the solvent under reduced pressure and chromatography on silica gel and gave 3-(4-bromo-4,4-difluorobutylthio)-5-phenyl-6-methyl-1,2,4-triazine. (0.509 g). $^1$H NMR: δ 2.12–2.24(2H,m); 2.48–2.68 (2H,m); 2.78(3H,s); 3.36(2H,t); 7.50–7.58(3H,m); 7.68–7.74(2H,m); (oil).

Step 2: 3-(4,4-difluorobut-3-enylthio)-5-phenyl-6-methyl-1,2,4-triazine 1,8-Diazabicyclo[5.4.0] undec-7-ene (DBU) (1 cm$^3$) was added dropwise to a stirred solution of the product from step 1 (0.5 g) in toluene (10 cm$^3$). The mixture was kept at ambient temperature for 20 hours, then excess ethyl acetate and saturated aqueous ammonium chloride were added and the organic phase separated. The aqueous phase was extracted with ethyl acetate and the combined organic phases were washed with saturated aqueous ammonium chloride, dried (MgSO$_4$), filtered and evaporated under reduced pressure to give an orange oil (0.43 g). Chromatography on silica gel using 1:4 ethyl acetate:hexane as eluant gave Compound XX.4 (0.281 g). M$^+$=293; $^1$H NMR: δ 2.48–2.58(2H,m); 2.76 (3H,s); 3.32(2H,t); 4.22–4.40(1H, m); 7.48–7.58(3H,m); 7.68–7.76(2H,m); (oil).

EXAMPLE XX.5

This Example illustrates a procedure suitable for the preparation of compounds according to the invention carrying an alkoxy, or substituted alkoxy, group on the 5-position of the triazine ring from a compound carrying alkenylthio groups in both the 3 and 5-positions, as demonstrated by the preparation of 3-(4,4-difluorobut-3-enylthio)-5-methoxy-1,2,4-triazine (Compound XX.221) from Compound XX.231.

Compound XX.231 (0.5 g) was stirred for one hour with sodium methoxide (0.083 g) in methanol (15 cm$^3$) at ambient temperature. The solvent was removed by evaporation under reduced pressure and the residue was chromatographed on silica gel, eluting with 15:85 ethyl acetate:hexane, and gave 0.12 g of Compound XX.221. M$^+$=233; $^1$H NMR: δ 2.50(2H,m); 3.29(2H,t); 4.02(3H,s); 4.22–4.42(1H,m); 8.55(1H,s) as a single isomer whose identity as the 5-methoxy compound was confirmed by nmr.

The following compounds according to the invention was prepared using the above procedure with the appropriate alkoxide in the corresponding alcohol as solvent:

(i) 3-(4,4-difluorobut-3-enylthio)-5-(1-methyl-ethoxy)-1,2,4-triazine (Compound XX.205). M$^+$=261; $^1$H NMR: δ 1.4(6H,d); 2.5(2H,m); 3.25(2H,t); 4.2–4.4(1H,m); 5.4 (1H,m); 8.45(1H,s).

(ii) 3-(4,4-difluorobut-3-enylthio)-5-ethoxy-1,2,4-triazine (Compound XX.218). M$^+$=247; $^1$H NMR: δ 1.43(3H,t); 2.50(2H,m); 3.26(2H,t); 4.2–4.4(1H,m); 4.46(2H,q); 8.5 (1H,s)

EXAMPLE XX.6

This Example illustrates a 2-step procedure used for the preparation of Compounds XX.52 and XX.116 as a 1:1 mixture.

Step 1: 3-(4-bromo-4,4-difluorobutylthio)-5-methyl-1,2,4-triazine and 3-(4-bromo-4,4-difluorobutylthio)-6-methyl-1,2,4-triazine 4-bromo-4,4-difluorobutyl methanesulfonate (1 g) and thiosemicarbazide (0.475 g) were stirred together and heated under reflux in ethanol (20 cm$^3$) for 5 hours. GC indicated complete consumption of the methanesulfonate. The mixture was allowed to cool and water (3 cm$^3$) and sodium bicarbonate (1 g) were added (effervescence). A 40% by weight solution of pyruvic aldehyde (1 cm$^3$) was then added and the mixture stirred at ambient temperature for 4 hours. TLC showed that product had formed. It was extracted into ethyl acetate and the organic layer was dried (MgSO$_4$), filtered and evaporated to give an oil (1.209 g). This intermediate product was purified by chromatography on silica gel, eluting with 1:4 ethyl acetate:hexane and gave a yellow oil (0.464 g) which had $^1$H NMR: δ 2.08–2.20(2H,m); 2.48–2.62(2H,m); 2.52 and 2.66 (total 3H,ea s); 3.28–3.38 (2H,m); 8.28 and 8.84 (total 1H, ea s), indicating it to be an approximately 1:1 mixture of the 5- and 6-methyl isomers.

Step 2: 3-(4,4-difluorobut-3-enylthio)-5-methyl-1,2,4-triazine and 3,-(4,4-difluorobut-3-enylthio)-6-methyl-1,2,4-triazine The mixture of products from Step 1 (0.46 g) were dehydrobrominated using DBU in a procedure analogous to Step 2 of Example XX.4 and the product (0.253 g) was purified by chromatography on silica gel eluting with dichloromethane. Under these conditions the 5- and 6-methyl isomers were inseparable and 0.232 g of a yellow oil was obtained which had M$^+$=217; $^1$H NMR: δ 2.44–2.54(2H,m); 2.50 and 2.66 (total 3H,ea s); 3.26–3.34(2H,m); 4.22–4.40 (1H,m); 8.28 and 8.82 (total 1H, ea s); this indicated it to be a 1:1 mixture of Compound XX.52 and Compound XX.116.

Compound XX.251 according to the invention was prepared using the above procedure but taking cyclohexane-1, 2-dione in Step 1 in place of pyruvic aldehyde. $^1$H NMR: δ 1.86–1.98(4H,m); 2.42–2.54(2H,m); 2.84–2.92(2H,m); 3.04–3.12(2H,m); 3.28(2H,t); 4.22–4.38(1H,m); (oil).

EXAMPLE XX.7

This Example illustrate an alternative procedure used for the preparation of Compounds XX.52 and XX.116 as a chromatographically separable mixture.

4,4-difluorobut-3-enyl 4-methyl-benzenesulfonate (1 g) and thiosemicarbazide (0.4 g) were stirred together and heated under reflux in ethanol (20 cm$^3$) for 6 hours. The mixture was allowed to cool overnight, whereupon a crystalline yellow precipitate of the S-alkylated compound was evident. This was not isolated but solvent was removed by evaportion at reduced pressure and the residue (1.3 g) was treated with sodium bicarbonate (0.928 g), water (3 cm$^3$) and ethanol (20 cm$^3$). A 40% by weight solution of pyruvic aldehyde (0.9 cm$^3$) was then added (slight effervescence)

and the mixture stirred at ambient temperature for 1 hour. The reaction was poured into water and the product was extracted into ethyl acetate (3 portions). The combined organic phases were dried (MgSO$_4$), filtered and evaporated to give a brown gum (0.85 g). Chromatography on silica gel, eluting with 10% ethyl acetate in hexane gave a fraction which was identified as Compound XX.116 (0.05 g) (containing 10% of Compound XX.52 by NMR). Continued elution gave a mixed fraction containing an approximately 1:1 mixture of Compounds XX.52 and XX.116 (0.16 g) and then a fraction identified as Compound XX.52 (0.1 g) (containing 15% of Compound XX.116 by NMR).

EXAMPLE XX.8

This Example illustrates a general procedure for the two-step preparation of compounds according to the invention by reaction of thiosemicarbazide with 4-bromo-1,1-difluorobut-1-ene and then cyclisation of the intermediate with a 1,2-dicarbonyl compound as demonstrated by the following preparation of 3-(4,4-difluorobut-3-enylthio)-1,2,4-triazine (Compound XX.137).

Thiosemicarbazide (2.6 g) was stirred with 4-bromo-1,1-difluorobut-1-ene in ethanol (75 cm$^3$) and the mixture heated under reflux for 7 hours and allowed to cool to the ambient temperature. Glyoxal (4.2 g of a 40% aqueous solution) and sodium hydrogen carbonate (7.37 g) were added and the resulting mixture was stirred at ambient temperature for 18 hours. Water was added and the product was extracted into three portion of ethyl acetate. The combined organic phases were washed with saturated brine, dried (MgSO$_4$), filtered and evaporated under reduced pressure to give a brown gum. Chromatography on silica gel, eluting with 20% ethyl acetate in hexane gave Compound XX.137. M$^+$=203; $^1$H NMR: δ 2.50(2H,m); 3.30(2H,t); 4.20–4.40(1H,m); 8.39 (1H,d); 8.95(1H,d) (oil).

The following compounds according to the invention were prepared using the above procedure with the appropriate 1,2-dicarbonyl compound in place of glyoxal:

(i) 3-(4,4-difluorobut-3-enylthio)-5-propyl-1,2,4-triazine (Compound XX.27) from 2-oxo-pentanal. M$^+$=245; $^1$H NMR: δ 1.0(3H,t); 1.7–1.85(2H,m); 2.45–2.55(2H,m); 2.6(2H,t); 3.3(2H,t); 4.2–4.4(1H,m); 8.8(1H,s) (oil). This preparation also gave the isomeric Compound XX.109; M$^+$=245; $^1$H NMR: δ 1.0(3H,t); 1.75–1.9(2H,m); 2.45–255(2H,m); 2.9(2H,t); 3.3(2H,t); 4.2–4.4(1H,m); 8.25(1H,s) (oil), the latter faster running isomer in the chromatography being approximately 8% of the mixture which was produced.

(ii) 3-(4,4-difluorobut-3-enylthio)-5-ethyl-1,2,4-triazine (Compound XX.30) from 2-oxo-butanal. M$^+$=231; $^1$H NMR: δ 1.3–1.3(3H,t); 2.45–2.55(2H,m); 2.75–2.85(2H, q); 3.25–3.35(2H,t); 4.2–4.4(1H,m); 8.85(1H,s) (oil). The isomeric Compound XX.110 was detected in the reaction mixture but was not isolated. However, it was the major product of the cyclisation when 1,1-diethoxy-butan-2-one was used in place of 2-oxo-butanal. Initial imine formation in water followed by cyclisation in aqueous acetone catalysed with pyridinium tosylate gave Compound XX.110. M$^+$=231; $^1$H NMR: δ 1.4(3H,t); 2.50(2H,m); 2.95(2H,q); 3.(2H,t); 4.2–4.4(1H,m); 8.29(1H,s) (oil).

(iii) 3-(4,4-difluorobut-3-enylthio)-6-methyl-1,2,4-triazine-5(4H)-one (Compound XX.226) from pyruvic acid. M$^+$=233; $^1$H NMR (DMSO-d$_6$): δ 2.05(3H,s); 2.30(2H, m); 3.12(2H,t); 4.4–4.6(1H,m) (gum).

The following compounds according to the invention were prepared using the above procedure with a 2,2-dichloro aldehyde in place of glyoxal:

(iv) 3-(4,4-difluorobut-3-enylthio)-5-(1-methyl-ethyl)-1,2,4-triazine (Compound XX.15). M$^+$=245; $^1$H NMR: δ 1.32(6H,d); 2.50(2H,m); 3.0(1H,m); 3.3(2H,t); 4.20–4.40 (1H,m); 8.82(1H,s) (oil) and the chromatographically faster-running isomer 3-(4,4-difluorobut-3-enylthio)-6-(1-methyl-ethyl)-1,2,4-triazine (Compound XX.98). M$^+$=245; $^1$H NMR: δ 1.4(6H,d): 2.50(2H,m); 3.18–3.35 (3H,m); 4.20–4.40(1H,m); 8.30(1H,s) (oil) from 2,2-dichloro-3-methyl-butanal.

EXAMPLE XX.9

This Example illustrates a preparation of 5-dichloromethyl-3-(4,4-difluorobut-3-enylthio)-1,2,4-triazine (Compound XX.65) from Compound XX.52.

Compound XX.52 (3.1 g) and N-chlorosuccinimide (2 g) were stirred and heated together under reflux in carbon tetrachloride (40 cm$^3$) for 1 hour. The mixture was allowed to cool and stirred at the ambient temperature for 4 hours. Solvent was removed by evaporation under reduced pressure and the black tarry residue was suspended in diethyl ether (40 cm$^3$) and passed through a bed of hi-flo filter aid. Insoluble material was washed with further diethyl ether and the combined solutions were evaporated under reduced pressure. The residue was purified by chromatography on silica, eluting with diethyl ether:hexane 1:1 and the fractions containing product were evaporated under reduced pressure and further purified by preparative tlc. eluting with 30% diethyl ether in hexane to give Compound XX.65 (0.2 g). $^1$H NMR: δ 2.50(2H,m); 3.3(2H,t); 4.20–4.40(1H,m); 6.50(1H, s); 9.37(1H,s); (oil).

EXAMPLE XX.10

This Example illustrates a preparation of 3-(4,4-difluorobut-3-enylsulfonyl)-5-propyl-1,2,4-triazine (Compound XX.28) from Compound XX.27.

Compound XX.27 (0.2 g) was stirred at 5° C. in dichloromethane (5 cm$^3$) and 3-chloro perbenzoic acid (0.282 g, 2 equiv.) was added. Stirring continued for 18 hours at the ambient temperature. The reaction was quenched by the addition of a saturated aqueous solution of sodium bicarbonate and the product was extracted into dichloromethane. The organic phase was separated, washed with saturated brine and dried (MgSO$_4$). After filtration and concentration by evaporation under reduced pressure, there was obtained an oil which was purified by chromatography on silica gel using 3:7 ethyl acetate:hexane as eluant to give Compound XX.28 (0.187 g). M$^+$=227; $^1$H NMR: δ 1.0–1.1(3H,t); 1.8–1.95(2H,m); 2.6–2.7(2,m); 2.9–3.0(2H,t); 3.7–3.8(2H, t); 4.2–4.4(1H,m); 9.3(1H,s); (oil).

The following compounds according to the invention were prepared by the above procedure, using 1.75 equivalents of oxidant:

(i) 3-(4,4-difluorobut-3-enylsulfinyl)-5-methyl-1,2,4-triazine (Compound XX.53); M$^+$=233; $^1$H NMR: δ 2.35–2.7(2H,m); 2.75(3H,s); 3.2–3.4(2H,m); 4.2–4.35 (1H,m); 9.25(1H,s); (oil) and 3-(4,4-difluorobut-3-enylsulfonyl)-5-methyl-1,2,4-triazine (Compound XX.54); MH$^+$=250; $^1$H NMR: δ 2.6–2.7(2H,m); 2.8(3H, s); 3.7–3.8(2H,t); 4.25–4.4(1H,m); 9.35(1H,s); (oil) from Compound XX.52.

(ii) 3-4,4-difluorobut-3-enylsulfinyl)-6-methyl-1,2,4-triazine (Compound XX.117); MH$^+$=234; $^1$H NMR: δ 2.3–2.75(2H,m); 2.85(3H,s); 3.2–3.4(2H,m); 4.15–4.3 (1H,m); 8.7(1H,s); (oil) and 3-(4,4-difluorobut-3-enylsulfonyl)-6-methyl-1,2,4-triazine (Compound XX.118); MH$^+$=250; $^1$H NMR: δ 2.6–2.7(2H,m); 2.9(3H, s); 3.65–3.75(2H,t); 4.2–4.4(1H,m); 8.75(1H,s); (oil) from Compound XX.116.

EXAMPLE XXI.1

This Example illustrates a preparation of 2-(4,4-difluorobut-3-enylthio)-1,3,5-triazine (Compound XXI.1).

(4,4-difluorobut-3-enyl)-thiourea (as its 4-methylbenzenesulfonate salt) (0.9 g) and 1,3,5-triazine (0.216 g) were heated together under reflux in ethanol (20 cm$^3$) for 4 hours. The reaction mixture was cooled and the solvent was removed by evaporation to give a solid which was triturated with hexane. The hexane-soluble material was recovered by evaporation under reduced pressure. This gave Compound XX.1 (0.4 g). M$^+$=203; $^1$H NMR: δ 2.45(2H,m); 3.20(2H,t); 4.20–4.40(1H,m);; 8.82(2H,s); (oil).

The compounds of formula (I) are nematicidal and can be used to control nematodes in plants. Thus, in a further aspect of the present invention, there is provided a method of killing or controlling nematodes, which comprises applying a compound of formula (I) to the nematode.

The term "controlling" extends to non-lethal effects which result in the prevention of damage to the host plant and the limitation of nematode population increase. The effects may be the result of chemical induced disorientation, immobilisation, or hatch prevention or induction. The chemical treatment may also have deleterious effects on nematode development or reproduction.

The compounds of the present invention can be used against both plant parasitic nematodes and nematodes living freely in the soil.

Examples of plant-parasitic nematodes are: ectoparasites, for example Xiphinema spp., Longidorus spp., and Trichodorus spp.; semi-parasites, for example, Tylenchulus spp.; migratory endoparasites, for example, Pratylenchus spp., Radopholus spp., and Scutellonema spp.; sedentary parasites, for example, Heterodera spp., Globodera spp. and Meloidogyne spp.; and stem and leaf endoparasites, for example, Ditylenchus spp., Aphelenchoides spp. and Hirshmaniella spp.

The compounds of formula (I) also display activity against different types of nematodes including cyst nematode.

The compounds of the present invention also exhibit activity against other pests of growing and stored agronomic crops, forestry, greenhouse crops, ornamentals, nursery crops, stored food and fiber products. These pests include:
Heteroptera/Homoptera including *Myzus persicae, Aphis gossypii, Aphis fabae, Rhopalosiphum padi,* Aonidiella spp., Trialeurodes spp,. *Bemisia tabaci, Nilaparvata lugens, Nephotettix cincticeps, Nezara viridula, Dysdercus suturellus, Dysdercus fasciatus,* and *Lygus lineoralis.*
Diptera including *Ceratitis capitata,* Tipula spp., *Oscinella frit,* Liriomyza spp., Delia spp., and Peromya spp.
Lepidoptera including *Pieris brassicae, Plutella xylostella, Spodoptera littoralis* and other Spodoptera spp., *Heliothis virescens* and other Heliothis and Helicoverpa spp., and *Chilo partellus.*
Coleoptera including *Phaedon cochleariae,* Diabrotica spp., Agrotis spp., and *Leptinotarsa decemlineata.*
Blattodea including *Blattella germanica, Periplaneta americana,* and *Blatta orientalis.* Orthoptera including *Chortiocetes terminifera,* Schistocerca spp., Locusta spp. and Scapteriscus spp.,
Acari including *Panonychus ulmi, Panoychus citri, Tetranychus urticae, Tetranychus cinnabarinus, Phyllocoptruta oleivora,* and Brevipalpus spp.

The compounds can also be used against livestock, household, public and animal health pests such as:
Siphonaptera including *Ctenocephalides felis, Ctenocephalides canis, Xenopsylla cheopis,* and *Pulex irritans.*
Mallophaga including *Menopon gallinae,* and *Cuclotogaster heterographus.*
Anoplura including *Pediculus humanus* capitis, *Pediculus humanus* humanus, and *Phthirus pubis.*
Diptera including *Musca domestica, Aedes aegypti, Anopheles gambiae, Culex quinquesfasciatus, Chrysops discalis,* and *Tabanus nigrovittatus.*
Sarcophagidae including *Sarcophaga haemorrhoidalis* and *Wohlfahrtia magnifica.*
Calliphoridae including *Lucilia cuprina* and *Cordylobia anthrophphaga.*
Oestridae including *Oestrus ovis.*

Generally, the compounds may be used to combat and control pest injurious to and/or associated with the transmission of diseases of man and animals. The pest which may be combated and controlled by the use of the compounds of the invention parasitic nematodes of animals, including mammals, which may be found in the gastrointestinal tract, the air passages or blood vessels of the respiratory tract and the heart, together with the associated blood vessels.

The compounds of formula (I) may be used to treat vertebrates, such as mammals (for example, man, pigs, sheep, cattle, equines, cats and dogs), birds (for example, chicken, ducks, turkeys, geese, canaries and budgerigas), and fish (for example, salmon, trout and ornamental fish).

The nematode and other pests may be killed/controlled by applying an effective amount of one or more of the compounds of the present invention to the environment of the pests, to the area to be protected, as well as directly on the pests.

In order to apply the compounds to the locus of the nematode, insect or acarid pest, or to a plant susceptible to attack by the nematode, insect or acarid pest, the compound is usually formulated into a composition which includes in addition to the compound of formula (I) suitable inert diluent or carrier materials, and/or surface active agents. Thus in two further aspects of the invention there is provided a nematicidal, insecticidal or acaricidal composition comprising an effective amount of a compound of formula (I) as defined herein and an inert diluent or carrier material and optionally a surface active agent.

The amount of composition generally applied for the control of nematode pests gives a rate of active ingredient from 0.01 to 10 kg per hectare, preferably from 0.1 to 6 kg per hectare.

The compositions can be applied to the soil, plant, seed, or other area to be protected, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite alumina, montmorillonite, kieslguhr, chalk, diatomaceous earths, calcium phosphates, calcium and magnesium carbonates, sulfur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulfates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated. For agricultural or horticultural purposes, an aqueous preparation containing between 0.0001% and 0.1% by weight of the active ingredient (approximately equivalent to from 5–2000 g/ha) is particularly useful.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulfuric acid, for example sodium lauryl sulfate, salts of sulfonated aromatic compounds, for example sodium dodecylbenzenesulfonate, sodium, calcium or ammonium lignosulfonate, or butylnaphthalene sulfonate, and a mixture of the sodium salts of diisopropyl- and triisopropylnaphthalene sulfonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 1–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrates FS, liquid seed treatment LS), or microcapsule suspensions CS for use in seed treatments. The formulations can be applied to the seed by standard techniques and through conventional seed treaters. In use the compositions are applied to the nematodes, to the locus of the nematodes, to the habitat of the nematodes, or to growing plants liable to infestation by the nematodes, by any of the known means of applying pesticidal compositions, for example, by dusting, spraying, or incorporation of granules.

The compounds of the invention may be the sole active ingredient of the composition or they may be admixed with one or more additional active ingredients such as nematicides or agents which modify the behaviour of nematodes such as hatching factors, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, bifenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avemectins or milbemycins, for example such as abamectin, ivemectin and milbemycin;

g) Hormones and pheromones;

h) Organochlorine compounds such as benzene hexachloride, DDT, endosulphan, chlordane or dieldrin;

i) Amidines, such as chlorodimeform or amitraz j) Fumigant agents;

k) Nitromethylenes such as imidacloprid.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, motilicides such as dicofol or propargite, general acaricides such as bromopropylate, chlorobenzilate, or growth regulators such as hydramethylnon, cyromazine, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

EXAMPLE 1

The activity of compounds of formula (I) according to the invention was determined using a variety of pests. The pests were treated with a liquid composition containing 500 parts per million (ppm) by weight of the compound unless otherwise stated. The compositions were made by dissolving the compound in acetone:ethanol (50:50) mixture and diluting the solutions with water containing 0.05% by weight of a wetting agent sold under the trade name "Synperonic" NP8 until the liquid composition contained the required concentration of the compound. "Synperonic" is a Registered Trade Mark.

The test procedure adopted with regard to each pest was basically the same and comprised supporting a number of the pests on a medium which was usually a host plant or a foodstuff on which the pests feed, and treating either or both the medium and the pests with the compositions. The mortality of the pests was then assessed at periods usually varying from one to three days after the treatment.

The results of the tests are presented in Table A for each of the compounds. The results indicate a grading of mortality designated as A, B or C wherein A indicates less than 40% mortality, B indicates 40–79% mortality and C indicates 80–100% mortality; – indicates that either the compound was not tested or no meaningful result was obtained.

Information regarding the pest species, the support medium or food, and the type and duration of the test is given in Table B. The pest species is designated by a letter code.

TABLE A

| Compound No. | SPECIES (see Table B) | | | | | |
|---|---|---|---|---|---|---|
| | TU | MPa | MD | HV | SE | DB |
| II.1 | B | A | A | A | A | — |
| II.2 | C | C | A | A | A | — |
| II.3 | A | A | A | A | A | — |
| II.4 | A | A | A | A | A | — |

TABLE A-continued

| Compound No. | SPECIES (see Table B) | | | | | |
|---|---|---|---|---|---|---|
| | TU | MPa | MD | HV | SE | DB |
| II.5 | A | C | A | A | A | — |
| II.6 | C | A | A | A | A | — |
| II.7 | A | A | A | B | A | — |
| II.8 | C | C | A | C | B | — |
| II.9 | B | C | A | A | A | — |
| III.1 | A | C | A | A | A | B |
| III.2 | C | C | A | C | A | — |
| III.3 | A | C | A | A | A | — |
| III.4 | A | A | A | A | A | — |
| III.5 | A | A | A | A | A | — |
| III.6 | A | A | A | C | A | — |
| III.7 | A | A | A | B | A | — |
| III.8 | A | A | A | A | A | — |
| III.9 | B | C | A | A | A | — |
| III.10 | A | C | A | B | A | — |
| III.11 | A | A | A | A | A | — |
| III.12 | B | A | A | A | A | — |
| IV.1 | C | C | A | C | B | C |
| IV.2 | C | C | A | C | B | C |
| IV.3 | C | C | A | B | A | B |
| IV.7 | C | C | A | C | A | — |
| IV.8 | C | C | A | C | A | — |
| IV.9 | C | C | A | C | A | — |
| IV.10 | C | C | — | B | A | — |
| IV.23 | C | C | A | C | B | — |
| IV.24 | C | C | A | A | A | — |
| IV.26 | C | C | A | A | A | — |
| V.2 | C | C | A | C | C | — |
| V.12 | C | C | A | C | A | — |
| V.15 | C | C | A | A | A | — |
| VI.1 | A | C | A | A | A | — |
| VI.4 | A | A | A | A | A | — |
| VI.5 | C | C | A | A | A | — |
| VI.6 | C | A | A | A | A | — |
| VI.13 | B | C | — | A | A | — |
| VI.14 | C | C | — | A | A | — |
| VI.15 | A | C | — | A | A | — |
| VI.16 | C | C | — | B | A | — |
| VI.18 | C | C | A | B | A | C |
| VI.19 | C | C | B | B | A | A |
| VI.20 | C | C | A | A | A | C |
| VI.25 | C | C | A | B | A | — |
| VI.31 | C | C | A | A | A | — |
| VI.32 | C | C | A | A | A | — |
| VI.36 | C | A | A | A | A | — |
| VI.37 | C | C | A | A | A | — |
| VI.38 | C | C | A | A | A | — |
| VI.40 | C | C | A | C | A | — |
| VII.1 | C | C | B | A | A | B |
| VII.2 | C | C | A | C | B | — |
| VII.3 | C | A | A | B | A | — |
| VII.4 | A | B | A | A | A | — |
| VII.6 | C | C | A | B | A | — |
| VII.7 | C | C | A | C | A | — |
| VII.8 | C | C | A | A | A | — |
| VII.9 | C | C | A | B | A | — |
| VII.10 | C | B | A | B | A | — |
| VII.11 | C | C | A | B | A | — |
| VII.13 | C | C | A | B | A | — |
| VII.14 | C | C | A | A | A | — |
| VII.15 | C | C | A | B | A | — |
| VII.16 | C | C | A | A | A | — |
| VII.17 | C | C | A | A | A | C |
| VII.21 | B | C | A | A | A | — |
| VII.23 | A | B | A | A | A | — |
| VII.24 | A | C | A | A | A | — |
| VII.25 | C | C | A | C | A | — |
| VII.26 | C | C | A | B | A | — |
| VII.27 | C | C | — | A | A | — |
| VII.28 | C | C | — | A | A | — |
| VII.32 | C | C | A | C | A | — |
| VII.36 | C | C | A | B | A | — |
| VII.41 | C | C | A | C | A | — |
| VII.43 | C | C | A | B | A | — |
| VII.45 | C | C | A | C | A | — |

TABLE A-continued

| Compound No. | TU | MPa | MD | HV | SE | DB |
|---|---|---|---|---|---|---|
| VII.47 | C | C | A | C | A | — |
| VII.52 | C | C | A | A | B | — |
| VII.53 | C | C | A | A | A | — |
| VII.56 | C | C | A | C | A | — |
| VII.82 | C | C | A | B | A | — |
| VII.83 | A | C | — | C | A | — |
| VII.84 | A | C | — | A | A | — |
| VII.90 | C | C | A | B | A | — |
| VII.94 | C | C | A | C | A | — |
| VII.98 | C | C | A | C | A | — |
| VII.102 | A | A | A | A | A | — |
| VII.114 | C | A | A | A | A | — |
| VII.115 | A | C | A | A | A | — |
| VII.116 | B | A | A | A | A | — |
| VII.128 | C | C | A | A | A | — |
| VII.130 | C | C | — | A | A | — |
| VII.134 | A | A | A | C | A | A |
| VIII.1 | C | C | A | B | A | — |
| VIII.2 | A | C | A | A | A | — |
| VIII.3 | C | C | A | B | A | — |
| VIII.4 | A | A | A | A | C | — |
| VIII.5 | C | C | A | C | A | C |
| VIII.7 | C | C | A | A | A | — |
| VIII.8 | C | A | A | A | A | — |
| VIII.9 | A | A | A | A | A | — |
| VIII.10 | C | C | A | A | A | — |
| VIII.11 | C | C | A | B | A | — |
| VIII.12 | C | C | A | B | A | — |
| VIII.13 | A | C | A | A | A | — |
| VIII.14 | C | C | A | A | A | — |
| VIII.15 | C | B | A | A | A | — |
| VIII.18 | C | C | A | A | A | — |
| VIII.19 | C | C | A | A | A | — |
| VIII.20 | C | C | A | A | A | — |
| VIII.21 | A | A | A | A | A | — |
| VIII.22 | C | C | A | A | A | — |
| VIII.23 | C | C | A | A | C | — |
| VIII.24 | C | C | A | A | B | — |
| VIII.27 | C | C | A | B | A | — |
| VIII.28 | A | C | A | A | A | — |
| VIII.29 | C | C | A | C | A | — |
| VIII.30 | A | C | A | A | A | — |
| VIII.31 | C | C | A | A | A | — |
| VIII.32 | B | C | A | A | A | — |
| VIII.33 | C | C | A | A | A | — |
| VIII.34 | B | B | A | A | A | — |
| VIII.36 | C | C | A | A | A | — |
| VIII.52 | A | C | — | A | A | — |
| VIII.53 | A | C | A | A | A | — |
| VIII.58 | C | C | A | C | A | — |
| VIII.59 | C | C | A | A | A | — |
| VIII.61 | C | C | A | A | A | — |
| VIII.63 | A | A | A | A | C | — |
| VIII.64 | C | C | A | A | A | — |
| VIII.65 | A | B | — | A | A | — |
| VIII.66 | A | A | A | A | A | — |
| VIII.67 | A | A | A | A | A | — |
| VIII.68 | C | C | A | A | A | — |
| VIII.151 | C | C | A | B | A | — |
| VIII.152 | C | C | — | A | A | — |
| IX.31 | C | C | A | A | A | — |
| IX.33 | A | A | A | A | A | — |
| IX.34 | B | C | A | A | A | — |
| IX.36 | A | C | A | A | A | — |
| IX.37 | C | C | A | A | B | — |
| IX.40 | A | A | A | A | A | — |
| IX.42 | A | A | A | A | A | — |
| IX.55 | C | A | A | A | A | — |
| IX.61 | A | C | A | A | A | — |
| IX.73 | C | C | A | A | C | — |
| IX.75 | C | C | A | A | A | — |
| IX.82 | C | C | A | C | B | — |
| IX.84 | C | A | A | C | A | — |
| IX.124 | C | A | A | A | A | — |
| IX.126 | A | A | A | A | A | — |
| X.3 | C | C | A | C | C | — |
| X.26 | C | C | A | C | A | — |
| X.32 | C | A | A | A | A | — |
| XI.5 | C | C | A | C | C | C |
| XI.9 | A | A | A | A | A | — |
| XI.11 | C | C | A | C | A | — |
| XI.23 | C | C | A | C | A | — |
| XI.24 | A | C | A | A | A | — |
| XI.25 | C | C | A | B | A | — |
| XI.30 | A | C | A | A | A | — |
| XI.31 | A | C | A | A | A | — |
| XI.34 | C | C | A | B | A | — |
| XI.35 | C | C | A | C | A | — |
| XI.36 | C | C | A | C | A | — |
| XI.38 | C | C | A | C | A | — |
| XI.40 | C | C | A | A | A | C |
| XI.87 | C | C | A | C | A | — |
| XI.102 | B | C | A | A | A | — |
| XI.108 | B | C | A | B | A | — |
| XI.109 | C | A | A | C | B | — |
| XI.110 | C | C | A | B | A | — |
| XI.125 | C | C | A | C | A | — |
| XI.127 | C | C | A | B | B | B |
| XII.1 | C | C | A | C | B | — |
| XII.3 | C | C | A | C | C | B |
| XII.4 | C | C | A | B | A | C |
| XII.5 | C | C | A | A | A | B |
| XII.8 | C | C | A | A | A | — |
| XII.9 | A | B | A | B | A | — |
| XII.11 | C | C | A | B | A | — |
| XII.12 | C | C | A | B | A | — |
| XII.13 | C | C | A | B | A | — |
| XII.14 | C | C | A | C | A | — |
| XII.15 | C | C | A | A | A | — |
| XII.19 | C | C | A | A | B | — |
| XII.23 | C | C | A | C | A | — |
| XII.25 | C | C | A | C | A | — |
| XII.26 | C | C | A | B | A | — |
| XII.27 | C | C | A | A | A | — |
| XII.28 | C | C | A | C | A | — |
| XII.29 | C | C | A | C | A | — |
| XII.30 | C | C | A | B | A | — |
| XII.31 | C | C | A | A | A | — |
| XII.32 | C | C | A | C | A | — |
| XII.33 | C | C | A | C | A | — |
| XII.35 | C | C | A | A | A | — |
| XII.49 | C | C | A | C | A | — |
| XII.51 | C | C | A | C | A | — |
| XII.54 | C | C | A | C | A | — |
| XII.55 | C | A | A | C | A | — |
| XII.68 | C | A | A | A | A | — |
| XII.128 | C | C | A | B | C | — |
| XII.129 | C | C | A | C | A | — |
| XII.130 | B | C | A | A | A | — |
| XII.131 | C | C | A | C | A | — |
| XII.132 | C | C | A | B | C | — |
| XII.133 | C | C | A | A | A | — |
| XII.134 | C | C | A | C | B | — |
| XII.142 | C | C | A | C | A | — |
| XII.143 | C | B | A | A | A | — |
| XII.144 | C | C | A | B | A | — |
| XII.145 | C | C | A | C | A | — |
| XII.146 | B | C | A | A | A | — |
| XII.147 | C | C | A | A | A | — |
| XII.148 | C | C | A | C | A | — |
| XIII.1 | C | A | A | B | A | — |
| XIII.2 | C | C | A | C | A | — |
| XIII.3 | C | C | A | B | A | — |
| XIII.4 | C | C | A | A | A | — |
| XIII.6 | C | A | A | C | A | — |
| XIII.7 | C | C | A | C | A | — |
| XIII.9 | C | C | A | C | A | — |
| XIII.10 | C | C | A | B | A | — |
| XIII.11 | C | C | A | A | A | — |
| XIII.14 | A | A | A | A | A | — |

TABLE A-continued

| Compound No. | TU | MPa | MD | HV | SE | DB |
|---|---|---|---|---|---|---|
| XIII.15 | C | C | A | A | A | — |
| XIII.16 | C | A | A | B | A | — |
| XIII.17 | C | C | A | C | A | — |
| XIII.18 | C | C | A | B | A | — |
| XIII.20 | C | C | A | B | A | — |
| XIII.24 | C | C | A | B | A | — |
| XIII.27 | C | A | A | C | A | — |
| XIII.28 | C | C | A | B | A | — |
| XIII.29 | C | C | A | B | A | — |
| XIII.40 | C | C | A | C | A | B |
| XIII.41 | C | C | A | C | A | — |
| XIII.42 | C | C | A | C | A | — |
| XIII.45 | C | C | A | A | A | — |
| XIII.63 | A | A | A | A | A | B |
| XIII.64 | C | C | A | C | A | — |
| XIII.65 | C | C | A | C | A | — |
| XIII.66 | C | C | A | B | A | — |
| XIII.69 | C | B | A | B | A | — |
| XIII.70 | A | C | A | B | A | A |
| XIII.101 | C | C | A | A | A | — |
| XIII.110 | C | C | A | C | A | C |
| XIII.114 | C | C | A | C | A | — |
| XIII.115 | C | C | A | C | A | — |
| XIII.116 | A | C | A | C | A | — |
| XIII.117 | C | C | B | A | B | B |
| XIII.119 | B | C | C | C | A | C |
| XIII.122 | C | C | A | A | A | — |
| XIII.124 | C | C | B | B | A | B |
| XIII.133 | C | C | A | C | A | C |
| XIII.134 | C | C | A | B | A | B |
| XIII.143 | C | A | A | C | A | — |
| XIV.1 | C | C | A | C | A | C |
| XV.1 | C | C | A | C | C | C |
| XVI.1 | A | C | A | C | B | — |
| XVI.2 | A | A | A | A | A | — |
| XVI.3 | C | A | A | C | A | — |
| XVI.5 | C | C | A | C | B | — |
| XVI.6 | C | C | A | C | A | — |
| XVI.7 | A | A | A | A | A | — |
| XVI.8 | C | C | A | C | A | — |
| XVI.9 | C | B | A | A | A | — |
| XVI.10 | C | C | A | C | B | C |
| XVI.11 | A | B | A | A | A | A |
| XVI.12 | C | C | A | A | C | — |
| XVI.13 | A | A | A | A | A | — |
| XVI.14 | A | A | A | A | A | — |
| XVI.15 | B | C | A | A | A | — |
| XVI.16 | C | C | A | A | A | — |
| XVI.17 | C | C | A | A | A | — |
| XVI.18 | C | C | A | A | A | — |
| XVI.19 | C | A | A | A | A | B |
| XVI.20 | A | A | A | A | A | — |
| XVI.21 | C | C | A | C | A | — |
| XVI.22 | C | A | A | B | A | — |
| XVI.23 | A | A | A | B | A | — |
| XVI.24 | C | C | A | B | A | — |
| XVII.1 | C | C | A | A | A | C |
| XVII.2 | C | C | A | A | A | C |
| XVII.3 | B | B | C | C | C | C |
| XVII.4 | C | C | A | A | A | B |
| XVII.5 | C | C | A | A | A | B |
| XVII.6 | A | A | A | A | A | A |
| XVII.7 | C | C | A | A | A | C |
| XVIII.1 | C | C | A | C | A | C |
| XVIII.3 | A | C | B | A | A | C |
| XVIII.4 | C | C | A | A | C | C |
| XVIII.7 | A | A | A | A | A | C |
| XVIII.10 | C | C | A | B | A | — |
| XVIII.13 | C | C | A | C | C | — |
| XVIII.14 | C | C | A | A | A | — |
| XVIII.15 | C | C | A | B | A | — |
| XVIII.16 | C | C | A | B | B | — |
| XIX.1 | C | C | B | C | A | C |
| XX.4 | C | B | A | C | A | C |
| XX.15 | C | A | A | A | A | — |
| XX.27 | C | C | A | B | A | — |
| XX.28 | C | C | A | A | B | — |
| XX.30 | C | C | A | A | A | — |
| XX.52 | C | C | A | B | A | — |
| XX.53 | C | C | A | C | A | — |
| XX.54 | C | C | A | B | A | — |
| XX.65 | C | C | A | A | A | — |
| XX.98 | C | C | A | A | A | — |
| XX.109 | C | C | A | C | A | — |
| XX.110 | C | C | A | A | A | — |
| XX.116 | C | C | A | B | A | — |
| XX.117 | C | C | A | C | A | — |
| XX.118 | C | C | A | C | A | — |
| XX.137 | C | C | A | B | A | — |
| XX.205 | C | C | A | C | A | — |
| XX.218 | C | C | A | C | A | — |
| XX.221 | C | C | A | C | A | — |
| XX.226 | C | A | A | C | C | — |
| XX.227 | C | C | B | A | A | A |
| XX.231 | C | C | A | C | A | — |
| XX.247 | C | C | A | C | A | — |
| XX.251 | C | C | A | A | A | B |
| XXI.1 | C | C | B | A | A | A |

TABLE B

| CODE LETTERS | TEST SPECIES | SUPPORT MEDIUM/FOOD | TYPE OF TEST | DURATION (days) |
|---|---|---|---|---|
| TU | *Tetranychus urticae* (spider mite) | French been leaf | Contact | 3 |
| MPa | *Myzus persicae* (green peach aphid) | Chinese Cabbage leaf | Contact | 3 |
| MD | *Musca domestica* (houseflies - adults) | Cotton wool/ sugar | Contact | 2 |
| HV | *Heliothis virescens* (Tobacco budworm - larva) | Soya leaf | Residual | 5 |

TABLE B-continued

| CODE LETTERS | TEST SPECIES | SUPPORT MEDIUM/FOOD | TYPE OF TEST | DURATION (days) |
|---|---|---|---|---|
| SE | *Spodoptera exigua* (lesser armyworm - larva) | Cotton leaf | Residual | 5 |
| DB | *Diabrotica balteata* (banded cucumber beetle - larva) | Filter paper/ maize seed | Residual | 2 |

"Contact" test indicates that both pests and medium were treated, and "Residual" indicates that the medium was treated before infestation with the pests.

EXAMPLE 2

This Example further illustrates the pesticidal activity of compounds of formula (I) according to the invention.

In Table C, further results are given for the activity of test compounds against four species, at various rates of application. The test procedures and details for tests TU (*Tetranychus urticae*, contact), MPa (*Myzus persicae*, contact) and DB (*Diabrotica balteata*, contact) are as described in Example 1 and Table B. Application rates are shown in the Table heading for each test type. The test procedure for test MPb (*Myzus persicae*, systemic) was as follows:

Upward systemicity of the test compounds was evaluated against the peach potato aphid, *Myzus persicae* by soil drenching 2–3 week old radish plants (cv. Cherrybelle) at 10 ppm or 2.5 ppm. Plants with 1st true leaves approximately 2×1 cm were used. The cotyledons, growing point and 1 true leaf were removed. The soil was covered with a clear lid. 12–18 mature aphids were added to each plant 1 day before treatment. On the treatment day, each pot was placed in a 250 cm$^3$ plastic pot with a fluon band to prevent aphid escape. Each pot was treated with 10 cm$^3$ of chemical in aqueous solution (prepared in 1% ethanol and acetone (1:1) and 0.01% Synperonic NP8—ICI Chemicals and Polymers). Each treatment was replicated 3 times. The treated plants were transferred to a constant environment room at 20° C., 60% relative humidity and a 16 hour photoperiod. The mortality was assessed at 3 and 5 days after treatment.

Activity against the root know nematode, *Meloidogyne incognita* (MI), was evaluated by applying the candidate nematicide as a drench solution to 2 week old cucumber plants (cultivar Telegraph) and infesting the soil with nematodes. 10 cm$^3$ of an aqueous solution of the test compound, (prepared in 1% ethanol and acetone (1:1) and 0.05% Synperonic NP8—ICI Chemicals & Polymers) was added to each plant such that the final soil concentration was 2 ppm. Each treatment was replicated twice. The cucumber plants were inoculated 48 hours after treatment with a 2 cm$^3$ suspension of freshly hatched juveniles at a concentration of 350 nematodes per cm$^3$. The test was maintained at 25° C. with a 16 hour photoperiod for 9 days. The roots of each plant were assessed for percentage root-knot reduction relative to an untreated, infested control and the results are recorded in Table C as % knot reduction compared to the control.

The results in Table C for the four species other than MI are expressed as % Control observed. A dash indicates that either the compound was not tested or that no meaningful result was obtained.

TABLE C

| Compound No. | TU 100 ppm | MPa 100 ppm | MPa 27 ppm | MPb 10 ppm | MPb 2.5 ppm | DB 25 ppm | MI 2 ppm |
|---|---|---|---|---|---|---|---|
| II.1 | — | — | — | — | 1 | — | 95 |
| II.2 | 88 | — | — | — | 100 | — | 100 |
| II.3 | — | — | — | — | — | — | 0 |
| II.4 | — | — | — | — | 4 | — | 96 |
| II.5 | — | — | — | — | — | — | 96 |
| II.6 | 39 | — | — | — | — | — | 88 |
| II.7 | — | — | — | — | 4 | — | 98 |
| II.8 | 74 | — | 24 | — | 100 | — | 97 |
| II.9 | — | — | 58 | — | 100 | — | 98 |
| III.1 | — | — | 5 | — | — | — | 98 |
| III.2 | 60 | — | 58 | — | 97 | — | 93 |
| III.3 | — | — | 8 | — | 41 | — | 83 |
| III.4 | — | — | — | — | — | — | 0 |
| III.5 | — | — | — | — | — | — | 30 |
| III.6 | — | — | — | — | — | — | 47 |
| III.7 | — | — | — | — | — | — | 48 |
| III.8 | — | — | — | — | — | — | 0 |
| III.9 | — | 7 | — | — | — | — | 88 |
| III.10 | — | 8 | — | — | — | — | 51 |
| III.11 | — | — | — | — | — | — | 0 |
| III.12 | — | — | — | — | — | — | 0 |
| IV.1 | 100 | — | 66 | 92 | — | 80 | 0 |
| IV.2 | 94 | — | 82 | 84 | — | 17 | 0 |
| IV.3 | 60 | — | 8 | 100 | — | — | 96 |
| IV.7 | 100 | 100 | — | — | 100 | — | 100 |
| IV.8 | 92 | — | 81 | — | 23 | — | 0 |

TABLE C-continued

| Compound No. | TU 100 ppm | MPa 100 ppm | MPa 27 ppm | MPb 10 ppm | MPb 2.5 ppm | DB 25 ppm | MI 2 ppm |
|---|---|---|---|---|---|---|---|
| IV.9 | 93 | — | 81 | — | 50 | — | 0 |
| IV.10 | — | — | — | — | — | — | 11 |
| IV.23 | — | — | — | 97 | — | — | 99 |
| IV.24 | — | — | — | — | — | — | 88 |
| V.2 | 100 | — | 84 | — | 55 | — | 0 |
| V.6 | — | — | — | — | — | — | 72 |
| V.12 | 100 | — | 100 | — | 10 | — | 0 |
| V.15 | 49 | — | 50 | — | 100 | — | 92 |
| VI.1 | — | — | 2 | — | — | — | 99 |
| VI.4 | — | — | — | — | 5 | — | 98 |
| VI.5 | 84 | 95 | — | — | 100 | — | 100 |
| VI.6 | — | — | — | 97 | — | — | 77 |
| VI.13 | — | — | — | — | — | — | 22 |
| VI.14 | — | — | — | — | — | — | 0 |
| VI.15 | — | — | — | — | — | — | 72 |
| VI.16 | — | — | — | — | — | — | 55 |
| VI.18 | 73 | — | 65 | 60 | — | 100 | 95 |
| VI.19 | 74 | — | 100 | 99 | — | — | 100 |
| VI.20 | 97 | — | 100 | 95 | 97 | 53 | 98 |
| VI.25 | 77 | — | 15 | — | 46 | — | 88 |
| VI.32 | 28 | — | 12 | — | 28 | — | 100 |
| VI.36 | — | — | — | 79 | — | — | 17 |
| VI.37 | 93 | — | 100 | — | 86 | — | 97 |
| VI.40 | 92 | — | 98 | — | 100 | — | 92 |
| VII.1 | 38 | — | 0 | — | 51 | — | 99 |
| VII.2 | 36 | — | 39 | — | 100 | — | 99 |
| VII.3 | 45 | — | — | — | — | — | 0 |
| VII.4 | — | — | 7 | — | — | — | 0 |
| VII.6 | 100 | — | 98 | — | 65 | — | 95 |
| VII.7 | 99 | — | 100 | — | 45 | — | 98 |
| VII.8 | 46 | — | 16 | — | 4 | — | 86 |
| VII.9 | 90 | 6 | — | — | — | — | 0 |
| VII.10 | 37 | 7 | — | — | — | — | 0 |
| VII.12 | — | — | — | 96 | — | — | 0 |
| VII.14 | — | — | — | — | — | — | 91 |
| VII.15 | — | — | — | — | — | — | 100 |
| VII.16 | 88 | 100 | — | — | 96 | — | 100 |
| VII.17 | 90 | — | 9 | — | — | 60 | 0 |
| VII.22 | — | — | — | — | — | — | 76 |
| VII.23 | — | — | — | — | — | — | 68 |
| VII.24 | — | — | 17 | — | 50 | — | 98 |
| VII.25 | — | — | — | — | 98 | — | 99 |
| VII.26 | 95 | — | 30 | — | 96 | — | 100 |
| VII.27 | — | — | — | — | — | — | 83 |
| VII.28 | — | — | — | — | — | — | 66 |
| VII.32 | 99 | — | 79 | — | 49 | — | 97 |
| VII.36 | 100 | — | 100 | — | 90 | — | 92 |
| VII.41 | 100 | — | 100 | — | 49 | — | 96 |
| VII.43 | 85 | 100 | — | — | — | — | 86 |
| VII.45 | 100 | 99 | — | — | — | — | 95 |
| VII.47 | — | — | — | — | — | — | 94 |
| VII.52 | — | — | — | 41 | — | — | 94 |
| VII.53 | — | — | — | 67 | — | — | 99 |
| VII.56 | — | — | — | 56 | — | — | — |
| VII.83 | — | — | — | — | — | — | 66 |
| VII.84 | — | — | — | — | — | — | 0 |
| VII.90 | 97 | — | 92 | — | 93 | — | 95 |
| VII.94 | 72 | — | 5 | — | — | — | 0 |
| VII.98 | 56 | — | 11 | — | — | — | 0 |
| VII.102 | — | — | — | — | — | — | 0 |
| VII.114 | — | — | — | 28 | — | — | 50 |
| VII.115 | — | — | — | — | — | — | 50 |
| VII.116 | — | — | — | — | — | — | 33 |
| VII.128 | — | — | — | 44 | — | — | 66 |
| VII.130 | — | — | — | — | — | — | 28 |
| VII.134 | — | — | — | — | — | — | 100 |
| VIII.1 | 100 | 100 | — | — | 100 | — | 98 |
| VIII.2 | — | 93 | — | — | 98 | — | 99 |
| VIII.3 | — | — | — | — | — | — | 88 |
| VIII.4 | — | — | — | 18 | — | — | 39 |
| VIII.5 | 45 | — | 26 | — | 96 | 87 | 98 |
| VIII.7 | 43 | 90 | — | — | 90 | — | 100 |
| VIII.8 | — | — | — | — | — | — | 59 |
| VIII.9 | — | — | — | — | — | — | 65 |
| VIII.10 | — | — | — | 42 | — | — | 39 |
| VIII.12 | — | — | — | — | — | — | 48 |

TABLE C-continued

| Compound No. | TU 100 ppm | MPa 100 ppm | MPa 27 ppm | MPb 10 ppm | MPb 2.5 ppm | DB 25 ppm | MI 2 ppm |
|---|---|---|---|---|---|---|---|
| VIII.13 | — | 4 | — | — | — | — | 86 |
| VIII.14 | — | — | — | — | — | — | 90 |
| VIII.15 | — | — | — | — | — | — | 97 |
| VIII.18 | 97 | 100 | — | — | — | — | 94 |
| VIII.19 | — | — | — | — | — | — | 66 |
| VIII.20 | — | — | — | 4 | — | — | 0 |
| VIII.21 | — | — | — | — | — | — | 0 |
| VIII.22 | — | — | — | — | — | — | 72 |
| VIII.23 | — | — | — | 76 | — | — | 44 |
| VIII.24 | — | — | — | 0 | — | — | 50 |
| VIII.27 | — | — | — | 0 | — | — | 0 |
| VIII.29 | — | — | — | — | — | — | 11 |
| VIII.30 | — | — | — | 29 | — | — | 44 |
| VIII.31 | — | — | — | — | — | — | 49 |
| VIII.32 | — | — | — | — | — | — | 99 |
| VIII.33 | — | — | — | — | — | — | 0 |
| VIII.34 | — | — | — | — | — | — | 22 |
| VIII.36 | — | — | — | — | — | — | 66 |
| VIII.52 | — | — | — | — | — | — | 22 |
| VIII.59 | — | — | — | — | — | — | 65 |
| VIII.61 | — | — | — | — | — | — | 66 |
| VIII.63 | — | — | — | — | — | — | 99 |
| VIII.64 | — | — | — | 29 | — | — | 0 |
| VIII.65 | — | — | — | 48 | — | — | 72 |
| VIII.66 | — | — | — | 16 | — | — | — |
| VIII.67 | — | — | — | — | — | — | 0 |
| VIII.151 | 100 | 100 | — | — | 30 | — | 99 |
| VIII.152 | — | — | — | — | — | — | 33 |
| IX.33 | — | — | — | 0 | — | — | 44 |
| IX.34 | — | — | — | 0 | — | — | 94 |
| IX.36 | — | — | — | 2 | — | — | 0 |
| IX.37 | — | — | — | — | — | — | 61 |
| IX.40 | — | — | — | 30 | — | — | 50 |
| IX.42 | — | — | — | 9 | — | — | 72 |
| IX.55 | — | — | — | — | — | — | 83 |
| IX.61 | — | — | — | 86 | — | — | 61 |
| IX.73 | — | — | — | 100 | — | — | 72 |
| IX.75 | — | — | — | — | — | — | 99 |
| IX.82 | 91 | 100 | — | — | — | — | 3 |
| IX.84 | 97 | — | — | — | 100 | — | 97 |
| IX.124 | — | — | — | — | — | — | 65 |
| IX.126 | — | — | — | — | — | — | 94 |
| IX.127 | — | — | — | — | — | — | 50 |
| X.3 | 100 | — | 100 | 52 | — | — | 94 |
| X.26 | — | — | — | 82 | — | — | 88 |
| X.32 | 54 | — | — | — | — | — | 96 |
| XI.5 | 100 | — | 100 | 30 | — | 13 | 100 |
| XI.9 | — | — | — | — | 26 | — | 99 |
| XI.11 | 84 | 100 | — | — | 100 | — | 95 |
| XI.23 | 40 | 14 | — | — | 48 | — | 98 |
| XI.24 | — | — | — | — | 95 | — | 86 |
| XI.25 | 41 | 100 | — | — | — | — | 97 |
| XI.30 | — | 81 | — | — | — | — | 4 |
| XI.31 | — | 29 | — | — | — | — | 14 |
| XI.34 | 100 | 100 | — | — | 99 | — | 100 |
| XI.35 | 97 | 100 | — | — | 98 | — | 98 |
| XI.36 | 100 | 100 | — | — | 100 | — | 92 |
| XI.38 | 100 | 100 | — | — | 52 | — | 93 |
| XI.40 | 36 | — | 100 | 100 | 95 | 77 | 100 |
| XI.87 | 82 | 100 | — | — | 92 | — | 100 |
| XI.102 | — | — | 2 | — | — | — | 0 |
| XI.108 | — | 100 | — | — | 93 | — | 92 |
| XI.109 | 100 | — | — | — | 35 | — | 93 |
| XI.110 | 70 | — | 96 | — | 59 | — | 90 |
| XI.125 | 100 | 100 | — | — | 80 | — | 97 |
| XI.127 | 100 | — | 100 | 26 | — | — | 0 |
| XII.1 | 86 | — | 9 | — | 100 | — | 95 |
| XII.3 | 100 | — | 46 | 9 | 65 | — | 88 |
| XII.4 | 100 | — | 93 | 49 | — | 67 | 98 |
| XII.5 | 37 | — | 0 | 72 | — | — | 89 |
| XII.8 | 59 | — | 4 | — | 100 | — | 96 |
| XII.9 | — | 42 | — | — | — | — | 68 |
| XII.11 | 81 | 100 | — | — | 50 | — | 100 |
| XII.12 | 73 | 100 | — | — | — | — | 97 |
| XII.13 | 43 | 20 | — | — | — | — | 76 |
| XII.14 | 93 | 100 | — | — | 95 | — | 93 |

TABLE C-continued

| Compound No. | TU 100 ppm | MPa 100 ppm | MPa 27 ppm | MPb 10 ppm | MPb 2.5 ppm | DB 25 ppm | MI 2 ppm |
|---|---|---|---|---|---|---|---|
| XII.15 | 47 | 11 | — | — | — | — | 94 |
| XII.19 | 50 | 30 | — | — | — | — | 69 |
| XII.23 | 95 | 100 | — | — | 97 | — | 97 |
| XII.25 | 100 | 100 | — | — | 56 | — | 99 |
| XII.26 | 73 | 100 | — | — | 77 | — | 99 |
| XII.27 | — | 98 | — | — | — | — | — |
| XII.28 | 100 | 100 | — | — | — | — | 84 |
| XII.29 | — | 100 | — | — | 100 | — | 99 |
| XII.30 | 15 | 100 | — | — | — | — | 94 |
| XII.31 | 73 | — | 22 | — | 100 | — | 95 |
| XII.32 | 100 | 100 | — | — | 98 | — | 99 |
| XII.33 | 45 | 37 | — | — | — | — | — |
| XII.35 | 100 | 87 | — | — | 95 | — | 98 |
| XII.49 | 38 | — | 18 | — | 97 | — | 95 |
| XII.51 | 40 | 8 | — | — | 51 | — | 91 |
| XII.54 | 100 | 80 | — | — | 100 | — | 98 |
| XII.55 | 96 | — | — | — | 100 | — | 90 |
| XII.68 | 53 | — | — | — | — | — | 0 |
| XII.128 | 100 | 100 | — | — | 26 | — | 61 |
| XII.129 | 100 | 100 | — | — | 86 | — | 89 |
| XII.130 | — | 77 | — | — | 5 | — | 87 |
| XII.131 | 87 | — | 26 | — | 54 | — | 86 |
| XII.132 | 98 | 100 | — | — | — | — | 31 |
| XII.133 | 99 | — | 85 | — | 6 | — | 0 |
| XII.134 | 75 | — | 88 | — | 97 | — | 0 |
| XII.142 | 54 | 100 | — | — | 92 | — | 95 |
| XII.143 | 48 | 39 | — | — | 65 | — | 94 |
| XII.144 | 100 | 100 | — | — | — | — | 53 |
| XII.145 | — | 100 | — | — | 32 | — | 97 |
| XII.146 | — | 45 | — | — | — | — | 69 |
| XII.147 | 39 | 56 | — | — | — | — | 37 |
| XII.148 | 97 | 97 | — | — | — | — | 84 |
| XIII.1 | 35 | — | — | — | — | — | 89 |
| XIII.2 | 95 | 100 | — | — | 100 | — | 98 |
| XIII.3 | 79 | 84 | — | — | 88 | — | 99 |
| XIII.4 | 100 | 100 | — | — | 100 | — | 96 |
| XIII.6 | 79 | — | — | — | 96 | — | 100 |
| XIII.7 | 88 | 100 | — | — | 100 | — | 99 |
| XIII.9 | 91 | — | 100 | — | 18 | — | 93 |
| XIII.10 | 94 | — | 100 | — | 32 | — | 96 |
| XIII.11 | 94 | — | 83 | — | 96 | — | 92 |
| XIII.14 | — | — | — | — | 7 | — | 95 |
| XIII.15 | 43 | 77 | — | — | — | — | 94 |
| XIII.16 | 89 | — | — | — | 89 | — | 96 |
| XIII.17 | 74 | 100 | — | — | 100 | — | 97 |
| XIII.18 | 85 | 100 | — | — | 96 | — | 99 |
| XIII.20 | 94 | — | 90 | — | 48 | — | 0 |
| XIII.24 | 89 | 100 | — | — | 45 | — | 100 |
| XIII.27 | 69 | — | — | — | 77 | — | 99 |
| XIII.28 | 100 | 100 | — | — | 100 | — | 96 |
| XIII.29 | 95 | 100 | — | — | 100 | — | 97 |
| XIII.40 | 100 | — | 5 | 100 | 100 | — | 100 |
| XIII.41 | 100 | — | 95 | — | 100 | — | 96 |
| XIII.42 | 98 | — | 35 | — | 100 | — | 95 |
| XIII.45 | 81 | — | 44 | — | 91 | — | 97 |
| XIII.63 | — | — | — | 98 | — | — | 100 |
| XIII.64 | 85 | — | 97 | — | 98 | — | 97 |
| XIII.65 | 73 | — | 42 | — | 100 | — | 98 |
| XIII.66 | 100 | 93 | — | — | — | — | 31 |
| XIII.69 | 84 | 18 | — | — | — | — | 63 |
| XIII.70 | — | — | 22 | — | — | — | 0 |
| XIII.101 | 79 | 98 | — | — | 99 | — | 100 |
| XIII.110 | 100 | — | 64 | 27 | — | 79 | 94 |
| XIII.114 | 96 | 100 | — | — | 18 | — | 97 |
| XIII.115 | 97 | 100 | — | — | 45 | — | 91 |
| XIII.116 | — | 100 | — | — | 19 | — | 100 |
| XIII.117 | 100 | — | 100 | 77 | — | — | 100 |
| XIII.119 | — | — | 13 | 29 | 82 | 53 | 91 |
| XIII.122 | 95 | 100 | — | — | 35 | — | 100 |
| XIII.124 | 78 | — | 12 | — | — | — | 0 |
| XIII.133 | 100 | — | 100 | 100 | — | 50 | 100 |
| XIII.134 | 97 | — | 100 | 100 | — | — | 100 |
| XIII.143 | — | — | — | — | — | — | 41 |
| XIV.1 | 45 | — | 15 | 100 | — | 33 | 0 |
| XV.1 | 82 | — | 18 | 80 | — | 70 | 91 |
| XVI.1 | — | 34 | — | — | — | — | 50 |

TABLE C-continued

| Compound No. | TU 100 ppm | MPa 100 ppm | MPa 27 ppm | MPb 10 ppm | MPb 2.5 ppm | DB 25 ppm | MI 2 ppm |
|---|---|---|---|---|---|---|---|
| XVI.2 | — | — | — | — | 7 | — | 82 |
| XVI.3 | 59 | — | — | — | 97 | — | 94 |
| XVI.5 | 56 | — | 39 | — | 62 | — | 100 |
| XVI.6 | 88 | 97 | — | — | 96 | — | 100 |
| XVI.7 | — | — | — | — | — | — | 0 |
| XVI.8 | 42 | 100 | — | — | — | — | 89 |
| XVI.9 | 68 | 29 | — | — | — | — | 12 |
| XVI.10 | 100 | — | 65 | 100 | — | 53 | 100 |
| XVI.11 | — | — | 2 | — | — | — | 0 |
| XVI.12 | 20 | 18 | — | — | — | — | 81 |
| XVI.13 | — | — | — | — | — | — | 32 |
| XVI.14 | — | — | — | — | — | — | 0 |
| XVI.15 | — | — | 53 | — | 48 | — | 94 |
| XVI.16 | 100 | 100 | — | — | — | — | 94 |
| XVI.17 | 46 | 45 | — | — | — | — | 24 |
| XVI.18 | 25 | 48 | — | — | — | — | 43 |
| XVI.19 | 26 | — | — | — | — | — | 0 |
| XVI.20 | — | — | — | — | — | — | 42 |
| XVI.21 | 82 | — | 100 | — | 8 | — | 100 |
| XVI.22 | 44 | — | — | — | — | — | 41 |
| XVI.23 | — | — | — | — | — | — | 38 |
| XVI.24 | 81 | 100 | — | — | 85 | — | 97 |
| XVII.1 | 30 | — | 7 | 74 | — | 50 | 0 |
| XVII.2 | 24 | — | 1 | — | — | 27 | 0 |
| XVII.3 | — | — | 0 | — | — | 87 | 0 |
| XVII.4 | 11 | — | 0 | — | — | — | 0 |
| XVII.5 | 32 | — | 7 | — | — | — | 0 |
| XVII.6 | — | — | — | — | — | — | 0 |
| XVII.7 | 49 | — | 7 | — | — | 30 | 0 |
| XVIII.1 | 95 | — | 100 | 35 | — | 80 | 92 |
| XVIII.3 | — | — | 45 | 100 | — | 23 | 98 |
| XVIII.4 | 96 | — | 100 | 15 | — | 93 | 94 |
| XVIII.7 | — | — | — | — | — | 83 | 0 |
| XVIII.10 | 49 | — | 65 | — | 29 | — | 100 |
| XVIII.13 | 100 | — | 74 | — | 53 | — | 0 |
| XVIII.14 | 56 | — | 7 | — | — | — | 0 |
| XVIII.15 | 62 | — | 38 | — | 89 | — | 100 |
| XVIII.16 | 55 | — | 5 | — | 94 | — | 100 |
| XIX.1 | 100 | — | 15 | 30 | — | 100 | 82 |
| XX.4 | 91 | — | 71 | 8 | — | 97 | 0 |
| XX.15 | 100 | — | — | — | 94 | — | 100 |
| XX.27 | 69 | 96 | — | — | 91 | — | 100 |
| XX.28 | 31 | 85 | — | — | — | — | 73 |
| XX.30 | 69 | 100 | — | — | 91 | — | 99 |
| XX.52 | 63 | — | 100 | — | 93 | — | 96 |
| XX.53 | 97 | 100 | — | — | 92 | — | 100 |
| XX.54 | 43 | 3 | — | — | — | — | 61 |
| XX.65 | 52 | 34 | — | — | — | — | 47 |
| XX.98 | 85 | — | — | — | 95 | — | 100 |
| XX.109 | 50 | 100 | — | — | 100 | — | 99 |
| XX.110 | 77 | 100 | — | — | 95 | — | 99 |
| XX.116 | 68 | — | 71 | — | 98 | — | 96 |
| XX.117 | 100 | 98 | — | — | 96 | — | 100 |
| XX.118 | 34 | 7 | — | — | — | — | 21 |
| XX.137 | 47 | — | 100 | — | 94 | — | 95 |
| XX.205 | 79 | 100 | — | — | — | — | 94 |
| XX.218 | 81 | 100 | — | — | — | — | 97 |
| XX.221 | 42 | — | 79 | — | 92 | — | 99 |
| XX.226 | 94 | — | — | — | 100 | — | 97 |
| XX.227 | 86 | — | 51 | 100 | — | — | 100 |
| XX.231 | 88 | — | 100 | — | 52 | — | 100 |
| XX.247 | 90 | 100 | — | — | 100 | — | 94 |
| XX.251 | 18 | — | 79 | 26 | — | — | 0 |
| XXI.1 | 28 | — | 0 | — | — | — | 0 |

EXAMPLE 3

The spectrum of nematicidal activity of compounds according to the invention was investigated in contact assays in the presence of soil and a host plant. Greatest activity was seen against *Meloidogyne incognita, Globodera rostochiensis, Pratylenchus brachyunus, Tylenchorhynchus claytoni, Hoplolaimus columbus* and *Radopholus similis*. Adequate activity was seen against *Rotylenchulus reniformis*, and *Belonolaimus longicaudatus*.

The following examples demonstrate formulations suitable for applying the compounds of the present invention. The amount of ingredient is expressed in parts by weight or grams per litre as indicated. A * indicates a trademark.

EXAMPLE 4

This example demonstrates granules suitable for soil application. The granules can be made by standard techniques such as impregnation, coating, extrusion or agglomeration.

|  |  | % w/w |
|---|---|---|
| Impregnated granule: | Active ingredient | 5 |
|  | Wood Rosin | 2.5 |
|  | Gypsum granules (20–40 mesh) | 92.5 |
| Coated granule: | Active ingredient | 0.5 |
|  | 'Solvessol'* 200 | 0.4 |
|  | Calcium carbonate granules (30–60 mesh) | 99.1 |
| Slow release granule: | Active ingredient | 10 |
|  | Polyvinylacetate/vinyl chloride copolymer latex | 5 |
|  | Attapulgus granules | 85 |

EXAMPLE 5

This Example demonstrates formulations for use as a spray. The compounds can be formulated as wettable powders, water dispersible granules, suspension concentrates, emulsifiable concentrates, emulsions or microcapsule suspensions for application diluted in water.

|  |  | g/l |
|---|---|---|
| Emulsifiable concentrate: | Active ingredient | 250 |
|  | Calcium dodecyl-benzene sulfonate | 50 |
|  | Nonyl phenol ethoxylate | 50 |
|  | Alkylbenzene solvent | to 1 litre |

|  |  | % w/w |
|---|---|---|
| Wettable powder: | Liquid active ingredient | 40 |
|  | lignosulfonate dispersant | 5 |
|  | silica | 25 |
|  | sodium lauryl sulfate | 3 |
|  | china clay (kaolin) | 27 |
| Microcapsule suspension: | Liquid active ingredient | 250 |
|  | toluene diisocyanate | 10 |
|  | polymethylene polyphenyl isocyanate | 20 |
|  | nonyl phenol ethoxylate | 6 |
|  | lignosulfonate dispersant | 15 |
|  | xanthan gum | 1 |
|  | bentonite | 10 |
|  | biocide 'Proxel'* | 0.1 |
|  | sodium carbonate | 5 |
|  | water | to 1 litre |

The microcapsule suspensions can be used as a spray, soil drench or as an intermediate to prepare slow release granulesfor application to the soil.

|  |  | g/l |
|---|---|---|
| Suspension concentrate: | Solid active ingredient | 400 |
|  | lignosulfonate dispersant | 50 |
|  | sodium lauryl sulfate | 30 |
|  | xanthan gum | 1 |
|  | biocide 'Proxel'* | 0.1 |
|  | bentonite | 10 |
|  | water | to 1 litre |

EXAMPLE 6

This Example demonstrates formulations suitable for use as seed treatments in conventional application machinery.

|  |  | % w/w |
|---|---|---|
| Dry seed treatment: | Active ingredient | 20 |
|  | dodecyl benzene | 3 |
|  | Rubine Toner (dyestuff) | 2.7 |
|  | Talc | 53.3 |
|  | Silica | to 100% |

The suspension concentrate and microcapsule suspension of Example 5 can be used as flowable concentrates for seed treatment.

EXAMPLE 7

This Example demonstrates the formulation of the compounds for electrostatic spraying.

|  | g/l |
|---|---|
| Active ingredient | 200 |
| N-methylpyrrolidone | 50 |
| Soyabean oil | 120 |
| 'Solvesso'* 200 | to 1 litre |

EXAMPLE 8

This Example demonstrates a formulations suitable for use as a bait.

|  | % w/w |
|---|---|
| Active ingredient | 0.25 |
| Icing sugar | 99.65 |
| Butylated hydroxy toluene | 0.10 |

EXAMPLE 9

This Example demonstrates a formulation suitable for use as a bolus.

|  | mg |
|---|---|
| Active ingredient | 1300 |
| Sodium starch glycollate | 300 |
| Microcrystalline cellulose | 1200 |
| Lactose | 2920 |
| Povidone | 250 |
| Magnesium stearate | 30 |

EXAMPLE 10

This Example demonstrates a formulation suitable for use as an injectable suspension.

|  | mg |
|---|---|
| Active ingredient | 40 |
| Sodium metabisulfite | 1 |
| Polysorbate 80 | 1 |
| Sodium methyl hydroxybenzoate | 2 |
| Water to | 1 ml |

EXAMPLE 11

This Example demonstrates a formulation suitable for use as an injectable solution.

|  | mg |
| --- | --- |
| Active ingredient | 20 |
| Sodium citrate | 6 |
| Citric acid | 1 |
| Sodium chloride | 7 |
| Chlorcresol | 1 |
| Water to | 1 ml |

EXAMPLE 12

This Example demonstrates a formulation suitable for use as an oral suspension.

|  | g |
| --- | --- |
| Active ingredient | 100.0 |
| Polysorbate 80 | 2.0 |
| Xanthan gum | 5.0 |
| Colloidal silicon dioxide | 10.0 |
| Methyl hydroxybenzoate | 1.5 |
| Citric acid monohydrate | 10.0 |
| Sodium citrate | 10.0 |
| Purified water to | 1000.0ml |

CHEMICAL FORMULAE
(IN DESCRIPTION)

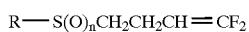     (I)

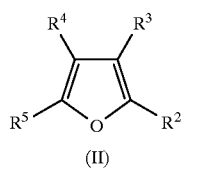 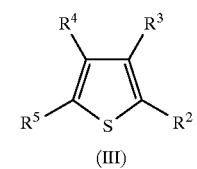

(II)           (III)

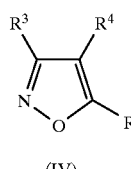 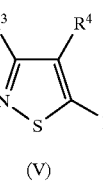 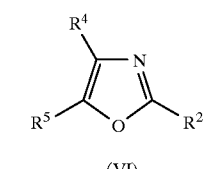

(IV)     (V)     (VI)

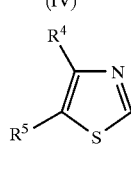 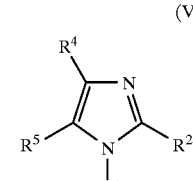

(VII)           (VIII)

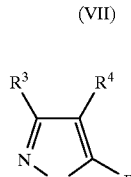 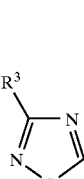 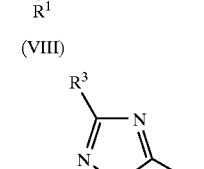

(IX)     (X)     (XI)

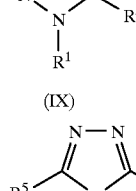 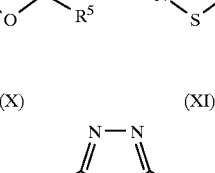

(XII)           (XIII)

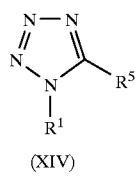 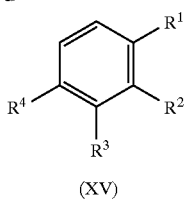

(XIV)           (XV)

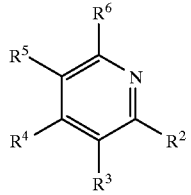 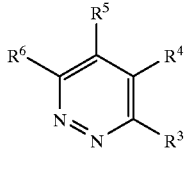

(XVI)           (XVII)

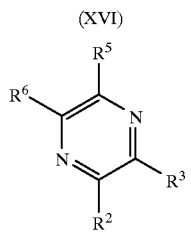 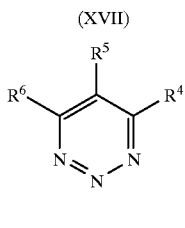

(XVIII)           (XIX)

(XX)           (XXI)

R—SH     (XXIII)

$CF_2$=$CHCH_2CH_2L$     (XXIV)

$CF_2$=$CHCH_2CH_2OSO_2R^b$     (XXV)

$CF_2$=$CHCH_2CH_2Br$     (XXVI)

R—L     (XXVII)

$CF_2$=$CHCH_2CH_2SH$     (XXVIII)

R—$NH_2$     (XXIX)

($CF_2$=$CHCH_2CH_2S)_2$     (XXX)

We claim:

1. A compound of formula (I),

or a salt thereof, wherein n is 0, 1 or 2; and R is a group of formula (V) or (VII)

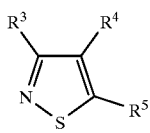

(V)

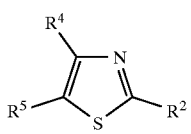

(VII)

wherein:
at least one of $R^2$, $R^3$, $R^4$ or $R^5$ is a S(O)$nCH_2CH_2CH=CF_2$ group; and the remainder of $R^2$, $R^3$, $R^4$ and $R^5$ are each independently selected from the group consisting of hydrogen, optionally substituted alkyl, optionally substituted alkenyl, alkynyl, cycloalkyl, alkylcycloalkyl, alkoxy, alkenyloxy, alkynyloxy, hydroxyalkyl, alkoxyalkyl, optionally substituted aryl, optionally substituted arylalkyl, optionally substituted heteroaryl, optionally substituted heteroarylalkyl, optionally substituted aryloxy, optionally substituted arylalkoxy, optionally substituted aryloxyalkyl, optionally substituted heteroaryloxy, optionally substituted heteroarylalkoxy, optionally substituted heteroaryloxyalkyl, haloalkyl, haloalkenyl, haloalkynyl, haloalkoxy, haloalkenyloxy, haloalkynyloxy, halogen, hydroxy, cyano, nitro, —$NR^7R^8$, —$NR^7COR^8$, $NR^7CSR^8$, —$NR^7SO_2R^8$, —$N(SO_2R^7)(SO_2R^8)$, —$COR^7$, —$CONR^7R^8$, —alkyl$CONR^7R^8$, —$CR^7NR^8$, —$COOR^7$, —$OCOR^7$, —$SR^7$, —$SOR^7$, —$SO_2R^7$, —alkyl$SR^7$, —alkyl$SOR^7$, —alkyl$SO_2R^7$, —$OSO_2R^7$, —$SO_2NR^7R^8$, —$CSNR^7R^8$, —$SiR^7R^8R^9$, —$OCH_2CO_2R^7$, —$OCH_2CH_2CO_2R^7$, —$CONR^7SO_2R^8$, —alkyl$CONR^7SO_2R^8$, —$NHCONR^7R^8$, —$NHCSNR^7R^8$; and $R^7$, $R^8$ and $R^9$ are each independently selected from the group consisting of hydrogen, optionally substituted alkyl, optionally substituted alkenyl, alkynyl, optionally substituted aryl or optionally substituted arylalkyl, haloalkyl, haloalkenyl, haloalkynyl, halogen, and hydroxy.

2. A compound according to claim 1, wherein:
at least one of $R^2$, $R^3$, $R^4$ or $R^5$ is a —S(O)$nCH_2CH_2CH=CF_2$ group; and the remainder of $R^2$, $R^3$, $R^4$ and $R^5$ are each independently selected from the group consisting of hydrogen, optionally substituted $C_{1-6}$ alkyl, optionally substituted $C_{2-6}$ alkenyl, optionally substituted $C_{2-6}$ alkynyl, $C_{3-6}$ cycloalkyl, $C_{4-7}$ alkylcycloalkyl, $C_{1-6}$ alkoxy, $C_{2-6}$ alkenyloxy, $C_{2-6}$ alkynyloxy, $C_{1-6}$ hydroxyalkyl, $C_{2-6}$ monoalkoxyalkyl, $C_{3-6}$ dialkoxyalkyl, optionally substituted $C_{6-10}$ aryl, optionally substituted $C_{6-10}$ aryl-$C_{1-2}$ alkyl group, optionally substituted 5 or 6 membered heteroaryl, optionally substituted 5 or 6 membered heteroaryl-$C_{1-6}$ alkyl, optionally substituted $C_{6-10}$ aryloxy, optionally substituted $C_{6-10}$ aryl-$C_{1-2}$ alkoxy, $C_{6-10}$ aryloxy-$C_{1-6}$ alkyl, optionally substituted 5 or 6 membered heteroaryloxy, optionally substituted 5 or 6 membered heteroaryl-$C_{1-6}$ alkoxy, 5 or 6 membered heteroaryloxy-$C_{1-2}$ alkyl, $C_{1-6}$ haloalkyl, $C_{2-6}$ haloalkenyl, $C_{2-6}$ haloalkynyl, $C_{1-6}$ haloalkoxy, $C_{2-6}$ haloalkenyloxy, $C_{2-6}$ haloalkynyloxy, halogen, hydroxy, cyano, nitro, —$NR^7R^8$, —$NR^7COR^8$, —$NR^7CSR^8$, —$NR^7SO_2R^8$, —$N(SO_2—R^7)(SO_2—R^8)$, —$COR^7$, —$CONR^7R^8$, —$C_{1-6}$ alkyl$CONR^7R^8$, —$CR^7NR^8$, —$COOR^7$, —$OCOR^7$, —$SR^7$, —$SOR^7$, —$SO_2R^7$, —$C_{1-6}$ alkyl$SR^7$, —$C_{1-6}$ alkyl$SOR^7$, —$C_{1-6}$ alkyl-$SO_2^7$, —$OSO_2R^7$, —$SO_2NR^7R^8$, —$CSNR^7R^8$, —$SiR^7R^8R^9$, —$OCH_2CO_2R^7$, —$OCH_2CH_2CO_2R^7$, —$CONR^7SO_2R^8$, —$C_{1-6}$ alkyl$CONR^7SO_2R^8$, —$NHCONR^7R^8$, —$NHCSNR^7R^8$; and $R^7$, $R^8$ and $R^9$ are each independently selected from the group consisting of hydrogen, optionally substituted $C_{1-6}$ alkyl, optionally substituted $C_{2-6}$ alkenyl, $C_{2-6}$ alkenyl, $C_{2-6}$ alkynyl, $C_{1-6}$ haloalkyl, $C_{2-6}$ haloalkenyl, $C_{2-6}$ haloalkynyl, optionally substituted $C_{4-6}$ aryl or optionally substituted $C_{4-6}$ aryl-$C_{1-6}$ alkyl, halogen and hydroxy.

3. A compound according to claim 2, wherein at least one of $R^2$, $R^3$, $R^4$ or $R^5$ is selected from the group consisting of:
substituted alkyl, or contains a substituted alkyl moiety, comprising one or more substituents, wherein the substituents are selected from the group consisting of halogen, nitro, cyano, —$COOR^7$ or a salt thereof, hydroxy, alkoxy, alkoxyimino, alkoxycarbonyl, carbamyl, mono- or di-alkylcarbamoyl, amino, mono- or di-alkylamino, acylamido, alkanesulfonyl and arylsulfonyl;
substituted alkenyl, which may contain one or more substituents selected from the group consisting of halogen, $COOR^7$ or a salt thereof, hydroxy, nitro and cyano;
substituted aryl or heteroaryl, which may contain one or more substituents selected from the group consisting of alkyl, alkoxy, haloalkyl, halogen, hydroxy, $COOR^7$ or a salt thereof, aminosulfonyl, cyano and nitro.

4. A compound according to claim 3 wherein at least one of $R^2$, $R^3$, $R^4$, or $R^5$ is —$SR^7$, and —$R^7$ is selected from the group consisting of optionally substituted $C_{1-6}$ alkylthio, $C_{2-6}$ alkenylthio, $C_{2-6}$ alkynylthio, $C_{1-6}$ haloalkyl, $C_{2-6}$ haloalkenylthio, $C_{2-6}$ haloalkynylthio and $C_{6-10}$ arylthio.

5. A compound according to claim 1 wherein:
the remainder of $R^2$, $R^3$, $R^4$ and $R^5$ are each independently selected from the group consisting of hydrogen; nitro; halogen; cyano; —CH=NOH; $C_{1-4}$ alkyl; $C_{1-4}$ haloalkyl; $C_{1-4}$ alkenyl; $C_{1-4}$ haloalkenyl; cyclopropyl; hydroxy; $C_{1-4}$ alkoxy; $C_{2-4}$ alkoxyalkyl; —COOH; $C_{2-4}$ alkoxycarbonyl; $C_{2-4}$ haloalkenyloxycarbonyl; —$CONH_2$; mono or di-$C_{1-2}$ alkylaminocarbonyl; $C_{2-4}$ alkanecarbonyl; phenyl optionally mono- or di- substituted with groups independently selected from the group consisting of halogen, nitro, $C_{1-4}$ alkyl, $C_{1-4}$ alkoxy and aminosulfonyl; —$CONHSO_2$—$C_{1-4}$ alkyl; benzyl optionally mono- or di- substituted with groups independently selected from the group consisting of halogen, nitro, $C_{1-4}$ alkyl and $C_{1-4}$ alkoxy; phenoxy optionally mono- or di- substituted with groups independently selected from the group consisting of halogen, cyano, $C_{1-4}$ alkyl and $C_{1-4}$ alkoxy; amino optionally mono- or di- substituted with $C_{1-4}$ alkyl groups; —SH; $C_{1-4}$ alkylthio; benzylthio optionally mono- or di- substituted with groups independently selected from the group consisting of halogen or $C_{1-4}$ haloalkyl; $C_{1-4}$ alkenylthio; $C_{2-4}$ haloalkenylthio; a second S(O)$nCH_2CH_2CH=CF_2$ group; $C_{1-4}$ alkanesulfonyl; $C_{1-4}$ haloalkanesulfonyl; fluorosulfonyl; mono- or di- $C_{1-4}$ alkylsulfamoyl; and a 5 or 6 membered heteroaryl group optionally substituted with halogen.

6. A compound according to claim 1 wherein the S(O)$_n$CH$_2$CH$_2$CH=CF$_2$ group is at least one of $R^2$, $R^3$, $R^4$ or $R^5$; and the remainder of $R^2$, $R^3$, $R^4$ and $R^5$ are each independently hydrogen, optionally substituted alkyl, optionally substituted aryl, optionally substituted heteroaryl, haloalkyl, halogen, cyano, nitro, —COR$^7$, —CONR$^7$R$^8$, —COOR$^7$, —SO$_2$R7, —SO$_2$NR$^7$R$^8$, —CONR$^7$SO2R$^8$, and $R^7$, $R^8$ and $R^9$ are each independently hydrogen, optionally substituted alkyl, halogen, or hydroxy.

7. A compound according to claim 6 wherein R is a group of formula VII, $R^2$ is S(O)nCH$_2$CH$_2$CH=CF$_2$ and R4 and 5 are selected from hydrogen, alkyl and halogen.

8. A compound according to claim 7 where R4 is hydrogen and R5 is chloro.

9. The compound according to claim 8 wherein n is 2.

10. An agricultural nematicidal, insecticidal or acaricidal composition comprising a nematicidally, insecticidally, or acaricidally effective amount of a compound of claim 1 as the active ingredient, in admixture with an agriculturally acceptable diluent or carrier.

11. An agricultural composition according to claim 10, further comprising a surface active material.

12. An agricultural composition according to claim 10, further comprising at least one other active ingredient which is an insecticide, fungicide, bactericide, acaricide or other biologically active compound.

13. A process for preparing an agricultural composition of claim 10, comprising admixing the compound of claim 1 and the agriculturally acceptable diluent or carrier.

14. A method for killing or controlling nematode, insect or acarid pests comprising applying a compound of claim 1, or a composition of claim 10, to the pests, their habitat, or a plant susceptible to attack by the pests.

* * * * *